United States Patent
Deisseroth et al.

(10) Patent No.: US 12,263,350 B2
(45) Date of Patent: Apr. 1, 2025

(54) LIGHT-RESPONSIVE POLYPEPTIDES AND METHODS OF USE THEREOF

(71) Applicants: The Board of Trustees of the Leland Stanford Junior University, Stanford, CA (US); The University of Tokyo, Tokyo (JP)

(72) Inventors: Karl A. Deisseroth, Stanford, CA (US); Yoon Kim, Stanford, CA (US); Hideaki Kato, Stanford, CA (US); Charu Ramakrishnan, Stanford, CA (US); Susumu Yoshizawa, Tokyo (JP)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 893 days.

(21) Appl. No.: 17/421,346

(22) PCT Filed: Jan. 10, 2020

(86) PCT No.: PCT/US2020/013098
§ 371 (c)(1),
(2) Date: Jul. 7, 2021

(87) PCT Pub. No.: WO2020/150093
PCT Pub. Date: Jul. 23, 2020

(65) Prior Publication Data
US 2022/0118271 A1    Apr. 21, 2022

Related U.S. Application Data

(60) Provisional application No. 62/792,297, filed on Jan. 14, 2019.

(51) Int. Cl.
*C07K 14/705*    (2006.01)
*A61N 5/06*    (2006.01)
*C12N 13/00*    (2006.01)
*A61N 5/067*    (2006.01)

(52) U.S. Cl.
CPC ........... *A61N 5/062* (2013.01); *A61N 5/0601* (2013.01); *C07K 14/705* (2013.01); *C12N 13/00* (2013.01); *A61N 2005/063* (2013.01); *A61N 2005/0652* (2013.01); *A61N 2005/0663* (2013.01); *A61N 5/067* (2021.08); *C07K 2319/04* (2013.01); *C07K 2319/10* (2013.01)

(58) Field of Classification Search
None
See application file for complete search history.

(56) References Cited

FOREIGN PATENT DOCUMENTS

WO    WO 2019/183376    9/2019

OTHER PUBLICATIONS

GenBank Accession QDS028931.1 ChRmine [synthetic construct]. Aug. 4, 2019 [2019]. [Retrieved Mar. 24, 2020]. Retrieved from the internet: <URL: https://www.ncbi.nlm.nih.gov/protein/1710560095>. p. 1.
UniProt Accession A0A172M4H4. Guith. Mar. 15, 2017 [online]. [Retrieved Mar. 24, 2020]. Retrieved from the Internet: URL:https://www.uniprot.org/uniprot/A0A172M4H4.txt?version=4. >. p. 1.

*Primary Examiner* — Nianxiang Zou
(74) *Attorney, Agent, or Firm* — Rudy J. Ng; Christian S. Hans; Bozicevic, Field & Francis LLP

(57) ABSTRACT

The present disclosure provides light-responsive polypeptides, and nucleic acids comprising nucleotide sequences encoding the light-responsive polypeptides. The present disclosure provides methods, devices, and systems for controlling the activity of a cell expressing a light-responsive polypeptide of the present disclosure.

22 Claims, 77 Drawing Sheets
Specification includes a Sequence Listing.

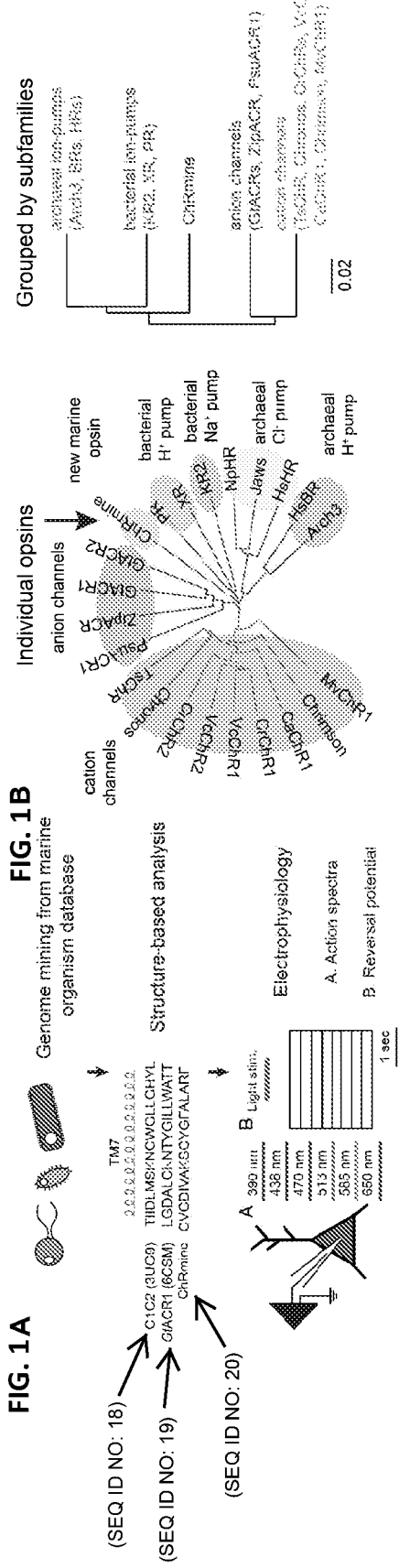
FIG. 1A
FIG. 1B
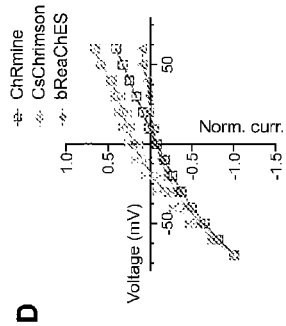
FIG. 1D
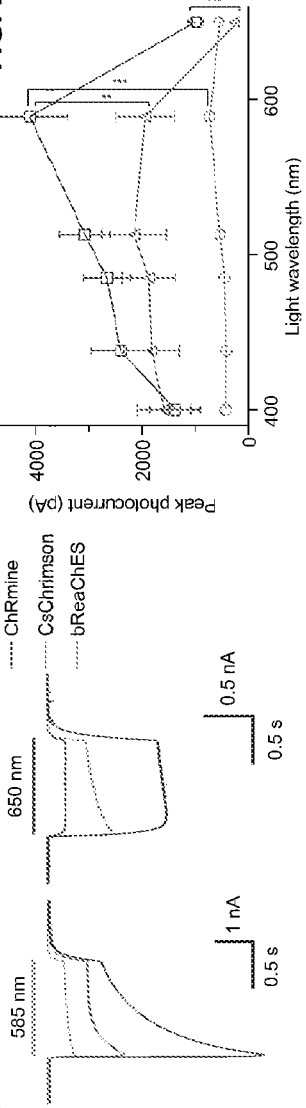
FIG. 1C

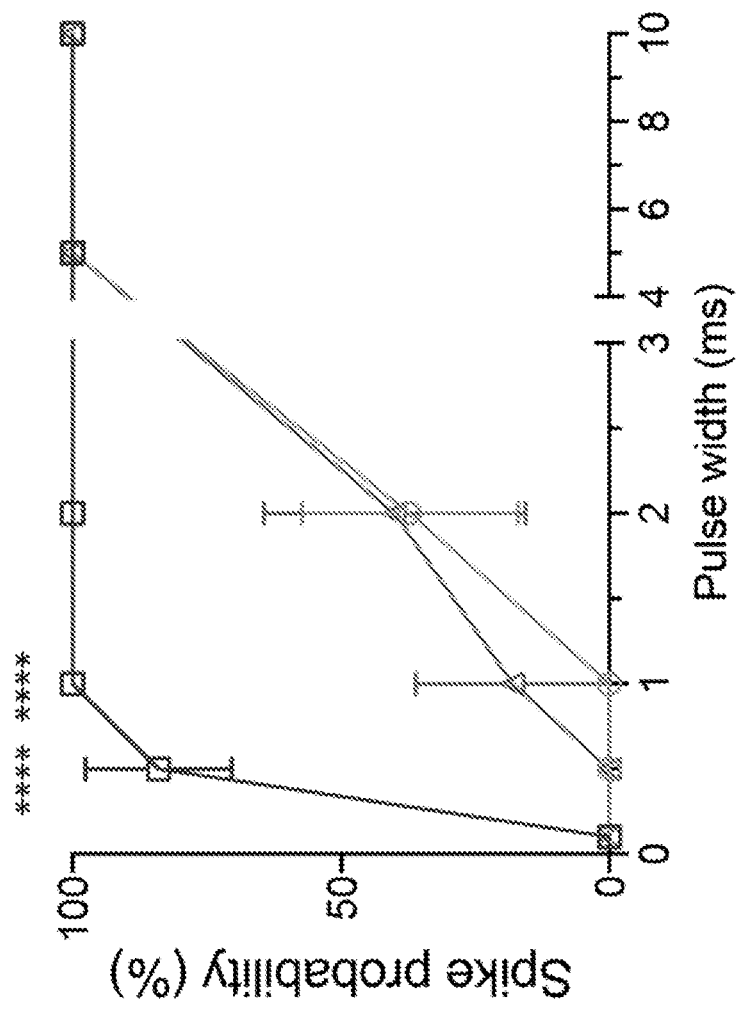

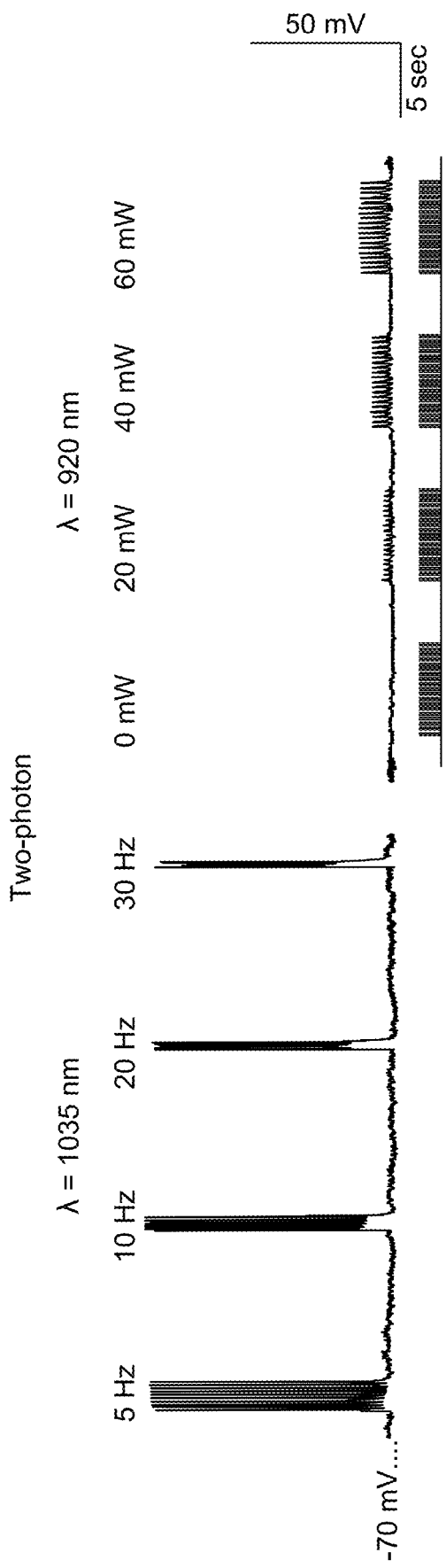
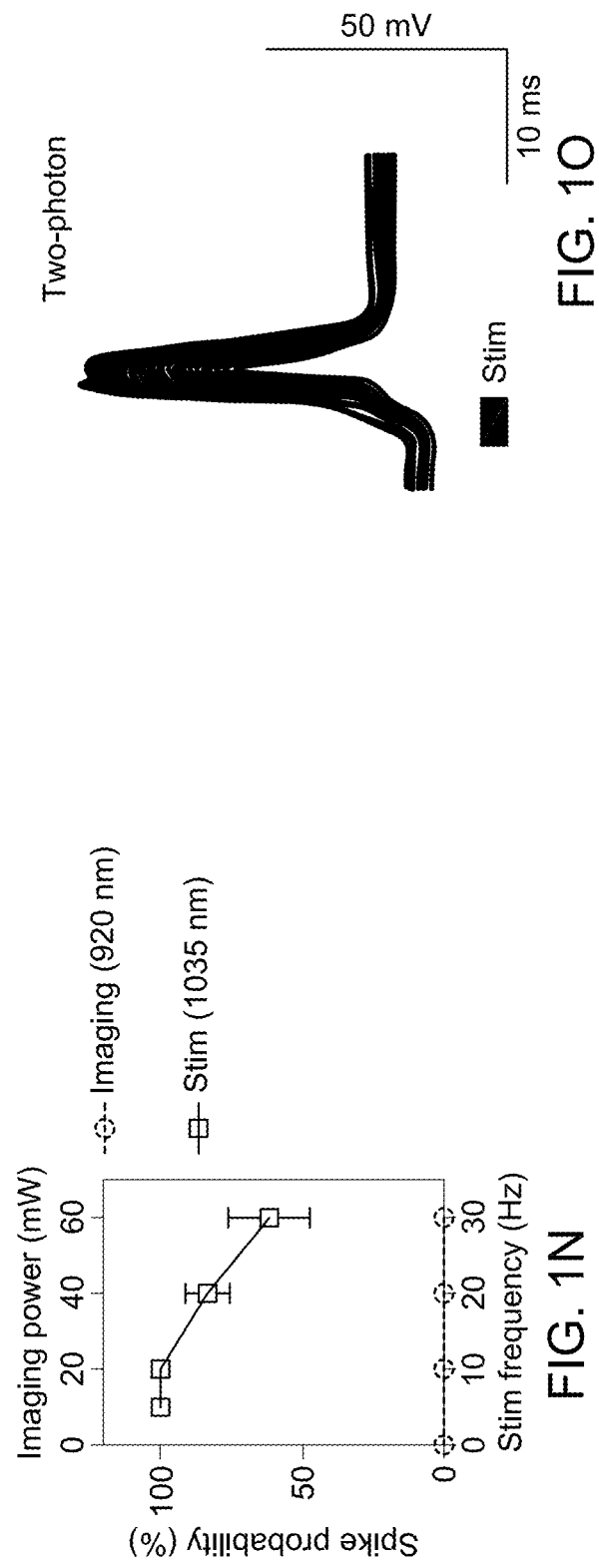
FIG. 1M
FIG. 1N
FIG. 1O

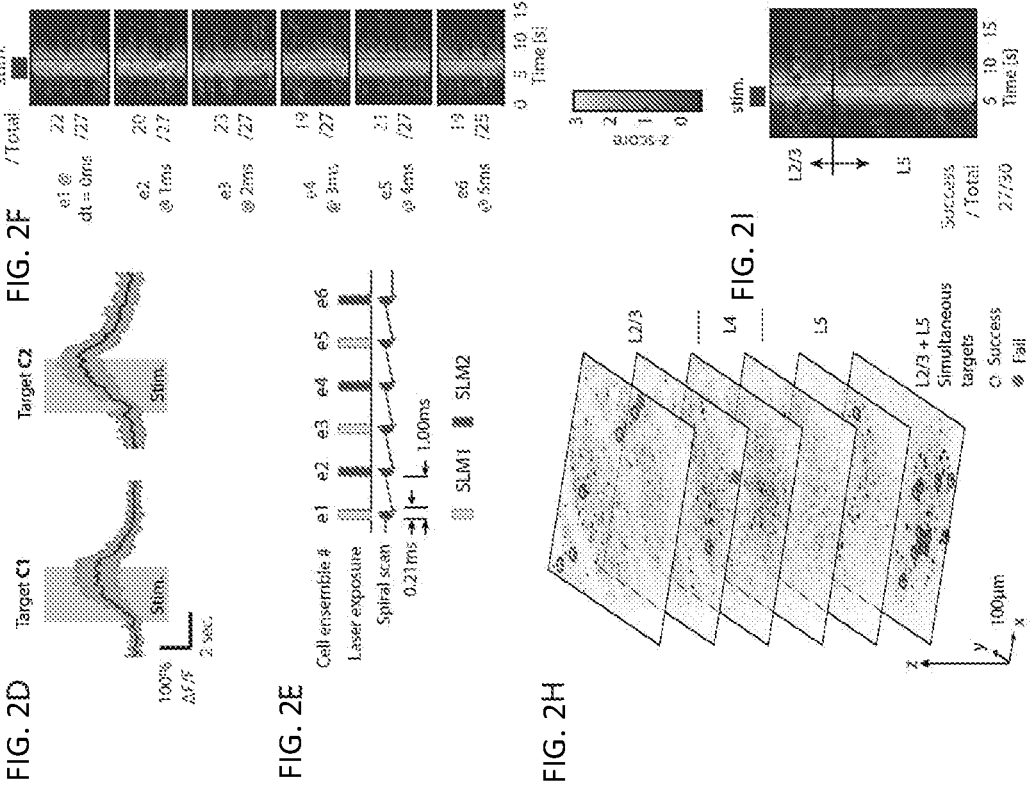
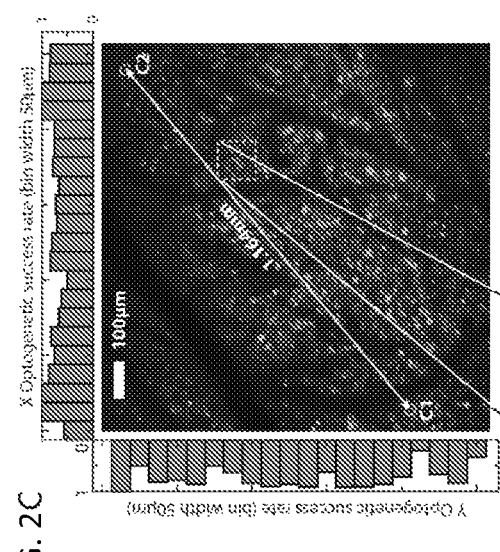
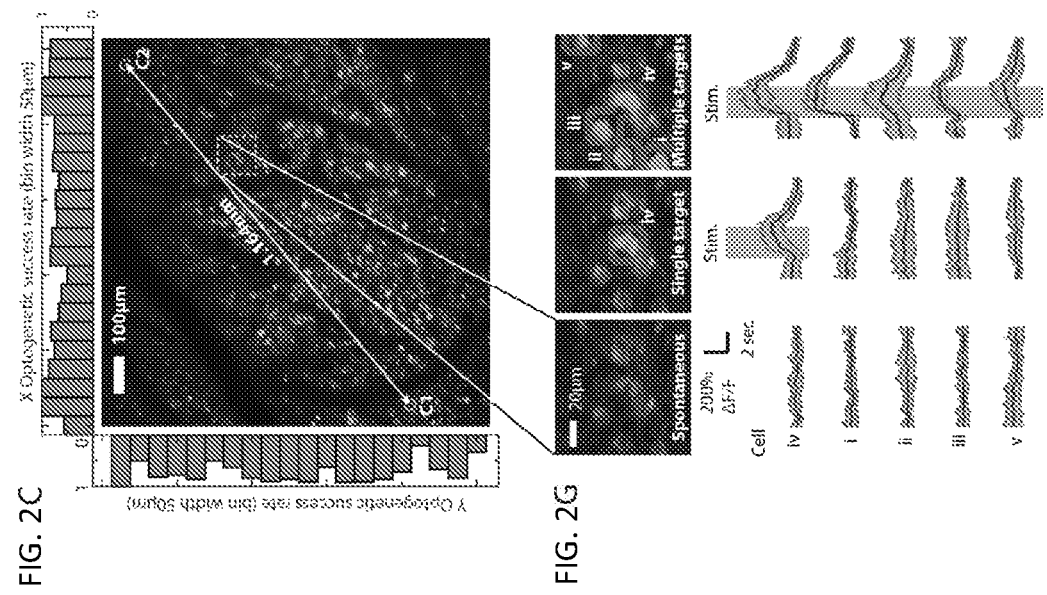

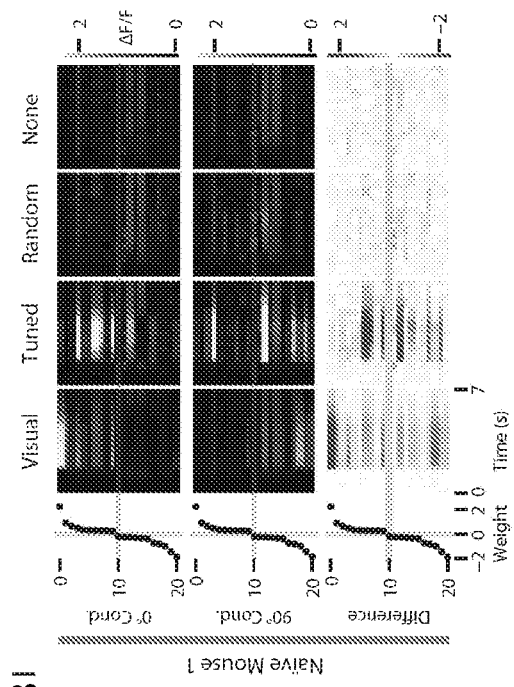
FIG. 3I
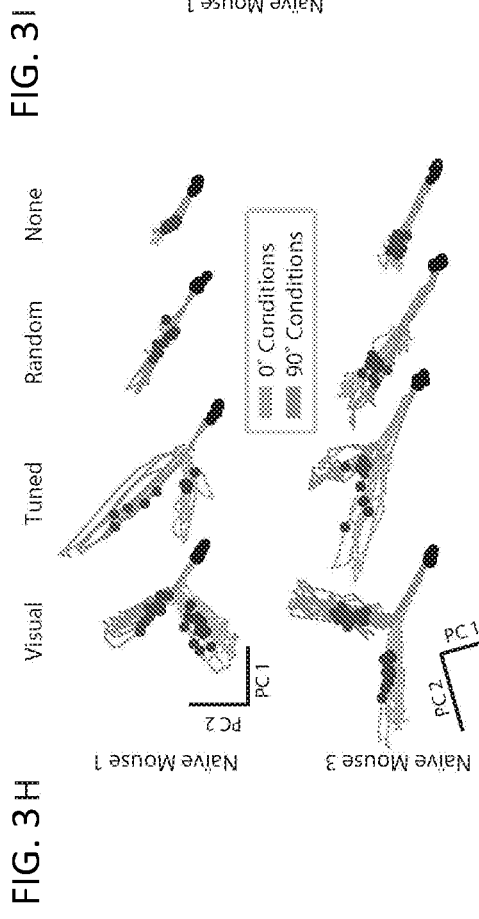
FIG. 3H
FIG. 3K
FIG. 3J

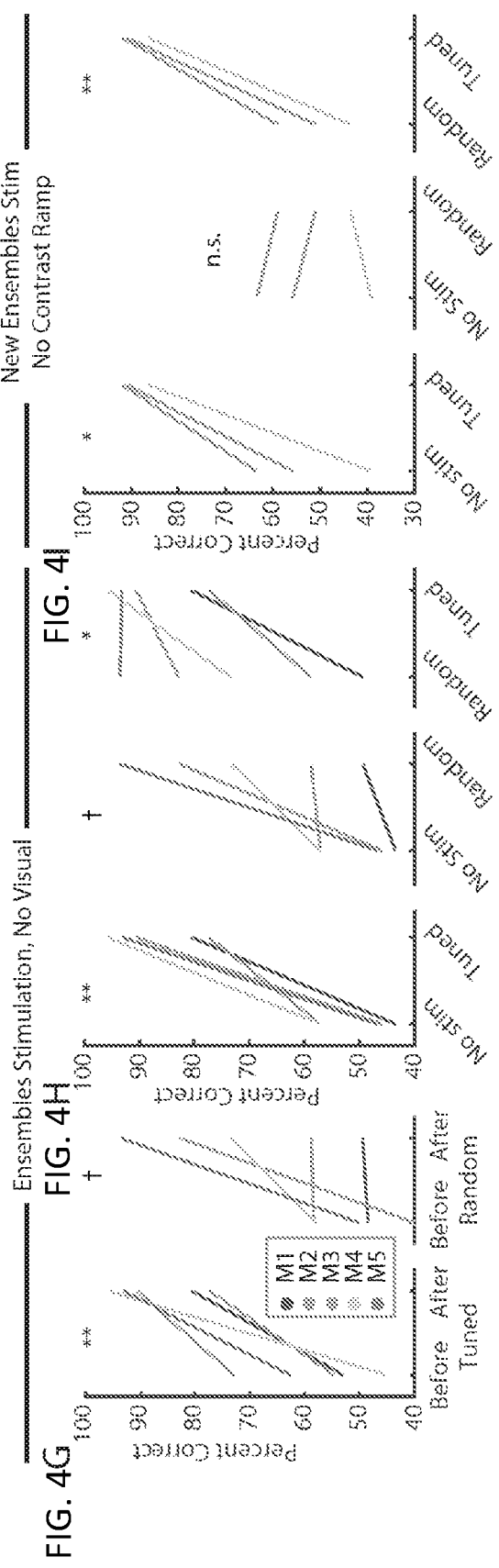

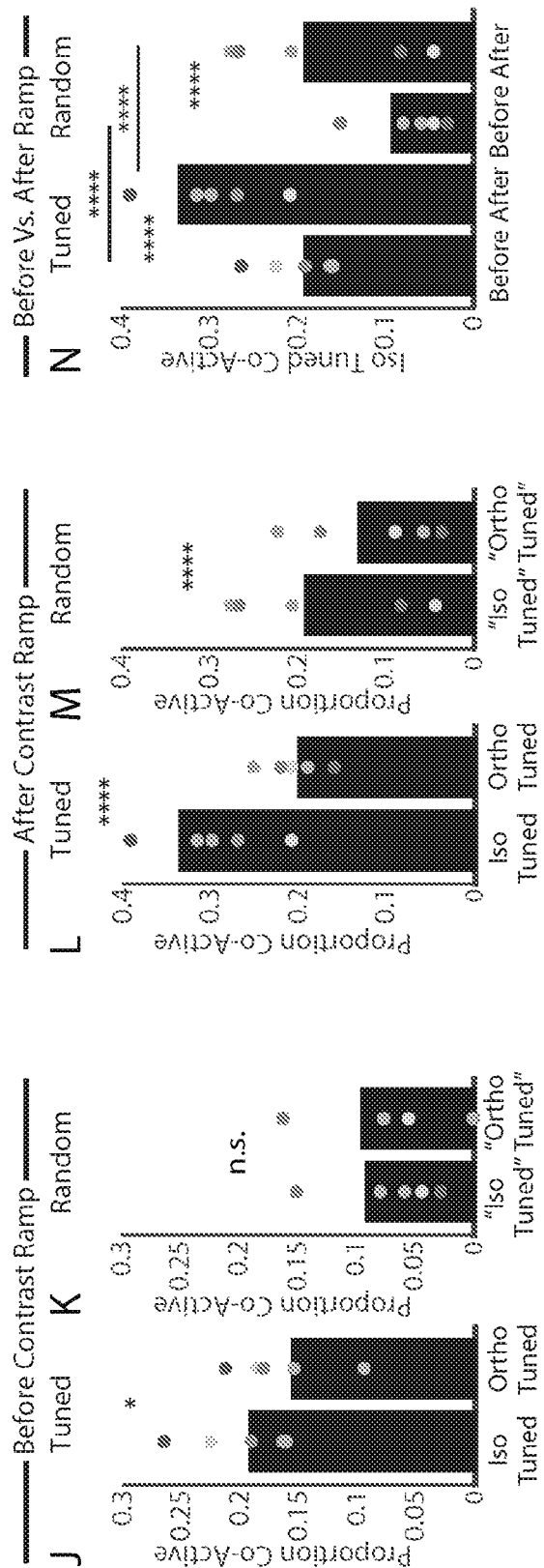
FIG. 4 J-N

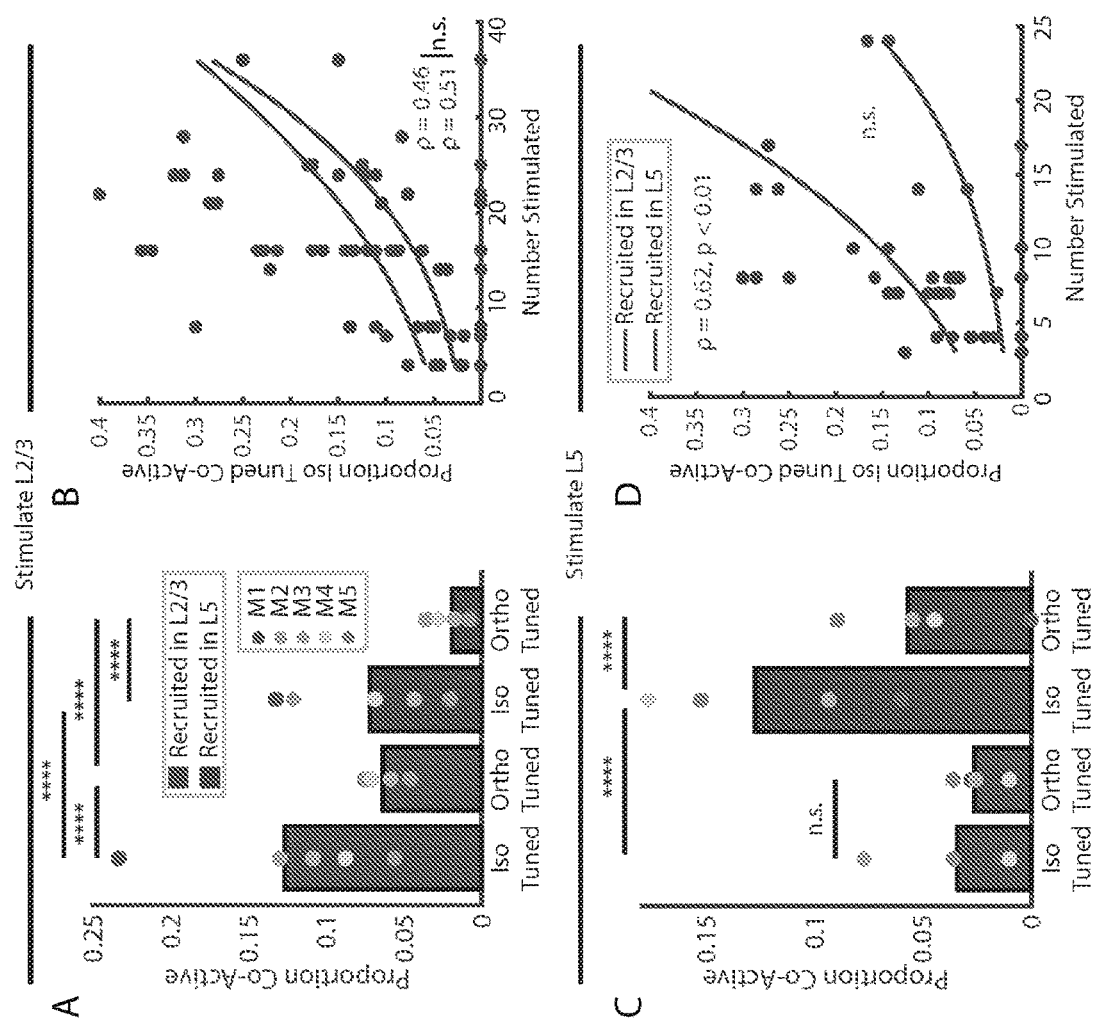
FIG. 6 A-D

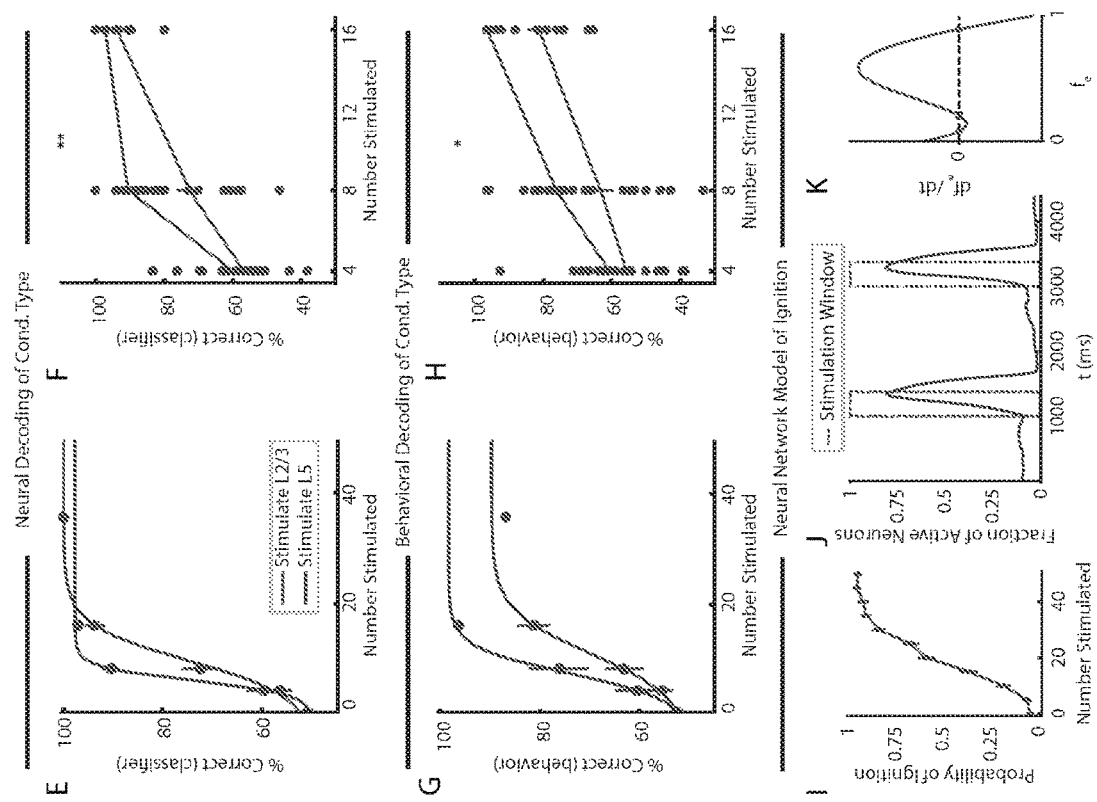
FIG. 6 E-K

FIG. 7

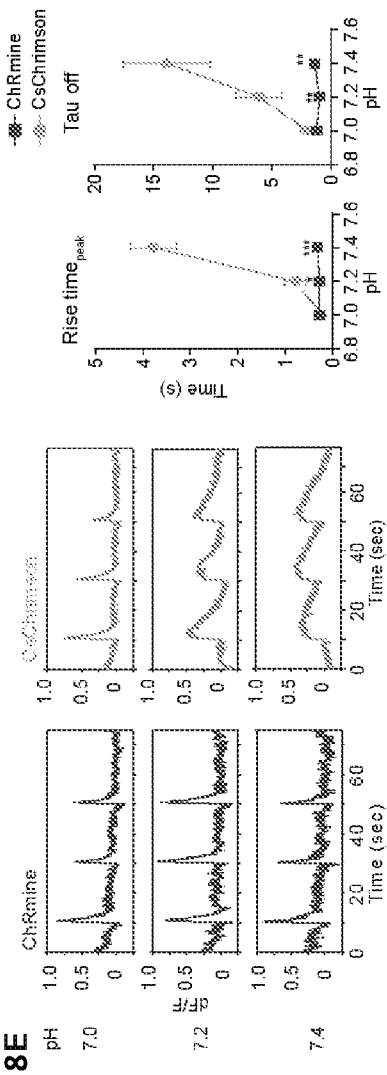
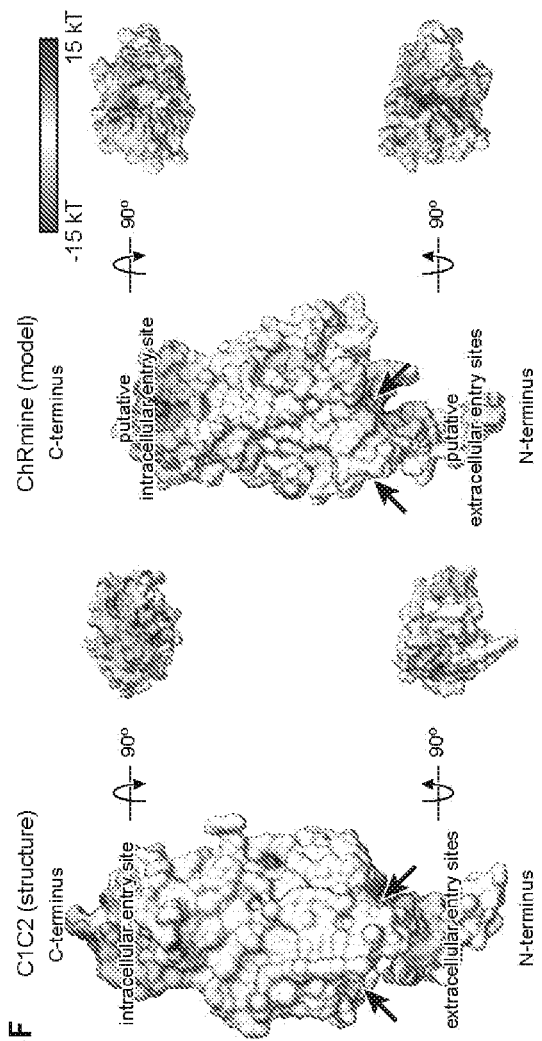
FIG. 8E
FIG. 8F

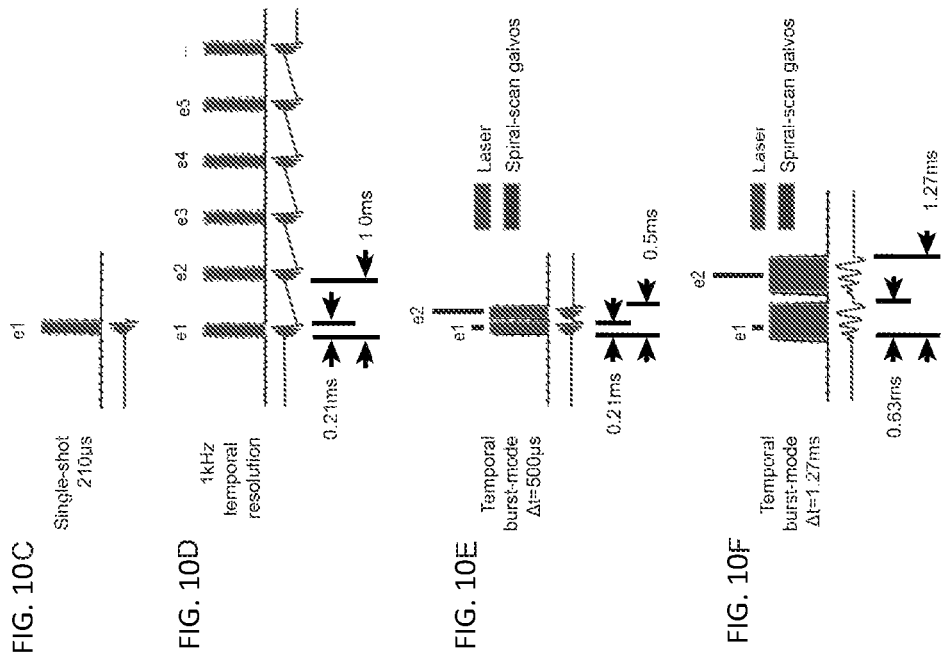
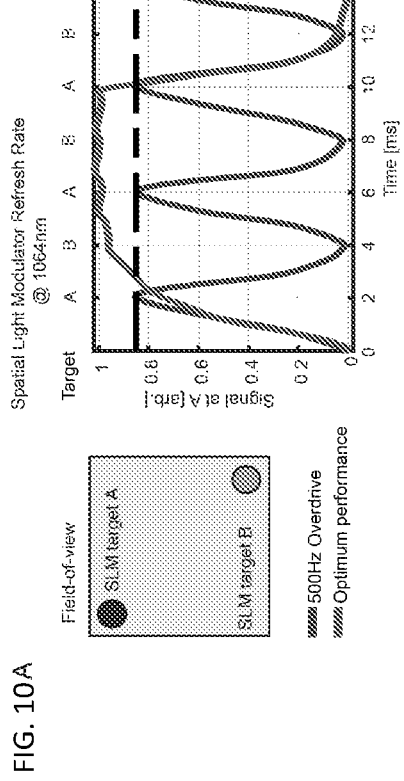
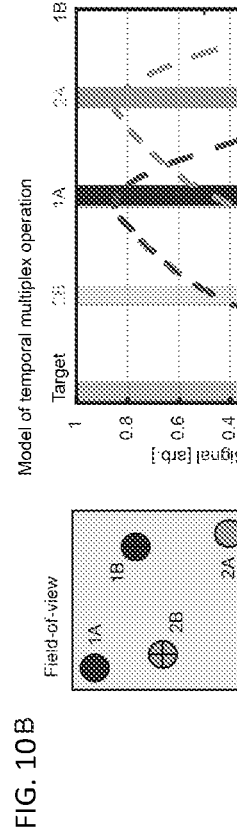
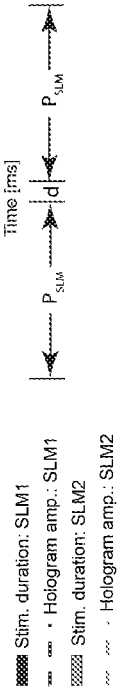
FIG. 10A
FIG. 10B
FIG. 10C
FIG. 10D
FIG. 10E
FIG. 10F

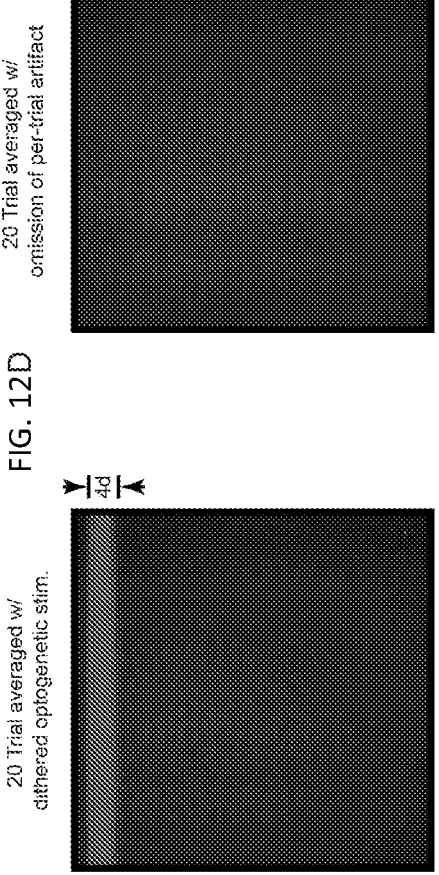
FIG. 12A
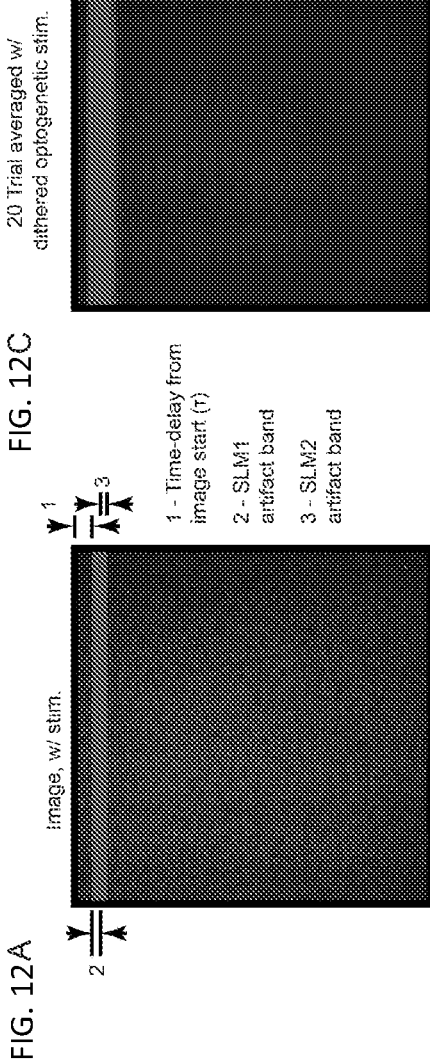
FIG. 12B
FIG. 12C
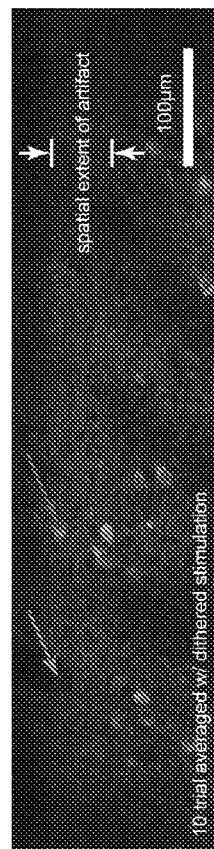
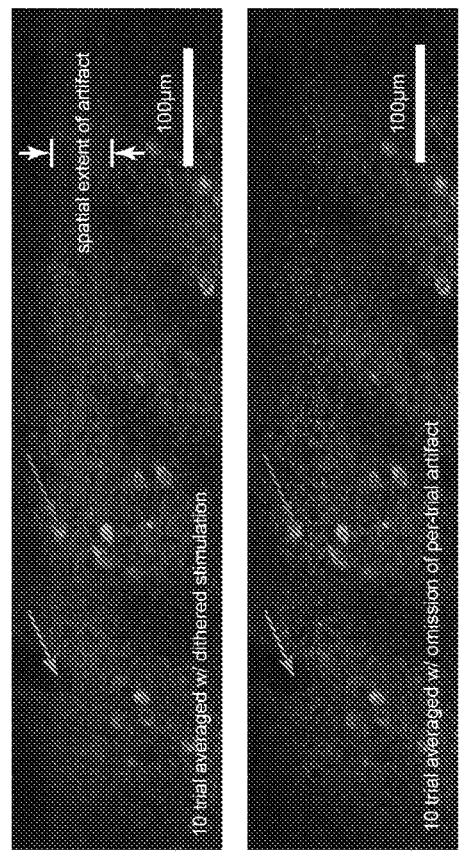
FIG. 12D
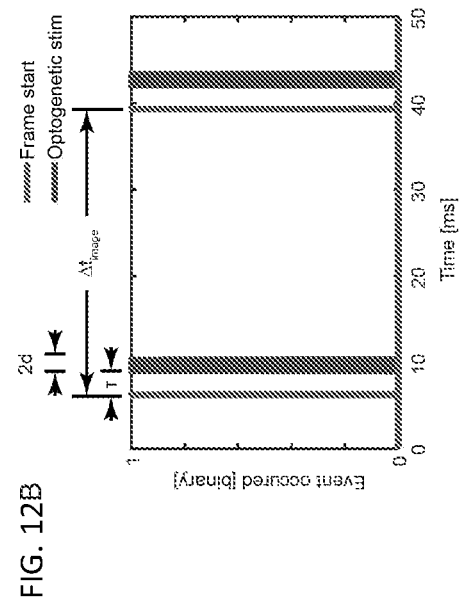
FIG. 12E

FIG. 14C

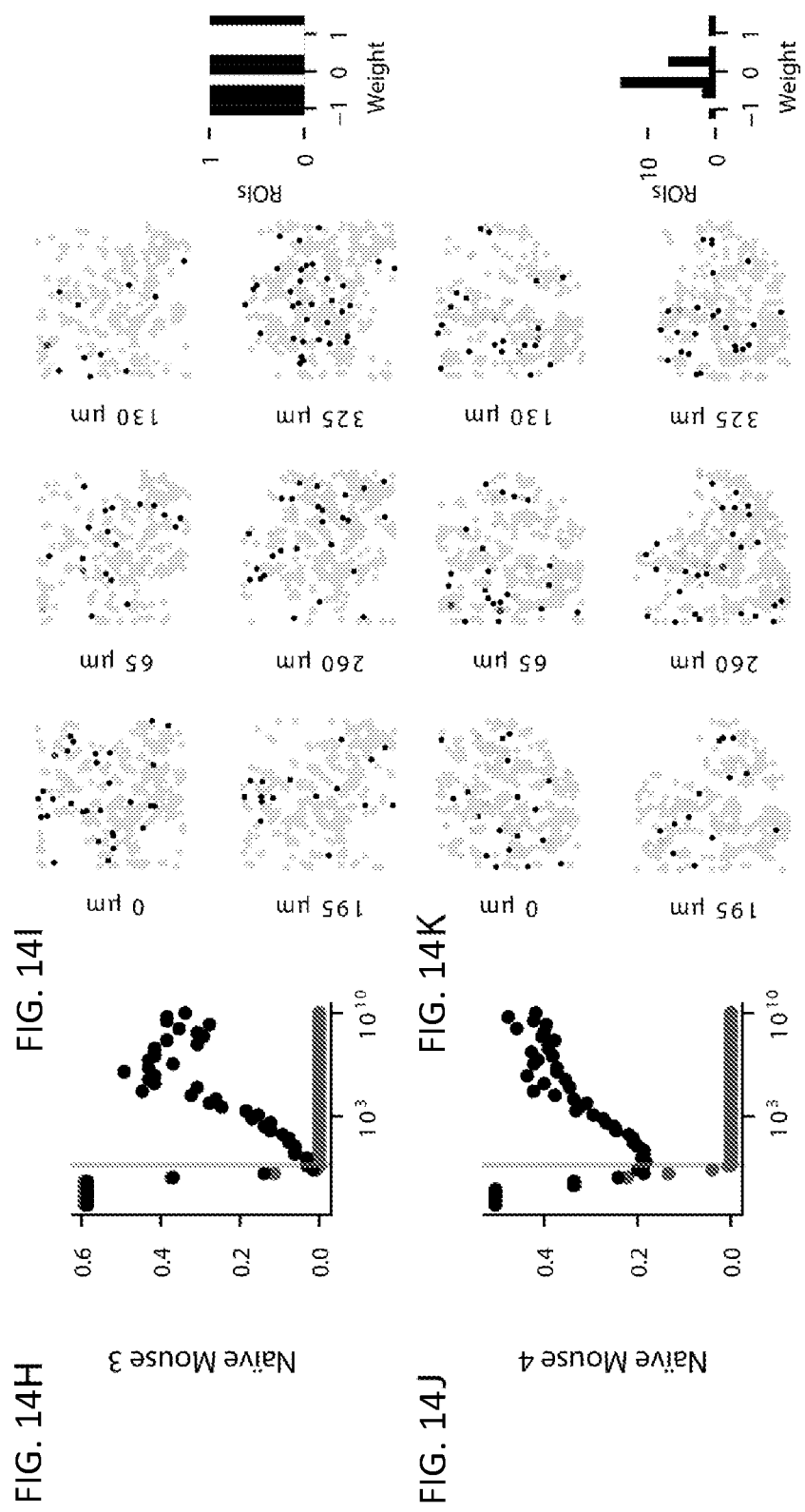

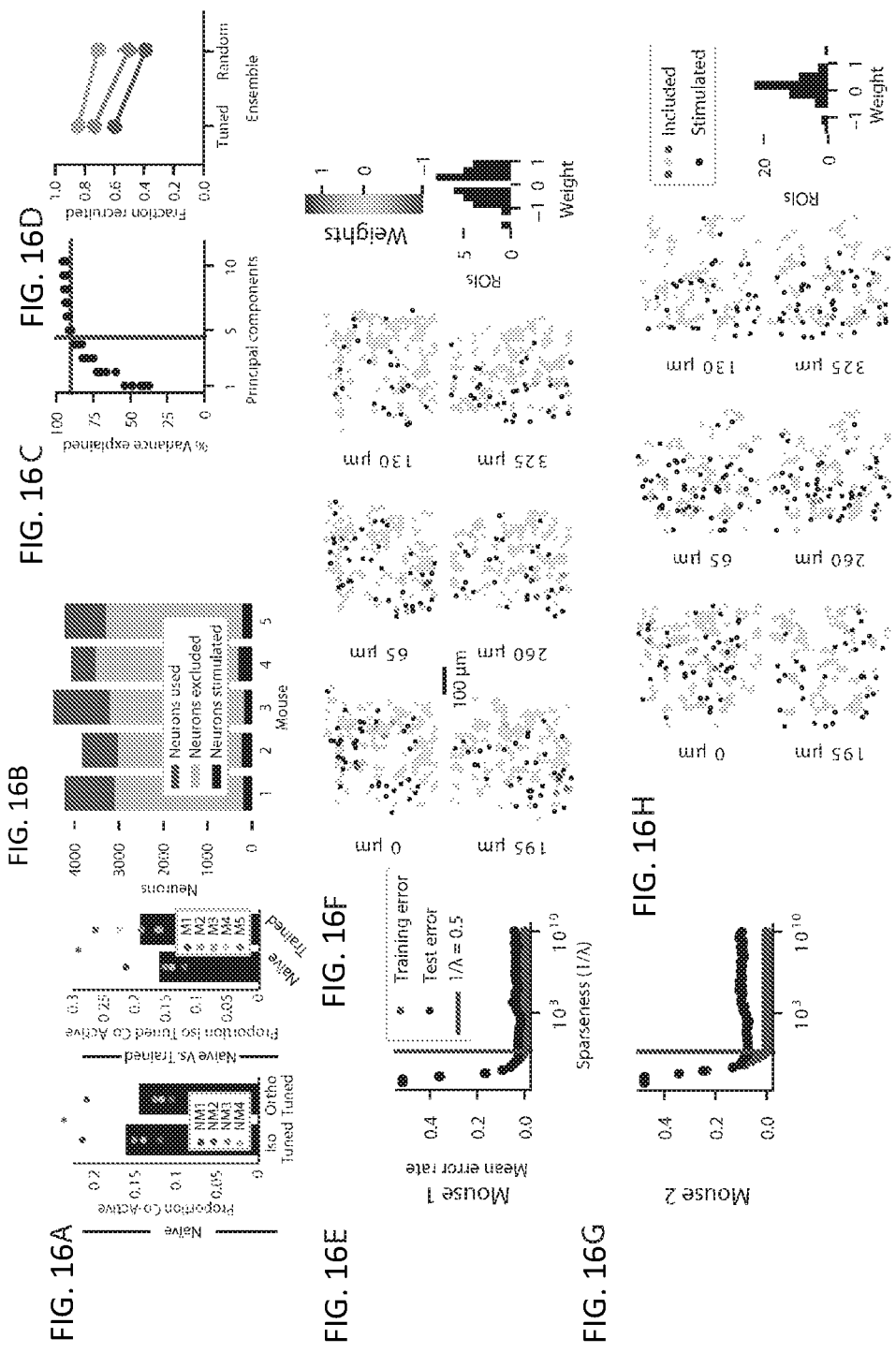

atggcacgcaccgaccaggcaccgaccagatgttctagtgggcacagatgtttactgtgggcaatccgtgcctgccatcgccactgtggtctttatcgtgctgacaatcaccaccattctacctggctat
gagtcctgacatctcggcgcctagcagaagaaacctcctttacgccggctatcaggaggagcagaacctgccctgtttgtgaatttcttttgccatgctgagctacttcgcaagatcgtgccgacactggccacaacttc
ggccgatgtgggccccttcatcatcggcttgccattacaggtatgccgactacatgctgacctgccatgtcgtgtatcagcttgaggcccccatcgcgtctttgtagcgccatcatcttgccatcctgatg
tctggcgtgctggccgagttctacgcagagggcgacctagcctgaggaatgccgcctacccgtgatagctcgctttatcttgctcgcctactcatcgtgatagccaagcagtatagccgctggccca
gctggccaggatacaggcgccgagcacagcctgtcgcatcgtgaagttgccgtgtttaccttctcatgctgtgattcgtttccctgttggccatctccctagaggcttcgctgatcgacgataactggacagagtg
gccactgcgtgtctgcgacatctggccaagtcctgttacgggctttgcccctgcccgggttcagaaagcctatgatgaggagctgttcgtctgagacagcagatgatcaagaagctgaagctgaatg
gaggctgagcagcagcgagcgcctgccgagacactgttctgcggctgcccaagaagcaggatgtctgcggagatcaccagccagggccagtacatcacccctgaccagatcaacgtgactgaagcgagcctgttcaccgggt
ggtgccccatcctggtcgagctggatcgaggcgacgtaaacgccacaagttcagcgtgccgagggcgagggcgatgccacctacgacaagctgaagttcatctcgaagtcgacctgaagttcatctcgaagtcgacctgaagttcaggacgacggcaagctccgccgccgtgcctgcc
ccacctcgtgacccactcggctacggcgtcgcagtgcttcgcccgaccactcttcgacgcaccactgcacctgcgccagagcagtcccagacatccgagggctactgccaggtccctacgtcgcccgaccgcacgcacccatctcttcgacgtcgcacctgcacctgcgccaggacgacggcaac
tacaagaccctgtgcaggtgaaagttcgagggtgacacccgtgtgaacctggccagagggcacaagtcgactgcggcacgtggggcacaaccctgggcacggcacaactgggacactacaactgcacagccacaacgtcta
tatcatggccgacaagcagaagaacgcatcaaggtgaacttcaagatccgccacaacatcgaggacgacgtcagccgtgcagccgcgtgaacaccctcgagctgccgtcctcgacccgccgactaccgactcacaccgtcttcccgagacaccagttcgagttcgactgaccgcgccaggtctccgactccgacggcgccaggatcactcgtcgagttcgtgaccgccgactcccgctgaggttcgtgaccgccgactcccgctgaggttcgtgaccgccgactcccgctgaggttcgtgaccgccgactcccgctgaggttcgtgaccgccgactcccgctgagg
aaccactacctagctaccagtccgccctgagccgcaaagaccccaacggcgatcacatggtcctgctggagttcgtgaccgccgactccgaccatggacgagctgctgccgac
ggtgtaa (SEQ ID NO:27)

Underlined: ChRmine
bold: Linker
double underlined: membrane trafficking signal
italicized: eYFP
bold and underlined: ER export signal

FIG. 23

ChRmine amino acid sequence mahapgtdqmfyvgtmdgwyldtklnsvaigahwscfivltittfylgyeswtsrgpskrtsfyagyqeeqnlalfvnffamls
yfgkivadtlghnfgdvgpfiigfgnyryadymltcpmlvydllyqlrapyrvscsaiifailmsgvlaefyaegdprlrngayawy
gfgcfwfifaysivmsivakqysrlaqlaqdtgaehslhvlkfavftfsmlwilfplvwaicprgfgwiddnwtevahcvcdivak
scygfalarfrktydeelfrlleqlghdedefqkleldmrlssngerlrrls (SEQ ID NO:1)

GCaMPK (SEQ ID NO:28)

MGSHHHHHHGMASMTGGQQMGRDLYDDDDKDLATMVDSSRRKWNKTG
HAVRAIGRLSSLENVYIKADKQKNGIKANFKIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTVMRSLGQNPTEAELQDMINEV
DADGDGTIDFPEFLTMMARKMKYTDSEEEIGEAFRVFDKDGNGYISAAELR
HVMTNLGEKLTDEEVDEMIREADIDGDGQVNYEEFVQMMTAK

FIG. 26B

GCaMP2 (SEQ ID NO:29)

MRGSHHHHHHGMASMTGGQQMGRDLYDDDDKDLATMVDSSRRKWNKTG
HAVRAIGRLSSLENVYIMADKQKNGIKANFKIRHNIEDGGVQLAYHYQQNTP
IGDGPVLLPDNHYLSTQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTVMRSLGQNPTEAELQDMINEV
DADGNGTIDFPEFLTMMARKMKDTDSEEEIREAFRVFDKDGNGYISAAELRH
VMTNLGEKLTDEEVDEMIREADIDGDGQVNYEEFVQMMTAK

FIG. 26C

GCaMP2.1 (SEQ ID NO:30)
MGSHHHHHHGMASMTGGQQMGRDLYDDDDKDLATMVDSSRRKWNKTG
HAVRAIGRLSSLENVYIMADKQKNGIKANFKIRHNIEDGGVQLAYHYQQNTP
IGDGPVLLPDNHYLSTQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTVMRSLGQNPTEAELQDMINEV
DADGNGTIDFPEFLTMMARKMKDTDSEEEIREAFRVFDKDGNGYISAAELRH
VMTNLGEKLTDEEVDEMIREADIDGDGQVNYEEFVQMMTAK

FIG. 26D

GCaMP2.2a (SEQ ID NO:31)
MGSHHHHHHGMASMTGGQQMGRDLYDDDDKDLATMVDSSRRKWNKTG
HAVRAIGRLSSLENVYIMADKQKNGIKANFKIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTVMRSLGQNPTEAELQDMINEV
DADGNGTIDFPEFLTMMARKMKDTDSEEEIREAFRVFDKDGNGYISAAELRH
VMTNLGEKLTDEEVDEMIREADIDGDGQVNYEEFVQMMTAK

FIG. 26E

GCaMP2.2b (SEQ ID NO:32)

MGSHHHHHHGMASMTGGQQMGRDLYDDDDKDLATMVDSSRRKWNKTG
HAVRAIGRLSSLENVYIMADKQKNGIKANFKIRHNIEDGGVQLAYHYQQNTP
IGDGPVLLPDNHYLSTQCKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTVMRSLGQNPTEAELQDMINEV
DADGNGTIDFPEFLTMMARKMKDTDSEEEIREAFRVFDKDGNGYISAAELRH
VMTNLGEKLTDEEVDEMIREADIDGDGQVNYEEFVQMMTAK

FIG. 26F

GCaMP2.3 (SEQ ID NO:33)

MGSHHHHHHGMASMTGGQQMGRDLYDDDDKDLATMVDSSRRKWNKTG
HAVRAIGRLSSLENVYIKADKQKNGIKANFKIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTVMRSLGQNPTEAELQDMINEV
DADGNGTIDFPEFLTMMARKMKDTDSEEEIREAFRVFDKDGNGYISAAELRH
VMTNLGEKLTDEEVDEMIREADIDGDGQVNYEEFVQMMTAK

FIG. 26G

GCaMP2.4 (SEQ ID NO:34)

MGSHHHHHHGMASMTGGQQMGRDLYDDDDKDLATMVDSSRRKWNKTG
HAVRAIGRLSSLENVYIMADKQKNGIKANFKIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTVMRSLGQNPTEAELQDMINEV
DADGDGTIDFPEFLTMMARKMKDTDSEEEIREAFRVFDKDGNGYISAAELRH
VMTNLGEKLTDEEVDEMIREADIDGDGQVNYEEFVQMMTAK

FIG. 26H

GCaMP3 (SEQ ID NO:35)

MGSHHHHHHGMASMTGGQQMGRDLYDDDDKDLATMVDSSRRKWNKTG
HAVRAIGRLSSLENVYIKADKQKNGIKANFKIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTVMRSLGQNPTEAELQDMINEV
DADGDGTIDFPEFLTMMARKMKDTDSEEEIREAFRVFDKDGNGYISAAELRH
VMTNLGEKLTDEEVDEMIREADIDGDGQVNYEEFVQMMTAK

FIG. 26I

GCaMP5g (SEQ ID NO:36)

MGSHHHHHHGMASMTGGQQMGRDLYDDDDKDLATMVDSSRRKWNKTG
HAVRAIGRLSSLENVYIKADKQKNGIKANFKIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNLPDQL
TEEQIAEFKEAFSLFDKDGDGTITTKELGTVMRSLGQNPTEAELQDMINEVD
ADGDGTIDFPEFLTMMARKMKYTDSEEEIREAFRVFDKDGNGYISAAELRHV
MTNLGEKLTDEEVDEMIREADIDGDGQVNYEEFVQMMTAK

FIG. 26J

GCaMP6m (SEQ ID NO:37)

MGSHHHHHHGMASMTGGQQMGRDLYDDDDKDLATMVDSSRRKWNKTG
HAVRAIGRLSSLENVYIKADKQKNGIKANFKIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNLPDQL
TEEQIAEFKEAFSLFDKDGDGTITTKELGTVMRSLGQNPTEAELQDMINEVD
ADGDGTIDFPEFLTMMARKGSYRDTEEEIREAFGVFDKDGNGYISAAELRHV
MTNLGEKLTDEEVDEMIREADIDGDGQVNYEEFVQMMTAK

FIG. 26K

GCaMP6s (SEQ ID NO:38)
MGSHHHHHHGMASMTGGQQMGRDLYDDDDKDLATMVDSSRRKWNKTG
HAVRAIGRLSSLENVYIKADKQKNGIKANFHIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNLPDQL
TEEQIAEFKEAFSLFDKDGDGTITTKELGTVMRSLGQNPTEAELQDMINEVD
ADGDGTIDFPEFLTMMARKMKYRDTEEEIREAFGVFDKDGNGYISAAELRH
VMTNLGEKLTDEEVDEMIREADIDGDGQVNYEEFVQMMTAK

FIG. 26L

GCaMP6f (SEQ ID NO:39)
MGSHHHHHHGMASMTGGQQMGRDLYDDDDKDLATMVDSSRRKWNKTG
HAVRAIGRLSSLENVYIKADKQKNGIKANFKIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNLPDQL
TEEQIAEFKEEFSLFDKDGDGTITTKELGTVMRSLGQNPTEAELQDMINEVD
ADGDGTIDFPEFLTMMARKMKYRDTEEEIREAFGVFDKDGNGYISAAELRH
VMTNLGEKLTDEEVDEMIREADIDGDGQVNYEEFVQMMTAK

FIG. 26M

GEM-GECO1 (GenBank ID: JN258409) (SEQ ID NO:40)
MVDSSRRKWNKTGHAVRAIGRLSSPENVYIKADEQKNGIKAYFKIRHNIEGG
GVQLAYHYQQITPIGDGPVLLPDNHYLSVQSILSKDPNEKRDHMVLLEFVTA
AGITLGMDELYKGGSGGMVSKGEELFTGVVPIQVELDGDVNGHKFSVSGEG
EGDATYGKLTLKFICTTGKLPVPWPTLVTTLSYGVQCFSRYPDHMKQHDFFK
SAMPEGYIQERTIFFKDDGNYKTRAEVKFEGDTLVNRIELKGIDFKEDGNILG
HKLEYSTRDQLTEEQIAEFKEAFSLFDKDGDGTITTKELGTVMRSLGQNPTE
AELQDMINEVDADGDGTIDFPEFLTMMAPKMQDTDSEEEIREAFRVFDKDG
NGYIGAAELRHVMTNLGEKLTDEEVDEMIRVADIDGDGQVNYEEFVQMMT
AK

FIG. 26N

GEX-GECO1 (GenBank ID: JN258410) (SEQ ID NO:41)
MVDSSRRKWNKTGHAVRAIGRLSSLENVYIKADEQKNGIKANFKIRHNIEDG
GVQLAYHYQQNTPIGDGPVLLPDNHYLSVQSILSKDPNEKRDHMVLLEFVT
AAGITLGMDELYKGGTGGSMVSKGEELFTGVVPIQVELDGDVNGHKFSVSG
EGEGDATYGKLTLKFICTTGKLPVPWPTLVTTLSYGVQCFSRYPDHMKQHDF
FKSAMPEGYIQERTIFFKDDGNYKTRAEVKFEGDTLVNRIELKGIDFKEDGNI
LGHKLEYNTRDQLTEEQIAELKEAFSLFDKDGDGTITTKELGTVMRSLGQNP
TEAELQDMINEVDADGDGTIDLPEFQTMMARKMNDTDSEEEIREAFRVFDK
DGNGYIGAAELRHVMTNLGEKLTDEEVDEMIRVADIDGDGQVNYEEFVQM
MTAK

FIG. 26O

R-GECO1 (GenBank ID: JN258411) (SEQ ID NO:42)
MVDSSRRKWNKAGHAVRAIGRLSSPVVSERMYPEDGALKSEIKKGLRLKDG
GHYAAEVKTTYKAKKPVQLPGAYIVDIKLDIVSHNEDYTIVEQCERAEGRHS
TGGMDELYKGGTGGSLVSKGEEDNMAIIKEFMRFKVHMEGSVNGHEFEIEG
EGEGRPYEAFQTAKLKVTKGGPLPFAWDILSPQFMYGSKAYIKHPADIPDYF
KLSFPEGFRWERVMNFEDGGIIHVNQDSSLQDGVFIYKVKLRGTNFPPDGPV
MQKKTMGWEATRDQLTEEQIAEFKEAFSLFDKDGDGTITTKELGTVMRSLG
QNPTEAELQDMINEVDADGDGTFDFPEFLTMMARKMNDTDSEEEIREAFRV
FDKDGNGYIGAAELRHVMTDLGEKLTDEEVDEMIRVADIDGDGQVNYEEFV
QMMTAK

FIG. 26P

B-GECO1 (GenBank ID: JN258412) (SEQ ID NO:43)
MVDSPRRKWNKTGHAVRAIGRLSSPENVYIKADKQKNGIKANFKIRHNIEG
GGVQLAYHYQQNTPIGDGPVLLPDNHYLSVQSILSKDPNEKRDHMVLLEFV
TAAGITLGMDELYKGGTGGSESMVSKGEELFTGVVPIQVELDGDVNGHKFS
VSGEGEGDATYGKLTLKFICTTGKLPVPWPTLVTTLSHGVQCFSRYPDHMKQ
HDFFKSAMPGGYIQERTIFFKDDGNYKTRAEVKFEGDTLVNRIELKGIDFKED
GNILGHKLEYNTRGQLTEEQIAEFKEAFSLFDKDGDGTITTKELGTVMRSLG
QNPTEAELQDMINEVDADGDGTIDFPEFLTMMAPKMQDTDSEEEIREAFRVF
DKDGNGYIGAAELRHVMTNLGEKLTDEEVDEMIREADIDGDGQVNYEEFV
QMMTAK

FIG. 26Q

G-GECO1 (GenBank ID: JN258413) (SEQ ID NO:44)

MVDSSRRKWNKTGHAVRAIGRLSSLENVYIKADKQKNGIKANFKIRHNIED
GGVQLAYHYQQNTPIGDGPVLLPDNHYLSVQSILSKDPNEKRDHMVLLEFV
TAAGITLGMDELYKGGTGGSMVSKGEELFTGVVPIQVELDGDVNGHKFSVS
GEGEGDATYGKLTLKFICTTGKLPVPWPTLVTTLTYGVQCFSRYPDHMKQHD
FFKSAMPEGYIQERTIFFKDDGNYKTRAEVKFEGDTLVNRIELKGIDFKEDGN
ILGHKLEYNTRDQLTEEQIAEFKEAFSLFDKDGDGTITTKELGTVMRSLGQNP
TEAELQDMINEVDADGDGTIDFPEFLTMMARKMKDTDSEEEIREAFRVFDK
DGNGYIGAAELRHVMTNLGEKLTDEEVDEMIRVADIDGDGQVNYEEFVQM
MTAK

FIG. 26R

G-GECO1.1 (GenBank ID: JN258414) (SEQ ID NO:45)

MVDSSRRKWNKTGHAVRAIGRLSSLENVYIKADEQKNGIKAYFKIRHNIEGG
GVQLAYHYQQNTPIGDGPVLLPDNHYLSVQSILSKDPNEKRDHMVLLEFVT
AAGITLGMDELYKGGTGGSMVSKGEELFTGVVPIQVELDGDVNGHKFSVSG
EGEGDATYGKLTLKFICTTGKLPVPWPTLVTTLTYGVQCFSRYPDHMKQHDF
FKSAMPEGYIQERTIFFKDDGNYKTRAEVKFEGDTLVNRIELKGIDFKEDGNI
LGHKLEYNTRDQLTEEQIAEFKEAFSLFDKDGDGTITTKELGTVMRSLGQNP
TEAELQDMINEVDADGDGTIDFPEFLTMMARKMNDTDSEEEIREAFRVFDK
DGNGYIGAAELRHVMTNLGEKLTDEEVDEMIRVADIDGDGQVNYEEFVQM
MTAK

FIG. 26S

G-GECO1.2 (GenBank ID: JN258415) (SEQ ID NO:46)
MVDSSRRKWNKTGHAVRAIGRLSSLENVYIKADEQKNGIKAYFKIRHNIEGG
GVQLAYHYQQNTPIGDGPVLLPDNHYLSVQSMLSKDPNEKRDHMVLLEFVT
AAGITLGMDELYKGGTGGSESMVSKGEELFTGVVPIQVELDGDVNGHKFSV
SGEGEGDATYGKLTLKFICTTGKLPVPWPTLVTTLTYGVQCFSRYPDHMKQH
DFFKSAMPEGYIQERTIFFKGDGNYKTRAEVKFEGDTLVNRIELKGIDFKEDG
NILGHKLEYNTRDQLTEEQIAEFKEAFSLFDKDGDGTITTKELGTVMRSLGQ
NPTEAELQDMINEVDADGDGTIDFPEFLTMMARKMKDTDSEEEIREAFRVFD
KDGNGYIGAAELRHVMTNLGEKLTDEEVDEMIRVADIDGDGQVNYEEFVQ
MMTAK

FIG. 27A

TN-XXL (SEQ ID NO:47)

MVSKGEELFTGVVPILVELDGDVNGHKFSVRGEGEGDATNGKLTLKFICTTG
KLPVPWPTLVTTLTWGVQCFSRYPDHMKQHDFFKSAMPEGYVQERTIFFKD
DGNYKTRAEVKFEGDTLVNRIELKGIDFKEDGNILGHKLEYNYISHNVYITA
DKQKNGIKAHFKIRHNIEDGSVQLADHYQQNTPIGDGPVLLPDNHYLSTQSK
LSKDPNEKRDHMVLLEFVTAARMLSEEELANCFRIFDKDANGFIDIEELGEIL
RATGEHVTEEDIEDLMKDSDKNNDGRIDFDEFLKMMEGVQGTSEEELANCF
RIFDKDANGFIDIEELGEILRATGEHVTEEDIEDLMKDSDKNNDGRIDFDEFL
KMMEGVQELMGGVQLADHYQQNTPIGDGPVLLPDNHYLSYQSKLSKDPNE
KRDHMVLLEFVTAAGITLGMDELYKGGTGGSMVSKGEELFTGVVPILVELD
GDVNGHKFSVRGEGEGDATNGKLTLKFICTTGKLPVPWPTLVTTLGYGLMC
FARYPDHMKQHDFFKSAMPEGYVQERTIFFKDDGNYKTRAEVKFEGDTLVN
RIELKGIDFKEDGNILGHKLEYNYNSHNVYIMADKQKNGIKANFKIRHNIED

FIG. 27B

YC3.6 (SEQ ID NO:48)

MVSKGEELFTGVVPILVELDGDVNGHRFSVSGEGEGDATYGKLTLKFICTTG
KLPVPWPTLVTTLTWGVQCFSRYPDHMKQHDFFKSAMPEGYVQERTIFFKD
DGNYKTRAEVKFEGDTLVNRIELKGIDFKEDGNILGHKLEYNYISHNVYITA
DKQKNGIKAHFKIRHNIEDGSVQLADHYQQNTPIGDGPVLLPDNHYLSTQSA
LSKDPNEKRDHMVLLEFVTAARMHDQLTEEQIAEFKEAFSLFDKDGDGTITT
KELGTVMRSLGQNPTEAELQDMINEVDADGNGTIYFPEFLTMMARKMKDT
DSEEEIREAFRVFDKDGNGYISAAQLRHVMTNLGEKLTDEEVDEMIREADID
GDGQVNYEEFVQMMTAKGGKRRWKKNFIAVSAANRFKKISSSGALELMDG
GVQLADHYQQNTPIGDGPVLLPDNHYLSYQSALSKDPNEKRDHMVLLEFVT
AAGITLGMDELYKGGSGGMVSKGEELFTGVVPILVELDGDVNGHKFSVSGE
GEGDATYGKLTLKLICTTGKLPVPWPTLVTTLGYGLQCFARYPDHMKQHDFF
KSAMPEGYVQERTIFFKDDGNYKTRAEVKFEGDTLVNRIELKGIDFKEDGNI
LGHKLEYNYNSHNVYITADKQKNGIKANFKIRHNIELSRGPGTSAEIYACRLE
ISN

FIG. 27C

D3CPVenus polypeptide (SEQ ID NO:49)
MVSKGEELFTGVVPILVELDGDVNGHRFSVSGEGEGDATYGKLTLKFICTTG
KLPVPWPTLVTTLTWGVQCFSRYPDHMKQHDFFKSAMPEGYVQERTIFFKD
DGNYKTRAEVKFEGDTLVNRIELKGIDFKEDGNILGHKLEYNYISHNVYITA
DKQKNGIKAHFKIRHNIEDGSVQLADHYQQNTPIGDGPVLLPDNHYLSTQSA
LSKDPNEKRDHMVLLEFVTAARMHDQLTEEQIAEFKEAFSLLDKDGDGTITT
KELGTALRSLGQNPTEAELQDMINEVDADGNGTIYFPEFLTMMARKMKDTD
SEEEIREAFRVFDKDGNGYISAAELRHVMTNLGEKLTDEEVDEMIREADIDG
DGQVNYEEFVQMMTAKGGKRRWQKTGHAVRAFGRLKKISSSGALELMDG
GVQLADHYQQNTPIGDGPVLLPDNHYLSYQSALSKDPNEKRDHMVLLEFVT
AAGITLGMDELYKGGSGGMVSKGEELFTGVVPILVELDGDVNGHKFSVSGE
GEGDATYGKLTLKLICTTGKLPVPWPTLVTTLGYGLQCFARYPDHMKQHDFF
KSAMPEGYVQERTIFFKDDGNYKTRAEVKFEGDTLVNRIELKGIDFKEDGNI
LGHKLEYNYNSHNVYITADKQKNGIKANFKIRHNIE

FIG. 28A

Amino acid sequence of ChR1 (SEQ ID NO: 50)

MSRRPWLLALALAVALAAGSAGASTGSDATVPVATQDGPDYVFHRAHERML
FQTSYTLENNGSVICIPNNGQCFCLAWLKSNGTNAEKLAANILQWITFALSAL
CLMFYGYQTWKSTCGWEEIYVATIEMIKFIIEYFHEFDEPAVIYSSNGNKTVW
LRYAEWLLTCPVILIHLSNLTGLANDYNKRTMGLLVSDIGTIVWGTTAALSKG
YVRVIFFLMGLCYGIYTFFNAAKVYIEAYHTVPKGICRDLVRYLAWLYFCSW
AMFPVLFLLGPEGFGHINQFNSAIAHAILDLASKNAWSMMGHFLRVKIHEHI
LLYGDIRKKQKVNVAGQEMEVETMVHEEDD

FIG. 28B

Amino acid sequence of ChR2 (SEQ ID NO: 51)

MDYGGALSAVGRELLFVTNPVVVNGSVLVPEDQCYCAGWIESRGTNGAQT
ASNVLQWLAAGFSILLLMFYAYQTWKSTCGWEEIYVCAIEMVKVILEFFFEF
KNPSMLYLATGHRVQWLRYAEWLLTCPVILIHLSNLTGLSNDYSRRTMGLLV
SDIGTIVWGATSAMATGYVKVIFFCLGLCYGANTFFHAAKAYIEGYHTVPKG
RCRQVVTGMAWLFFVSWGMFPILFILGPEGFGVLSVYGSTVGHTIIDLMSKN
CWGLLGHYLRVLIHEHILIHGDIRKTTKLNIGGTEIEVETLVEDEAEAGAVP

FIG. 28C

Amino acid sequence of ChR2 SFO (SEQ ID NO: 52)

MDYGGALSAVGRELLFVTNPVVVNGSVLVPEDQCYCAGWIESRGTNGAQT
ASNVLQWLAAGFSILLLMFYAYQTWKSTCGWEEIYVCAIEMVKVILEFFFEF
KNPSMLYLATGHRVQWLRYAEWLLTSPVILIHLSNLTGLSNDYSRRTMGLLV
SDIGTIVWGATSAMATGYVKVIFFCLGLCYGANTFFHAAKAYIEGYHTVPKG
RCRQVVTGMAWLFFVSWGMFPILFILGPEGFGVLSVYGSTVGHTIIDLMSKN
CWGLLGHYLRVLIHEHILIHGDIRKTTKLNIGGTEIEVETLVEDEAEAGAVP

FIG. 28D

Amino acid sequence of ChR2 SSFO (SEQ ID NO:53)

MDYGGALSAVGRELLFVTNPVVVNGSVLVPEDQCYCAGWIESRGTNGAQT
ASNVLQWLAAGFSILLLMFYAYQTWKSTCGWEEIYVCAIEMVKVILEFFFEF
KNPSMLYLATGHRVQWLRYAEWLLTSPVILIHLSNLTGLSNDYSRRTMGLLV
SAIGTIVWGATSAMATGYVKVIFFCLGLCYGANTFFHAAKAYIEGYHTVPKG
RCRQVVTGMAWLFFVSWGMFPILFILGPEGFGVLSVYGSTVGHTIIDLMSKN
CWGLLGHYLRVLIHEHILIHGDIRKTTKLNIGGTEIEVETLVEDEAEAGAVP

FIG. 28E

Amino acid sequence of VChR1 (SEQ ID NO:54)

MDYPVARSLIVRYPTDLGNGTVCMPRGQCYCEGWLRSRGTSIEKTIAITLQW
VVFALSVACLGWYAYQAWRATCGWEEVYVALIEMMKSIIEAFHEFDSPATLW
LSSGNGVVWMRYGEWLLTCPVLLIHLSNLTGLKDDYSKRTMGLLVSDVGCI
VWGATSAMCTGWTKILFFLISLSYGMYTYFHAAKVYIEAFHTVPKGICRELV
RVMAWTFFVAWGMFPVLFLLGTEGFGHISPYGSAIGHSILDLIAKNMWGVLG
NYLRVKIHEHILLYGDIRKKQKITIAGQEMEVETLVAEEED

FIG. 28F

Amino acid sequence of VChR1 SFO (SEQ ID NO: 55)

MDYPVARSLIVRYPTDLGNGTVCMPRGQCYCEGWLRSRGTSIEKTIAITLQW
VVFALSVACLGWYAYQAWRATCGWEEVYVALIEMMKSIIEAFHEFDSPATLW
LSSGNGVVWMRYGEWLLTSPVLLIHLSNLTGLKDDYSKRTMGLLVSDVGCI
VWGATSAMCTGWTKILFFLISLSYGMYTYFHAAKVYIEAFHTVPKGICRELV
RVMAWTFFVAWGMFPVLFLLGTEGFGHISPYGSAIGHSILDLIAKNMWGVLG
NYLRVKIHEHILLYGDIRKKQKITIAGQEMEVETLVAEEED

FIG. 28G

Amino acid sequence of VChR1 SSFO (SEQ ID NO:56)

MDYPVARSLIVRYPTDLGNGTVCMPRGQCYCEGWLRSRGTSIEKTIAITLQW
VVFALSVACLGWYAYQAWRATCGWEEVYVALIEMMKSIIEAFHEFDSPATLW
LSSGNGVVWMRYGEWLLTCPVLLIHLSNLTGLKDDYSKRTMGLLVSAVGCI
VWGATSAMCTGWTKILFFLISLSYGMYTYFHAAKVYIEAFHTVPKGICRELV
RVMAWTFFVAWGMFPVLFLLGTEGFGHISPYGSAIGHSILDLIAKNMWGVLG
NYLRVKIHEHILLYGDIRKKQKITIAGQEMEVETLVAEEED

FIG. 28H

Amino acid sequence of C1V1 (SEQ ID NO: 57)

MSRRPWLLALALAVALAAGSAGASTGSDATVPVATQDGPDYVFHRAHERML
FQTSYTLENNGSVICIPNNGQCFCLAWLKSNGTNAEKLAANILQWITFALSAL
CLMFYGYQTWKSTCGWEEIYVATIEMIKFIIEYFHEFDEPAVIYSSNGNKTVW
LRYAEWLLTCPVLLIHLSNLTGLKDDYSKRTMGLLVSDVGCIVWGATSAMCT
GWTKILFFLISLSYGMYTYFHAAKVYIEAFHTVPKGICRELVRVMAWTFFVA
WGMFPVLFLLGTEGFGHISPYGSAIGHSILDLIAKNMWGVLGNYLRVKIHEH
ILLYGDIRKKQKITIAGQEMEVETLVAEEED

FIG. 28I

Amino acid sequence of C1C2 (SEQ ID NO:58)

MSRRPWLLALALAVALAAGSAGASTGSDATVPVATQDGPDYVFHRAHERML
FQTSYTLENNGSVICIPNNGQCFCLAWLKSNGTNAEKLAANILQWITFALSAL
CLMFYGYQTWKSTCGWEEIYVATIEMIKFIIEYFHEFDEPAVIYSSNGNKTVW
LRYAEWLLTCPVILIHLSNLTGLANDYNKRTMGLLVSDIGTIVWGTTAALSKG
YVRVIFFLMGLCYGIYTFFNAAKVYIEAYHTVPKGRCRQVVTGMAWLFFVS
WGMFPILFILGPEGFGVLSVYGSTVGHTIIDLMSKNCWGLLGHYLRVLIHEHI
LIHGDIRKTTKLNIGGTEIEVETLVEDEAEAGAV

FIG. 28J

Amino acid sequence of SdChR (SEQ ID NO:59)

MGGAPAPDAHSAPPGNDSAGGSEYHAPAGYQVNPPYHPVHGYEEQCSSIYI
YYGALWEQETARGFQWFAVFLSALFLAFYGWHAYKASVGWEEVYVCSVEL
IKVILEIYFEFTSPAMLFLYGGNITPWLRYAEWLLTCPVILIHLSNITGLSEEYN
KRTMALLVSDLGTICMGVTAALATGWVKWLFYCIGLVYGTQTFYNAGIIYV
ESYYIMPAGGCKKLVLAMTAVYYSSWLMFPGLFIFGPEGMHTLSVAGSTIGH
TIADLLSKNIWGLLGHFLRIKIHEHIIMYGDIRRPVSSQFLGRKVDVLAFVTEE
DKV

FIG. 28K

Amino acid sequence of CnChR2 (SEQ ID NO:60)

MEPVLGLASTAVRELTAGGSGNPYESYKPPEDPCALTPFGCLTNFWCDPQFG
LADAKYDYCYVKAAYGELAIVETSRLPWLYSHGSDAEHQGALAMQWMAF
ALCIICLVFYAYHSWKATTGWEEVYVCVVELVKVLLEIYKEFESPASIYLPTA
NAALWLRYGEWLLTCPVILIHLSNITGLKDDYNKRTMQLLVSDIGCVVWGIT
AAFSVGWLKWVFFVLGLLYGSNTYFHAAKVYIESYHTVPKGHCRLIVRLMA
YCFYVAWTMYPILFILGPEGLGHMSAYMSTALHGVADMLSKQIWGLLGHHL
RVKIFEHILIHGDIRKTTTMQVGGQMVQVEEMVDEEDEDTI

FIG. 28L

Amino acid sequence of CsChrimson (SEQ ID NO:61)

MSRLVAASWLLALLLCGITSTTTASSAPAASSTDGTAAAAVSHYAMNGFDEL
AKGAVVPEDHFVCGPADKCYCSAWLHSRGTPGEKIGAQVCQWIAFSIAIALL
TFYGFSAWKATCGWEEVYVCCVEVLFVTLEIFKEFSSPATVYLSTGNHAYCL
RYFEWLLSCPVILIKLSNLSGLKNDYSKRTMGLIVSCVGMIVFGMAAGLATD
WLKWLLYIVSCIYGGYMYFQAAKCYVEANHSVPKGHCRMVVKLMAYAYF
ASWGSYPILWAVGPEGLLKLSPYANSIGHSICDIIAKEFWTFLAHHLRIKIHEHI
LIHGDIRKTTKMEIGGEEVEVEEFVEEEDEDTV

FIG. 28M

Amino acid sequence of ShChR1 (SEQ ID NO:62)

METAATMTHAFISAVPSAEATIRGLLSAAAVVTPAADAHGETSNATTAGADH
GCFPHINHGTELQHKIAVGLQWFTVIVAIVQLIFYGWHSFKATTGWEEVYVC
VIELVKCFIELFHEVDSPATVYQTNGGAVIWLRYSMWLLTCPVILIHLSNLTGL
HEEYSKRTMTILVTDIGNIVWGITAAFTKGPLKILFFMIGLFYGVTCFFQIAKV
YIESYHTLPKGVCRKICKIMAYVFFCSWLMFPVMFIAGHEGLGLITPYTSGIG
HLILDLISKNTWGFLGHHLRVKIHEHILIHGDIRKTTTINVAGENMEIETFVDE
EEEGGV

FIG. 28N

Amino acid sequence of Arch (SEQ ID NO:63)

MDPIALQAGYDLLGDGRPETLWLGIGTLLMLIGTFYFLVRGWGVTDKDARE
YYAVTILVPGIASAAYLSMFFGIGLTEVTVGGEMLDIYYARYADWLFTTPLLL
LDLALLAKVDRVTIGTLVGVDALMIVTGLIGALSHTAIARYSWWLFSTICMIV
VLYFLATSLRSAAKERGPEVASTFNTLTALVLVLWTAYPILWIIGTEGAGVVGL
GIETLLFMVLDVTAKVGFGFILLRSRAILGDTEAPEPSAGADVSAAD

FIG. 28O

Amino acid sequence of ArchT (SEQ ID NO:64)

MDPIALQAGYDLLGDGRPETLWLGIGTLLMLIGTFYFIVKGWGVTDKEARE
YYSITILVPGIASAAYLSMFFGIGLTEVTVAGEVLDIYYARYADWLFTTPLLLL
DLALLAKVDRVSIGTLVGVDALMIVTGLIGALSHTPLARYSWWLFSTICMIV
VLYFLATSLRAAAKERGPEVASTFNTLTALVLVLWTAYPILWIIGTEGAGVVGL
GIETLLFMVLDVTAKVGFGFILLRSRAILGDTEAPEP

FIG. 28P

Amino acid sequence of GtR3 (SEQ ID NO:65)
ASSFGKALLEFVFIVFACITLLLGINAAKSKAASRVLFPATFVTGIASIAYFSMA
SGGGWVIAPDCRQLFVARYLDWLITTPLLLIDLGLVAGVSRWDIMALCLSDV
LMIATGAFGSLTVGNVKWVWWFFGMCWFLHIIFALGKSWAEAAKAKGGDS
ASVYSKIAGITVITWFCYPVVWVFAEGFGNFSVTFEVLIYGVLDVISKAVFGLI
LMSGAATGYESI

FIG. 28Q

Amino acid sequence of Oxy (SEQ ID NO:66)
MAPLAQDWTYAEWSAVYNALSFGIAGMGSATIFFWLQLPNVTKNYRTALTIT
GIVTLIATYHYFRIFNSWVAAFNVGLGVNGAYEVTVSGTPFNDAYRYVDWLL
TVPLLLVELILVMKLPAKETVCLAWTLGIASAVMVALGYPGEIQDDLSVRWF
WWACAMVPFVYVVGTLVVGLGAATAKQPEGVVDLVSAARYLTVVSWLTYP
FVYIVKNIGLAGSTATMYEQIGYSAADVTAKAVFGVLIWAIANAKSRLEEEG
KLRA

FIG. 28R

Amino acid sequence of Mac (SEQ ID NO: 67)
MIVDQFEEVLMKTSQLFPLPTATQSAQPTHVAPVPTVLPDTPIYETVGDSGSK
TLWVVFVLMLIASAAFTALSWKIPVNRRLYHVITTIITLTAALSYFAMATGHG
VALNKIVIRTQHDHVPDTYETVYRQVYYARYIDWAITTPLLLLDLGLLAGMS
GAHIFMAIVADLIMVLTGLFAAFGSEGTPQKWGWYTIACIAYIFVVWHLVLN
GGANARVKGEKLRSFFVAIGAYTLILWTAYPIVWGLADGARKIGVDGEIIAYA
VLDVLAKGVFGAWLLVTHANLRESDVELNGFWANGLNREGAIRIGEDDGA

FIG. 28S

Amino acid sequence of NpHR (SEQ ID NO:68)
VTQRELFEFVLNDPLLASSLYINIALAGLSILLFVFMTRGLDDPRAKLIAVSTIL
VPVVSIASYTGLASGLTISVLEMPAGHFAEGSSVMLGGEEVDGVVTMWGRY
LTWALSTPMILLALGLLAGSNATKLFTAITFDIAMCVTGLAAALTTSSHLMRW
FWYAISCACFLVVLYILLVEWAQDAKAAGTADMFNTLKLLTVVMWLGYPIV
WALGVEGIAVLPVGVTSWGYSFLDIVAKYIFAFLLLNYLTSNESVVSGSILDV
PSASGTPADD

FIG. 28T

Amino acid sequence of DsChR (SEQ ID NO:69)
MRRRESQLAYLCLFVLIAGWAPRLTESAPDLAERRPPSERNTPYANIKKVPNI
TEPNANVQLDGWALYQDFYYLAGSDKEWVVGPSDQCYCRAWSKSHGTDR
EGEAAVVWAYIVFAICIVQLVYFMFAAWKATVGWEEVYVNIIELVHIALVIWV
EFDKPAMLYLNDGQMVPWLRYSAWLLSCPVILIHLSNLTGLKGDYSKRTMG
LLVSDIGTIVFGTSAALAPPNHVKVILFTIGLLYGLFTFFTAAKVYIEAYHTVP
KGQCRNLVRAMAWTYFVSWAMFPILFILGREGFGHITYFGSSIGHFILEIFSKN
LWSLLGHGLRYRIRQHIIIHGNLTKKNKINIAGDNVEVEEYVDSNDKSDV

FIG. 28U

Amino acid sequence of Champ (SEQ ID NO: 70)
MDPIALQAGYDLLGDGRPETLWLGIGTLLMLIGTFYFLVRGWGVTDKDARE
YYAVTILVPGIASAAYLSMFFGIGLTEVTVGGEMLDIYYARYADWLFTTPLLL
LDLALLAKVDRVTIGTLVGVDALMIVTGLIGALSHTAIARYSWWLFSTICMIV
VLYFLATSLRSAAKERGPEVASTFNTLTALVLVLWTAYPILWIIGTEGAGVVGL
GIETLLFMVLDVTAKVGFGFILLRSRAILGDTEAPEPSAGADVSAADKSRITSE
GEYIPLDQIDINVGAPGSGATNFSLLKQAGDVEENPGPMDLKESPSEGSLQPS
SIQIFANTSTLHGIRHIFVYGPLTIRRVLWAVAFVGSLGLLLVESSERVSYYFSY
QHVTKVDEVVAQSLVFPAVTLCNLNGFRFSRLTTNDLYHAGELLALLDVNLQ
IPDPHLADPTVLEALRQKANFKHYKPKQFSMLEFLHRVGHDLKDMMLYCKF
KGQECGHQDFTTVFTKYGKCYMFNSGEDGKPLLTTVKGGTGNGLEIMLDIQ
QDEYLPIWGETEETTFEAGVKVQIHSQSEPPFIQELGFGVAPGFQTFVATQEQR
LTYLPPPWGECRSSEMGLDFFPVYSITACRIDCETRYIVENCNCRMVHMPGD
APFCTPEQHKECAEPALGLLAEKDSNYCLCRTPCNLTRYNKELSMVKIPSKTS
AKYLEKKFNKSEKYISENILVLDIFFEALNYETIEQKKAYEVAALLGDIGGQM
GLFIGASLLTILELFDYIYELIKEKLLDLLGKEEEEGSHDENMSTCDTMPNHSE
TISHTVNVPLQTALGTLEEIACAAAKSRITSEGEYIPLDQIDINVVSKGEELFTG
VVPILVELDGDVNGHKFSVSGEGEGDATYGKLTLKFICTTGKLPVPWPTLVT
TFGYGLQCFARYPDHMKQHDFFKSAMPEGYVQERTIFFKDDGNYKTRAEVK
FEGDTLVNRIELKGIDFREDGNILGHKLEYNYNSHNVYIMADKQKNGIKVNF
KIRHNIEDGSVQLADHYQQNTPIGDGPVLLPDNHYLSYQSALSKDPNEKRDH
MVLLEFVTAAGITLGMDELYKFCYENEV

SEQUENCE LISTING

<160> NUMBER OF SEQ ID NOS: 70

<210> SEQ ID NO 1
<211> LENGTH: 309
<212> TYPE: PRT
<213> ORGANISM: Artificial Sequence
<220> FEATURE:
<223> OTHER INFORMATION: Synthetic sequence

<400> SEQUENCE: 1

Met Ala His Ala Pro Gly Thr Asp Gln Met Phe Tyr Val Gly Thr Met
1               5                   10                  15

Asp Gly Trp Tyr Leu Asp Thr Lys Leu Asn Ser Val Ala Ile Gly Ala
            20                  25                  30

His Trp Ser Cys Phe Ile Val Leu Thr Ile Thr Thr Phe Tyr Leu Gly
        35                  40                  45

Tyr Glu Ser Trp Thr Ser Arg Gly Pro Ser Lys Arg Thr Ser Phe Tyr
    50                  55                  60

Ala Gly Tyr Gln Glu Glu Gln Asn Leu Ala Leu Phe Val Asn Phe Phe
65                  70                  75                  80

Ala Met Leu Ser Tyr Phe Gly Lys Ile Val Ala Asp Thr Leu Gly His
                85                  90                  95

-continued

Asn Phe Gly Asp Val Gly Pro Phe Ile Ile Gly Phe Gly Asn Tyr Arg
            100                 105                 110

Tyr Ala Asp Tyr Met Leu Thr Cys Pro Met Leu Val Tyr Asp Leu Leu
            115                 120                 125

Tyr Gln Leu Arg Ala Pro Tyr Arg Val Ser Cys Ser Ala Ile Ile Phe
            130                 135                 140

Ala Ile Leu Met Ser Gly Val Leu Ala Glu Phe Tyr Ala Glu Gly Asp
145                 150                 155                 160

Pro Arg Leu Arg Asn Gly Ala Tyr Ala Trp Tyr Gly Phe Gly Cys Phe
                165                 170                 175

Trp Phe Ile Phe Ala Tyr Ser Ile Val Met Ser Ile Val Ala Lys Gln
            180                 185                 190

Tyr Ser Arg Leu Ala Gln Leu Ala Gln Asp Thr Gly Ala Glu His Ser
            195                 200                 205

Leu His Val Leu Lys Phe Ala Val Phe Thr Phe Ser Met Leu Trp Ile
            210                 215                 220

Leu Phe Pro Leu Val Trp Ala Ile Cys Pro Arg Gly Phe Gly Trp Ile
225                 230                 235                 240

Asp Asp Asn Trp Thr Glu Val Ala His Cys Val Cys Asp Ile Val Ala
                245                 250                 255

Lys Ser Cys Tyr Gly Phe Ala Leu Ala Arg Phe Arg Lys Thr Tyr Asp
            260                 265                 270

Glu Glu Leu Phe Arg Leu Leu Glu Gln Leu Gly His Asp Glu Asp Glu
            275                 280                 285

Phe Gln Lys Leu Glu Leu Asp Met Arg Leu Ser Ser Asn Gly Glu Arg
            290                 295                 300

Leu Arg Arg Leu Ser
305

<210> SEQ ID NO 2
<211> LENGTH: 309
<212> TYPE: PRT
<213> ORGANISM: Artificial Sequence
<220> FEATURE:
<223> OTHER INFORMATION: Synthetic sequence

<400> SEQUENCE: 2

Met Ala His Ala Pro Gly Thr Asp Gln Met Phe Tyr Val Gly Thr Met
1               5                   10                  15

Asp Gly Trp Tyr Leu Asp Thr Lys Leu Asn Ser Val Ala Ile Gly Ala
            20                  25                  30

Arg Trp Ser Cys Phe Ile Val Leu Thr Ile Thr Thr Phe Tyr Leu Gly
            35                  40                  45

Tyr Glu Ser Trp Thr Ser Arg Gly Pro Ser Lys Arg Thr Ser Phe Tyr
        50                  55                  60

Ala Gly Tyr Gln Glu Glu Gln Asn Leu Ala Leu Phe Val Asn Phe Phe
65              70                  75                  80

Ala Met Leu Ser Tyr Phe Gly Lys Ile Val Ala Asp Thr Leu Gly His
                85                  90                  95

Asn Phe Gly Asp Val Gly Pro Phe Ile Ile Gly Phe Gly Asn Tyr Arg
            100                 105                 110

Tyr Ala Asp Tyr Met Leu Thr Cys Pro Met Leu Val Tyr Asp Leu Leu
            115                 120                 125

Tyr Gln Leu Arg Ala Pro Tyr Arg Val Ser Cys Ser Ala Ile Ile Phe
            130                 135                 140

```
Ala Ile Leu Met Ser Gly Val Leu Ala Glu Phe Tyr Ala Glu Gly Asp
145                 150                 155                 160

Pro Arg Leu Arg Asn Gly Ala Tyr Ala Trp Tyr Gly Phe Gly Cys Phe
                165                 170                 175

Trp Phe Ile Phe Ala Tyr Ser Ile Val Met Ser Ile Val Ala Lys Gln
            180                 185                 190

Tyr Ser Arg Leu Ala Gln Leu Ala Gln Asp Thr Gly Ala Glu His Ser
        195                 200                 205

Leu His Val Leu Lys Phe Ala Val Phe Thr Phe Ser Met Leu Trp Ile
        210                 215                 220

Leu Phe Pro Leu Val Trp Ala Ile Cys Pro Arg Gly Phe Gly Trp Ile
225                 230                 235                 240

Asp Asp Asn Trp Thr Glu Val Ala His Cys Val Cys Asp Ile Val Ala
                245                 250                 255

Lys Ser Cys Tyr Gly Phe Ala Leu Ala Arg Phe Arg Lys Thr Tyr Asp
            260                 265                 270

Glu Glu Leu Phe Arg Leu Leu Glu Gln Leu Gly His Asp Glu Asp Glu
        275                 280                 285

Phe Gln Lys Leu Glu Leu Asp Met Arg Leu Ser Ser Asn Gly Glu Arg
290                 295                 300

Leu Arg Arg Leu Ser
305

<210> SEQ ID NO 3
<211> LENGTH: 309
<212> TYPE: PRT
<213> ORGANISM: Artificial Sequence
<220> FEATURE:
<223> OTHER INFORMATION: Synthetic sequence

<400> SEQUENCE: 3

Met Ala His Ala Pro Gly Thr Asp Gln Met Phe Tyr Val Gly Thr Met
1               5                   10                  15

Asp Gly Trp Tyr Leu Asp Thr Lys Leu Asn Ser Val Ala Ile Gly Ala
                20                  25                  30

His Trp Ser Cys Phe Ile Val Leu Thr Ile Thr Thr Phe Tyr Leu Gly
            35                  40                  45

Tyr Glu Ser Trp Thr Ser Arg Gly Pro Ser Lys Arg Thr Ser Phe Tyr
        50                  55                  60

Ala Gly Tyr Gln Glu Glu Gln Asn Leu Ala Leu Phe Val Asn Phe Phe
65                  70                  75                  80

Ala Met Leu Ser Tyr Phe Gly Lys Ile Val Ala Asp Thr Leu Gly His
                85                  90                  95

Asn Phe Gly Asp Val Gly Pro Phe Ile Ile Gly Phe Gly Asn Tyr Arg
            100                 105                 110

Tyr Ala Asp Tyr Met Leu Thr Cys Pro Met Leu Val Tyr Asp Leu Leu
        115                 120                 125

Tyr Gln Leu Arg Ala Pro Tyr His Val Ser Cys Ser Ala Ile Ile Phe
130                 135                 140

Ala Ile Leu Met Ser Gly Val Leu Ala Glu Phe Tyr Ala Glu Gly Asp
145                 150                 155                 160

Pro Arg Leu Arg Asn Gly Ala Tyr Ala Trp Tyr Gly Phe Gly Cys Phe
                165                 170                 175

Trp Phe Ile Phe Ala Tyr Ser Ile Val Met Ser Ile Val Ala Lys Gln
            180                 185                 190
```

```
Tyr Ser Arg Leu Ala Gln Leu Ala Gln Asp Thr Gly Ala Glu His Ser
            195                 200                 205
Leu His Val Leu Lys Phe Ala Val Phe Thr Phe Ser Met Leu Trp Ile
        210                 215                 220
Leu Phe Pro Leu Val Trp Ala Ile Cys Pro Arg Gly Phe Gly Trp Ile
225                 230                 235                 240
Asp Asp Asn Trp Thr Glu Val Ala His Cys Val Cys Asp Ile Val Ala
                245                 250                 255
Lys Ser Cys Tyr Gly Phe Ala Leu Ala Arg Phe Arg Lys Thr Tyr Asp
            260                 265                 270
Glu Glu Leu Phe Arg Leu Leu Glu Gln Leu Gly His Asp Glu Asp Glu
        275                 280                 285
Phe Gln Lys Leu Glu Leu Asp Met Arg Leu Ser Ser Asn Gly Glu Arg
290                 295                 300
Leu Arg Arg Leu Ser
305

<210> SEQ ID NO 4
<211> LENGTH: 309
<212> TYPE: PRT
<213> ORGANISM: Artificial Sequence
<220> FEATURE:
<223> OTHER INFORMATION: Synthetic sequence

<400> SEQUENCE: 4

Met Ala His Ala Pro Gly Thr Asp Gln Met Phe Tyr Val Gly Thr Met
1               5                   10                  15
Asp Gly Trp Tyr Leu Asp Thr Lys Leu Asn Ser Val Ala Ile Gly Ala
            20                  25                  30
Arg Trp Ser Cys Phe Ile Val Leu Thr Ile Thr Thr Phe Tyr Leu Gly
        35                  40                  45
Tyr Glu Ser Trp Thr Ser Arg Gly Pro Ser Lys Arg Thr Ser Phe Tyr
    50                  55                  60
Ala Gly Tyr Gln Glu Glu Gln Asn Leu Ala Leu Phe Val Asn Phe Phe
65                  70                  75                  80
Ala Met Leu Ser Tyr Phe Gly Lys Ile Val Ala Asp Thr Leu Gly His
                85                  90                  95
Asn Phe Gly Asp Val Gly Pro Phe Ile Ile Gly Phe Gly Asn Tyr Arg
            100                 105                 110
Tyr Ala Asp Tyr Met Leu Thr Cys Pro Met Leu Val Tyr Asp Leu Leu
        115                 120                 125
Tyr Gln Leu Arg Ala Pro Tyr His Val Ser Cys Ser Ala Ile Ile Phe
    130                 135                 140
Ala Ile Leu Met Ser Gly Val Leu Ala Glu Phe Tyr Ala Glu Gly Asp
145                 150                 155                 160
Pro Arg Leu Arg Asn Gly Ala Tyr Ala Trp Tyr Gly Phe Gly Cys Phe
                165                 170                 175
Trp Phe Ile Phe Ala Tyr Ser Ile Val Met Ser Ile Val Ala Lys Gln
            180                 185                 190
Tyr Ser Arg Leu Ala Gln Leu Ala Gln Asp Thr Gly Ala Glu His Ser
        195                 200                 205
Leu His Val Leu Lys Phe Ala Val Phe Thr Phe Ser Met Leu Trp Ile
    210                 215                 220
Leu Phe Pro Leu Val Trp Ala Ile Cys Pro Arg Gly Phe Gly Trp Ile
225                 230                 235                 240
```

Asp Asp Asn Trp Thr Glu Val Ala His Cys Val Cys Asp Ile Val Ala
                245                 250                 255

Lys Ser Cys Tyr Gly Phe Ala Leu Ala Arg Phe Arg Lys Thr Tyr Asp
            260                 265                 270

Glu Glu Leu Phe Arg Leu Leu Glu Gln Leu Gly His Asp Glu Asp Glu
        275                 280                 285

Phe Gln Lys Leu Glu Leu Asp Met Arg Leu Ser Ser Asn Gly Glu Arg
    290                 295                 300

Leu Arg Arg Leu Ser
305

<210> SEQ ID NO 5
<211> LENGTH: 309
<212> TYPE: PRT
<213> ORGANISM: Artificial Sequence
<220> FEATURE:
<223> OTHER INFORMATION: Synthetic sequence

<400> SEQUENCE: 5

Met Ala His Ala Pro Gly Thr Asp Gln Met Phe Tyr Val Gly Thr Met
1               5                   10                  15

Asp Gly Trp Tyr Leu Asp Thr Lys Leu Asn Ser Val Ala Ile Gly Ala
            20                  25                  30

His Trp Ser Cys Phe Ile Val Leu Thr Ile Thr Thr Phe Tyr Leu Gly
        35                  40                  45

Tyr Glu Ser Trp Thr Ser Arg Gly Pro Ser Lys Arg Thr Ser Phe Tyr
    50                  55                  60

Ala Gly Tyr Gln Glu Gln Asn Leu Ala Leu Phe Val Asn Phe Phe
65                  70                  75                  80

Ala Met Leu Ser Tyr Phe Gly Lys Ile Val Ala Asp Thr Leu Gly His
                85                  90                  95

Asn Phe Gly Asp Val Gly Pro Phe Ile Ile Gly Phe Gly Asn Tyr Arg
            100                 105                 110

Tyr Ala Asp Tyr Met Leu Thr Cys Pro Met Leu Val Tyr Asp Leu Leu
        115                 120                 125

Tyr Gln Leu Arg Ala Pro Tyr Arg Val Ser Cys Ser Ala Ile Ile Phe
    130                 135                 140

Ala Ile Leu Met Ser Gly Val Leu Ala Glu Phe Tyr Ala Glu Gly Asp
145                 150                 155                 160

Pro Arg Leu Arg Asn Gly Ala Tyr Ala Trp Tyr Gly Phe Gly Cys Phe
                165                 170                 175

Trp Phe Ile Phe Ala Tyr Ser Ile Val Met Ser Ile Val Ala Lys Gln
            180                 185                 190

Tyr Ser Arg Leu Ala Gln Leu Ala Gln Asp Thr Gly Ala Glu His Ser
        195                 200                 205

Leu His Val Leu Lys Phe Ala Val Phe Thr Phe Ser Met Leu Trp Ile
    210                 215                 220

Leu Phe Pro Leu Val Trp Ala Ile Cys Pro Arg Gly Phe Gly Trp Ile
225                 230                 235                 240

Asp Asp Asn Trp Thr Glu Val Ala His Cys Val Cys Asp Ile Val Ala
                245                 250                 255

Lys Ser Cys Tyr Gly Phe Ala Leu Ala Arg Phe Arg Lys Thr Tyr Asp
            260                 265                 270

Glu Glu Leu Phe Arg Leu Leu Glu Gln Leu Gly His Asp Glu Asp Glu
        275                 280                 285

```
Phe Gln Lys Leu Glu Leu Asp Met Arg Leu Ser Ser Asn Gly Glu Arg
    290                 295                 300

Leu Arg Arg Leu Ser
305

<210> SEQ ID NO 6
<211> LENGTH: 20
<212> TYPE: PRT
<213> ORGANISM: Artificial Sequence
<220> FEATURE:
<223> OTHER INFORMATION: Synthetic sequence

<400> SEQUENCE: 6

Lys Ser Arg Ile Thr Ser Glu Gly Glu Tyr Ile Pro Leu Asp Gln Ile
1               5                   10                  15

Asp Ile Asn Val
            20

<210> SEQ ID NO 7
<211> LENGTH: 19
<212> TYPE: PRT
<213> ORGANISM: Artificial Sequence
<220> FEATURE:
<223> OTHER INFORMATION: Synthetic sequence

<400> SEQUENCE: 7

Lys Ser Arg Ile Thr Ser Glu Gly Glu Tyr Ile Pro Leu Asp Gln Ile
1               5                   10                  15

Asp Ile Asn

<210> SEQ ID NO 8
<211> LENGTH: 5
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 8

Val Xaa Xaa Ser Leu
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic sequence

<400> SEQUENCE: 9

Val Lys Glu Ser Leu
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic sequence

<400> SEQUENCE: 10

Val Leu Gly Ser Leu
1               5
```

<210> SEQ ID NO 11
<211> LENGTH: 16
<212> TYPE: PRT
<213> ORGANISM: Artificial Sequence
<220> FEATURE:
<223> OTHER INFORMATION: Synthetic sequence

<400> SEQUENCE: 11

Asn Ala Asn Ser Phe Cys Tyr Glu Asn Glu Val Ala Leu Thr Ser Lys
1               5                   10                  15

<210> SEQ ID NO 12
<211> LENGTH: 6
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa can be any naturally occurring amino acid

<400> SEQUENCE: 12

Phe Xaa Tyr Glu Asn Glu
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic sequence

<400> SEQUENCE: 13

Phe Cys Tyr Glu Asn Glu Val
1               5

<210> SEQ ID NO 14
<211> LENGTH: 309
<212> TYPE: PRT
<213> ORGANISM: Artificial Sequence
<220> FEATURE:
<223> OTHER INFORMATION: Synthetic sequence

<400> SEQUENCE: 14

Met Ala His Ala Pro Gly Thr Asp Gln Met Phe Tyr Val Gly Thr Met
1               5                   10                  15

Asp Gly Trp Tyr Leu Asp Thr Lys Leu Asn Ser Val Ala Ile Gly Ala
                20                  25                  30

His Trp Ser Cys Phe Ile Val Leu Thr Ile Thr Thr Phe Tyr Leu Gly
            35                  40                  45

Tyr Glu Ser Trp Thr Ser Arg Gly Pro Ser Lys Arg Thr Ser Phe Tyr
        50                  55                  60

Ala Gly Tyr Gln Glu Gln Asn Leu Ala Leu Phe Val Asn Phe Phe
65                  70                  75                  80

Ala Met Leu Ser Tyr Phe Gly Lys Ile Val Ala Asp Thr Leu Gly His
                85                  90                  95

Asn Phe Gly Asp Val Gly Pro Phe Ile Ile Gly Phe Gly Asn Tyr Arg
                100                 105                 110

Tyr Ala Asp Tyr Met Leu Thr Cys Pro Met Leu Val Tyr Asp Leu Leu
            115                 120                 125

Tyr Gln Leu Arg Ala Pro Tyr Arg Val Ser Cys Ser Ala Ile Ile Phe

```
                130             135             140
Ala Ile Leu Met Ser Gly Val Leu Ala Glu Phe Tyr Ala Glu Gly Asp
145                 150                 155                 160

Pro Arg Leu Arg Asn Gly Ala Tyr Ala Trp Tyr Gly Phe Gly Cys Phe
                165                 170                 175

Trp Phe Ile Phe Ala Tyr Ser Ile Val Met Ser Ile Val Ala Lys Gln
            180                 185                 190

Tyr Ser Arg Leu Ala Gln Leu Ala Gln Asp Thr Gly Ala Glu His Ser
        195                 200                 205

Leu His Val Leu Lys Phe Ala Val Phe Thr Phe Ser Met Leu Trp Ile
    210                 215                 220

Leu Phe Pro Leu Val Trp Ala Ile Cys Pro Arg Gly Phe Gly Trp Ile
225                 230                 235                 240

Asp Asp Asn Trp Thr Glu Val Ala His Cys Val Cys Asp Ile Val Ala
                245                 250                 255

Lys Ser Cys Tyr Gly Phe Ala Leu Ala Arg Phe Arg Lys Thr Tyr Asp
                260                 265                 270

Glu Glu Leu Phe Arg Leu Leu Glu Gln Leu Gly His Asp Glu Asp Glu
            275                 280                 285

Phe Gln Lys Leu Glu Leu Asp Met Arg Leu Ser Ser Asn Gly Glu Arg
        290                 295                 300

Leu Arg Arg Leu Ser
305

<210> SEQ ID NO 15
<211> LENGTH: 309
<212> TYPE: PRT
<213> ORGANISM: Artificial Sequence
<220> FEATURE:
<223> OTHER INFORMATION: Synthetic sequence

<400> SEQUENCE: 15

Met Ala His Ala Pro Gly Thr Asp Gln Met Phe Tyr Val Gly Thr Met
1               5                   10                  15

Asp Gly Trp Tyr Leu Asp Thr Lys Leu Asn Ser Val Ala Ile Gly Ala
            20                  25                  30

His Trp Ser Cys Phe Ile Val Leu Thr Ile Thr Thr Phe Tyr Leu Gly
        35                  40                  45

Tyr Glu Ser Trp Thr Ser Arg Gly Pro Ser Lys Arg Thr Ser Phe Tyr
    50                  55                  60

Ala Gly Tyr Gln Glu Gln Asn Leu Ala Leu Phe Val Asn Phe Phe
65                  70                  75                  80

Ala Met Leu Ser Tyr Phe Gly Lys Ile Val Ala Asp Thr Leu Gly His
                85                  90                  95

Asn Phe Gly Asp Val Gly Pro Phe Ile Ile Gly Phe Gly Asn Tyr Arg
            100                 105                 110

Tyr Ala Asp Tyr Met Leu Thr Cys Pro Met Leu Val Tyr Asp Leu Leu
        115                 120                 125

Tyr Gln Leu Arg Ala Pro Tyr Arg Val Ser Cys Ser Ala Ile Ile Phe
    130                 135                 140

Ala Ile Leu Met Ser Gly Val Leu Ala Glu Phe Tyr Ala Glu Gly Asp
145                 150                 155                 160

Pro Arg Leu Arg Asn Gly Ala Tyr Ala Trp Tyr Gly Phe Gly Cys Phe
                165                 170                 175

Trp Phe Ile Phe Ala Tyr Ser Ile Val Met Ser Ile Val Ala Lys Gln
```

```
                180                 185                 190
Tyr Ser Arg Leu Ala Gln Leu Ala Gln Asp Thr Gly Ala Glu His Ser
            195                 200                 205

Leu His Val Leu Lys Phe Ala Val Phe Thr Phe Ser Met Leu Trp Ile
    210                 215                 220

Leu Phe Pro Leu Val Trp Ala Ile Cys Pro Arg Gly Phe Gly Trp Ile
225                 230                 235                 240

Asp Asp Asn Trp Thr Glu Val Ala His Cys Val Cys Asp Ile Val Ala
                245                 250                 255

Lys Ser Cys Tyr Gly Phe Ala Leu Ala Arg Phe Arg Lys Thr Tyr Asp
            260                 265                 270

Glu Glu Leu Phe Arg Leu Leu Glu Gln Leu Gly His Asp Glu Asp Glu
        275                 280                 285

Phe Gln Lys Leu Glu Leu Asp Met Arg Leu Ser Ser Asn Gly Glu Arg
    290                 295                 300

Leu Arg Arg Leu Ser
305

<210> SEQ ID NO 16
<211> LENGTH: 339
<212> TYPE: PRT
<213> ORGANISM: Artificial Sequence
<220> FEATURE:
<223> OTHER INFORMATION: Synthetic sequence

<400> SEQUENCE: 16

Met Ala His Ala Pro Gly Thr Asp Gln Met Phe Tyr Val Gly Thr Met
1               5                   10                  15

Asp Gly Trp Tyr Leu Asp Thr Lys Leu Asn Ser Val Ala Ile Gly Ala
            20                  25                  30

His Trp Ser Cys Phe Ile Val Leu Thr Ile Thr Thr Phe Tyr Leu Gly
        35                  40                  45

Tyr Glu Ser Trp Thr Ser Arg Gly Pro Ser Lys Arg Thr Ser Phe Tyr
    50                  55                  60

Ala Gly Tyr Gln Glu Glu Gln Asn Leu Ala Leu Phe Val Asn Phe Phe
65                  70                  75                  80

Ala Met Leu Ser Tyr Phe Gly Lys Ile Val Ala Asp Thr Leu Gly His
                85                  90                  95

Asn Phe Gly Asp Val Gly Pro Phe Ile Gly Phe Gly Asn Tyr Arg
            100                 105                 110

Tyr Ala Asp Tyr Met Leu Thr Cys Pro Met Leu Val Tyr Asp Leu Leu
        115                 120                 125

Tyr Gln Leu Arg Ala Pro Tyr Arg Val Ser Cys Ser Ala Ile Ile Phe
    130                 135                 140

Ala Ile Leu Met Ser Gly Val Leu Ala Glu Phe Tyr Ala Glu Gly Asp
145                 150                 155                 160

Pro Arg Leu Arg Asn Gly Ala Tyr Ala Trp Tyr Gly Phe Gly Cys Phe
                165                 170                 175

Trp Phe Ile Phe Ala Tyr Ser Ile Val Met Ser Ile Val Ala Lys Gln
            180                 185                 190

Tyr Ser Arg Leu Ala Gln Leu Ala Gln Asp Thr Gly Ala Glu His Ser
        195                 200                 205

Leu His Val Leu Lys Phe Ala Val Phe Thr Phe Ser Met Leu Trp Ile
    210                 215                 220

Leu Phe Pro Leu Val Trp Ala Ile Cys Pro Arg Gly Phe Gly Trp Ile
```

|   |   |   |   |   |   |   |   |   |   |   |   |   |   |   |
|---|---|---|---|---|---|---|---|---|---|---|---|---|---|---|
| 225 | | | | 230 | | | | 235 | | | | 240 | | |

Asp Asp Asn Trp Thr Glu Val Ala His Cys Val Cys Asp Ile Val Ala
                          245                        250                        255

Lys Ser Cys Tyr Gly Phe Ala Leu Ala Arg Phe Arg Lys Thr Tyr Asp
                        260                        265                        270

Glu Glu Leu Phe Arg Leu Leu Glu Gln Leu Gly His Asp Glu Asp Glu
                        275                        280                        285

Phe Gln Lys Leu Glu Leu Asp Met Arg Leu Ser Ser Asn Gly Glu Arg
                        290                        295                        300

Leu Arg Arg Leu Ser Ala Ala Lys Ser Arg Ile Thr Ser Glu Gly
    305                        310                        315                        320

Glu Tyr Ile Pro Leu Asp Gln Ile Asp Ile Asn Val Phe Cys Tyr Glu
                        325                        330                        335

Asn Glu Val

<210> SEQ ID NO 17
<211> LENGTH: 927
<212> TYPE: DNA
<213> ORGANISM: Artificial Sequence
<220> FEATURE:
<223> OTHER INFORMATION: Synthetic sequence

<400> SEQUENCE: 17

```
atggcacacg caccaggcac cgaccagatg ttctacgtgg gcacaatgga cggctggtat      60
ctggatacca agctgaactc cgtggccatc ggcgcccact ggtcttgctt tatcgtgctg     120
acaatcacca cattctacct gggctatgag tcctggacat ctcggggccc tagcaagaga     180
acctcctttt acgccggcta tcaggaggag cagaacctgg ccctgtttgt gaatttcttt     240
gccatgctga gctacttcgg caagatcgtg gccgacacac tgggccacaa cttcggcgat     300
gtgggcccct tcatcatcgg cttcggcaat tacaggtatg ccgactacat gctgacctgc     360
ccaatgctgg tgtacgatct gctgtatcag ctgagggccc cctatcgcgt gtcttgtagc     420
gccatcatct ttgccatcct gatgtctggc gtgctggccg agttctacgc agagggcgac     480
cctaggctga ggaatggcgc ctacgcctgg tatggctttg ctgtttctg gtttatcttc     540 gcctactcta tcgtgatgag catcgtggcc aagcagtata gccggctggc ccagctggcc     600
caggatacag cgccgagca cagcctgcac gtgctgaagt cgccgtgtt taccttctcc     660 atgctgtgga ttctgtttcc cctggtgtgg gccatctgcc ctagaggctt cggctggatc     720
gacgataact ggacagaggt ggcccactgc gtgtgcgaca tcgtggccaa gtcctgttac     780
ggctttgccc tggcccggtt cagaaagacc tatgatgagg agctgtttcg gctgctggag     840
cagctgggac acgacgagga tgagttccag aagctggagc tggatatgag gctgagcagc     900
aatggcgagc gcctgcggag actgtct                                        927
```

<210> SEQ ID NO 18
<211> LENGTH: 18
<212> TYPE: PRT
<213> ORGANISM: Artificial Sequence
<220> FEATURE:
<223> OTHER INFORMATION: Synthetic sequence

<400> SEQUENCE: 18

Thr Ile Ile Asp Leu Met Ser Lys Asn Cys Trp Gly Leu Leu Gly His
1                 5                    10                   15

Tyr Leu

<210> SEQ ID NO 19
<211> LENGTH: 18
<212> TYPE: PRT
<213> ORGANISM: Artificial Sequence
<220> FEATURE:
<223> OTHER INFORMATION: Synthetic sequence

<400> SEQUENCE: 19

Leu Gly Asp Ala Leu Cys Lys Asn Thr Tyr Gly Ile Leu Leu Trp Ala
1               5                   10                  15

Thr Thr

<210> SEQ ID NO 20
<211> LENGTH: 18
<212> TYPE: PRT
<213> ORGANISM: Artificial Sequence
<220> FEATURE:
<223> OTHER INFORMATION: Synthetic sequence

<400> SEQUENCE: 20

Cys Val Cys Asp Ile Val Ala Lys Ser Cys Tyr Gly Phe Ala Leu Ala
1               5                   10                  15

Arg Phe

<210> SEQ ID NO 21
<211> LENGTH: 295
<212> TYPE: PRT
<213> ORGANISM: Tiarina fusus

<400> SEQUENCE: 21

Met Ser Ser Ile Thr Cys Asp Pro Ala Ile Tyr Gly Glu Trp Ser Arg
1               5                   10                  15

Glu Asn Gln Phe Cys Val Glu Lys Ser Leu Ile Thr Leu Asp Gly Ile
                20                  25                  30

Lys Tyr Val Gln Leu Val Met Ala Val Ser Ala Cys Gln Val Phe
            35                  40                  45

Phe Met Val Thr Arg Ala Pro Lys Val Pro Trp Glu Ala Ile Tyr Leu
50                  55                  60

Pro Thr Thr Glu Met Ile Thr Tyr Ser Leu Ala Phe Thr Gly Asn Gly
65                  70                  75                  80

Tyr Ile Arg Val Ala Asn Gly Lys Tyr Leu Pro Trp Ala Arg Met Ala
                85                  90                  95

Ser Trp Leu Cys Thr Cys Pro Ile Met Leu Gly Leu Val Ser Asn Met
            100                 105                 110

Ala Leu Val Lys Tyr Lys Ser Ile Pro Leu Asn Pro Met Met Ile Ala
            115                 120                 125

Ala Ser Ser Ile Cys Thr Val Phe Gly Thr Ile Ala Ser Val Val Leu
            130                 135                 140

Asp Pro Leu His Val Trp Leu Tyr Cys Phe Ile Ser Ser Ile Phe Phe
145                 150                 155                 160

Ile Phe Glu Met Val Val Ala Phe Ala Ile Phe Ala Ile Thr Ile His
                165                 170                 175

Asp Phe Gln Thr Ile Gly Ser Pro Met Ser Leu Lys Val Glu Arg
            180                 185                 190

Leu Lys Leu Met Arg Ile Val Phe Tyr Val Ser Trp Met Ala Tyr Pro
            195                 200                 205

Ile Leu Trp Ser Phe Ser Ser Thr Gly Ala Cys Ile Met Ser Glu Asn
210                 215                 220

```
Thr Ser Ser Val Leu Tyr Leu Leu Gly Asp Ala Leu Cys Lys Asn Thr
225                 230                 235                 240

Tyr Gly Ile Leu Leu Trp Ala Thr Thr Trp Gly Leu Leu Asn Gly Lys
            245                 250                 255

Trp Asp Arg Asp Tyr Val Lys Gly Arg Asn Val Asp Gly Thr Leu Met
        260                 265                 270

Pro Glu Tyr Glu Gln Asp Leu Glu Lys Gly Asn Thr Glu Arg Tyr Glu
            275                 280                 285

Asp Ala Arg Ala Gly Glu Thr
        290                 295

<210> SEQ ID NO 22
<211> LENGTH: 291
<212> TYPE: PRT
<213> ORGANISM: Tiarina fusus

<400> SEQUENCE: 22

Met Ala Ser Gln Val Val Tyr Gly Glu Trp Ala Ser Thr His Thr Glu
1               5                   10                  15

Cys Tyr Asn Met Ser Arg Ile Asp Ser Thr Phe Val Ser Leu Leu Gln
            20                  25                  30

Leu Val Trp Ala Val Val Ser Gly Cys Gln Thr Ile Phe Met Ile Ser
        35                  40                  45

Arg Ala Pro Lys Val Pro Trp Glu Ser Val Tyr Leu Pro Phe Val Glu
50                  55                  60

Ser Ile Thr Tyr Ala Leu Ala Ser Thr Gly Asn Gly Thr Leu Gln Met
65                  70                  75                  80

Arg Asp Gly Arg Phe Phe Pro Trp Ser Arg Met Ala Ser Trp Leu Cys
                85                  90                  95

Thr Cys Pro Ile Met Leu Gly Gln Ile Ser Asn Met Ala Leu Val Lys
            100                 105                 110

Tyr Lys Ser Ile Pro Leu Asn Pro Ile Ala Gln Ala Ser Ile Ile
        115                 120                 125

Arg Val Val Met Gly Ile Thr Ala Thr Ile Ser Pro Ala Glu Tyr Met
130                 135                 140

Lys Trp Leu Phe Phe Phe Gly Ala Thr Cys Leu Val Phe Glu Tyr
145                 150                 155                 160

Ser Val Val Phe Thr Ile Phe Gln Val Gly Leu Tyr Gly Phe Glu Ser
                165                 170                 175

Val Gly Thr Pro Leu Ala Gln Lys Val Val Arg Ile Lys Met Leu
            180                 185                 190

Arg Leu Ile Phe Phe Ile Ala Trp Thr Met Phe Pro Ile Val Trp Leu
        195                 200                 205

Ile Ser Pro Thr Gly Val Cys Val Ile His Glu Asn Val Ser Ala Ile
210                 215                 220

Leu Tyr Leu Leu Ala Asp Gly Leu Cys Lys Asn Thr Tyr Gly Val Ile
225                 230                 235                 240

Leu Trp Ser Thr Ala Trp Gly Val Leu Glu Gly Lys Trp Asp Pro Ala
            245                 250                 255

Cys Leu Pro Gly Gln Glu Lys Pro Glu Ala Asp Pro Phe Gly Leu
        260                 265                 270

Asn His Glu Lys Asn Ala Pro Pro Asn Asp Glu Val Asn Ile Arg Met
            275                 280                 285

Phe Gly Arg
```

```
<210> SEQ ID NO 23
<211> LENGTH: 359
<212> TYPE: PRT
<213> ORGANISM: Tiarina fusus

<400> SEQUENCE: 23

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Phe Val His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Ile Leu Ile His Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Ala Ala Leu Ser Lys
        195                 200                 205

Gly Tyr Val Arg Val Ile Phe Phe Leu Met Gly Leu Cys Tyr Gly Ile
210                 215                 220

Tyr Thr Phe Phe Asn Ala Ala Lys Val Tyr Ile Glu Ala Tyr His Thr
225                 230                 235                 240

Val Pro Lys Gly Ile Cys Arg Asp Leu Val Arg Tyr Leu Ala Trp Leu
                245                 250                 255

Tyr Phe Cys Ser Trp Ala Met Phe Pro Val Leu Phe Leu Leu Gly Pro
            260                 265                 270

Glu Gly Phe Gly His Ile Asn Gln Phe Asn Ser Ala Ile Ala His Ala
        275                 280                 285

Ile Leu Asp Leu Ala Ser Lys Asn Ala Trp Ser Met Met Gly His Phe
290                 295                 300

Leu Arg Val Lys Ile His Glu His Ile Leu Leu Tyr Gly Asp Ile Arg
305                 310                 315                 320

Lys Lys Gln Lys Val Asn Val Ala Gly Gln Glu Met Glu Val Glu Thr
                325                 330                 335

Met Val His Glu Glu Asp Asp Glu Thr Gln Lys Val Pro Thr Ala Lys
            340                 345                 350

Tyr Ala Asn Arg Asp Ser Phe
        355
```

```
<210> SEQ ID NO 24
<211> LENGTH: 309
<212> TYPE: PRT
<213> ORGANISM: Tiarina fusus

<400> SEQUENCE: 24

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
            115                 120                 125

Pro Val Ile Leu Ile His Leu Ser Asn Leu Thr Gly Leu Ser Asn Asp
            130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300

Glu Ala Gly Ala Val
305

<210> SEQ ID NO 25
<211> LENGTH: 331
<212> TYPE: PRT
<213> ORGANISM: Tiarina fusus

<400> SEQUENCE: 25

Met Asp Tyr Pro Val Ala Arg Ser Leu Ile Val Arg Tyr Pro Thr Asp
1               5                   10                  15
```

```
Leu Gly Asn Gly Thr Val Cys Met Pro Arg Gly Gln Cys Tyr Cys Glu
            20                  25                  30

Gly Trp Leu Arg Ser Arg Gly Thr Ser Ile Glu Lys Thr Ile Ala Ile
        35                  40                  45

Thr Leu Gln Trp Val Val Phe Ala Leu Ser Val Ala Cys Leu Gly Trp
50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
                85                  90                  95

Phe Asp Ser Pro Ala Thr Leu Trp Leu Ser Ser Gly Asn Gly Val Val
            100                 105                 110

Trp Met Arg Tyr Gly Glu Trp Leu Leu Thr Cys Pro Val Leu Leu Ile
        115                 120                 125

His Leu Ser Asn Leu Thr Gly Leu Lys Asp Asp Tyr Ser Lys Arg Thr
130                 135                 140

Met Gly Leu Leu Val Ser Asp Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
            180                 185                 190

Glu Ala Phe His Thr Val Pro Lys Gly Ile Cys Arg Glu Leu Val Arg
        195                 200                 205

Val Met Ala Trp Thr Phe Phe Val Ala Trp Gly Met Phe Pro Val Leu
210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
            260                 265                 270

Tyr Gly Asp Ile Arg Lys Lys Gln Lys Ile Thr Ile Ala Gly Gln Glu
        275                 280                 285

Met Glu Val Glu Thr Leu Val Ala Glu Glu Asp Asp Thr Val Lys
290                 295                 300

Gln Ser Thr Ala Lys Tyr Ala Ser Arg Asp Ser Phe Ile Thr Met Arg
305                 310                 315                 320

Asn Arg Met Arg Glu Lys Gly Leu Glu Val Arg
                325                 330

<210> SEQ ID NO 26
<211> LENGTH: 350
<212> TYPE: PRT
<213> ORGANISM: Tiarina fusus

<400> SEQUENCE: 26

Met Ala Glu Leu Ile Ser Ser Ala Thr Arg Ser Leu Phe Ala Ala Gly
1               5                   10                  15

Gly Ile Asn Pro Trp Pro Asn Pro Tyr His His Glu Asp Met Gly Cys
            20                  25                  30

Gly Gly Met Thr Pro Thr Gly Glu Cys Phe Ser Thr Glu Trp Trp Cys
        35                  40                  45

Asp Pro Ser Tyr Gly Leu Ser Asp Ala Gly Tyr Gly Tyr Cys Phe Val
50                  55                  60
```

Glu Ala Thr Gly Gly Tyr Leu Val Val Gly Val Lys Lys Gln Ala
65                  70                  75                  80

Trp Leu His Ser Arg Gly Thr Pro Gly Glu Lys Ile Gly Ala Gln Val
            85                  90                  95

Cys Gln Trp Ile Ala Phe Ser Ile Ala Ile Ala Leu Leu Thr Phe Tyr
            100                 105                 110

Gly Phe Ser Ala Trp Lys Ala Thr Cys Gly Trp Glu Glu Val Tyr Val
            115                 120                 125

Cys Cys Val Glu Val Leu Phe Val Thr Leu Glu Ile Phe Lys Glu Phe
130                 135                 140

Ser Ser Pro Ala Thr Val Tyr Leu Ser Thr Gly Asn His Ala Tyr Cys
145                 150                 155                 160

Leu Arg Tyr Phe Glu Trp Leu Leu Ser Cys Pro Val Ile Leu Ile Lys
            165                 170                 175

Leu Ser Asn Leu Ser Gly Leu Lys Asn Asp Tyr Ser Lys Arg Thr Met
            180                 185                 190

Gly Leu Ile Val Ser Cys Val Gly Met Ile Val Phe Gly Met Ala Ala
            195                 200                 205

Gly Leu Ala Thr Asp Trp Leu Lys Trp Leu Leu Tyr Ile Val Ser Cys
210                 215                 220

Ile Tyr Gly Gly Tyr Met Tyr Phe Gln Ala Ala Lys Cys Tyr Val Glu
225                 230                 235                 240

Ala Asn His Ser Val Pro Lys Gly His Cys Arg Met Val Val Lys Leu
            245                 250                 255

Met Ala Tyr Ala Tyr Phe Ala Ser Trp Gly Ser Tyr Pro Ile Leu Trp
            260                 265                 270

Ala Val Gly Pro Glu Gly Leu Leu Lys Leu Ser Pro Tyr Ala Asn Ser
            275                 280                 285

Ile Gly His Ser Ile Cys Asp Ile Ile Ala Lys Glu Phe Trp Thr Phe
            290                 295                 300

Leu Ala His His Leu Arg Ile Lys Ile His Glu His Ile Leu Ile His
305                 310                 315                 320

Gly Asp Ile Arg Lys Thr Thr Lys Met Glu Ile Gly Gly Glu Glu Val
            325                 330                 335

Glu Val Glu Glu Phe Val Glu Glu Glu Asp Glu Asp Thr Val
            340                 345                 350

<210> SEQ ID NO 27
<211> LENGTH: 1734
<212> TYPE: DNA
<213> ORGANISM: Artificial Sequence
<220> FEATURE:
<223> OTHER INFORMATION: Synthetic sequence

<400> SEQUENCE: 27
atggcacacg caccaggcac cgaccagatg ttctacgtgg gcacaatgga cggctggtat      60
ctggatacca agctgaactc cgtggccatc ggcgcccact ggtcttgctt tatcgtgctg     120
acaatcacca cattctacct gggctatgag tcctggacat ctcggggccc tagcaagaga     180
acctcctttt acgccggcta tcaggaggag cagaacctgg ccctgtttgt gaatttcttt     240
gccatgctga gctacttcgg caagatcgtg gccgacacac tgggccacaa cttcggcgat     300
gtgggcccct tcatcatcgg cttcggcaat acaggtatg ccgactacat gctgacctgc     360
ccaatgctgg tgtacgatct gctgtatcag ctgagggccc cctatcgcgt gtcttgtagc     420

```
gccatcatct tgccatcct gatgtctggc gtgctggccg agttctacgc agagggcgac      480
cctaggctga ggaatggcgc ctacgcctgg tatggctttg ctgtttctg gtttatcttc      540 gcctactcta tcgtgatgag catcgtggcc aagcagtata gccggctggc ccagctggcc      600
caggatacag gcgccgagca cagcctgcac gtgctgaagt cgccgtgtt taccttctcc      660 atgctgtgga ttctgtttcc cctggtgtgg gccatctgcc ctagaggctt cggctggatc      720
gacgataact ggacagaggt ggcccactgc gtgtgcgaca tcgtggccaa gtcctgttac      780
ggctttgccc tggcccggtt cagaaagacc tatgatgagg agctgtttcg gctgctggag      840
cagctgggac acgacgagga tgagttccag aagctggagc tggatatgag gctgagcagc      900
aatggcgagc gcctgcggag actgtctcgg gccgccaaga gcaggatcac cagcgagggc      960
gagtacatcc ccctggacca gatcgacatc aacgtggtga gcaagggcga ggagctgttc     1020
accggggtgg tgcccatcct ggtcgagctg gacggcgacg taaacggcca agttcagc      1080 gtgtccggcg agggcgaggg cgatgccacc tacggcaagc tgaccctgaa gttcatctgc     1140
accaccggca agctgcccgt gccctggccc accctcgtga ccaccttcgg ctacggcctg     1200
cagtgcttcg cccgctaccc cgaccacatg aagcagcacg acttcttcaa gtccgccatg     1260
cccgaaggct acgtccagga gcgcaccatc ttcttcaagg acgacggcaa ctacaagacc     1320
cgcgccgagg tgaagttcga gggcgacacc ctggtgaacc gcatcgagct gaagggcatc     1380
gacttcaagg aggacggcaa catcctgggg cacaagctgg agtacaacta caacagccac     1440
aacgtctata tcatggccga caagcagaag aacggcatca aggtgaactt caagatccgc     1500
cacaacatcg aggacggcag cgtgcagctc gccgaccact accagcagaa cacccccatc     1560
ggcgacggcc ccgtgctgct gcccgacaac cactacctga gctaccagtc cgccctgagc     1620
aaagacccca cgagaagcg cgatcacatg gtcctgctgg agttcgtgac cgccgccggg     1680
atcactctcg gcatggacga gctgtacaag ttctgctacg agaacgaggt gtaa          1734
```

<210> SEQ ID NO 28
<211> LENGTH: 450
<212> TYPE: PRT
<213> ORGANISM: Artificial Sequence
<220> FEATURE:
<223> OTHER INFORMATION: Synthetic sequence

<400> SEQUENCE: 28

```
Met Gly Ser His His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Leu Glu Asn Val Tyr Ile
    50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly
```

```
            130                 135                 140
Met Asp Glu Leu Tyr Lys Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
                180                 185                 190

Asp Ala Thr Tyr Gly Lys Leu Thr Leu Lys Phe Ile Cys Thr Thr Gly
                195                 200                 205

Lys Leu Pro Val Pro Trp Pro Thr Leu Val Thr Thr Leu Thr Tyr Gly
    210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
                260                 265                 270

Gly Asp Thr Leu Val Asn Arg Ile Glu Leu Lys Gly Ile Asp Phe Lys
                275                 280                 285

Glu Asp Gly Asn Ile Leu Gly His Lys Leu Glu Tyr Asn Thr Arg Asp
    290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
                340                 345                 350

Met Ile Asn Glu Val Asp Ala Asp Gly Asp Gly Thr Ile Asp Phe Pro
    355                 360                 365

Glu Phe Leu Thr Met Met Ala Arg Lys Met Lys Tyr Thr Asp Ser Glu
    370                 375                 380

Glu Glu Ile Gly Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
                420                 425                 430

Asp Gly Asp Gly Gln Val Asn Tyr Glu Glu Phe Val Gln Met Met Thr
                435                 440                 445

Ala Lys
    450

<210> SEQ ID NO 29
<211> LENGTH: 451
<212> TYPE: PRT
<213> ORGANISM: Artificial Sequence
<220> FEATURE:
<223> OTHER INFORMATION: Synthetic sequence

<400> SEQUENCE: 29

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Leu Ala Thr Met Val Asp Ser Ser Arg Arg Lys Trp Asn Lys Thr Gly
```

```
                35                  40                  45
His Ala Val Arg Ala Ile Gly Arg Leu Ser Ser Leu Glu Asn Val Tyr
 50                  55                  60
Ile Met Ala Asp Lys Gln Lys Asn Gly Ile Lys Ala Asn Phe Lys Ile
65                  70                  75                  80
Arg His Asn Ile Glu Asp Gly Gly Val Gln Leu Ala Tyr His Tyr Gln
                85                  90                  95
Gln Asn Thr Pro Ile Gly Asp Gly Pro Val Leu Leu Pro Asp Asn His
                100                 105                 110
Tyr Leu Ser Thr Gln Ser Lys Leu Ser Lys Asp Pro Asn Glu Lys Arg
                115                 120                 125
Asp His Met Val Leu Leu Glu Phe Val Thr Ala Ala Gly Ile Thr Leu
                130                 135                 140
Gly Met Asp Glu Leu Tyr Lys Gly Gly Thr Gly Gly Ser Met Val Ser
145                 150                 155                 160
Lys Gly Glu Glu Leu Phe Thr Gly Val Val Pro Ile Leu Val Glu Leu
                165                 170                 175
Asp Gly Asp Val Asn Gly His Lys Phe Ser Val Ser Gly Glu Gly Glu
                180                 185                 190
Gly Asp Ala Thr Tyr Gly Lys Leu Thr Leu Lys Phe Ile Cys Thr Thr
                195                 200                 205
Gly Lys Leu Pro Val Pro Trp Pro Thr Leu Val Thr Thr Leu Thr Tyr
                210                 215                 220
Gly Val Gln Cys Phe Ser Arg Tyr Pro Asp His Met Lys Gln His Asp
225                 230                 235                 240
Phe Phe Lys Ser Ala Met Pro Glu Gly Tyr Ile Gln Glu Arg Thr Ile
                245                 250                 255
Phe Phe Lys Asp Asp Gly Asn Tyr Lys Thr Arg Ala Glu Val Lys Phe
                260                 265                 270
Glu Gly Asp Thr Leu Val Asn Arg Ile Glu Leu Lys Gly Ile Asp Phe
                275                 280                 285
Lys Glu Asp Gly Asn Ile Leu Gly His Lys Leu Glu Tyr Asn Thr Arg
                290                 295                 300
Asp Gln Leu Thr Glu Glu Gln Ile Ala Glu Phe Lys Glu Ala Phe Ser
305                 310                 315                 320
Leu Phe Asp Lys Asp Gly Asp Gly Thr Ile Thr Thr Lys Glu Leu Gly
                325                 330                 335
Thr Val Met Arg Ser Leu Gly Gln Asn Pro Thr Glu Ala Glu Leu Gln
                340                 345                 350
Asp Met Ile Asn Glu Val Asp Ala Asp Gly Asn Gly Thr Ile Asp Phe
                355                 360                 365
Pro Glu Phe Leu Thr Met Met Ala Arg Lys Met Lys Asp Thr Asp Ser
                370                 375                 380
Glu Glu Glu Ile Arg Glu Ala Phe Arg Val Phe Asp Lys Asp Gly Asn
385                 390                 395                 400
Gly Tyr Ile Ser Ala Ala Glu Leu Arg His Val Met Thr Asn Leu Gly
                405                 410                 415
Glu Lys Leu Thr Asp Glu Glu Val Asp Glu Met Ile Arg Glu Ala Asp
                420                 425                 430
Ile Asp Gly Asp Gly Gln Val Asn Tyr Glu Glu Phe Val Gln Met Met
                435                 440                 445
Thr Ala Lys
450
```

```
<210> SEQ ID NO 30
<211> LENGTH: 450
<212> TYPE: PRT
<213> ORGANISM: Artificial Sequence
<220> FEATURE:
<223> OTHER INFORMATION: Synthetic sequence

<400> SEQUENCE: 30

Met Gly Ser His His His His His Gly Met Ala Ser Met Thr Gly
1               5                   10                  15

Gly Gln Gln Met Gly Arg Asp Leu Tyr Asp Asp Asp Lys Asp Leu
                20                  25                  30

Ala Thr Met Val Asp Ser Ser Arg Arg Lys Trp Asn Lys Thr Gly His
            35                  40                  45

Ala Val Arg Ala Ile Gly Arg Leu Ser Ser Leu Glu Asn Val Tyr Ile
    50                  55                  60

Met Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
                100                 105                 110

Leu Ser Thr Gln Ser Lys Leu Ser Lys Asp Pro Asn Glu Lys Arg Asp
            115                 120                 125

His Met Val Leu Leu Glu Phe Val Thr Ala Ala Gly Ile Thr Leu Gly
130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
                180                 185                 190

Asp Ala Thr Tyr Gly Lys Leu Thr Leu Lys Phe Ile Cys Thr Thr Gly
            195                 200                 205

Lys Leu Pro Val Pro Trp Pro Thr Leu Val Thr Thr Leu Thr Tyr Gly
210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
                260                 265                 270

Gly Asp Thr Leu Val Asn Arg Ile Glu Leu Lys Gly Ile Asp Phe Lys
            275                 280                 285

Glu Asp Gly Asn Ile Leu Gly His Lys Leu Glu Tyr Asn Thr Arg Asp
        290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asn Gly Thr Ile Asp Phe Pro
        355                 360                 365
```

```
Glu Phe Leu Thr Met Met Ala Arg Lys Met Lys Asp Thr Asp Ser Glu
            370                 375                 380

Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
            435                 440                 445

Ala Lys
    450

<210> SEQ ID NO 31
<211> LENGTH: 450
<212> TYPE: PRT
<213> ORGANISM: Artificial Sequence
<220> FEATURE:
<223> OTHER INFORMATION: Synthetic sequence

<400> SEQUENCE: 31

Met Gly Ser His His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
            35                  40                  45

Ala Val Arg Ala Ile Gly Arg Leu Ser Ser Leu Glu Asn Val Tyr Ile
50                  55                  60

Met Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly
    130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
    210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270
```

-continued

```
Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Thr Arg Asp
    290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asn Gly Thr Ile Asp Phe Pro
        355                 360                 365

Glu Phe Leu Thr Met Met Ala Arg Lys Met Lys Asp Thr Asp Ser Glu
    370                 375                 380

Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
        435                 440                 445

Ala Lys
    450

<210> SEQ ID NO 32
<211> LENGTH: 450
<212> TYPE: PRT
<213> ORGANISM: Artificial Sequence
<220> FEATURE:
<223> OTHER INFORMATION: Synthetic sequence

<400> SEQUENCE: 32

Met Gly Ser His His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Leu Glu Asn Val Tyr Ile
    50                  55                  60

Met Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Thr Gln Cys Lys Leu Ser Lys Asp Pro Asn Glu Lys Arg Asp
        115                 120                 125

His Met Val Leu Leu Glu Phe Val Thr Ala Ala Gly Ile Thr Leu Gly
    130                 135                 140

Met Asp Glu Leu Tyr Lys Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175
```

```
Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
            195                 200                 205

Lys Leu Pro Val Pro Trp Pro Thr Leu Val Thr Thr Leu Thr Tyr Gly
210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
                260                 265                 270

Gly Asp Thr Leu Val Asn Arg Ile Glu Leu Lys Gly Ile Asp Phe Lys
            275                 280                 285

Glu Asp Gly Asn Ile Leu Gly His Lys Leu Glu Tyr Asn Thr Arg Asp
290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asn Gly Thr Ile Asp Phe Pro
            355                 360                 365

Glu Phe Leu Thr Met Met Ala Arg Lys Met Lys Asp Thr Asp Ser Glu
370                 375                 380

Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
                420                 425                 430

Asp Gly Asp Gly Gln Val Asn Tyr Glu Glu Phe Val Gln Met Met Thr
            435                 440                 445

Ala Lys
    450

<210> SEQ ID NO 33
<211> LENGTH: 450
<212> TYPE: PRT
<213> ORGANISM: Artificial Sequence
<220> FEATURE:
<223> OTHER INFORMATION: Synthetic sequence

<400> SEQUENCE: 33

Met Gly Ser His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
            35                  40                  45

Ala Val Arg Ala Ile Gly Arg Leu Ser Ser Leu Glu Asn Val Tyr Ile
        50                  55                  60

Lys Ala Asp Lys Gln Lys Asn Gly Ile Lys Ala Asn Phe Lys Ile Arg
65                  70                  75                  80
```

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly
    130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
    210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Thr Arg Asp
290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asn Gly Thr Ile Asp Phe Pro
        355                 360                 365

Glu Phe Leu Thr Met Met Ala Arg Lys Met Lys Asp Thr Asp Ser Glu
370                 375                 380

Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
        435                 440                 445

Ala Lys
    450

<210> SEQ ID NO 34
<211> LENGTH: 450
<212> TYPE: PRT
<213> ORGANISM: Artificial Sequence
<220> FEATURE:

<223> OTHER INFORMATION: Synthetic sequence

<400> SEQUENCE: 34

| | | | | | | | | | | | | | | |
|---|---|---|---|---|---|---|---|---|---|---|---|---|---|---|
| Met | Gly | Ser | His | His | His | His | His | Gly | Met | Ala | Ser | Met | Thr | Gly |
| 1 | | | | 5 | | | | | 10 | | | | | 15 |
| Gly | Gln | Gln | Met | Gly | Arg | Asp | Leu | Tyr | Asp | Asp | Asp | Lys | Asp | Leu |
| | | | 20 | | | | | 25 | | | | 30 | | |
| Ala | Thr | Met | Val | Asp | Ser | Ser | Arg | Arg | Lys | Trp | Asn | Lys | Thr | Gly | His |
| | | 35 | | | | | 40 | | | | | 45 | | |
| Ala | Val | Arg | Ala | Ile | Gly | Arg | Leu | Ser | Ser | Leu | Glu | Asn | Val | Tyr | Ile |
| | 50 | | | | | 55 | | | | | 60 | | | | |
| Met | Ala | Asp | Lys | Gln | Lys | Asn | Gly | Ile | Lys | Ala | Asn | Phe | Lys | Ile | Arg |
| 65 | | | | | 70 | | | | | 75 | | | | | 80 |
| His | Asn | Ile | Glu | Asp | Gly | Gly | Val | Gln | Leu | Ala | Tyr | His | Tyr | Gln | Gln |
| | | | | 85 | | | | | 90 | | | | | 95 | |
| Asn | Thr | Pro | Ile | Gly | Asp | Gly | Pro | Val | Leu | Leu | Pro | Asp | Asn | His | Tyr |
| | | | 100 | | | | | 105 | | | | | 110 | | |
| Leu | Ser | Val | Gln | Ser | Lys | Leu | Ser | Lys | Asp | Pro | Asn | Glu | Lys | Arg | Asp |
| | | | 115 | | | | | 120 | | | | | 125 | | |
| His | Met | Val | Leu | Leu | Glu | Phe | Val | Thr | Ala | Ala | Gly | Ile | Thr | Leu | Gly |
| | 130 | | | | | 135 | | | | | 140 | | | | |
| Met | Asp | Glu | Leu | Tyr | Lys | Gly | Gly | Thr | Gly | Gly | Ser | Met | Val | Ser | Lys |
| 145 | | | | | 150 | | | | | 155 | | | | | 160 |
| Gly | Glu | Glu | Leu | Phe | Thr | Gly | Val | Val | Pro | Ile | Leu | Val | Glu | Leu | Asp |
| | | | | 165 | | | | | 170 | | | | | 175 | |
| Gly | Asp | Val | Asn | Gly | His | Lys | Phe | Ser | Val | Ser | Gly | Glu | Gly | Glu | Gly |
| | | | 180 | | | | | 185 | | | | | 190 | | |
| Asp | Ala | Thr | Tyr | Gly | Lys | Leu | Thr | Leu | Lys | Phe | Ile | Cys | Thr | Thr | Gly |
| | | 195 | | | | | 200 | | | | | 205 | | | |
| Lys | Leu | Pro | Val | Pro | Trp | Pro | Thr | Leu | Val | Thr | Thr | Leu | Thr | Tyr | Gly |
| 210 | | | | | 215 | | | | | 220 | | | | | |
| Val | Gln | Cys | Phe | Ser | Arg | Tyr | Pro | Asp | His | Met | Lys | Gln | His | Asp | Phe |
| 225 | | | | | 230 | | | | | 235 | | | | | 240 |
| Phe | Lys | Ser | Ala | Met | Pro | Glu | Gly | Tyr | Ile | Gln | Glu | Arg | Thr | Ile | Phe |
| | | | | 245 | | | | | 250 | | | | | 255 | |
| Phe | Lys | Asp | Asp | Gly | Asn | Tyr | Lys | Thr | Arg | Ala | Glu | Val | Lys | Phe | Glu |
| | | | 260 | | | | | 265 | | | | | 270 | | |
| Gly | Asp | Thr | Leu | Val | Asn | Arg | Ile | Glu | Leu | Lys | Gly | Ile | Asp | Phe | Lys |
| | | 275 | | | | | 280 | | | | | 285 | | | |
| Glu | Asp | Gly | Asn | Ile | Leu | Gly | His | Lys | Leu | Glu | Tyr | Asn | Thr | Arg | Asp |
| | 290 | | | | | 295 | | | | | 300 | | | | |
| Gln | Leu | Thr | Glu | Glu | Gln | Ile | Ala | Glu | Phe | Lys | Glu | Ala | Phe | Ser | Leu |
| 305 | | | | | 310 | | | | | 315 | | | | | 320 |
| Phe | Asp | Lys | Asp | Gly | Asp | Gly | Thr | Ile | Thr | Thr | Lys | Glu | Leu | Gly | Thr |
| | | | | 325 | | | | | 330 | | | | | 335 | |
| Val | Met | Arg | Ser | Leu | Gly | Gln | Asn | Pro | Thr | Glu | Ala | Glu | Leu | Gln | Asp |
| | | | 340 | | | | | 345 | | | | | 350 | | |
| Met | Ile | Asn | Glu | Val | Asp | Ala | Asp | Gly | Asp | Gly | Thr | Ile | Asp | Phe | Pro |
| | | 355 | | | | | 360 | | | | | 365 | | | |
| Glu | Phe | Leu | Thr | Met | Met | Ala | Arg | Lys | Met | Lys | Asp | Thr | Asp | Ser | Glu |
| | 370 | | | | | 375 | | | | | 380 | | | | |
| Glu | Glu | Ile | Arg | Glu | Ala | Phe | Arg | Val | Phe | Asp | Lys | Asp | Gly | Asn | Gly |
| 385 | | | | | 390 | | | | | 395 | | | | | 400 |

```
Tyr Ile Ser Ala Ala Glu Leu Arg His Val Met Thr Asn Leu Gly Glu
            405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
            435                 440                 445

Ala Lys
    450

<210> SEQ ID NO 35
<211> LENGTH: 450
<212> TYPE: PRT
<213> ORGANISM: Artificial Sequence
<220> FEATURE:
<223> OTHER INFORMATION: Synthetic sequence

<400> SEQUENCE: 35

Met Gly Ser His His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
            35                  40                  45

Ala Val Arg Ala Ile Gly Arg Leu Ser Ser Leu Glu Asn Val Tyr Ile
50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
            85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
            115                 120                 125

His Met Val Leu Leu Glu Phe Val Thr Ala Ala Gly Ile Thr Leu Gly
            130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
            165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
            195                 200                 205

Lys Leu Pro Val Pro Trp Pro Thr Leu Val Thr Thr Leu Thr Tyr Gly
            210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
            245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
            275                 280                 285

Glu Asp Gly Asn Ile Leu Gly His Lys Leu Glu Tyr Asn Thr Arg Asp
            290                 295                 300
```

```
Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
            325                 330                 335

Val Met Arg Ser Leu Gly Gln Asn Pro Thr Glu Ala Glu Leu Gln Asp
        340                 345                 350

Met Ile Asn Glu Val Asp Ala Asp Gly Asp Gly Thr Ile Asp Phe Pro
    355                 360                 365

Glu Phe Leu Thr Met Met Ala Arg Lys Met Lys Asp Thr Asp Ser Glu
    370                 375                 380

Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
            405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
            435                 440                 445

Ala Lys
    450

<210> SEQ ID NO 36
<211> LENGTH: 450
<212> TYPE: PRT
<213> ORGANISM: Artificial Sequence
<220> FEATURE:
<223> OTHER INFORMATION: Synthetic sequence

<400> SEQUENCE: 36

Met Gly Ser His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Leu Glu Asn Val Tyr Ile
    50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
            85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly
130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
            165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205
```

```
Lys Leu Pro Val Pro Trp Pro Thr Leu Val Thr Thr Leu Thr Tyr Gly
    210             215                 220

Val Gln Cys Phe Ser Arg Tyr Pro Asp His Met Lys Gln His Asp Phe
225             230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
                260                 265                 270

Gly Asp Thr Leu Val Asn Arg Ile Glu Leu Lys Gly Ile Asp Phe Lys
            275                 280                 285

Glu Asp Gly Asn Ile Leu Gly His Lys Leu Glu Tyr Asn Leu Pro Asp
290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asp Gly Thr Ile Asp Phe Pro
            355                 360                 365

Glu Phe Leu Thr Met Met Ala Arg Lys Met Lys Tyr Thr Asp Ser Glu
370                 375                 380

Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
            435                 440                 445

Ala Lys
    450

<210> SEQ ID NO 37
<211> LENGTH: 450
<212> TYPE: PRT
<213> ORGANISM: Artificial Sequence
<220> FEATURE:
<223> OTHER INFORMATION: Synthetic sequence

<400> SEQUENCE: 37

Met Gly Ser His His His His His Gly Met Ala Ser Met Thr Gly Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
            35                  40                  45

Ala Val Arg Ala Ile Gly Arg Leu Ser Ser Leu Glu Asn Val Tyr Ile
        50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110
```

```
Leu Ser Val Gln Ser Lys Leu Ser Lys Asp Pro Asn Glu Lys Arg Asp
            115                 120                 125

His Met Val Leu Leu Glu Phe Val Thr Ala Ala Gly Ile Thr Leu Gly
        130                 135                 140

Met Asp Glu Leu Tyr Lys Gly Thr Gly Gly Ser Met Val Ser Lys
145                 150                 155                 160

Gly Glu Glu Leu Phe Thr Gly Val Val Pro Ile Leu Val Glu Leu Asp
                    165                 170                 175

Gly Asp Val Asn Gly His Lys Phe Ser Val Ser Gly Glu Gly Glu Gly
                180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
                260                 265                 270

Gly Asp Thr Leu Val Asn Arg Ile Glu Leu Lys Gly Ile Asp Phe Lys
            275                 280                 285

Glu Asp Gly Asn Ile Leu Gly His Lys Leu Glu Tyr Asn Leu Pro Asp
290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
                340                 345                 350

Met Ile Asn Glu Val Asp Ala Asp Gly Asp Gly Thr Ile Asp Phe Pro
            355                 360                 365

Glu Phe Leu Thr Met Met Ala Arg Lys Gly Ser Tyr Arg Asp Thr Glu
370                 375                 380

Glu Glu Ile Arg Glu Ala Phe Gly Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
                420                 425                 430

Asp Gly Asp Gly Gln Val Asn Tyr Glu Glu Phe Val Gln Met Met Thr
            435                 440                 445

Ala Lys
450

<210> SEQ ID NO 38
<211> LENGTH: 450
<212> TYPE: PRT
<213> ORGANISM: Artificial Sequence
<220> FEATURE:
<223> OTHER INFORMATION: Synthetic sequence

<400> SEQUENCE: 38

Met Gly Ser His His His His His Gly Met Ala Ser Met Thr Gly
1               5                   10                  15
```

```
Gly Gln Gln Met Gly Arg Asp Leu Tyr Asp Asp Asp Lys Asp Leu
             20                  25                  30

Ala Thr Met Val Asp Ser Ser Arg Arg Lys Trp Asn Lys Thr Gly His
         35                  40                  45

Ala Val Arg Ala Ile Gly Arg Leu Ser Ser Leu Glu Asn Val Tyr Ile
 50                  55                  60

Lys Ala Asp Lys Gln Lys Asn Gly Ile Lys Ala Asn Phe His Ile Arg
 65                  70                  75                  80

His Asn Ile Glu Asp Gly Gly Val Gln Leu Ala Tyr His Tyr Gln Gln
             85                  90                  95

Asn Thr Pro Ile Gly Asp Gly Pro Val Leu Leu Pro Asp Asn His Tyr
             100                 105                 110

Leu Ser Val Gln Ser Lys Leu Ser Lys Asp Pro Asn Glu Lys Arg Asp
             115                 120                 125

His Met Val Leu Leu Glu Phe Val Thr Ala Ala Gly Ile Thr Leu Gly
             130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                    165                 170                 175

Gly Asp Val Asn Gly His Lys Phe Ser Val Ser Gly Glu Gly Glu Gly
             180                 185                 190

Asp Ala Thr Tyr Gly Lys Leu Thr Leu Lys Phe Ile Cys Thr Thr Gly
             195                 200                 205

Lys Leu Pro Val Pro Trp Pro Thr Leu Val Thr Thr Leu Thr Tyr Gly
 210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                    245                 250                 255

Phe Lys Asp Asp Gly Asn Tyr Lys Thr Arg Ala Glu Val Lys Phe Glu
             260                 265                 270

Gly Asp Thr Leu Val Asn Arg Ile Glu Leu Lys Gly Ile Asp Phe Lys
             275                 280                 285

Glu Asp Gly Asn Ile Leu Gly His Lys Leu Glu Tyr Asn Leu Pro Asp
 290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                    325                 330                 335

Val Met Arg Ser Leu Gly Gln Asn Pro Thr Glu Ala Glu Leu Gln Asp
             340                 345                 350

Met Ile Asn Glu Val Asp Ala Asp Gly Asp Gly Thr Ile Asp Phe Pro
             355                 360                 365

Glu Phe Leu Thr Met Met Ala Arg Lys Met Lys Tyr Arg Asp Thr Glu
             370                 375                 380

Glu Glu Ile Arg Glu Ala Phe Gly Val Phe Asp Lys Asp Gly Asn Gly
385                 390                 395                 400

Tyr Ile Ser Ala Ala Glu Leu Arg His Val Met Thr Asn Leu Gly Glu
                    405                 410                 415

Lys Leu Thr Asp Glu Glu Val Asp Glu Met Ile Arg Glu Ala Asp Ile
             420                 425                 430

Asp Gly Asp Gly Gln Val Asn Tyr Glu Glu Phe Val Gln Met Met Thr
```

435                 440                 445

Ala Lys
    450

<210> SEQ ID NO 39
<211> LENGTH: 450
<212> TYPE: PRT
<213> ORGANISM: Artificial Sequence
<220> FEATURE:
<223> OTHER INFORMATION: Synthetic sequence

<400> SEQUENCE: 39

Met Gly Ser His His His His His Gly Met Ala Ser Met Thr Gly Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Leu Glu Asn Val Tyr Ile
    50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly
    130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
    210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Leu Pro Asp
    290                 295                 300

Gln Leu Thr Glu Glu Gln Ile Ala Glu Phe Lys Glu Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp

```
                340                 345                 350
Met Ile Asn Glu Val Asp Ala Asp Gly Asp Gly Thr Ile Asp Phe Pro
                355                 360                 365

Glu Phe Leu Thr Met Met Ala Arg Lys Met Lys Tyr Arg Asp Thr Glu
    370                 375                 380

Glu Glu Ile Arg Glu Ala Phe Gly Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
                420                 425                 430

Asp Gly Asp Gly Gln Val Asn Tyr Glu Glu Phe Val Gln Met Met Thr
            435                 440                 445

Ala Lys
    450

<210> SEQ ID NO 40
<211> LENGTH: 415
<212> TYPE: PRT
<213> ORGANISM: Artificial Sequence
<220> FEATURE:
<223> OTHER INFORMATION: Synthetic sequence

<400> SEQUENCE: 40

Met Val Asp Ser Ser Arg Arg Lys Trp Asn Lys Thr Gly His Ala Val
1               5                   10                  15

Arg Ala Ile Gly Arg Leu Ser Ser Pro Glu Asn Val Tyr Ile Lys Ala
                20                  25                  30

Asp Glu Gln Lys Asn Gly Ile Lys Ala Tyr Phe Lys Ile Arg His Asn
            35                  40                  45

Ile Glu Gly Gly Gly Val Gln Leu Ala Tyr His Tyr Gln Gln Ile Thr
        50                  55                  60

Pro Ile Gly Asp Gly Pro Val Leu Leu Pro Asp Asn His Tyr Leu Ser
65                  70                  75                  80

Val Gln Ser Ile Leu Ser Lys Asp Pro Asn Glu Lys Arg Asp His Met
                85                  90                  95

Val Leu Leu Glu Phe Val Thr Ala Ala Gly Ile Thr Leu Gly Met Asp
            100                 105                 110

Glu Leu Tyr Lys Gly Gly Ser Gly Gly Met Val Ser Lys Gly Glu Glu
        115                 120                 125

Leu Phe Thr Gly Val Val Pro Ile Gln Val Glu Leu Asp Gly Asp Val
    130                 135                 140

Asn Gly His Lys Phe Ser Val Ser Gly Glu Gly Glu Gly Asp Ala Thr
145                 150                 155                 160

Tyr Gly Lys Leu Thr Leu Lys Phe Ile Cys Thr Thr Gly Lys Leu Pro
                165                 170                 175

Val Pro Trp Pro Thr Leu Val Thr Thr Leu Ser Tyr Gly Val Gln Cys
            180                 185                 190

Phe Ser Arg Tyr Pro Asp His Met Lys Gln His Asp Phe Phe Lys Ser
        195                 200                 205

Ala Met Pro Glu Gly Tyr Ile Gln Glu Arg Thr Ile Phe Phe Lys Asp
    210                 215                 220

Asp Gly Asn Tyr Lys Thr Arg Ala Glu Val Lys Phe Glu Gly Asp Thr
225                 230                 235                 240

Leu Val Asn Arg Ile Glu Leu Lys Gly Ile Asp Phe Lys Glu Asp Gly
```

```
                    245                 250                 255
Asn Ile Leu Gly His Lys Leu Glu Tyr Ser Thr Arg Asp Gln Leu Thr
                260                 265                 270

Glu Glu Gln Ile Ala Glu Phe Lys Glu Ala Phe Ser Leu Phe Asp Lys
            275                 280                 285

Asp Gly Asp Gly Thr Ile Thr Thr Lys Glu Leu Gly Thr Val Met Arg
        290                 295                 300

Ser Leu Gly Gln Asn Pro Thr Glu Ala Glu Leu Gln Asp Met Ile Asn
305                 310                 315                 320

Glu Val Asp Ala Asp Gly Asp Gly Thr Ile Asp Phe Pro Glu Phe Leu
                325                 330                 335

Thr Met Met Ala Pro Lys Met Gln Asp Thr Asp Ser Glu Glu Glu Ile
                340                 345                 350

Arg Glu Ala Phe Arg Val Phe Asp Lys Asp Gly Asn Gly Tyr Ile Gly
            355                 360                 365

Ala Ala Glu Leu Arg His Val Met Thr Asn Leu Gly Glu Lys Leu Thr
        370                 375                 380

Asp Glu Glu Val Asp Glu Met Ile Arg Val Ala Asp Ile Asp Gly Asp
385                 390                 395                 400

Gly Gln Val Asn Tyr Glu Glu Phe Val Gln Met Met Thr Ala Lys
                405                 410                 415

<210> SEQ ID NO 41
<211> LENGTH: 416
<212> TYPE: PRT
<213> ORGANISM: Artificial Sequence
<220> FEATURE:
<223> OTHER INFORMATION: Synthetic sequence

<400> SEQUENCE: 41

Met Val Asp Ser Ser Arg Arg Lys Trp Asn Lys Thr Gly His Ala Val
1               5                   10                  15

Arg Ala Ile Gly Arg Leu Ser Ser Leu Glu Asn Val Tyr Ile Lys Ala
            20                  25                  30

Asp Glu Gln Lys Asn Gly Ile Lys Ala Asn Phe Lys Ile Arg His Asn
        35                  40                  45

Ile Glu Asp Gly Gly Val Gln Leu Ala Tyr His Tyr Gln Gln Asn Thr
    50                  55                  60

Pro Ile Gly Asp Gly Pro Val Leu Leu Pro Asp Asn His Tyr Leu Ser
65                  70                  75                  80

Val Gln Ser Ile Leu Ser Lys Asp Pro Asn Glu Lys Arg Asp His Met
                85                  90                  95

Val Leu Leu Glu Phe Val Thr Ala Ala Gly Ile Thr Leu Gly Met Asp
            100                 105                 110

Glu Leu Tyr Lys Gly Gly Thr Gly Gly Ser Met Val Ser Lys Gly Glu
        115                 120                 125

Glu Leu Phe Thr Gly Val Val Pro Ile Gln Val Glu Leu Asp Gly Asp
    130                 135                 140

Val Asn Gly His Lys Phe Ser Val Ser Gly Glu Gly Glu Gly Asp Ala
145                 150                 155                 160

Thr Tyr Gly Lys Leu Thr Leu Lys Phe Ile Cys Thr Thr Gly Lys Leu
                165                 170                 175

Pro Val Pro Trp Pro Thr Leu Val Thr Thr Leu Ser Tyr Gly Val Gln
            180                 185                 190

Cys Phe Ser Arg Tyr Pro Asp His Met Lys Gln His Asp Phe Phe Lys
```

```
            195                 200                 205
Ser Ala Met Pro Glu Gly Tyr Ile Gln Glu Arg Thr Ile Phe Phe Lys
210                 215                 220

Asp Asp Gly Asn Tyr Lys Thr Arg Ala Glu Val Lys Phe Glu Gly Asp
225                 230                 235                 240

Thr Leu Val Asn Arg Ile Glu Leu Lys Gly Ile Asp Phe Lys Glu Asp
                    245                 250                 255

Gly Asn Ile Leu Gly His Lys Leu Glu Tyr Asn Thr Arg Asp Gln Leu
                260                 265                 270

Thr Glu Glu Gln Ile Ala Glu Leu Lys Glu Ala Phe Ser Leu Phe Asp
            275                 280                 285

Lys Asp Gly Asp Gly Thr Ile Thr Thr Lys Glu Leu Gly Thr Val Met
290                 295                 300

Arg Ser Leu Gly Gln Asn Pro Thr Glu Ala Glu Leu Gln Asp Met Ile
305                 310                 315                 320

Asn Glu Val Asp Ala Asp Gly Asp Gly Thr Ile Asp Leu Pro Glu Phe
                    325                 330                 335

Gln Thr Met Met Ala Arg Lys Met Asn Asp Thr Asp Ser Glu Glu Glu
                340                 345                 350

Ile Arg Glu Ala Phe Arg Val Phe Asp Lys Asp Gly Asn Gly Tyr Ile
            355                 360                 365

Gly Ala Ala Glu Leu Arg His Val Met Thr Asn Leu Gly Glu Lys Leu
370                 375                 380

Thr Asp Glu Glu Val Asp Glu Met Ile Arg Val Ala Asp Ile Asp Gly
385                 390                 395                 400

Asp Gly Gln Val Asn Tyr Glu Phe Val Gln Met Met Thr Ala Lys
                    405                 410                 415

<210> SEQ ID NO 42
<211> LENGTH: 417
<212> TYPE: PRT
<213> ORGANISM: Artificial Sequence
<220> FEATURE:
<223> OTHER INFORMATION: Synthetic sequence

<400> SEQUENCE: 42

Met Val Asp Ser Ser Arg Arg Lys Trp Asn Lys Ala Gly His Ala Val
1               5                   10                  15

Arg Ala Ile Gly Arg Leu Ser Ser Pro Val Val Ser Glu Arg Met Tyr
                20                  25                  30

Pro Glu Asp Gly Ala Leu Lys Ser Glu Ile Lys Lys Gly Leu Arg Leu
            35                  40                  45

Lys Asp Gly Gly His Tyr Ala Ala Glu Val Lys Thr Thr Tyr Lys Ala
50                  55                  60

Lys Lys Pro Val Gln Leu Pro Gly Ala Tyr Ile Val Asp Ile Lys Leu
65                  70                  75                  80

Asp Ile Val Ser His Asn Glu Asp Tyr Thr Ile Val Glu Gln Cys Glu
                85                  90                  95

Arg Ala Glu Gly Arg His Ser Thr Gly Gly Met Asp Glu Leu Tyr Lys
            100                 105                 110

Gly Gly Thr Gly Gly Ser Leu Val Ser Lys Gly Glu Glu Asp Asn Met
                115                 120                 125

Ala Ile Ile Lys Glu Phe Met Arg Phe Lys Val His Met Glu Gly Ser
130                 135                 140

Val Asn Gly His Glu Phe Glu Ile Glu Gly Glu Gly Glu Gly Arg Pro
```

```
145                 150                 155                 160
Tyr Glu Ala Phe Gln Thr Ala Lys Leu Lys Val Thr Lys Gly Gly Pro
                165                 170                 175

Leu Pro Phe Ala Trp Asp Ile Leu Ser Pro Gln Phe Met Tyr Gly Ser
                180                 185                 190

Lys Ala Tyr Ile Lys His Pro Ala Asp Ile Pro Asp Tyr Phe Lys Leu
                195                 200                 205

Ser Phe Pro Glu Gly Phe Arg Trp Glu Arg Val Met Asn Phe Glu Asp
    210                 215                 220

Gly Gly Ile Ile His Val Asn Gln Asp Ser Ser Leu Gln Asp Gly Val
225                 230                 235                 240

Phe Ile Tyr Lys Val Lys Leu Arg Gly Thr Asn Phe Pro Pro Asp Gly
                245                 250                 255

Pro Val Met Gln Lys Lys Thr Met Gly Trp Glu Ala Thr Arg Asp Gln
                260                 265                 270

Leu Thr Glu Glu Gln Ile Ala Glu Phe Lys Glu Ala Phe Ser Leu Phe
                275                 280                 285

Asp Lys Asp Gly Asp Gly Thr Ile Thr Thr Lys Glu Leu Gly Thr Val
    290                 295                 300

Met Arg Ser Leu Gly Gln Asn Pro Thr Glu Ala Glu Leu Gln Asp Met
305                 310                 315                 320

Ile Asn Glu Val Asp Ala Asp Gly Asp Gly Thr Phe Asp Phe Pro Glu
                325                 330                 335

Phe Leu Thr Met Met Ala Arg Lys Met Asn Asp Thr Asp Ser Glu Glu
                340                 345                 350

Glu Ile Arg Glu Ala Phe Arg Val Phe Asp Lys Asp Gly Asn Gly Tyr
                355                 360                 365

Ile Gly Ala Ala Glu Leu Arg His Val Met Thr Asp Leu Gly Glu Lys
                370                 375                 380

Leu Thr Asp Glu Glu Val Asp Glu Met Ile Arg Val Ala Asp Ile Asp
385                 390                 395                 400

Gly Asp Gly Gln Val Asn Tyr Glu Glu Phe Val Gln Met Met Thr Ala
                405                 410                 415

Lys

<210> SEQ ID NO 43
<211> LENGTH: 418
<212> TYPE: PRT
<213> ORGANISM: Artificial Sequence
<220> FEATURE:
<223> OTHER INFORMATION: Synthetic sequence

<400> SEQUENCE: 43

Met Val Asp Ser Pro Arg Arg Lys Trp Asn Lys Thr Gly His Ala Val
1               5                   10                  15

Arg Ala Ile Gly Arg Leu Ser Ser Pro Glu Asn Val Tyr Ile Lys Ala
                20                  25                  30

Asp Lys Gln Lys Asn Gly Ile Lys Ala Asn Phe Lys Ile Arg His Asn
                35                  40                  45

Ile Glu Gly Gly Gly Val Gln Leu Ala Tyr His Tyr Gln Gln Asn Thr
                50                  55                  60

Pro Ile Gly Asp Gly Pro Val Leu Leu Pro Asp Asn His Tyr Leu Ser
65                  70                  75                  80

Val Gln Ser Ile Leu Ser Lys Asp Pro Asn Glu Lys Arg Asp His Met
                85                  90                  95
```

Val Leu Leu Glu Phe Val Thr Ala Ala Gly Ile Thr Leu Gly Met Asp
            100                 105                 110

Glu Leu Tyr Lys Gly Gly Thr Gly Gly Ser Glu Ser Met Val Ser Lys
        115                 120                 125

Gly Glu Glu Leu Phe Thr Gly Val Val Pro Ile Gln Val Glu Leu Asp
    130                 135                 140

Gly Asp Val Asn Gly His Lys Phe Ser Val Ser Gly Glu Gly Glu Gly
145                 150                 155                 160

Asp Ala Thr Tyr Gly Lys Leu Thr Leu Lys Phe Ile Cys Thr Thr Gly
                165                 170                 175

Lys Leu Pro Val Pro Trp Pro Thr Leu Val Thr Thr Leu Ser His Gly
            180                 185                 190

Val Gln Cys Phe Ser Arg Tyr Pro Asp His Met Lys Gln His Asp Phe
        195                 200                 205

Phe Lys Ser Ala Met Pro Gly Gly Tyr Ile Gln Glu Arg Thr Ile Phe
    210                 215                 220

Phe Lys Asp Asp Gly Asn Tyr Lys Thr Arg Ala Glu Val Lys Phe Glu
225                 230                 235                 240

Gly Asp Thr Leu Val Asn Arg Ile Glu Leu Lys Gly Ile Asp Phe Lys
                245                 250                 255

Glu Asp Gly Asn Ile Leu Gly His Lys Leu Glu Tyr Asn Thr Arg Gly
            260                 265                 270

Gln Leu Thr Glu Glu Gln Ile Ala Glu Phe Lys Glu Ala Phe Ser Leu
        275                 280                 285

Phe Asp Lys Asp Gly Asp Gly Thr Ile Thr Thr Lys Glu Leu Gly Thr
    290                 295                 300

Val Met Arg Ser Leu Gly Gln Asn Pro Thr Glu Ala Glu Leu Gln Asp
305                 310                 315                 320

Met Ile Asn Glu Val Asp Ala Asp Gly Asp Gly Thr Ile Asp Phe Pro
                325                 330                 335

Glu Phe Leu Thr Met Met Ala Pro Lys Met Gln Asp Thr Asp Ser Glu
            340                 345                 350

Glu Glu Ile Arg Glu Ala Phe Arg Val Phe Asp Lys Asp Gly Asn Gly
        355                 360                 365

Tyr Ile Gly Ala Ala Glu Leu Arg His Val Met Thr Asn Leu Gly Glu
    370                 375                 380

Lys Leu Thr Asp Glu Glu Val Asp Glu Met Ile Arg Glu Ala Asp Ile
385                 390                 395                 400

Asp Gly Asp Gly Gln Val Asn Tyr Glu Glu Phe Val Gln Met Met Thr
                405                 410                 415

Ala Lys

<210> SEQ ID NO 44
<211> LENGTH: 416
<212> TYPE: PRT
<213> ORGANISM: Artificial Sequence
<220> FEATURE:
<223> OTHER INFORMATION: Synthetic sequence

<400> SEQUENCE: 44

Met Val Asp Ser Ser Arg Arg Lys Trp Asn Lys Thr Gly His Ala Val
1               5                   10                  15

Arg Ala Ile Gly Arg Leu Ser Ser Leu Glu Asn Val Tyr Ile Lys Ala
            20                  25                  30

Asp Lys Gln Lys Asn Gly Ile Lys Ala Asn Phe Lys Ile Arg His Asn
                35                  40                  45

Ile Glu Asp Gly Gly Val Gln Leu Ala Tyr His Tyr Gln Gln Asn Thr
 50                  55                  60

Pro Ile Gly Asp Gly Pro Val Leu Leu Pro Asp Asn His Tyr Leu Ser
 65                  70                  75                  80

Val Gln Ser Ile Leu Ser Lys Asp Pro Asn Glu Lys Arg Asp His Met
                 85                  90                  95

Val Leu Leu Glu Phe Val Thr Ala Ala Gly Ile Thr Leu Gly Met Asp
                100                 105                 110

Glu Leu Tyr Lys Gly Gly Thr Gly Gly Ser Met Val Ser Lys Gly Glu
                115                 120                 125

Glu Leu Phe Thr Gly Val Val Pro Ile Gln Val Glu Leu Asp Gly Asp
                130                 135                 140

Val Asn Gly His Lys Phe Ser Val Ser Gly Glu Gly Glu Gly Asp Ala
145                 150                 155                 160

Thr Tyr Gly Lys Leu Thr Leu Lys Phe Ile Cys Thr Thr Gly Lys Leu
                165                 170                 175

Pro Val Pro Trp Pro Thr Leu Val Thr Thr Leu Thr Tyr Gly Val Gln
                180                 185                 190

Cys Phe Ser Arg Tyr Pro Asp His Met Lys Gln His Asp Phe Phe Lys
                195                 200                 205

Ser Ala Met Pro Glu Gly Tyr Ile Gln Glu Arg Thr Ile Phe Phe Lys
                210                 215                 220

Asp Asp Gly Asn Tyr Lys Thr Arg Ala Glu Val Lys Phe Glu Gly Asp
225                 230                 235                 240

Thr Leu Val Asn Arg Ile Glu Leu Lys Gly Ile Asp Phe Lys Glu Asp
                245                 250                 255

Gly Asn Ile Leu Gly His Lys Leu Glu Tyr Asn Thr Arg Asp Gln Leu
                260                 265                 270

Thr Glu Glu Gln Ile Ala Glu Phe Lys Glu Ala Phe Ser Leu Phe Asp
                275                 280                 285

Lys Asp Gly Asp Gly Thr Ile Thr Thr Lys Glu Leu Gly Thr Val Met
290                 295                 300

Arg Ser Leu Gly Gln Asn Pro Thr Glu Ala Glu Leu Gln Asp Met Ile
305                 310                 315                 320

Asn Glu Val Asp Ala Asp Gly Asp Gly Thr Ile Asp Phe Pro Glu Phe
                325                 330                 335

Leu Thr Met Met Ala Arg Lys Met Lys Asp Thr Asp Ser Glu Glu Glu
                340                 345                 350

Ile Arg Glu Ala Phe Arg Val Phe Asp Lys Asp Gly Asn Gly Tyr Ile
                355                 360                 365

Gly Ala Ala Glu Leu Arg His Val Met Thr Asn Leu Gly Glu Lys Leu
                370                 375                 380

Thr Asp Glu Glu Val Asp Glu Met Ile Arg Val Ala Asp Ile Asp Gly
385                 390                 395                 400

Asp Gly Gln Val Asn Tyr Glu Glu Phe Val Gln Met Met Thr Ala Lys
                405                 410                 415

<210> SEQ ID NO 45
<211> LENGTH: 416
<212> TYPE: PRT
<213> ORGANISM: Artificial Sequence
<220> FEATURE:
<223> OTHER INFORMATION: Synthetic sequence

<400> SEQUENCE: 45

Met Val Asp Ser Ser Arg Arg Lys Trp Asn Lys Thr Gly His Ala Val
1               5                   10                  15

Arg Ala Ile Gly Arg Leu Ser Ser Leu Glu Asn Val Tyr Ile Lys Ala
            20                  25                  30

Asp Glu Gln Lys Asn Gly Ile Lys Ala Tyr Phe Lys Ile Arg His Asn
        35                  40                  45

Ile Glu Gly Gly Val Gln Leu Ala Tyr His Tyr Gln Gln Asn Thr
    50                  55                  60

Pro Ile Gly Asp Gly Pro Val Leu Leu Pro Asp Asn His Tyr Leu Ser
65              70                  75                  80

Val Gln Ser Ile Leu Ser Lys Asp Pro Asn Glu Lys Arg Asp His Met
                85                  90                  95

Val Leu Leu Glu Phe Val Thr Ala Ala Gly Ile Thr Leu Gly Met Asp
            100                 105                 110

Glu Leu Tyr Lys Gly Gly Thr Gly Gly Ser Met Val Ser Lys Gly Glu
        115                 120                 125

Glu Leu Phe Thr Gly Val Val Pro Ile Gln Val Glu Leu Asp Gly Asp
    130                 135                 140

Val Asn Gly His Lys Phe Ser Val Ser Gly Glu Gly Glu Gly Asp Ala
145             150                 155                 160

Thr Tyr Gly Lys Leu Thr Leu Lys Phe Ile Cys Thr Thr Gly Lys Leu
                165                 170                 175

Pro Val Pro Trp Pro Thr Leu Val Thr Thr Leu Thr Tyr Gly Val Gln
            180                 185                 190

Cys Phe Ser Arg Tyr Pro Asp His Met Lys Gln His Asp Phe Phe Lys
        195                 200                 205

Ser Ala Met Pro Glu Gly Tyr Ile Gln Glu Arg Thr Ile Phe Phe Lys
    210                 215                 220

Asp Asp Gly Asn Tyr Lys Thr Arg Ala Glu Val Lys Phe Glu Gly Asp
225             230                 235                 240

Thr Leu Val Asn Arg Ile Glu Leu Lys Gly Ile Asp Phe Lys Glu Asp
                245                 250                 255

Gly Asn Ile Leu Gly His Lys Leu Glu Tyr Asn Thr Arg Asp Gln Leu
            260                 265                 270

Thr Glu Glu Gln Ile Ala Glu Phe Lys Glu Ala Phe Ser Leu Phe Asp
        275                 280                 285

Lys Asp Gly Asp Gly Thr Ile Thr Thr Lys Glu Leu Gly Thr Val Met
290                 295                 300

Arg Ser Leu Gly Gln Asn Pro Thr Glu Ala Glu Leu Gln Asp Met Ile
305             310                 315                 320

Asn Glu Val Asp Ala Asp Gly Asp Gly Thr Ile Asp Phe Pro Glu Phe
                325                 330                 335

Leu Thr Met Met Ala Arg Lys Met Asn Asp Thr Asp Ser Glu Glu Glu
            340                 345                 350

Ile Arg Glu Ala Phe Arg Val Phe Asp Lys Asp Gly Asn Gly Tyr Ile
        355                 360                 365

Gly Ala Ala Glu Leu Arg His Val Met Thr Asn Leu Gly Glu Lys Leu
    370                 375                 380

Thr Asp Glu Glu Val Asp Glu Met Ile Arg Val Ala Asp Ile Asp Gly
385                 390                 395                 400

Asp Gly Gln Val Asn Tyr Glu Glu Phe Val Gln Met Met Thr Ala Lys

<210> SEQ ID NO 46
<211> LENGTH: 418
<212> TYPE: PRT
<213> ORGANISM: Artificial Sequence
<220> FEATURE:
<223> OTHER INFORMATION: Synthetic sequence

<400> SEQUENCE: 46

Met Val Asp Ser Ser Arg Arg Lys Trp Asn Lys Thr Gly His Ala Val
1               5                   10                  15

Arg Ala Ile Gly Arg Leu Ser Ser Leu Glu Asn Val Tyr Ile Lys Ala
            20                  25                  30

Asp Glu Gln Lys Asn Gly Ile Lys Ala Tyr Phe Lys Ile Arg His Asn
        35                  40                  45

Ile Glu Gly Gly Gly Val Gln Leu Ala Tyr His Tyr Gln Gln Asn Thr
    50                  55                  60

Pro Ile Gly Asp Gly Pro Val Leu Leu Pro Asp Asn His Tyr Leu Ser
65                  70                  75                  80

Val Gln Ser Met Leu Ser Lys Asp Pro Asn Glu Lys Arg Asp His Met
                85                  90                  95

Val Leu Leu Glu Phe Val Thr Ala Ala Gly Ile Thr Leu Gly Met Asp
            100                 105                 110

Glu Leu Tyr Lys Gly Gly Thr Gly Gly Ser Glu Ser Met Val Ser Lys
        115                 120                 125

Gly Glu Glu Leu Phe Thr Gly Val Val Pro Ile Gln Val Glu Leu Asp
    130                 135                 140

Gly Asp Val Asn Gly His Lys Phe Ser Val Ser Gly Glu Gly Glu Gly
145                 150                 155                 160

Asp Ala Thr Tyr Gly Lys Leu Thr Leu Lys Phe Ile Cys Thr Thr Gly
                165                 170                 175

Lys Leu Pro Val Pro Trp Pro Thr Leu Val Thr Thr Leu Thr Tyr Gly
            180                 185                 190

Val Gln Cys Phe Ser Arg Tyr Pro Asp His Met Lys Gln His Asp Phe
        195                 200                 205

Phe Lys Ser Ala Met Pro Glu Gly Tyr Ile Gln Glu Arg Thr Ile Phe
    210                 215                 220

Phe Lys Gly Asp Gly Asn Tyr Lys Thr Arg Ala Glu Val Lys Phe Glu
225                 230                 235                 240

Gly Asp Thr Leu Val Asn Arg Ile Glu Leu Lys Gly Ile Asp Phe Lys
                245                 250                 255

Glu Asp Gly Asn Ile Leu Gly His Lys Leu Glu Tyr Asn Thr Arg Asp
            260                 265                 270

Gln Leu Thr Glu Glu Gln Ile Ala Glu Phe Lys Glu Ala Phe Ser Leu
        275                 280                 285

Phe Asp Lys Asp Gly Asp Gly Thr Ile Thr Thr Lys Glu Leu Gly Thr
    290                 295                 300

Val Met Arg Ser Leu Gly Gln Asn Pro Thr Glu Ala Glu Leu Gln Asp
305                 310                 315                 320

Met Ile Asn Glu Val Asp Ala Asp Gly Asp Gly Thr Ile Asp Phe Pro
                325                 330                 335

Glu Phe Leu Thr Met Met Ala Arg Lys Met Lys Asp Thr Asp Ser Glu
            340                 345                 350

Glu Glu Ile Arg Glu Ala Phe Arg Val Phe Asp Lys Asp Gly Asn Gly

```
                355                 360                 365
Tyr Ile Gly Ala Ala Glu Leu Arg His Val Met Thr Asn Leu Gly Glu
            370                 375                 380
Lys Leu Thr Asp Glu Glu Val Asp Glu Met Ile Arg Val Ala Asp Ile
385                 390                 395                 400
Asp Gly Asp Gly Gln Val Asn Tyr Glu Glu Phe Val Gln Met Met Thr
                405                 410                 415
Ala Lys

<210> SEQ ID NO 47
<211> LENGTH: 619
<212> TYPE: PRT
<213> ORGANISM: Artificial Sequence
<220> FEATURE:
<223> OTHER INFORMATION: Synthetic sequence

<400> SEQUENCE: 47

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Arg Gly
            20                  25                  30

Glu Gly Glu Gly Asp Ala Thr Asn Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
        195                 200                 205

Ser Lys Asp Pro Asn Glu Lys Arg Asp His Met Val Leu Leu Glu Phe
    210                 215                 220

Val Thr Ala Ala Arg Met Leu Ser Glu Glu Leu Ala Asn Cys Phe
225                 230                 235                 240

Arg Ile Phe Asp Lys Asp Ala Asn Gly Phe Ile Asp Ile Glu Glu Leu
                245                 250                 255

Gly Glu Ile Leu Arg Ala Thr Gly Glu His Val Thr Glu Glu Asp Ile
            260                 265                 270

Glu Asp Leu Met Lys Asp Ser Asp Lys Asn Asn Asp Gly Arg Ile Asp
        275                 280                 285

Phe Asp Glu Phe Leu Lys Met Met Glu Gly Val Gln Gly Thr Ser Glu
    290                 295                 300
```

Glu Glu Leu Ala Asn Cys Phe Arg Ile Phe Asp Lys Asp Ala Asn Gly
305                 310                 315                 320

Phe Ile Asp Ile Glu Glu Leu Gly Glu Ile Leu Arg Ala Thr Gly Glu
            325                 330                 335

His Val Thr Glu Glu Asp Ile Glu Asp Leu Met Lys Asp Ser Asp Lys
            340                 345                 350

Asn Asn Asp Gly Arg Ile Asp Phe Asp Glu Phe Leu Lys Met Met Glu
        355                 360                 365

Gly Val Gln Glu Leu Met Gly Gly Val Gln Leu Ala Asp His Tyr Gln
        370                 375                 380

Gln Asn Thr Pro Ile Gly Asp Gly Pro Val Leu Leu Pro Asp Asn His
385                 390                 395                 400

Tyr Leu Ser Tyr Gln Ser Lys Leu Ser Lys Asp Pro Asn Glu Lys Arg
            405                 410                 415

Asp His Met Val Leu Leu Glu Phe Val Thr Ala Ala Gly Ile Thr Leu
            420                 425                 430

Gly Met Asp Glu Leu Tyr Lys Gly Gly Thr Gly Gly Ser Met Val Ser
        435                 440                 445

Lys Gly Glu Glu Leu Phe Thr Gly Val Val Pro Ile Leu Val Glu Leu
450                 455                 460

Asp Gly Asp Val Asn Gly His Lys Phe Ser Val Arg Gly Glu Gly Glu
465                 470                 475                 480

Gly Asp Ala Thr Asn Gly Lys Leu Thr Leu Lys Phe Ile Cys Thr Thr
            485                 490                 495

Gly Lys Leu Pro Val Pro Trp Pro Thr Leu Val Thr Thr Leu Gly Tyr
            500                 505                 510

Gly Leu Met Cys Phe Ala Arg Tyr Pro Asp His Met Lys Gln His Asp
        515                 520                 525

Phe Phe Lys Ser Ala Met Pro Glu Gly Tyr Val Gln Glu Arg Thr Ile
        530                 535                 540

Phe Phe Lys Asp Asp Gly Asn Tyr Lys Thr Arg Ala Glu Val Lys Phe
545                 550                 555                 560

Glu Gly Asp Thr Leu Val Asn Arg Ile Glu Leu Lys Gly Ile Asp Phe
            565                 570                 575

Lys Glu Asp Gly Asn Ile Leu Gly His Lys Leu Glu Tyr Asn Tyr Asn
            580                 585                 590

Ser His Asn Val Tyr Ile Met Ala Asp Lys Gln Lys Asn Gly Ile Lys
        595                 600                 605

Ala Asn Phe Lys Ile Arg His Asn Ile Glu Asp
    610                 615

<210> SEQ ID NO 48
<211> LENGTH: 673
<212> TYPE: PRT
<213> ORGANISM: Artificial Sequence
<220> FEATURE:
<223> OTHER INFORMATION: Synthetic sequence

<400> SEQUENCE: 48

Met Val Ser Lys Gly Glu Glu Leu Phe Thr Gly Val Val Pro Ile Leu
1               5                   10                  15

Val Glu Leu Asp Gly Asp Val Asn Gly His Arg Phe Ser Val Ser Gly
            20                  25                  30

Glu Gly Glu Gly Asp Ala Thr Tyr Gly Lys Leu Thr Leu Lys Phe Ile
        35                  40                  45

-continued

```
Cys Thr Thr Gly Lys Leu Pro Val Pro Trp Pro Thr Leu Val Thr Thr
 50                  55                  60

Leu Thr Trp Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
                130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Ser
                165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Ala Leu
                195                 200                 205

Ser Lys Asp Pro Asn Glu Lys Arg Asp His Met Val Leu Leu Glu Phe
210                 215                 220

Val Thr Ala Ala Arg Met His Asp Gln Leu Thr Glu Glu Gln Ile Ala
225                 230                 235                 240

Glu Phe Lys Glu Ala Phe Ser Leu Phe Asp Lys Asp Gly Asp Gly Thr
                245                 250                 255

Ile Thr Thr Lys Glu Leu Gly Thr Val Met Arg Ser Leu Gly Gln Asn
                260                 265                 270

Pro Thr Glu Ala Glu Leu Gln Asp Met Ile Asn Glu Val Asp Ala Asp
                275                 280                 285

Gly Asn Gly Thr Ile Tyr Phe Pro Glu Phe Leu Thr Met Met Ala Arg
                290                 295                 300

Lys Met Lys Asp Thr Asp Ser Glu Glu Glu Ile Arg Glu Ala Phe Arg
305                 310                 315                 320

Val Phe Asp Lys Asp Gly Asn Gly Tyr Ile Ser Ala Ala Gln Leu Arg
                325                 330                 335

His Val Met Thr Asn Leu Gly Glu Lys Leu Thr Asp Glu Glu Val Asp
                340                 345                 350

Glu Met Ile Arg Glu Ala Asp Ile Asp Gly Asp Gly Gln Val Asn Tyr
                355                 360                 365

Glu Glu Phe Val Gln Met Met Thr Ala Lys Gly Gly Lys Arg Arg Trp
                370                 375                 380

Lys Lys Asn Phe Ile Ala Val Ser Ala Ala Asn Arg Phe Lys Lys Ile
385                 390                 395                 400

Ser Ser Ser Gly Ala Leu Glu Leu Met Asp Gly Gly Val Gln Leu Ala
                405                 410                 415

Asp His Tyr Gln Gln Asn Thr Pro Ile Gly Asp Gly Pro Val Leu Leu
                420                 425                 430

Pro Asp Asn His Tyr Leu Ser Tyr Gln Ser Ala Leu Ser Lys Asp Pro
                435                 440                 445

Asn Glu Lys Arg Asp His Met Val Leu Leu Glu Phe Val Thr Ala Ala
450                 455                 460
```

```
Gly Ile Thr Leu Gly Met Asp Glu Leu Tyr Lys Gly Gly Ser Gly Gly
465                 470                 475                 480

Met Val Ser Lys Gly Glu Glu Leu Phe Thr Gly Val Val Pro Ile Leu
                485                 490                 495

Val Glu Leu Asp Gly Asp Val Asn Gly His Lys Phe Ser Val Ser Gly
            500                 505                 510

Glu Gly Glu Gly Asp Ala Thr Tyr Gly Lys Leu Thr Leu Lys Leu Ile
        515                 520                 525

Cys Thr Thr Gly Lys Leu Pro Val Pro Trp Pro Thr Leu Val Thr Thr
    530                 535                 540

Leu Gly Tyr Gly Leu Gln Cys Phe Ala Arg Tyr Pro Asp His Met Lys
545                 550                 555                 560

Gln His Asp Phe Phe Lys Ser Ala Met Pro Glu Gly Tyr Val Gln Glu
                565                 570                 575

Arg Thr Ile Phe Phe Lys Asp Asp Gly Asn Tyr Lys Thr Arg Ala Glu
            580                 585                 590

Val Lys Phe Glu Gly Asp Thr Leu Val Asn Arg Ile Glu Leu Lys Gly
        595                 600                 605

Ile Asp Phe Lys Glu Asp Gly Asn Ile Leu Gly His Lys Leu Glu Tyr
    610                 615                 620

Asn Tyr Asn Ser His Asn Val Tyr Ile Thr Ala Asp Lys Gln Lys Asn
625                 630                 635                 640

Gly Ile Lys Ala Asn Phe Lys Ile Arg His Asn Ile Glu Leu Ser Arg
                645                 650                 655

Gly Pro Gly Thr Ser Ala Glu Ile Tyr Ala Cys Arg Leu Glu Ile Ser
            660                 665                 670

Asn

<210> SEQ ID NO 49
<211> LENGTH: 653
<212> TYPE: PRT
<213> ORGANISM: Artificial Sequence
<220> FEATURE:
<223> OTHER INFORMATION: Synthetic sequence

<400> SEQUENCE: 49

Met Val Ser Lys Gly Glu Glu Leu Phe Thr Gly Val Val Pro Ile Leu
1               5                   10                  15

Val Glu Leu Asp Gly Asp Val Asn Gly His Arg Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
```

```
            145                 150                 155                 160
        Gly Ile Lys Ala His Phe Lys Ile Arg His Asn Ile Glu Asp Gly Ser
                        165                 170                 175
        Val Gln Leu Ala Asp His Tyr Gln Gln Asn Thr Pro Ile Gly Asp Gly
                        180                 185                 190
        Pro Val Leu Leu Pro Asp Asn His Tyr Leu Ser Thr Gln Ser Ala Leu
                        195                 200                 205
        Ser Lys Asp Pro Asn Glu Lys Arg Asp His Met Val Leu Leu Glu Phe
            210                 215                 220
        Val Thr Ala Ala Arg Met His Asp Gln Leu Thr Glu Glu Gln Ile Ala
        225                 230                 235                 240
        Glu Phe Lys Glu Ala Phe Ser Leu Leu Asp Lys Asp Gly Asp Gly Thr
                        245                 250                 255
        Ile Thr Thr Lys Glu Leu Gly Thr Ala Leu Arg Ser Leu Gly Gln Asn
                        260                 265                 270
        Pro Thr Glu Ala Glu Leu Gln Asp Met Ile Asn Glu Val Asp Ala Asp
                        275                 280                 285
        Gly Asn Gly Thr Ile Tyr Phe Pro Glu Phe Leu Thr Met Met Ala Arg
            290                 295                 300
        Lys Met Lys Asp Thr Asp Ser Glu Glu Glu Ile Arg Glu Ala Phe Arg
        305                 310                 315                 320
        Val Phe Asp Lys Asp Gly Asn Gly Tyr Ile Ser Ala Ala Glu Leu Arg
                        325                 330                 335
        His Val Met Thr Asn Leu Gly Glu Lys Leu Thr Asp Glu Glu Val Asp
                        340                 345                 350
        Glu Met Ile Arg Glu Ala Asp Ile Asp Gly Asp Gly Gln Val Asn Tyr
                        355                 360                 365
        Glu Glu Phe Val Gln Met Met Thr Ala Lys Gly Lys Arg Arg Trp
                        370                 375                 380
        Gln Lys Thr Gly His Ala Val Arg Ala Phe Gly Arg Leu Lys Lys Ile
        385                 390                 395                 400
        Ser Ser Ser Gly Ala Leu Glu Leu Met Asp Gly Gly Val Gln Leu Ala
                        405                 410                 415
        Asp His Tyr Gln Gln Asn Thr Pro Ile Gly Asp Gly Pro Val Leu Leu
                        420                 425                 430
        Pro Asp Asn His Tyr Leu Ser Tyr Gln Ser Ala Leu Ser Lys Asp Pro
                        435                 440                 445
        Asn Glu Lys Arg Asp His Met Val Leu Leu Glu Phe Val Thr Ala Ala
            450                 455                 460
        Gly Ile Thr Leu Gly Met Asp Glu Leu Tyr Lys Gly Gly Ser Gly Gly
        465                 470                 475                 480
        Met Val Ser Lys Gly Glu Glu Leu Phe Thr Gly Val Val Pro Ile Leu
                        485                 490                 495
        Val Glu Leu Asp Gly Asp Val Asn Gly His Lys Phe Ser Val Ser Gly
                        500                 505                 510
        Glu Gly Glu Gly Asp Ala Thr Tyr Gly Lys Leu Thr Leu Lys Leu Ile
                        515                 520                 525
        Cys Thr Thr Gly Lys Leu Pro Val Pro Trp Pro Thr Leu Val Thr Thr
            530                 535                 540
        Leu Gly Tyr Gly Leu Gln Cys Phe Ala Arg Tyr Pro Asp His Met Lys
        545                 550                 555                 560
        Gln His Asp Phe Phe Lys Ser Ala Met Pro Glu Gly Tyr Val Gln Glu
                        565                 570                 575
```

-continued

Arg Thr Ile Phe Phe Lys Asp Asp Gly Asn Tyr Lys Thr Arg Ala Glu
            580                 585                 590

Val Lys Phe Glu Gly Asp Thr Leu Val Asn Arg Ile Glu Leu Lys Gly
        595                 600                 605

Ile Asp Phe Lys Glu Asp Gly Asn Ile Leu Gly His Lys Leu Glu Tyr
    610                 615                 620

Asn Tyr Asn Ser His Asn Val Tyr Ile Thr Ala Asp Lys Gln Lys Asn
625                 630                 635                 640

Gly Ile Lys Ala Asn Phe Lys Ile Arg His Asn Ile Glu
                645                 650

<210> SEQ ID NO 50
<211> LENGTH: 344
<212> TYPE: PRT
<213> ORGANISM: Artificial Sequence
<220> FEATURE:
<223> OTHER INFORMATION: Synthetic sequence

<400> SEQUENCE: 50

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Ile Leu Ile His Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Ile Cys Arg Asp Leu Val Arg Tyr Leu Ala Trp
                245                 250                 255

Leu Tyr Phe Cys Ser Trp Ala Met Phe Pro Val Leu Phe Leu Leu Gly
            260                 265                 270

Pro Glu Gly Phe Gly His Ile Asn Gln Phe Asn Ser Ala Ile Ala His
        275                 280                 285

Ala Ile Leu Asp Leu Ala Ser Lys Asn Ala Trp Ser Met Met Gly His
            290                 295                 300

Phe Leu Arg Val Lys Ile His Glu His Ile Leu Leu Tyr Gly Asp Ile
305                 310                 315                 320

Arg Lys Lys Gln Lys Val Asn Val Ala Gly Gln Glu Met Glu Val Glu
                325                 330                 335

Thr Met Val His Glu Glu Asp Asp
            340

<210> SEQ ID NO 51
<211> LENGTH: 310
<212> TYPE: PRT
<213> ORGANISM: Chlamydomonas reinhardtii

<400> SEQUENCE: 51

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 52
<211> LENGTH: 310
<212> TYPE: PRT
<213> ORGANISM: Artificial Sequence
<220> FEATURE:
<223> OTHER INFORMATION: Synthetic sequence

<400> SEQUENCE: 52

```
Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Ser
        115                 120                 125

Pro Val Ile Leu Ile His Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
290                 295                 300

Glu Ala Gly Ala Val Pro
305                 310
```

<210> SEQ ID NO 53
<211> LENGTH: 310
<212> TYPE: PRT
<213> ORGANISM: Artificial Sequence
<220> FEATURE:
<223> OTHER INFORMATION: Synthetic sequence

<400> SEQUENCE: 53

```
Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65              70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Ser
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Ala Ile Gly Thr Ile
145             150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225             230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310
```

<210> SEQ ID NO 54
<211> LENGTH: 300
<212> TYPE: PRT
<213> ORGANISM: Volvox carteri

<400> SEQUENCE: 54

```
Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
            20                  25                  30

Gly Trp Leu Arg Ser Arg Gly Thr Ser Ile Glu Lys Thr Ile Ala Ile
        35                  40                  45
```

Thr Leu Gln Trp Val Val Phe Ala Leu Ser Val Ala Cys Leu Gly Trp
        50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
                85                  90                  95

Phe Asp Ser Pro Ala Thr Leu Trp Leu Ser Ser Gly Asn Gly Val Val
                100                 105                 110

Trp Met Arg Tyr Gly Glu Trp Leu Leu Thr Cys Pro Val Leu Leu Ile
            115                 120                 125

His Leu Ser Asn Leu Thr Gly Leu Lys Asp Asp Tyr Ser Lys Arg Thr
            130                 135                 140

Met Gly Leu Leu Val Ser Asp Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
                180                 185                 190

Glu Ala Phe His Thr Val Pro Lys Gly Ile Cys Arg Glu Leu Val Arg
            195                 200                 205

Val Met Ala Trp Thr Phe Phe Val Ala Trp Gly Met Phe Pro Val Leu
210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
                260                 265                 270

Tyr Gly Asp Ile Arg Lys Lys Gln Lys Ile Thr Ile Ala Gly Gln Glu
            275                 280                 285

Met Glu Val Glu Thr Leu Val Ala Glu Glu Glu Asp
            290                 295                 300

<210> SEQ ID NO 55
<211> LENGTH: 300
<212> TYPE: PRT
<213> ORGANISM: Artificial Sequence
<220> FEATURE:
<223> OTHER INFORMATION: Synthetic sequence

<400> SEQUENCE: 55

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
            20                  25                  30

Gly Trp Leu Arg Ser Arg Gly Thr Ser Ile Glu Lys Thr Ile Ala Ile
            35                  40                  45

Thr Leu Gln Trp Val Val Phe Ala Leu Ser Val Ala Cys Leu Gly Trp
        50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
                85                  90                  95

Phe Asp Ser Pro Ala Thr Leu Trp Leu Ser Ser Gly Asn Gly Val Val
                100                 105                 110

```
Trp Met Arg Tyr Gly Glu Trp Leu Leu Thr Ser Pro Val Leu Leu Ile
        115                 120                 125

His Leu Ser Asn Leu Thr Gly Leu Lys Asp Asp Tyr Ser Lys Arg Thr
    130                 135                 140

Met Gly Leu Leu Val Ser Asp Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
            180                 185                 190

Glu Ala Phe His Thr Val Pro Lys Gly Ile Cys Arg Glu Leu Val Arg
        195                 200                 205

Val Met Ala Trp Thr Phe Phe Val Ala Trp Gly Met Phe Pro Val Leu
    210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
            260                 265                 270

Tyr Gly Asp Ile Arg Lys Lys Gln Lys Ile Thr Ile Ala Gly Gln Glu
        275                 280                 285

Met Glu Val Glu Thr Leu Val Ala Glu Glu Asp
    290                 295                 300

<210> SEQ ID NO 56
<211> LENGTH: 300
<212> TYPE: PRT
<213> ORGANISM: Artificial Sequence
<220> FEATURE:
<223> OTHER INFORMATION: Synthetic sequence

<400> SEQUENCE: 56

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
            20                  25                  30

Gly Trp Leu Arg Ser Arg Gly Thr Ser Ile Glu Lys Thr Ile Ala Ile
        35                  40                  45

Thr Leu Gln Trp Val Val Phe Ala Leu Ser Val Ala Cys Leu Gly Trp
    50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
                85                  90                  95

Phe Asp Ser Pro Ala Thr Leu Trp Leu Ser Ser Gly Asn Gly Val Val
            100                 105                 110

Trp Met Arg Tyr Gly Glu Trp Leu Leu Thr Cys Pro Val Leu Leu Ile
        115                 120                 125

His Leu Ser Asn Leu Thr Gly Leu Lys Asp Asp Tyr Ser Lys Arg Thr
    130                 135                 140

Met Gly Leu Leu Val Ser Ala Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175
```

```
Leu Ser Tyr Gly Met Tyr Thr Tyr Phe His Ala Ala Lys Val Tyr Ile
            180                 185                 190

Glu Ala Phe His Thr Val Pro Lys Gly Ile Cys Arg Glu Leu Val Arg
            195                 200                 205

Val Met Ala Trp Thr Phe Phe Val Ala Trp Gly Met Phe Pro Val Leu
    210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
            260                 265                 270

Tyr Gly Asp Ile Arg Lys Lys Gln Lys Ile Thr Ile Ala Gly Gln Glu
            275                 280                 285

Met Glu Val Glu Thr Leu Val Ala Glu Glu Asp
    290                 295                 300

<210> SEQ ID NO 57
<211> LENGTH: 344
<212> TYPE: PRT
<213> ORGANISM: Artificial Sequence
<220> FEATURE:
<223> OTHER INFORMATION: Synthetic sequence

<400> SEQUENCE: 57

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240
```

```
Thr Val Pro Lys Gly Ile Cys Arg Glu Leu Val Arg Val Met Ala Trp
            245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
            275                 280                 285

Ser Ile Leu Asp Leu Ile Ala Lys Asn Met Trp Gly Val Leu Gly Asn
            290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
            325                 330                 335

Thr Leu Val Ala Glu Glu Glu Asp
            340

<210> SEQ ID NO 58
<211> LENGTH: 348
<212> TYPE: PRT
<213> ORGANISM: Chlamydomonas reinhardti

<400> SEQUENCE: 58

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
            50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
            85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
            115                 120                 125

Glu Met Ile Lys Phe Ile Ile Glu Tyr Phe His Glu Phe Asp Glu Pro
            130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Ile Leu Ile His Leu Ser Asn
            165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
            195                 200                 205

Lys Gly Tyr Val Arg Val Ile Phe Phe Leu Met Gly Leu Cys Tyr Gly
            210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
            245                 250                 255

Leu Phe Phe Val Ser Trp Gly Met Phe Pro Ile Leu Phe Ile Leu Gly
```

```
                260                 265                 270
Pro Glu Gly Phe Gly Val Leu Ser Val Tyr Gly Ser Thr Val Gly His
            275                 280                 285

Thr Ile Ile Asp Leu Met Ser Lys Asn Cys Trp Gly Leu Leu Gly His
            290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
            340                 345

<210> SEQ ID NO 59
<211> LENGTH: 316
<212> TYPE: PRT
<213> ORGANISM: Scherffelia dubia

<400> SEQUENCE: 59

Met Gly Gly Ala Pro Ala Pro Asp Ala His Ser Ala Pro Pro Gly Asn
1               5                   10                  15

Asp Ser Ala Gly Gly Ser Glu Tyr His Ala Pro Ala Gly Tyr Gln Val
            20                  25                  30

Asn Pro Pro Tyr His Pro Val His Gly Tyr Glu Glu Gln Cys Ser Ser
        35                  40                  45

Ile Tyr Ile Tyr Tyr Gly Ala Leu Trp Glu Gln Glu Thr Ala Arg Gly
    50                  55                  60

Phe Gln Trp Phe Ala Val Phe Leu Ser Ala Leu Phe Leu Ala Phe Tyr
65                  70                  75                  80

Gly Trp His Ala Tyr Lys Ala Ser Val Gly Trp Glu Glu Val Tyr Val
                85                  90                  95

Cys Ser Val Glu Leu Ile Lys Val Ile Leu Glu Ile Tyr Phe Glu Phe
            100                 105                 110

Thr Ser Pro Ala Met Leu Phe Leu Tyr Gly Gly Asn Ile Thr Pro Trp
        115                 120                 125

Leu Arg Tyr Ala Glu Trp Leu Leu Thr Cys Pro Val Ile Leu Ile His
    130                 135                 140

Leu Ser Asn Ile Thr Gly Leu Ser Glu Glu Tyr Asn Lys Arg Thr Met
145                 150                 155                 160

Ala Leu Leu Val Ser Asp Leu Gly Thr Ile Cys Met Gly Val Thr Ala
                165                 170                 175

Ala Leu Ala Thr Gly Trp Val Lys Trp Leu Phe Tyr Cys Ile Gly Leu
            180                 185                 190

Val Tyr Gly Thr Gln Thr Phe Tyr Asn Ala Gly Ile Ile Tyr Val Glu
        195                 200                 205

Ser Tyr Tyr Ile Met Pro Ala Gly Gly Cys Lys Lys Leu Val Leu Ala
    210                 215                 220

Met Thr Ala Val Tyr Tyr Ser Ser Trp Leu Met Phe Pro Gly Leu Phe
225                 230                 235                 240

Ile Phe Gly Pro Glu Gly Met His Thr Leu Ser Val Ala Gly Ser Thr
                245                 250                 255

Ile Gly His Thr Ile Ala Asp Leu Leu Ser Lys Asn Ile Trp Gly Leu
            260                 265                 270

Leu Gly His Phe Leu Arg Ile Lys Ile His Glu His Ile Ile Met Tyr
        275                 280                 285
```

Gly Asp Ile Arg Arg Pro Val Ser Ser Gln Phe Leu Gly Arg Lys Val
290                 295                 300

Asp Val Leu Ala Phe Val Thr Glu Glu Asp Lys Val
305                 310                 315

<210> SEQ ID NO 60
<211> LENGTH: 349
<212> TYPE: PRT
<213> ORGANISM: Chlamydomonas noctigama

<400> SEQUENCE: 60

Met Glu Pro Val Leu Gly Leu Ala Ser Thr Ala Val Arg Glu Leu Thr
1               5                   10                  15

Ala Gly Gly Ser Gly Asn Pro Tyr Glu Ser Tyr Lys Pro Pro Glu Asp
                20                  25                  30

Pro Cys Ala Leu Thr Pro Phe Gly Cys Leu Thr Asn Phe Trp Cys Asp
            35                  40                  45

Pro Gln Phe Gly Leu Ala Asp Ala Lys Tyr Asp Tyr Cys Tyr Val Lys
        50                  55                  60

Ala Ala Tyr Gly Glu Leu Ala Ile Val Glu Thr Ser Arg Leu Pro Trp
65                  70                  75                  80

Leu Tyr Ser His Gly Ser Asp Ala Glu His Gln Gly Ala Leu Ala Met
                85                  90                  95

Gln Trp Met Ala Phe Ala Leu Cys Ile Ile Cys Leu Val Phe Tyr Ala
            100                 105                 110

Tyr His Ser Trp Lys Ala Thr Thr Gly Trp Glu Glu Val Tyr Val Cys
        115                 120                 125

Val Val Glu Leu Val Lys Val Leu Leu Glu Ile Tyr Lys Glu Phe Glu
130                 135                 140

Ser Pro Ala Ser Ile Tyr Leu Pro Thr Ala Asn Ala Ala Leu Trp Leu
145                 150                 155                 160

Arg Tyr Gly Glu Trp Leu Leu Thr Cys Pro Val Ile Leu Ile His Leu
                165                 170                 175

Ser Asn Ile Thr Gly Leu Lys Asp Asp Tyr Asn Lys Arg Thr Met Gln
            180                 185                 190

Leu Leu Val Ser Asp Ile Gly Cys Val Val Trp Gly Ile Thr Ala Ala
        195                 200                 205

Phe Ser Val Gly Trp Leu Lys Trp Val Phe Phe Val Leu Gly Leu Leu
210                 215                 220

Tyr Gly Ser Asn Thr Tyr Phe His Ala Ala Lys Val Tyr Ile Glu Ser
225                 230                 235                 240

Tyr His Thr Val Pro Lys Gly His Cys Arg Leu Ile Val Arg Leu Met
                245                 250                 255

Ala Tyr Cys Phe Tyr Val Ala Trp Thr Met Tyr Pro Ile Leu Phe Ile
            260                 265                 270

Leu Gly Pro Glu Gly Leu Gly His Met Ser Ala Tyr Met Ser Thr Ala
        275                 280                 285

Leu His Gly Val Ala Asp Met Leu Ser Lys Gln Ile Trp Gly Leu Leu
290                 295                 300

Gly His His Leu Arg Val Lys Ile Phe Glu His Ile Leu Ile His Gly
305                 310                 315                 320

Asp Ile Arg Lys Thr Thr Thr Met Gln Val Gly Gly Gln Met Val Gln
                325                 330                 335

Val Glu Glu Met Val Asp Glu Glu Asp Glu Asp Thr Ile
            340                 345

```
<210> SEQ ID NO 61
<211> LENGTH: 345
<212> TYPE: PRT
<213> ORGANISM: Chloromonas subdivisa

<400> SEQUENCE: 61

Met Ser Arg Leu Val Ala Ala Ser Trp Leu Ala Leu Leu Leu Cys
1               5                   10                  15

Gly Ile Thr Ser Thr Thr Thr Ala Ser Ala Pro Ala Ala Ser Ser
                20                  25                  30

Thr Asp Gly Thr Ala Ala Ala Val Ser His Tyr Ala Met Asn Gly
                35                  40                  45

Phe Asp Glu Leu Ala Lys Gly Ala Val Val Pro Glu Asp His Phe Val
        50                  55                  60

Cys Gly Pro Ala Asp Lys Cys Tyr Cys Ser Ala Trp Leu His Ser Arg
65                  70                  75                  80

Gly Thr Pro Gly Glu Lys Ile Gly Ala Gln Val Cys Gln Trp Ile Ala
                85                  90                  95

Phe Ser Ile Ala Ile Ala Leu Leu Thr Phe Tyr Gly Phe Ser Ala Trp
                100                 105                 110

Lys Ala Thr Cys Gly Trp Glu Glu Val Tyr Val Cys Cys Val Glu Val
                115                 120                 125

Leu Phe Val Thr Leu Glu Ile Phe Lys Glu Phe Ser Ser Pro Ala Thr
        130                 135                 140

Val Tyr Leu Ser Thr Gly Asn His Ala Tyr Cys Leu Arg Tyr Phe Glu
145                 150                 155                 160

Trp Leu Leu Ser Cys Pro Val Ile Leu Ile Lys Leu Ser Asn Leu Ser
                165                 170                 175

Gly Leu Lys Asn Asp Tyr Ser Lys Arg Thr Met Gly Leu Ile Val Ser
                180                 185                 190

Cys Val Gly Met Ile Val Phe Gly Met Ala Ala Gly Leu Ala Thr Asp
                195                 200                 205

Trp Leu Lys Trp Leu Leu Tyr Ile Val Ser Cys Ile Tyr Gly Gly Tyr
        210                 215                 220

Met Tyr Phe Gln Ala Ala Lys Cys Tyr Val Glu Ala Asn His Ser Val
225                 230                 235                 240

Pro Lys Gly His Cys Arg Met Val Val Lys Leu Met Ala Tyr Ala Tyr
                245                 250                 255

Phe Ala Ser Trp Gly Ser Tyr Pro Ile Leu Trp Ala Val Gly Pro Glu
                260                 265                 270

Gly Leu Leu Lys Leu Ser Pro Tyr Ala Asn Ser Ile Gly His Ser Ile
        275                 280                 285

Cys Asp Ile Ile Ala Lys Glu Phe Trp Thr Phe Leu Ala His His Leu
290                 295                 300

Arg Ile Lys Ile His Glu His Ile Leu Ile His Gly Asp Ile Arg Lys
305                 310                 315                 320

Thr Thr Lys Met Glu Ile Gly Gly Glu Glu Val Glu Val Glu Phe
                325                 330                 335

Val Glu Glu Glu Asp Glu Asp Thr Val
                340                 345

<210> SEQ ID NO 62
<211> LENGTH: 325
<212> TYPE: PRT
```

<213> ORGANISM: Stigeoclonium helveticum

<400> SEQUENCE: 62

```
Met Glu Thr Ala Ala Thr Met Thr His Ala Phe Ile Ser Ala Val Pro
1               5                   10                  15

Ser Ala Glu Ala Thr Ile Arg Gly Leu Leu Ser Ala Ala Val Val
            20                  25                  30

Thr Pro Ala Ala Asp Ala His Gly Glu Thr Ser Asn Ala Thr Thr Ala
            35                  40                  45

Gly Ala Asp His Gly Cys Phe Pro His Ile Asn His Gly Thr Glu Leu
50                  55                  60

Gln His Lys Ile Ala Val Gly Leu Gln Trp Phe Thr Val Ile Val Ala
65                  70                  75                  80

Ile Val Gln Leu Ile Phe Tyr Gly Trp His Ser Phe Lys Ala Thr Thr
                85                  90                  95

Gly Trp Glu Glu Val Tyr Val Cys Val Ile Glu Leu Val Lys Cys Phe
            100                 105                 110

Ile Glu Leu Phe His Glu Val Asp Ser Pro Ala Thr Val Tyr Gln Thr
            115                 120                 125

Asn Gly Gly Ala Val Ile Trp Leu Arg Tyr Ser Met Trp Leu Leu Thr
130                 135                 140

Cys Pro Val Ile Leu Ile His Leu Ser Asn Leu Thr Gly Leu His Glu
145                 150                 155                 160

Glu Tyr Ser Lys Arg Thr Met Thr Ile Leu Val Thr Asp Ile Gly Asn
                165                 170                 175

Ile Val Trp Gly Ile Thr Ala Ala Phe Thr Lys Gly Pro Leu Lys Ile
            180                 185                 190

Leu Phe Phe Met Ile Gly Leu Phe Tyr Gly Val Thr Cys Phe Phe Gln
            195                 200                 205

Ile Ala Lys Val Tyr Ile Glu Ser Tyr His Thr Leu Pro Lys Gly Val
210                 215                 220

Cys Arg Lys Ile Cys Lys Ile Met Ala Tyr Val Phe Phe Cys Ser Trp
225                 230                 235                 240

Leu Met Phe Pro Val Met Phe Ile Ala Gly His Glu Gly Leu Gly Leu
                245                 250                 255

Ile Thr Pro Tyr Thr Ser Gly Ile Gly His Leu Ile Leu Asp Leu Ile
            260                 265                 270

Ser Lys Asn Thr Trp Gly Phe Leu Gly His His Leu Arg Val Lys Ile
            275                 280                 285

His Glu His Ile Leu Ile His Gly Asp Ile Arg Lys Thr Thr Thr Ile
290                 295                 300

Asn Val Ala Gly Glu Asn Met Glu Ile Glu Thr Phe Val Asp Glu Glu
305                 310                 315                 320

Glu Glu Gly Gly Val
                325
```

<210> SEQ ID NO 63
<211> LENGTH: 258
<212> TYPE: PRT
<213> ORGANISM: Halorubrum sodomense

<400> SEQUENCE: 63

```
Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
```

```
            20                  25                  30

Gly Thr Phe Tyr Phe Leu Val Arg Gly Trp Gly Val Thr Asp Lys Asp
                35                  40                  45

Ala Arg Glu Tyr Tyr Ala Val Thr Ile Leu Val Pro Gly Ile Ala Ser
 50                  55                  60

Ala Ala Tyr Leu Ser Met Phe Phe Gly Ile Gly Leu Thr Glu Val Thr
 65                  70                  75                  80

Val Gly Gly Glu Met Leu Asp Ile Tyr Tyr Ala Arg Tyr Ala Asp Trp
                85                  90                  95

Leu Phe Thr Thr Pro Leu Leu Leu Asp Leu Ala Leu Leu Ala Lys
                100                 105                 110

Val Asp Arg Val Thr Ile Gly Thr Leu Val Gly Val Asp Ala Leu Met
                115                 120                 125

Ile Val Thr Gly Leu Ile Gly Ala Leu Ser His Thr Ala Ile Ala Arg
                130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
                180                 185                 190

Thr Ala Tyr Pro Ile Leu Trp Ile Ile Gly Thr Glu Gly Ala Gly Val
                195                 200                 205

Val Gly Leu Gly Ile Glu Thr Leu Leu Phe Met Val Leu Asp Val Thr
                210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp

<210> SEQ ID NO 64
<211> LENGTH: 248
<212> TYPE: PRT
<213> ORGANISM: Halorubrum sp.

<400> SEQUENCE: 64

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
                20                  25                  30

Gly Thr Phe Tyr Phe Ile Val Lys Gly Trp Gly Val Thr Asp Lys Glu
                35                  40                  45

Ala Arg Glu Tyr Tyr Ser Ile Thr Ile Leu Val Pro Gly Ile Ala Ser
 50                  55                  60

Ala Ala Tyr Leu Ser Met Phe Phe Gly Ile Gly Leu Thr Glu Val Thr
 65                  70                  75                  80

Val Ala Gly Glu Val Leu Asp Ile Tyr Tyr Ala Arg Tyr Ala Asp Trp
                85                  90                  95

Leu Phe Thr Thr Pro Leu Leu Leu Asp Leu Ala Leu Leu Ala Lys
                100                 105                 110

Val Asp Arg Val Ser Ile Gly Thr Leu Val Gly Val Asp Ala Leu Met
                115                 120                 125

Ile Val Thr Gly Leu Ile Gly Ala Leu Ser His Thr Pro Leu Ala Arg
```

```
                    130                 135                 140
Tyr Ser Trp Trp Leu Phe Ser Thr Ile Cys Met Ile Val Val Leu Tyr
145                 150                 155                 160

Phe Leu Ala Thr Ser Leu Arg Ala Ala Lys Glu Arg Gly Pro Glu
                165                 170                 175

Val Ala Ser Thr Phe Asn Thr Leu Thr Ala Leu Val Leu Val Leu Trp
                180                 185                 190

Thr Ala Tyr Pro Ile Leu Trp Ile Ile Gly Thr Glu Gly Ala Gly Val
                195                 200                 205

Val Gly Leu Gly Ile Glu Thr Leu Leu Phe Met Val Leu Asp Val Thr
                210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro
                245

<210> SEQ ID NO 65
<211> LENGTH: 223
<212> TYPE: PRT
<213> ORGANISM: Guillardia theta

<400> SEQUENCE: 65

Ala Ser Ser Phe Gly Lys Ala Leu Leu Glu Phe Val Phe Ile Val Phe
1               5                   10                  15

Ala Cys Ile Thr Leu Leu Leu Gly Ile Asn Ala Ala Lys Ser Lys Ala
                20                  25                  30

Ala Ser Arg Val Leu Phe Pro Ala Thr Phe Val Thr Gly Ile Ala Ser
                35                  40                  45

Ile Ala Tyr Phe Ser Met Ala Ser Gly Gly Trp Val Ile Ala Pro
50                  55                  60

Asp Cys Arg Gln Leu Phe Val Ala Arg Tyr Leu Asp Trp Leu Ile Thr
65                  70                  75                  80

Thr Pro Leu Leu Leu Ile Asp Leu Gly Leu Val Ala Gly Val Ser Arg
                85                  90                  95

Trp Asp Ile Met Ala Leu Cys Leu Ser Asp Val Leu Met Ile Ala Thr
                100                 105                 110

Gly Ala Phe Gly Ser Leu Thr Val Gly Asn Val Lys Trp Val Trp Trp
                115                 120                 125

Phe Phe Gly Met Cys Trp Phe Leu His Ile Ile Phe Ala Leu Gly Lys
130                 135                 140

Ser Trp Ala Glu Ala Ala Lys Ala Lys Gly Gly Asp Ser Ala Ser Val
145                 150                 155                 160

Tyr Ser Lys Ile Ala Gly Ile Thr Val Ile Thr Trp Phe Cys Tyr Pro
                165                 170                 175

Val Val Trp Val Phe Ala Glu Gly Phe Gly Asn Phe Ser Val Thr Phe
                180                 185                 190

Glu Val Leu Ile Tyr Gly Val Leu Asp Val Ile Ser Lys Ala Val Phe
                195                 200                 205

Gly Leu Ile Leu Met Ser Gly Ala Ala Thr Gly Tyr Glu Ser Ile
210                 215                 220

<210> SEQ ID NO 66
<211> LENGTH: 262
<212> TYPE: PRT
<213> ORGANISM: Oxyrrhis marina
```

<400> SEQUENCE: 66

```
Met Ala Pro Leu Ala Gln Asp Trp Thr Tyr Ala Glu Trp Ser Ala Val
1               5                   10                  15

Tyr Asn Ala Leu Ser Phe Gly Ile Ala Gly Met Gly Ser Ala Thr Ile
            20                  25                  30

Phe Phe Trp Leu Gln Leu Pro Asn Val Thr Lys Asn Tyr Arg Thr Ala
        35                  40                  45

Leu Thr Ile Thr Gly Ile Val Thr Leu Ile Ala Thr Tyr His Tyr Phe
    50                  55                  60

Arg Ile Phe Asn Ser Trp Val Ala Ala Phe Asn Val Gly Leu Gly Val
65                  70                  75                  80

Asn Gly Ala Tyr Glu Val Thr Val Ser Gly Thr Pro Phe Asn Asp Ala
                85                  90                  95

Tyr Arg Tyr Val Asp Trp Leu Leu Thr Val Pro Leu Leu Leu Val Glu
            100                 105                 110

Leu Ile Leu Val Met Lys Leu Pro Ala Lys Glu Thr Val Cys Leu Ala
        115                 120                 125

Trp Thr Leu Gly Ile Ala Ser Ala Val Met Val Ala Leu Gly Tyr Pro
    130                 135                 140

Gly Glu Ile Gln Asp Asp Leu Ser Val Arg Trp Phe Trp Ala Cys
145                 150                 155                 160

Ala Met Val Pro Phe Val Tyr Val Val Gly Thr Leu Val Val Gly Leu
                165                 170                 175

Gly Ala Ala Thr Ala Lys Gln Pro Glu Gly Val Val Asp Leu Val Ser
            180                 185                 190

Ala Ala Arg Tyr Leu Thr Val Val Ser Trp Leu Thr Tyr Pro Phe Val
        195                 200                 205

Tyr Ile Val Lys Asn Ile Gly Leu Ala Gly Ser Thr Ala Thr Met Tyr
    210                 215                 220

Glu Gln Ile Gly Tyr Ser Ala Ala Asp Val Thr Ala Lys Ala Val Phe
225                 230                 235                 240

Gly Val Leu Ile Trp Ala Ile Ala Asn Ala Lys Ser Arg Leu Glu Glu
                245                 250                 255

Glu Gly Lys Leu Arg Ala
            260
```

<210> SEQ ID NO 67
<211> LENGTH: 313
<212> TYPE: PRT
<213> ORGANISM: Leptosphaeria maculans

<400> SEQUENCE: 67

```
Met Ile Val Asp Gln Phe Glu Glu Val Leu Met Lys Thr Ser Gln Leu
1               5                   10                  15

Phe Pro Leu Pro Thr Ala Thr Gln Ser Ala Gln Pro Thr His Val Ala
            20                  25                  30

Pro Val Pro Thr Val Leu Pro Asp Thr Pro Ile Tyr Glu Thr Val Gly
        35                  40                  45

Asp Ser Gly Ser Lys Thr Leu Trp Val Val Phe Val Leu Met Leu Ile
    50                  55                  60

Ala Ser Ala Ala Phe Thr Ala Leu Ser Trp Lys Ile Pro Val Asn Arg
65                  70                  75                  80

Arg Leu Tyr His Val Ile Thr Thr Ile Ile Thr Leu Thr Ala Ala Leu
                85                  90                  95
```

Ser Tyr Phe Ala Met Ala Thr Gly His Gly Val Ala Leu Asn Lys Ile
            100                 105                 110

Val Ile Arg Thr Gln His Asp His Val Pro Asp Thr Tyr Glu Thr Val
        115                 120                 125

Tyr Arg Gln Val Tyr Ala Arg Tyr Ile Asp Trp Ala Ile Thr Thr
130                 135                 140

Pro Leu Leu Leu Leu Asp Leu Gly Leu Leu Ala Gly Met Ser Gly Ala
145                 150                 155                 160

His Ile Phe Met Ala Ile Val Ala Asp Leu Ile Met Val Leu Thr Gly
                165                 170                 175

Leu Phe Ala Ala Phe Gly Ser Glu Gly Thr Pro Gln Lys Trp Gly Trp
            180                 185                 190

Tyr Thr Ile Ala Cys Ile Ala Tyr Ile Phe Val Val Trp His Leu Val
        195                 200                 205

Leu Asn Gly Gly Ala Asn Ala Arg Val Lys Gly Glu Lys Leu Arg Ser
210                 215                 220

Phe Phe Val Ala Ile Gly Ala Tyr Thr Leu Ile Leu Trp Thr Ala Tyr
225                 230                 235                 240

Pro Ile Val Trp Gly Leu Ala Asp Gly Ala Arg Lys Ile Gly Val Asp
                245                 250                 255

Gly Glu Ile Ile Ala Tyr Ala Val Leu Asp Val Leu Ala Lys Gly Val
            260                 265                 270

Phe Gly Ala Trp Leu Leu Val Thr His Ala Asn Leu Arg Glu Ser Asp
        275                 280                 285

Val Glu Leu Asn Gly Phe Trp Ala Asn Gly Leu Asn Arg Glu Gly Ala
290                 295                 300

Ile Arg Ile Gly Glu Asp Asp Gly Ala
305                 310

<210> SEQ ID NO 68
<211> LENGTH: 273
<212> TYPE: PRT
<213> ORGANISM: Natronomonas pharaonis

<400> SEQUENCE: 68

Val Thr Gln Arg Glu Leu Phe Glu Phe Val Leu Asn Asp Pro Leu Leu
1               5                   10                  15

Ala Ser Ser Leu Tyr Ile Asn Ile Ala Leu Ala Gly Leu Ser Ile Leu
            20                  25                  30

Leu Phe Val Phe Met Thr Arg Gly Leu Asp Asp Pro Arg Ala Lys Leu
        35                  40                  45

Ile Ala Val Ser Thr Ile Leu Val Pro Val Val Ser Ile Ala Ser Tyr
50                  55                  60

Thr Gly Leu Ala Ser Gly Leu Thr Ile Ser Val Leu Glu Met Pro Ala
65                  70                  75                  80

Gly His Phe Ala Glu Gly Ser Ser Val Met Leu Gly Gly Glu Glu Val
                85                  90                  95

Asp Gly Val Val Thr Met Trp Gly Arg Tyr Leu Thr Trp Ala Leu Ser
            100                 105                 110

Thr Pro Met Ile Leu Leu Ala Leu Gly Leu Leu Ala Gly Ser Asn Ala
        115                 120                 125

Thr Lys Leu Phe Thr Ala Ile Thr Phe Asp Ile Ala Met Cys Val Thr
130                 135                 140

Gly Leu Ala Ala Ala Leu Thr Thr Ser Ser His Leu Met Arg Trp Phe
145                 150                 155                 160

```
Trp Tyr Ala Ile Ser Cys Ala Cys Phe Leu Val Val Leu Tyr Ile Leu
                165                 170                 175

Leu Val Glu Trp Ala Gln Asp Ala Lys Ala Ala Gly Thr Ala Asp Met
        180                 185                 190

Phe Asn Thr Leu Lys Leu Leu Thr Val Val Met Trp Leu Gly Tyr Pro
            195                 200                 205

Ile Val Trp Ala Leu Gly Val Glu Gly Ile Ala Val Leu Pro Val Gly
    210                 215                 220

Val Thr Ser Trp Gly Tyr Ser Phe Leu Asp Ile Val Ala Lys Tyr Ile
225                 230                 235                 240

Phe Ala Phe Leu Leu Asn Tyr Leu Thr Ser Asn Glu Ser Val Val
                245                 250                 255

Ser Gly Ser Ile Leu Asp Val Pro Ser Ala Ser Gly Thr Pro Ala Asp
                260                 265                 270

Asp

<210> SEQ ID NO 69
<211> LENGTH: 365
<212> TYPE: PRT
<213> ORGANISM: Dunaliella salina

<400> SEQUENCE: 69

Met Arg Arg Arg Glu Ser Gln Leu Ala Tyr Leu Cys Leu Phe Val Leu
1               5                   10                  15

Ile Ala Gly Trp Ala Pro Arg Leu Thr Glu Ser Ala Pro Asp Leu Ala
            20                  25                  30

Glu Arg Arg Pro Pro Ser Glu Arg Asn Thr Pro Tyr Ala Asn Ile Lys
        35                  40                  45

Lys Val Pro Asn Ile Thr Glu Pro Asn Ala Asn Val Gln Leu Asp Gly
    50                  55                  60

Trp Ala Leu Tyr Gln Asp Phe Tyr Tyr Leu Ala Gly Ser Asp Lys Glu
65                  70                  75                  80

Trp Val Val Gly Pro Ser Asp Gln Cys Tyr Cys Arg Ala Trp Ser Lys
                85                  90                  95

Ser His Gly Thr Asp Arg Glu Gly Glu Ala Ala Val Val Trp Ala Tyr
            100                 105                 110

Ile Val Phe Ala Ile Cys Ile Val Gln Leu Val Tyr Phe Met Phe Ala
        115                 120                 125

Ala Trp Lys Ala Thr Val Gly Trp Glu Glu Val Tyr Val Asn Ile Ile
    130                 135                 140

Glu Leu Val His Ile Ala Leu Val Ile Trp Val Glu Phe Asp Lys Pro
145                 150                 155                 160

Ala Met Leu Tyr Leu Asn Asp Gly Gln Met Val Pro Trp Leu Arg Tyr
                165                 170                 175

Ser Ala Trp Leu Leu Ser Cys Pro Val Ile Leu Ile His Leu Ser Asn
            180                 185                 190

Leu Thr Gly Leu Lys Gly Asp Tyr Ser Lys Arg Thr Met Gly Leu Leu
        195                 200                 205

Val Ser Asp Ile Gly Thr Ile Val Phe Gly Thr Ser Ala Ala Leu Ala
    210                 215                 220

Pro Pro Asn His Val Lys Val Ile Leu Phe Thr Ile Gly Leu Leu Tyr
225                 230                 235                 240

Gly Leu Phe Thr Phe Phe Thr Ala Ala Lys Val Tyr Ile Glu Ala Tyr
                245                 250                 255
```

```
His Thr Val Pro Lys Gly Gln Cys Arg Asn Leu Val Arg Ala Met Ala
            260                 265                 270

Trp Thr Tyr Phe Val Ser Trp Ala Met Phe Pro Ile Leu Phe Ile Leu
            275                 280                 285

Gly Arg Glu Gly Phe Gly His Ile Thr Tyr Phe Gly Ser Ser Ile Gly
            290                 295                 300

His Phe Ile Leu Glu Ile Phe Ser Lys Asn Leu Trp Ser Leu Leu Gly
305                 310                 315                 320

His Gly Leu Arg Tyr Arg Ile Arg Gln His Ile Ile His Gly Asn
            325                 330                 335

Leu Thr Lys Lys Asn Lys Ile Asn Ile Ala Gly Asp Asn Val Glu Val
            340                 345                 350

Glu Glu Tyr Val Asp Ser Asn Asp Lys Asp Ser Asp Val
            355                 360                 365

<210> SEQ ID NO 70
<211> LENGTH: 1083
<212> TYPE: PRT
<213> ORGANISM: Artificial Sequence
<220> FEATURE:
<223> OTHER INFORMATION: Synthetic sequence

<400> SEQUENCE: 70

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
            35                  40                  45

Ala Arg Glu Tyr Tyr Ala Val Thr Ile Leu Val Pro Gly Ile Ala Ser
        50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Asp Trp
            85                  90                  95

Leu Phe Thr Thr Pro Leu Leu Leu Asp Leu Ala Leu Leu Ala Lys
            100                 105                 110

Val Asp Arg Val Thr Ile Gly Thr Leu Val Gly Val Asp Ala Leu Met
            115                 120                 125

Ile Val Thr Gly Leu Ile Gly Ala Leu Ser His Thr Ala Ile Ala Arg
        130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
            195                 200                 205

Val Gly Leu Gly Ile Glu Thr Leu Leu Phe Met Val Leu Asp Val Thr
        210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255
```

```
Ala Asp Lys Ser Arg Ile Thr Ser Glu Gly Glu Tyr Ile Pro Leu Asp
                260                 265                 270

Gln Ile Asp Ile Asn Val Gly Ala Pro Gly Ser Gly Ala Thr Asn Phe
            275                 280                 285

Ser Leu Leu Lys Gln Ala Gly Asp Val Glu Glu Asn Pro Gly Pro Met
        290                 295                 300

Asp Leu Lys Glu Ser Pro Ser Glu Gly Ser Leu Gln Pro Ser Ser Ile
305                 310                 315                 320

Gln Ile Phe Ala Asn Thr Ser Thr Leu His Gly Ile Arg His Ile Phe
                325                 330                 335

Val Tyr Gly Pro Leu Thr Ile Arg Arg Val Leu Trp Ala Val Ala Phe
            340                 345                 350

Val Gly Ser Leu Gly Leu Leu Val Glu Ser Ser Glu Arg Val Ser
        355                 360                 365

Tyr Tyr Phe Ser Tyr Gln His Val Thr Lys Val Asp Glu Val Val Ala
    370                 375                 380

Gln Ser Leu Val Phe Pro Ala Val Thr Leu Cys Asn Leu Asn Gly Phe
385                 390                 395                 400

Arg Phe Ser Arg Leu Thr Thr Asn Asp Leu Tyr His Ala Gly Glu Leu
                405                 410                 415

Leu Ala Leu Leu Asp Val Asn Leu Gln Ile Pro Asp Pro His Leu Ala
            420                 425                 430

Asp Pro Thr Val Leu Glu Ala Leu Arg Gln Lys Ala Asn Phe Lys His
        435                 440                 445

Tyr Lys Pro Lys Gln Phe Ser Met Leu Glu Phe Leu His Arg Val Gly
    450                 455                 460

His Asp Leu Lys Asp Met Met Leu Tyr Cys Lys Phe Lys Gly Gln Glu
465                 470                 475                 480

Cys Gly His Gln Asp Phe Thr Thr Val Phe Thr Lys Tyr Gly Lys Cys
                485                 490                 495

Tyr Met Phe Asn Ser Gly Glu Asp Gly Lys Pro Leu Leu Thr Thr Val
            500                 505                 510

Lys Gly Gly Thr Gly Asn Gly Leu Glu Ile Met Leu Asp Ile Gln Gln
        515                 520                 525

Asp Glu Tyr Leu Pro Ile Trp Gly Glu Thr Glu Glu Thr Thr Phe Glu
    530                 535                 540

Ala Gly Val Lys Val Gln Ile His Ser Gln Ser Glu Pro Pro Phe Ile
545                 550                 555                 560

Gln Glu Leu Gly Phe Gly Val Ala Pro Gly Phe Gln Thr Phe Val Ala
                565                 570                 575

Thr Gln Glu Gln Arg Leu Thr Tyr Leu Pro Pro Pro Trp Gly Glu Cys
            580                 585                 590

Arg Ser Ser Glu Met Gly Leu Asp Phe Phe Pro Val Tyr Ser Ile Thr
        595                 600                 605

Ala Cys Arg Ile Asp Cys Glu Thr Arg Tyr Ile Val Glu Asn Cys Asn
    610                 615                 620

Cys Arg Met Val His Met Pro Gly Asp Ala Pro Phe Cys Thr Pro Glu
625                 630                 635                 640

Gln His Lys Glu Cys Ala Glu Pro Ala Leu Gly Leu Leu Ala Glu Lys
                645                 650                 655

Asp Ser Asn Tyr Cys Leu Cys Arg Thr Pro Cys Asn Leu Thr Arg Tyr
            660                 665                 670
```

Asn Lys Glu Leu Ser Met Val Lys Ile Pro Ser Lys Thr Ser Ala Lys
    675                 680                 685

Tyr Leu Glu Lys Lys Phe Asn Lys Ser Glu Lys Tyr Ile Ser Glu Asn
    690                 695                 700

Ile Leu Val Leu Asp Ile Phe Phe Glu Ala Leu Asn Tyr Glu Thr Ile
705                 710                 715                 720

Glu Gln Lys Lys Ala Tyr Glu Val Ala Ala Leu Leu Gly Asp Ile Gly
                725                 730                 735

Gly Gln Met Gly Leu Phe Ile Gly Ala Ser Leu Leu Thr Ile Leu Glu
            740                 745                 750

Leu Phe Asp Tyr Ile Tyr Glu Leu Ile Lys Glu Lys Leu Leu Asp Leu
        755                 760                 765

Leu Gly Lys Glu Glu Glu Gly Ser His Asp Glu Asn Met Ser Thr
    770                 775                 780

Cys Asp Thr Met Pro Asn His Ser Glu Thr Ile Ser His Thr Val Asn
785                 790                 795                 800

Val Pro Leu Gln Thr Ala Leu Gly Thr Leu Glu Ile Ala Cys Ala
                805                 810                 815

Ala Ala Lys Ser Arg Ile Thr Ser Glu Gly Glu Tyr Ile Pro Leu Asp
            820                 825                 830

Gln Ile Asp Ile Asn Val Val Ser Lys Gly Glu Glu Leu Phe Thr Gly
        835                 840                 845

Val Val Pro Ile Leu Val Glu Leu Asp Gly Asp Val Asn Gly His Lys
    850                 855                 860

Phe Ser Val Ser Gly Glu Gly Glu Gly Asp Ala Thr Tyr Gly Lys Leu
865                 870                 875                 880

Thr Leu Lys Phe Ile Cys Thr Thr Gly Lys Leu Pro Val Pro Trp Pro
                885                 890                 895

Thr Leu Val Thr Thr Phe Gly Tyr Gly Leu Gln Cys Phe Ala Arg Tyr
            900                 905                 910

Pro Asp His Met Lys Gln His Asp Phe Phe Lys Ser Ala Met Pro Glu
        915                 920                 925

Gly Tyr Val Gln Glu Arg Thr Ile Phe Phe Lys Asp Asp Gly Asn Tyr
    930                 935                 940

Lys Thr Arg Ala Glu Val Lys Phe Glu Gly Asp Thr Leu Val Asn Arg
945                 950                 955                 960

Ile Glu Leu Lys Gly Ile Asp Phe Arg Glu Asp Gly Asn Ile Leu Gly
                965                 970                 975

His Lys Leu Glu Tyr Asn Tyr Asn Ser His Asn Val Tyr Ile Met Ala
            980                 985                 990

Asp Lys Gln Lys Asn Gly Ile Lys Val Asn Phe Lys Ile Arg His Asn
        995                 1000                1005

Ile Glu Asp Gly Ser Val Gln Leu Ala Asp His Tyr Gln Gln Asn
    1010                1015                1020

Thr Pro Ile Gly Asp Gly Pro Val Leu Leu Pro Asp Asn His Tyr
    1025                1030                1035

Leu Ser Tyr Gln Ser Ala Leu Ser Lys Asp Pro Asn Glu Lys Arg
    1040                1045                1050

Asp His Met Val Leu Leu Glu Phe Val Thr Ala Ala Gly Ile Thr
    1055                1060                1065

Leu Gly Met Asp Glu Leu Tyr Lys Phe Cys Tyr Glu Asn Glu Val
    1070                1075                1080

LIGHT-RESPONSIVE POLYPEPTIDES AND METHODS OF USE THEREOF

CROSS-REFERENCE

This application claims the benefit of U.S. Provisional Patent Application No. 62/792,297, filed Jan. 14, 2019, which application is incorporated herein by reference in its entirety.

INTRODUCTION

Optogenetics involves the use of light-activated proteins to change the membrane voltage potentials of excitable cells, such as neurons, upon exposure to light of various wavelengths. In neurons, membrane depolarization leads to the activation of transient electrical signals (also called action potentials or "spikes"), which are the basis of neuronal communication. Conversely, membrane hyperpolarization leads to the inhibition of such signals. By expressing, in a neuron or other excitable cell, a light-activated protein that changes the membrane potential, light can be utilized as a triggering means to induce inhibition or excitation.

SUMMARY

The present disclosure provides light-responsive polypeptides, and nucleic acids comprising nucleotide sequences encoding the light-responsive polypeptides. The present disclosure provides methods, devices, and systems for controlling the activity of a cell expressing a light-responsive polypeptide of the present disclosure.

BRIEF DESCRIPTION OF THE DRAWINGS

FIGS. 2A-2I depict a schematic of a large volume temporally-precise all-optical microscope (MultiSLM) and imaging of cells.

FIGS. 3A-3K depict selective visual network recruitment by functionally-defined-ensemble stimulation.

FIG. 6A-6K depict circuit architecture underlying layer-specific perceptual thresholds.

FIG. 7 depicts a structure-based sequence alignment of natural channelrhodopsin genes.

FIGS. 8A-8F depict the electrophysiological and structural characterization of ChRmine.

FIGS. 10A-10F depict the temporal precision of the MultiSLM.

FIGS. 12A-12E depict removal of photostimulation artifact in imaging channel of MultiSLM.

FIGS. 14A-14K depict parameter estimation for classifier analysis of behaviorally naïve mice.

FIGS. 16A-16N depict parameter estimation for classifier analysis and tuned visual network recruitment in behaviorally trained mice.

FIG. 23 depicts nucleotide sequence encoding a fusion polypeptide comprising: a) a light-responsive polypeptide of the present disclosure.

FIG. 24 depicts a ChRmine amino acid sequence (SEQ ID NO: 1).

FIG. 26A-26S provide amino acid sequences of single-fluorescent protein genetically encoded calcium indicators.

FIG. 27A-27C provide amino acid sequences of multi-fluorescent protein genetically encoded calcium indicators.

FIG. 28A-28U provide amino acid sequences of various light-responsive polypeptides.

DEFINITIONS

Figure 1F:
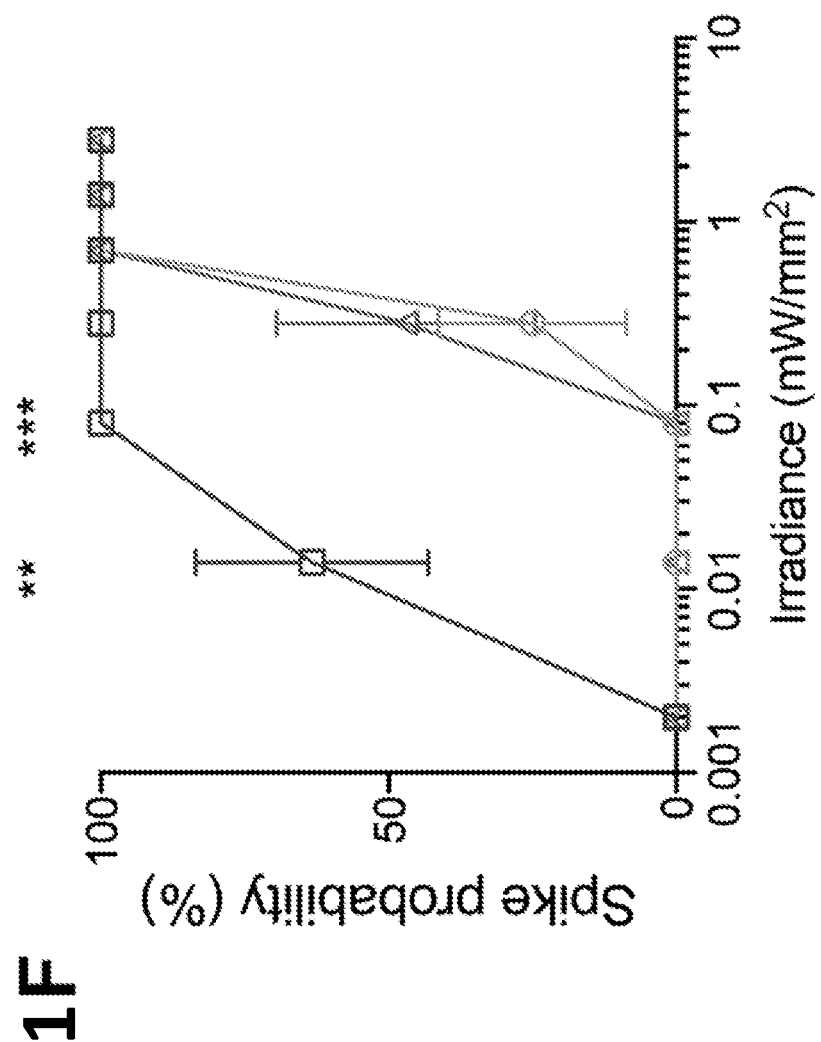
FIGS. 1A-1O depict schematics of opsin screening, a phylogenetic categorization of opsins, and characteristics of an opsin (ChRmine).

The terms "polynucleotide", "nucleotide", "nucleotide sequence", "nucleic acid", "nucleic acid molecule", "nucleic acid sequence" and "oligonucleotide" are used interchangeably, and can also include plurals of each respectively depending on the context in which the terms are utilized. They refer to a polymeric form of nucleotides of any length, either deoxyribonucleotides (DNA) or ribonucleotides (RNA), or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA, ribozymes, small interfering RNA, (siRNA), microRNA (miRNA), small nuclear RNA (snRNA), cDNA, recombinant polynucleotides, branched polynucleotides, plasmids, vectors, isolated DNA (A, B and Z structures) of any sequence, PNA, locked nucleic acid (LNA), TNA (treose nucleic acid), isolated RNA of any sequence, nucleic acid probes, and primers. LNA, often referred to as inaccessible RNA, is a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA, which can significantly improve thermal stability.

The terms "polypeptide", "peptide" and "protein" are used interchangeably herein to refer to polymers of amino acids of any length. The polymer may be linear, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

As used herein, "sequence identity" or "identity" in the context of two nucleic acid sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and, therefore, do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Any suitable means for making this adjustment may be used. This may involve scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may include additions or deletions (i.e., gaps) as compared to the reference sequence (which does not include additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Any suitable methods of alignment of sequences for comparison may be employed. Thus, the determination of percent identity between any two sequences can be accomplished using a mathematical algorithm. Examples of such mathematical algorithms are the algorithm of Myers and Miller, CABIOS, 4:11 (1988), which is hereby incorporated by reference in its entirety; the local homology algorithm of Smith et al, Adv. Appl. Math., 2:482 (1981), which is hereby incorporated by reference in its entirety; the homology alignment algorithm of Needleman and Wunsch, J. Mol. Biol, 48:443 (1970), which is hereby incorporated by reference in its entirety; the search-for-similarity-method of Pearson and Lipman, Proc. Natl. Acad. Sci. USA, 85:2444 (1988), which is hereby incorporated by reference in its entirety; the algorithm of Karlin and Altschul, Proc. Natl. Acad. Sci. USA, 87:2264 (1990), which is hereby incorporated by reference in its entirety; modified as in Karhn and Altschul, Proc. Natl. Acad. Sci. USA, 90:5873 (1993), which is hereby incorporated by reference in its entirety.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., Gene, 73:237 (1988), Higgins et al., CABIOS, 5:151 (1989); Corpet et al., Nucl. Acids Res., 16:10881 (1988); Huang et al., CABIOS, 8:155 (1992); and Pearson et al., Meth. Mol. Biol., 24:307 (1994), which are hereby incorporated by reference in their entirety. The ALIGN program is based on the algorithm of Myers and Miller, supra. The BLAST programs of Altschul et al., JMB, 215:403 (1990); Nucl. Acids Res., 25:3389 (1990), which are hereby incorporated by reference in their entirety, are based on the algorithm of Karlin and Altschul supra.

Software for performing BLAST analyses is publicly available through the National Center for Biotechnology Information (NCBI; worldwideweb.ncbi.nlm.nih.gov).

Amino acid substitutions in an amino acid sequence, relative to a reference amino acid sequence, may be "conservative" or "non-conservative" and such substituted amino acid residues may or may not be one encoded by the genetic code. A "conservative amino acid substitution" is one in which the amino acid residue is replaced with an amino acid residue having a chemically similar side chain (i.e., replacing an amino acid possessing a basic side chain with another amino acid with a basic side chain). A "non-conservative amino acid substitution" is one in which the amino acid residue is replaced with an amino acid residue having a chemically different side chain (i.e., replacing an amino acid having a basic side chain with an amino acid having an aromatic side chain). The standard (coded) twenty amino acids divided into chemical families based on chemical properties of their side chains. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and side chains having aromatic groups (e.g., tyrosine, phenylalanine, tryptophan, histidine).

The term "genetic modification" refers to a permanent or transient genetic change induced in a cell following introduction into the cell of a heterologous nucleic acid (e.g., a nucleic acid exogenous to the cell). Genetic change ("modification") can be accomplished by incorporation of the heterologous nucleic acid into the genome of the host cell, or by transient or stable maintenance of the heterologous nucleic acid as an extrachromosomal element. Where the cell is a eukaryotic cell, a permanent genetic change can be achieved by introduction of the nucleic acid into the genome of the cell. Suitable methods of genetic modification include viral infection, transfection, conjugation, protoplast fusion, electroporation, particle gun technology, calcium phosphate precipitation, direct microinjection, and the like.

The term "promoter" as used herein refers to a sequence of DNA that directs the expression (transcription) of a gene. A promoter may direct the transcription of a prokaryotic or eukaryotic gene. A promoter may be "inducible", initiating transcription in response to an inducing agent or, in contrast, a promoter may be "constitutive", whereby an inducing agent does not regulate the rate of transcription. A promoter may be regulated in a tissue-specific or tissue-preferred manner, such that it is only active in transcribing the operable linked coding region in a specific tissue type or types.

The term "operably-linked" refers to a functional linkage between a regulatory sequence and a coding sequence. The components so described are thus in a relationship permitting them to function in their intended manner. For example, placing a coding sequence under regulatory control of a promoter means positioning the coding sequence such that the expression of the coding sequence is controlled by the promoter.

As used herein, an "individual," "subject," or "patient" can be a mammal, including a human. Mammals include, but are not limited to, ungulates, canines, felines, bovines, ovines, non-human primates, lagomorphs, and rodents (e.g., mice and rats). In one aspect, an individual is a human. In another aspect, an individual is a non-human mammal.

As used herein, "treatment" or "treating" refers to obtaining beneficial or desired results, including clinical results. For purposes of this disclosure, beneficial or desired clinical results include, but are not limited to, one or more of the following: decreasing symptoms (ameliorating adverse symptoms) resulting from a disease, increasing the quality of life of those suffering from a disease, decreasing the dose of other medications required to treat a disease, delaying the progression of a disease, and/or prolonging survival of individuals having a disease.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a light-responsive polypeptide" includes a plurality of such light-responsive polypeptides and reference to "the GECI" includes reference to one or more GECIs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides light-responsive polypeptides, and nucleic acids comprising nucleotide sequences encoding the light-responsive polypeptides. The present disclosure provides methods, devices, and systems for controlling the activity of a cell expressing a light-responsive polypeptide of the present disclosure.

Light-Responsive Polypeptides

The present disclosure provides light-responsive polypeptides. A light-responsive-polypeptide of the present disclosure is also referred to as a "light-activated polypeptide." A light-responsive polypeptide of the present disclosure, when expressed in a eukaryotic cell (e.g., a mammalian cell; e.g., an excitable cell such as a neuronal cell) and when exposed to light of an activating wavelength, induces depolarization of the cell membrane.

In some cases, a light-responsive polypeptide of the present disclosure comprises an amino acid sequence having at least 80%, at least 85%, at least 90%, at least 95%, at least 98%, at least 99%, or 100%, amino acid sequence identity with at least 250 contiguous amino acids, at least 275 contiguous amino acids, at least 300 contiguous amino acids, or 309 contiguous amino acids, of the following amino acid sequence:

```
                                           (SEQ ID NO: 1)
MAHAPGTDQMFYVGTMDGWYLDTKLNSVAIGAHWSCFIVLTITTFYLGYE

SWTSRGPSKRTSFYAGYQEEQNLALFVNFFAMLSYFGKIVADTLGHNFGD

VGPFIIGFGNYRYADYMLTCPMLVYDLLYQLRAPYRVSCSAIIFAILMSG

VLAEFYAEGDPRLRNGAYAWYGFGCFWFIFAYSIVMSIVAKQYSRLAQLA

QDTGAEHSLHVLKFAVFTFSMLWILFPLVWAICPRGFGWIDDNWTEVAHC

VCDIVAKSCYGFALARFRKTYDEELFRLLEQLGHDEDEFQKLELDMRLSS

NGERLRRLS.
```

In some cases, a light-responsive polypeptide of the present disclosure comprises an amino acid sequence having at least 80%, at least 85%, at least 90%, at least 95%, at least 98%, at least 99%, or 100%, amino acid sequence identity with at least 250 contiguous amino acids, at least 275 contiguous amino acids, at least 300 contiguous amino acids, or 309 contiguous amino acids, of the following amino acid sequence:

(SEQ ID NO: 2)
MAHAPGTDQMFYVGTMDGWYLDTKLNSVAIGARWSCFIVLTITTFYLGYE

SWTSRGPSKRTSFYAGYQEEQNLALFVNFFAMLSYFGKIVADTLGHNFGD

VGPFIIGFGNYRYADYMLTCPMLVYDLLYQLRAPYRVSCSAIIFAILMSG

VLAEFYAEGDPRLRNGAYAWYGFGCFWFIFAYSIVMSIVAKQYSRLAQLA

QDTGAEHSLHVLKFAVFTFSMLWILFPLVWAICPRGFGWIDDNWTEVAHC

VCDIVAKSCYGFALARFRKTYDEELFRLLEQLGHDEDEFQKLELDMRLSS

NGERLRRLS, where amino acid 33 is Arg.

In some cases, a light-responsive polypeptide of the present disclosure comprises an amino acid sequence having at least 80%, at least 85%, at least 90%, at least 95%, at least 98%, at least 99%, or 100%, amino acid sequence identity with at least 250 contiguous amino acids, at least 275 contiguous amino acids, at least 300 contiguous amino acids, or 309 contiguous amino acids, of the following amino acid sequence:

(SEQ ID NO: 3)
MAHAPGTDQMFYVGTMDGWYLDTKLNSVAIGAHWSCFIVLTITTFYLGYE

SWTSRGPSKRTSFYAGYQEEQNLALFVNFFAMLSYFGKIVADTLGHNFGD

VGPFIIGFGNYRYADYMLTCPMLVYDLLYQLRAPYHVSCSAIIFAILMSG

VLAEFYAEGDPRLRNGAYAWYGFGCFWFIFAYSIVMSIVAKQYSRLAQLA

QDTGAEHSLHVLKFAVFTFSMLWILFPLVWAICPRGFGWIDDNWTEVAHC

VCDIVAKSCYGFALARFRKTYDEELFRLLEQLGHDEDEFQKLELDMRLSS

NGERLRRLS, where amino acid 136 is His.

In some cases, a light-responsive polypeptide of the present disclosure comprises an amino acid sequence having at least 80%, at least 85%, at least 90%, at least 95%, at least 98%, at least 99%, or 100%, amino acid sequence identity with at least 250 contiguous amino acids, at least 275 contiguous amino acids, at least 300 contiguous amino acids, or 309 contiguous amino acids, of the following amino acid sequence:

(SEQ ID NO: 4)
MAHAPGTDQMFYVGTMDGWYLDTKLNSVAIGARWSCFIVLTITTFYLGYE

SWTSRGPSKRTSFYAGYQEEQNLALFVNFFAMLSYFGKIVADTLGHNFGD

VGPFIIGFGNYRYADYMLTCPMLVYDLLYQLRAPYHVSCSAIIFAILMSG

VLAEFYAEGDPRLRNGAYAWYGFGCFWFIFAYSIVMSIVAKQYSRLAQLA

QDTGAEHSLHVLKFAVFTFSMLWILFPLVWAICPRGFGWIDDNWTEVAHC

VCDIVAKSCYGFALARFRKTYDEELFRLLEQLGHDEDEFQKLELDMRLSS

NGERLRRLS, where amino acid 33 is Arg and amino acid 136 is His.

In some cases, a light-responsive polypeptide of the present disclosure comprises an amino acid sequence having at least 80%, at least 85%, at least 90%, at least 95%, at least 98%, or at least 99%, amino acid sequence identity with at least 250 contiguous amino acids, at least 275 contiguous amino acids, at least 300 contiguous amino acids, or 309 contiguous amino acids, of the following amino acid sequence:

(SEQ ID NO: 5)
MAHAPGTDQMFYVGTMDGWYLDTKLNSVAIGAHWSCFIVLTITTFYLGYE

SWTSRGPSKRTSFYAGYQEEQNLALFVNFFAMLSYFGKIVADTLGHNFGD

VGPFIIGFGNYRYADYMLTCPMLVYDLLYQLRAPYRVSCSAIIFAILMSG

VLAEFYAEGDPRLRNGAYAWYGFGCFWFIFAYSIVMSIVAKQYSRLAQLA

QDTGAEHSLHVLKFAVFTFSMLWILFPLVWAICPRGFGWIDDNWTEVAHC

VCDIVAKSCYGFALARFRKTYDEELFRLLEQLGHDEDEFQKLELDMRLSS

NGERLRRLS;

and comprises from 1 to 50 conservative amino acid substitutions, e.g., comprises from 1 to 5, from 5 to 10, from 10 to 15, from 15 to 20, from 20 to 25, from 25 to 30, from 30 to 35, from 35 to 40, from 40 to 45, from 45 to 50, from 1 to 30, or from 1 to 15, conservative amino acid substitutions.

A light-responsive polypeptide of the present disclosure can have a length of from about 275 amino acids to about 280 amino acids, from about 280 amino acids to about 285 amino acids, from about 285 amino acids to about 290 amino acids, from about 290 amino acids to about 295 amino acids, from about 295 amino acids to about 300 amino acids, from about 300 amino acids to about 305 amino acids, or from about 305 amino acids to 309 amino acids.

Figure 7:
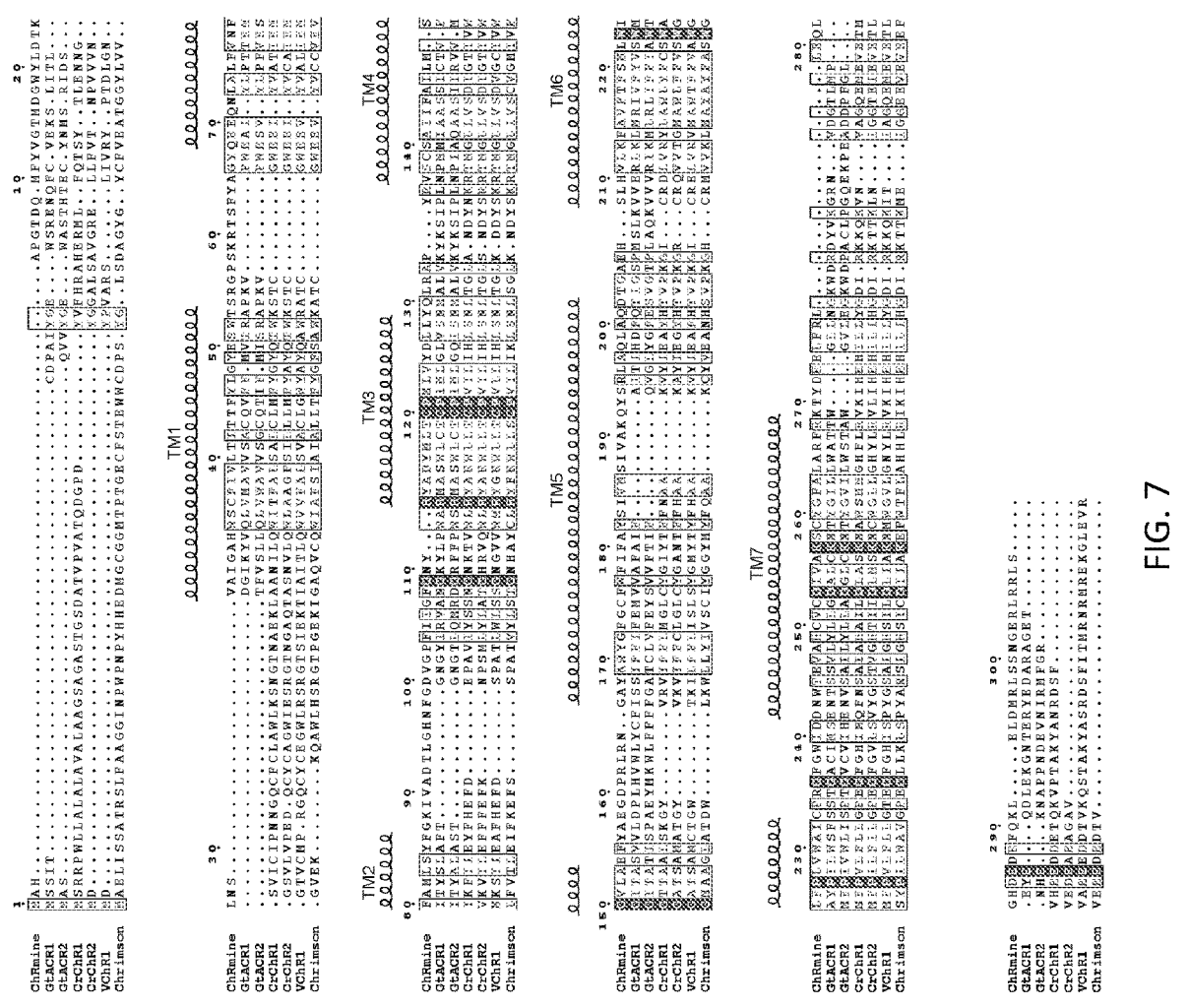

A light-responsive polypeptide of the present disclosure is a 7-transmembrane protein, as depicted schematically in FIG. 7. A light-responsive polypeptide of the present disclosure is a cation-conducting ion channel; e.g., can be permeable to $Na^+$ or $K^+$. A light-responsive polypeptide of the present disclosure can be derived from Tiarinafusus, or can be a variant of a light-responsive polypeptide derived from Tiarinafusus.

A light-responsive polypeptide of the present disclosure is activated by light of an activating wavelength, e.g., light having a wavelength of from 600 nm to 700 nm, e.g., from 600 nm to 625 nm, from 625 nm to 650 nm, from 650 nm to 675 nm, or from 675 nm to 700 nm. In some cases, a light-responsive polypeptide of the present disclosure is activated by light having a wavelength of from 625 nm to 650 nm. In some cases, a light-responsive polypeptide of the present disclosure is activated by light having a wavelength of 650 nm.

A light-responsive polypeptide of the present disclosure exhibits, in cultured hippocampal neurons, a half-recovery time from desensitization in darkness of about 0.63±0.08 seconds.

A light-responsive polypeptide of the present disclosure exhibits, in cultured hippocampal neurons, channel closure having a tau value of less than 300 ms, less than 200 ms, or less than 100 ms, when measured in cultured rat hippocampal neurons. A light-responsive polypeptide of the present disclosure exhibits channel closure having kinetics of channel closure that are at least 2-fold, at least 2.5-fold, at least 3-fold, at least 5-fold, at least 7-fold, at least 10-fold, at least 13-fold, or at least 15-fold, faster than the kinetics of channel closure of an opsin comprising the GtACR1, GtACR2, CrChR1, CrChR2, VChR1, or Chrimson amino acid sequence depicted in FIG. 7.

A light-responsive polypeptide of the present disclosure gives rise to, in cultured hippocampal neurons, inward (excitatory) photocurrents driven by red-shifted light of about 4.1±0.53 nA at 585 nm. A light-responsive polypeptide of the present disclosure gives rise to, in cultured hippocampal neurons, inward (excitatory) photocurrents driven by red-shifted light that are at least 2-fold stronger than those provided by CsChrimson or bReaChES.

A light-responsive polypeptide of the present disclosure exhibits an effective power density (EPD50; a measure of light sensitivity) of about 0.02 mW/mm$^2$, about 0.03 mW/mm$^2$, or about 0.04 mW/mm$^2$. A light-responsive polypeptide of the present disclosure exhibits an EPD50 that is at least 50%, at least 2-fold, at least 2.5-fold, at least 5-fold, or at least 10-fold, greater than that of an opsin comprising the GtACR1, GtACR2, CrChR1, CrChR2, VChR1, or Chrimson amino acid sequence depicted in FIG. 7.

A light-responsive polypeptide of the present disclosure can, when exposed to light of an activating wavelength, evoke action potentials at a higher frequency (e.g., 10% higher, 25% higher, 50% higher, 2-fold higher, or more than 2-fold higher) than the frequency of action potentials evoked by an opsin comprising the GtACR1, GtACR2, CrChR1, CrChR2, VChR1, or Chrimson amino acid sequence depicted in FIG. 7, e.g., when expressed in a mammalian neuron. A light-responsive polypeptide of the present disclosure can, when exposed to light of an activating wavelength, evoke action potentials at a frequency of greater than 2 Hz, greater than 5 Hz, greater than 10 Hz, greater than 15 Hz, greater than 20 Hz, greater than 25 Hz, greater than 30 Hz, or greater than 35 Hz, in a cell expressing the light-responsive polypeptide. For example, a light-responsive polypeptide of the present disclosure can, when exposed to light of an activating wavelength (e.g., red light), evoke action potentials at a frequency of from 10 Hz to 15 Hz, from 15 Hz to 20 Hz, from 20 Hz to 25 Hz, from 25 Hz to 30 Hz, from 30 Hz to 35 Hz, or from 35 Hz to 40 Hz. In some cases, a light-responsive polypeptide of the present disclosure can, when exposed to light of an activating wavelength, evoke action potentials at a frequency of from 20 Hz to 40 Hz.

A light-responsive polypeptide of the present disclosure can, when exposed to short red-shifted light pulses, induce spiking in a neuron. For example, a light-responsive polypeptide of the present disclosure can induce a 100% spike success rate at 1 ms pulses. A light-responsive polypeptide of the present disclosure can, when activated by red light, depolarize the membrane of an excitable cell (e.g., a neuron) when the red light is provided in pulses at a frequency of less than 5 milliseconds (ms), less than 4 ms, less than 3 ms, or less than 2 ms. A light-responsive polypeptide of the present disclosure can, when activated by red light, depolarize the membrane of an excitable cell (e.g., a neuron) when the red light is provided in pulses at a frequency of from about 0.5 ms to about 1 ms, from about 1 ms to about 1.5 ms, or from about 1.5 ms to about 2 ms.

A light-responsive polypeptide of the present disclosure can, when exposed to red light, spiking at low irradiance values. For example, a light-responsive polypeptide of the present disclosure can induce a 100% spike success rate at 0.08 mW/mm$^2$. A light-responsive polypeptide of the present disclosure can, when activated by red light, depolarize the membrane of an excitable cell (e.g., a neuron) when the red light is provided at less than 0.5 mW/mm$^2$, less than 0.4 mW/mm$^2$, less than 0.3 mW/mm$^2$, less than 0.2 mW/mm$^2$, or less than 0.1 mW/mm$^2$.

Fusion Polypeptides

The present disclosure provides a fusion polypeptide comprising: a) a light-responsive polypeptide of the present disclosure; and b) a heterologous fusion partner, where the heterologous fusion partner is a polypeptide that is not part of the light-responsive polypeptide in nature. The heterologous fusion partner can be present at the N-terminus of the light-responsive polypeptide, at the C-terminus of the light-responsive polypeptide, or internally within the light-responsive polypeptide.

A light-responsive polypeptide of the present disclosure can be fused to one or more amino acid sequence motifs selected from the group consisting of a signal peptide, an endoplasmic reticulum (ER) export signal, a membrane trafficking signal, and an N-terminal Golgi export signal. The one or more amino acid sequence motifs that enhance protein transport to the plasma membranes of mammalian cells can be fused to the N-terminus, the C-terminus, or to both the N- and C-termini of a protein in order to facilitate optimal expression and/or localization of the protein in the plasma membrane of a cell. Optionally, a light-responsive polypeptide of the present disclosure and the one or more amino acid sequence motifs may be separated by a linker. In some cases, a light-responsive polypeptide of the present disclosure can be modified by the addition of a trafficking signal (ts) which enhances transport of the protein to the cell plasma membrane. In some cases, the trafficking signal can be derived from the amino acid sequence of the human inward rectifier potassium channel Kir2.1. In other cases, the trafficking signal can comprise the amino acid sequence KSRITSEGEYIPLDQIDINV (SEQ ID NO: 6). In some cases, the heterologous membrane trafficking signal can comprise the amino acid sequence KSRITSEGEYIPLDQIDIN (SEQ ID NO: 7).

Trafficking sequences that are suitable for use can comprise an amino acid sequence having 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO: 6)).

A trafficking sequence can have a length of from about 10 amino acids to about 50 amino acids, e.g., from about 10 amino acids to about 20 amino acids, from about 20 amino acids to about 30 amino acids, from about 30 amino acids to about 40 amino acids, or from about 40 amino acids to about 50 amino acids.

A signal sequence can have a length of from about 10 amino acids to about 50 amino acids, e.g., from about 10 amino acids to about 20 amino acids, from about 20 amino acids to about 30 amino acids, from about 30 amino acids to about 40 amino acids, or from about 40 amino acids to about 50 amino acids.

Endoplasmic reticulum (ER) export sequences that are suitable for use with a light-responsive polypeptide of the present disclosure include, e.g., VXXSL (SEQ ID NO: 8; where X is any amino acid) (e.g., VKESL (SEQ ID NO: 9); VLGSL (SEQ ID NO: 10); etc.); NANSFCYENEVALTSK (SEQ ID NO: 11); FXYENE (SEQ ID NO: 12) (where X is any amino acid), e.g., FCYENEV (SEQ ID NO: 13); and the like. An ER export sequence can have a length of from about 5 amino acids to about 25 amino acids, e.g., from about 5 amino acids to about 10 amino acids, from about 10 amino acids to about 15 amino acids, from about 15 amino acids to about 20 amino acids, or from about 20 amino acids to about 25 amino acids.

For example, a light-responsive fusion polypeptide of the present disclosure can comprise: a) an amino acid sequence having at least 80%, at least 85%, at least 90%, at least 95%, at least 98%, at least 99%, or 100%, amino acid sequence identity with at least 250 contiguous amino acids, at least 275 contiguous amino acids, at least 300 contiguous amino acids, or 309 contiguous amino acids, of the following amino acid sequence:

(SEQ ID NO: 14)
MAHAPGTDQMFYVGTMDGWYLDTKLNSVAIGAHWSCFIVLTITTFYLGYE

SWTSRGPSKRTSFYAGYQEEQNLALFVNFFAMLSYFGKIVADTLGHNFGD

VGPFIIGFGNYRYADYMLTCPMLVYDLLYQLRAPYRVSCSAIIFAILMSG

VLAEFYAEGDPRLRNGAYAWYGFGCFWFIFAYSIVMSIVAKQYSRLAQLA

QDTGAEHSLHVLKFAVFTFSMLWILFPLVWAICPRGFGWIDDNWTEVAHC

VCDIVAKSCYGFALARFRKTYDEELFRLLEQLGHDEDEFQKLELDMRLSS

NGERLRRLS;

b) a membrane trafficking signal; and c) an ER export signal.

For example, a light-responsive fusion polypeptide of the present disclosure can comprise, in order from N-terminus to C-terminus: a) an amino acid sequence having at least 80%, at least 85%, at least 90%, at least 95%, at least 98%, at least 99%, or 100%, amino acid sequence identity with at least 250 contiguous amino acids, at least 275 contiguous amino acids, at least 300 contiguous amino acids, or 309 contiguous amino acids, of the following amino acid sequence:

(SEQ ID NO: 15)
MAHAPGTDQMFYVGTMDGWYLDTKLNSVAIGAHWSCFIVLTITTFYLGYE

SWTSRGPSKRTSFYAGYQEEQNLALFVNFFAMLSYFGKIVADTLGHNFGD

VGPFIIGFGNYRYADYMLTCPMLVYDLLYQLRAPYRVSCSAIIFAILMSG

VLAEFYAEGDPRLRNGAYAWYGFGCFWFIFAYSIVMSIVAKQYSRLAQLA

QDTGAEHSLHVLKFAVFTFSMLWILFPLVWAICPRGFGWIDDNWTEVAHC

VCDIVAKSCYGFALARFRKTYDEELFRLLEQLGHDEDEFQKLELDMRLSS

NGERLRRLS;

b) a membrane trafficking signal; and c) an ER export signal.

As one non-limiting example, a light-responsive fusion polypeptide of the present disclosure can comprise the following amino acid sequence:

```
                                        (SEQ ID NO: 16)
MAHAPGTDQM  FYVGTMDGWY  LDTKLNSVAI  GAHWSCFIVL

TITTFYLGYE  SWTSRGPSKR  TSFYAGYQEE  QNLALFVNFF

AMLSYFGKIV  ADTLGHNFGD  VGPFIIGFGN  YRYADYMLTC

PMLVYDLLYQ  LRAPYRVSCS  AIIFAILMSG  VLAEFYAEGD

PRLRNGAYAW  YGFGCFWFIF  AYSIVMSIVA  KQYSRLAQLA

QDTGAEHSLH  VLKFAVFTFS  MLWILFPLVW  AICPRGFGWI
```

-continued
```
DDNWTEVAHC  VCDIVAKSCY  GFALARFRKT  YDEELFRLLE

QLGHDEDEFQ  KLELDMRLSS  NGERLRRLSA  AAKSRITSEG

EYIPLDQIDI  NVFCYENEV,
``` where the amino acid sequence KSRITSEGEYIPLDQID-INV (SEQ ID NO: 6) is a membrane trafficking signal, and the amino acid sequence FCYENEV (SEQ ID NO: 13) is an ER export signal. A linker sequence (e.g., AAA, as depicted here) can be provided between the light-responsive polypeptide and the membrane trafficking signal.

A light-responsive polypeptide of the present disclosure can further include one or more additional polypeptides. For example, a light-responsive polypeptide of the present disclosure can include a linker; an epitope tag; a fluorescent protein; a peptide that provides for ease of purification; a cleavable linker peptide; and the like.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilized EGFP (dEGFP), destabilized ECFP (dECFP), destabilized EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, Renilla GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) *Nat. Methods* 2:905-909), and the like. Any of a variety of fluorescent and colored proteins from Anthozoan species, as described in, e.g., Matz et al. (1999) *Nature Biotechnol.* 17:969-973, is suitable for use.

Nucleic Acids, Expression Vectors, and Host Cells

The present disclosure provides nucleic acids that comprise a nucleotide sequence that encodes one or more of the subject proteins described herein (e.g., one or more light-responsive polypeptides, as described above). The present disclosure also provides recombinant expression vectors comprising a nucleic acid that comprises a light-responsive polypeptide of the present disclosure. The present disclosure also provides host cells genetically modified to include a nucleic acid of the present disclosure or a recombinant expression vector of the present disclosure.

Nucleic Acids and Recombinant Expression Vectors

The present disclosure provides nucleic acids that comprise a nucleotide sequence that encodes one or more of the subject proteins described herein (e.g., one or more light-responsive polypeptides, as described above). In some cases, a subject polynucleotide comprises an expression cassette, wherein the expression cassette contains a plurality of components (e.g., a plurality of coding sequences) that are utilized to express one or more proteins encoded by the polynucleotide in a target cell.

In some cases, a nucleotide sequence encoding a light-responsive polypeptide of the present disclosure is codon optimized for expression in a mammalian cell. In some cases, a nucleotide sequence encoding a light-responsive polypeptide of the present disclosure is codon optimized for expression in a human cell.

In some cases, a nucleic acid of the present disclosure comprises nucleotide sequence having at least 75%, at least 80%, at least 85%, at least 90%, at least 95%, at least 98%, at least 99%, or 100%, nucleotide sequence identity to a contiguous stretch of from about 800 nucleotides to about 850 nucleotides, from about 850 nucleotides to about 900 nucleotides, or from about 900 nucleotides to 927 nucleotides, of the following nucleotide sequence:

(SEQ ID NO: 17)
atggcacacgcaccaggcaccgaccagatgttctacgtgggcacaatgga cggctggtatctggataccaagctgaactccgtggccatcggcgcccact ggtcttgctttatcgtgctgacaatcaccacattctacctgggctatgag tcctggacatctcggggccctagcaagagaacctccttttacgccggcta tcaggaggagcagaacctggccctgtttgtgaatttctttgccatgctga gctacttcggcaagatcgtggccgacacactgggccacaacttcggcgat gtgggcccttcatcatcggcttcggcaattacaggtatgccgactacat gctgacctgcccaatgctggtgtacgatctgctgtatcagctgagggccc cctatcgcgtgtcttgtagcgccatcatctttgccatcctgatgtctggc gtgctggccgagttctacgcagagggcgacctaggctgaggaatggcgc ctacgcctggtatggctttggctgtttctggtttatcttcgcctactcta tcgtgatgagcatcgtggccaagcagtatagccggctggcccagctggcc caggatacaggcgccgagcacagcctgcacgtgctgaagttcgccgtgtt taccttctccatgctgtggattctgtttccctggtgtgggccatctgcc ctagaggcttcggctggatcgacgataactggacagaggtggcccactgc gtgtgcgacatcgtggccaagtcctgttacggctttgccctggcccggtt cagaaagacctatgatgaggagctgtttcggctgctggagcagctgggac acgacgaggatgagttccagaagctggagctggatatgaggctgagcagc aatggcgagcgcctgcggagactgtct.

In some cases, a nucleotide sequence encoding a light-responsive polypeptide of the present disclosure is operably linked to a transcriptional control element, e.g., a promoter. Any suitable promoter that functions in a target cell is suitable for use. In certain cases, a promoter can be a promoter that is specific to a particular target cell type or to a particular tissue type, such as a particular neuron or a pan-neuronal promoter. Initiation control regions of promoters, which are useful to drive expression of polynucleotides in a specific animal cell, are numerous and familiar to those skilled in the art. Virtually any promoter capable of driving expression of the subject polynucleotides can be used. In some embodiments, the promoter used to drive expression of a light-responsive polypeptide of the present disclosure can be a Thy1 promoter (See, e.g., Llewellyn, et al. (2010) Nat. Med., 16(10):1161-1166). In some cases, the promoter used to drive expression of a light-responsive polypeptide of the present disclosure is a human synapsin (hSyn) promoter, a human elongation factor 1-α (EF1α) promoter, a cytomegalovirus (CMV) promoter, a CMV early enhancer/chicken β actin (CAG) promoter, a synapsin-I promoter (e.g., a human synapsin-I promoter), a human synuclein 1 promoter, a human Thy1 promoter, a calcium/calmodulin-dependent kinase II alpha (CAMKIIa) promoter, a vesicular γ-amino butyric acid (VGAT) promoter, a glial fibrillary acidic protein (GFAP) promoter, a Pet1 promoter, a neuropeptide Y (NPY) promoter, a somatostatin (SST) promoter, an arginine vasopressin (AVP) promoter, a hypocretin (Hcrt) promoter, or any other promoter capable of driving expression of a nucleotide sequence encoding a light-responsive polypeptide of the present disclosure in a target cell.

In some cases, a suitable promoter is an inducible promoter. For example, the promoter may be induced by a trans-acting factor that responds to an exogenously administered drug. Examples of inducible promoters include, but are not limited to, tetracycline-on or tetracycline-off promoters, or tamoxifen-inducible CreER.

In some cases, a suitable promoter is a constitutive promoter. Such constitutive promoters are active in all circumstances, and are not regulated.

In some cases, a subject polynucleotide may comprise a ribosomal skip sequence that can be used to generate two separate proteins from the same transcript. In such cases, a subject polynucleotide will typically include a coding sequence that encodes a light-activated protein as well as a response protein. In these embodiments, a ribosomal skip sequence may be placed between the two coding sequences to produce two distinct proteins (namely, the light-activated protein and the response protein) from the same transcript.

Also provided herein are recombinant expression vectors comprising a subject polynucleotide (comprising a nucleotide sequence encoding a light-responsive polypeptide of the present disclosure) or any variant thereof as described herein. Vectors according to the present disclosure also include vectors comprising a nucleotide sequence that encodes an RNA (e.g., an mRNA) that when transcribed from the polynucleotides of the vector will result in the accumulation of a light-responsive polypeptide of the present disclosure on the plasma membranes of target cells. Vectors which may be used include, without limitation, lentiviral, retroviral, herpes simplex virus (HSV), adenoviral, and adeno-associated viral (AAV) vectors. Lentivirus vectors include, but are not limited to vectors based on human immunodeficiency virus (e.g., HIV-1, HIV-2), simian immunodeficiency virus (SIV), feline immunodeficiency virus (FIV), and equine infectious anemia virus (EIAV). Lentiviruses may be pseudotyped with the envelope proteins of other viruses, including, but not limited to vesicular stomatitis virus (VSV), rabies virus, Moloney-murine leukemia virus (Mo-MLV), baculovirus, and Ebola virus. Such vectors may be prepared using standard methods in the art. Retroviruses include, but are not limited to Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus, and the like.

In some cases, a suitable vector is a recombinant AAV vector. AAV vectors are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome that contains the rep gene involved in viral replication and expression of the viral genes; and the right-hand part of the genome that contains the cap gene encoding the capsid proteins of the virus.

AAV vectors may be prepared using standard methods in the art. Adeno-associated viruses of any serotype are suitable (see, e.g., Blacklow, pp. 165-174 of "Parvoviruses and Human Disease" J. R. Pattison, ed. (1988); Rose, Comprehensive Virology 3:1, 1974; P. Tattersall "The Evolution of Parvovirus Taxonomy" In Parvoviruses (J R Kerr, S F Cotmore. M E Bloom, R M Linden, C R Parrish, Eds.) p 5-14, Hudder Arnold, London, UK (2006); and D E Bowles, J E Rabinowitz, R J Samulski "The Genus Dependovirus" (J R Kerr, S F Cotmore. M E Bloom, R M Linden, C R Parrish, Eds.) p 15-23, Hudder Arnold, London, UK (2006), the disclosures of each of which are hereby incorporated by reference herein in their entireties). Methods for purifying for vectors may be found in, for example, U.S. Pat. Nos. 6,566,118, 6,989,264, and 6,995,006 and WO/1999/011764 titled "Methods for Generating High Titer Helper-free Preparation of Recombinant AAV Vectors", the disclosures of which are herein incorporated by reference in their entirety. Methods of preparing AAV vectors in a baculovirus system are described in, e.g., WO 2008/024998. AAV vectors can be self-complementary or single-stranded. Preparation of hybrid vectors is described in, for example, PCT Application No. PCT/US2005/027091, the disclosure of which is herein incorporated by reference in its entirety. The use of vectors derived from the AAVs for transferring genes in vitro and in vivo has been described (See e.g., International Patent Application Publication Nos.: 91/18088 and WO 93/09239; U.S. Pat. Nos. 4,797,368, 6,596,535, and 5,139,941; and European Patent No.: 0488528, all of which are hereby incorporated by reference herein in their entireties). These publications describe various AAV-derived constructs in which the rep and/or cap genes are deleted and replaced by a gene of interest, and the use of these constructs for transferring the gene of interest in vitro (into cultured cells) or in vivo (directly into an organism). A replication-defective recombinant AAV can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In some cases, the vector(s) for use in the methods of the present disclosure are encapsidated into a virus particle (e.g. AAV virus particle including, but not limited to, AAV1, AAV2, AAV3, AAV4, AAV5, AAV6, AAV7, AAV8, AAV9, AAV10, AAV11, AAV12, AAV13, AAV14, AAV15, and AAV16). Accordingly, the present disclosure includes a recombinant virus particle (recombinant because it contains a recombinant polynucleotide) comprising any of the vectors described herein. Methods of producing such particles are known in the art and are described in U.S. Pat. No. 6,596, 535, the disclosure of which is hereby incorporated by reference in its entirety.

In some cases, a nucleotide sequence encoding a light-responsive polypeptide of the present disclosure can be operably linked to various promoters for targeting specific neuronal populations in mammalian brains. Suitable promoters include, e.g., a CamKII promoter, a human synapsin promoter, a Thy1 promoter, a glial fibrillary acid protein (GFAP) promoter (see, e.g., Lee et al. (2008) Glia 56:481), a vesicular gamma amino butyric acid transporter (VGAT) promoter, where a PET1 promoter (see, e.g., Liu et al. (2010) Nat. Neurosci. 13:1190), a neuropeptide Y (NPY) promoter, a somatostatin (SST) promoter, an arginine vasopressin promoter (see, e.g., Pak et al. (2007) 148:3371), an Ef1a promoter, a cytomegalovirus early enhancer/chicken R actin (CAG) promoter (see, e.g., Alexopoulou et al. (2008) MBC Cell Biol. 9:2), Another major viral transduction system utilizes lentivirus including the following potential expression vectors.

Neuron-specific promoters and other control elements (e.g., enhancers) are known in the art. Suitable neuron-specific control sequences include, but are not limited to, a neuron-specific enolase (NSE) promoter (see, e.g., EMBL HSENO2, X51956; see also, e.g., U.S. Pat. Nos. 6,649,811, 5,387,742); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19; and Llewellyn et al. (2010) Nat. Med. 16:1161); a serotonin receptor promoter (see, e.g., GenBank S62283); a tyrosine hydroxylase promoter (TH) (see, e.g., Nucl. Acids. Res. 15:2363-2384 (1987) and Neuron 6:583-594 (1991)); a GnRH promoter (see, e.g., Radovick et al., Proc. Natl. Acad. Sci. USA 88:3402-3406 (1991)); an L7 promoter (see, e.g., Oberdick et al., Science 248:223-226 (1990)); a DNMT promoter (see, e.g., Bartge et al., Proc. Natl. Acad. Sci. USA 85:3648-3652 (1988)); an enkephalin promoter (see, e.g., Comb et al., EMBO J. 17:3793-3805 (1988)); a myelin basic protein (MBP) promoter; a CMV enhancer/platelet-derived growth factor-β promoter (see, e.g., Liu et al. (2004) Gene Therapy 11:52-60); a motor neuron-specific gene Hb9 promoter (see, e.g., U.S. Pat. No. 7,632,679; and Lee et al. (2004) Development 131:3295-3306); an alpha subunit of $Ca^{2+}$-calmodulin-dependent protein kinase II (CaMKIIα) promoter (see, e.g., Mayford et al. (1996) Proc. Natl. Acad. Sci. USA 93:13250); a methyl-CpG-binding protein-2 (MeCP2); a Pax6 promoter; an Nkx6.1 promoter; a latency-associated promoter 2 (LAP2) promoter; a ETS domain transcription factor PET1 promoter (see, e.g., Liu et al. (2011) Nat. Neurosci. 13(10): 1190-1198); a glial fibrillary acidic protein (GFAP) promoter (see, e.g., Brenner et al. (1994) J. Neurosci. 14:1030-1037); a vesicular GABA transporter (VGAT) promoter (see, e.g., Ebihara et al. (2003) Brain Res. Mol. Brain Res. 110:126-139); a neuropeptide tyrosine (NPY) promoter (see, e.g., Andersson et al. (1994) Cell Growth Differ. 5:27-36); a somatostatin (SST) promoter (see, e.g., Grosser et al. (2014) Neurosci. Lett. 566:241-246); an arginine vasopressin (AVP) promoter (e.g., AVP5.5 promoter; see, e.g., Pak et al. (2007) Endocrinology. 148:3371-3382); an elongation factor 1a (EF1a) promoter (see, e.g., Zhu et al. (2001) Biochim. Biophys. Acta. 1521:19-29); a hypocretin neuropeptide precursor (HCRT) promoter (see, e.g., Dong et al. (2013) Sleep Med. 14:482-487); and the like.

In some cases, a recombinant expression vector of the present disclosure can comprise a control element such as a Cre-dependent genetic switch (FLEX switch) which in the presence of Cre turns the expression of an operably linked gene "on" or "off" depending on the orientation of the gene (see, e.g., Atasoy et al. (2008) J. Neurosci. 28:7025-7030). In some cases, in the presence of Cre, a FLEX switch of the present disclosure will turn "on" the expression of an operably linked gene that is of forward orientation (e.g., a FLEX-for switch). In other cases, in the presence of Cre, a FLEX switch of the present disclosure will turn "off" the expression of an operably linked gene that is of reverse orientation (e.g., a FLEX-rev switch).

In some cases, a recombinant expression vector of the present disclosure can comprise a nucleotide sequence encoding a light-responsive polypeptide of the present disclosure, and a nucleotide sequence encoding a calcium indicator, e.g., a genetically encoded calcium indicator (GECI). In some cases, a light-responsive polypeptide of the present disclosure and a GECI are encoded on two separate expression vectors.

A light-responsive polypeptide of the present disclosure can be used as tools for the effective mapping of functional connection between brain regions. In some cases, the effective mapping of functional connections is achieved in combination with a GECI. In general, GECIs are fluorescent molecules that can respond to the intracellular level of calcium ions, and as such, have a wide range of use in the study of calcium signaling in a variety of cell types (e.g., neuronal activity). GECIs can be easily targeted to specific cell types or sub-cellular compartments, and when expressed together with light-responsive polypeptides, can provide long-term repeated in vivo measurements of cell activity. A GECI comprises a fluorescent protein, a calcium-binding domain (e.g., calmodulin, troponin C, and the like), and a domain that binds the calcium-binding domain (e.g., the M13 domain of the myosin light chain kinase, which binds calmodulin). Examples of GECI include Pericams, Cameleons, GCaMP, TN-XXL, and Twitch.

Fluorescent polypeptides that are suitable for use in a GECI include, but are not limited to, green fluorescent protein (GFP), blue fluorescent variant of GFP (BFP), cyan fluorescent variant of GFP(CFP), yellow fluorescent variant of GFP (YFP), enhanced GFP (EGFP), enhanced CFP (ECFP), enhanced YFP (EYFP), Venus, GFPS65T, Emerald, Topaz, GFPuv, destabilized EGFP (dEGFP), destabilized ECFP (dECFP), destabilized EYFP (dEYFP), HcRed, t-HcRed, DsRed, DsRed2, mCherry, t-dimer2, t-dimer2(12), mRFP1, mEos, pocilloporin, Renilla GFP, Monster GFP, paGFP, Kaede protein or a Phycobiliprotein, or a biologically active variant or fragment of any one thereof.

GECIs comprise a calcium-binding domain such as calmodulin or troponin C, fused to one or more (e.g., one, two, three, four, or more) fluorescent proteins (FPs). In single-FP GECIs, upon calcium binding, the fluorescence intensity of a circularly permutated FP (cpFP) may be modulated by calcium binding-dependent changes in the chromophore environment. In multiple-FP GECIs (e.g., two-FP GECIs, three-FP GECIs, four-FP GECIs), calcium binding modulates Förster resonance energy transfer (FRET) between FPs.

For example, in some cases, single-FP GECIs may find use in combination with light-responsive polypeptides as tools for the effective mapping of functional connection between brain regions. Single-FP GECIs that find use in the present disclosure may be a fusion product of a fluorescent protein, calmodulin and an M13 peptide sequence (e.g., GFP calmodulin-M13 GECI (GCaMP)), including, but are not limited to, GCaMPK (SEQ ID NO: 28), GCaMP2 (SEQ ID NO: 29), GCaMP2.1 (SEQ ID NO: 30), GCaMP2.2a (SEQ ID NO: 31), GCaMP2.2b (SEQ ID NO: 32), GCaMP2.3 (SEQ ID NO: 33), GCaMP2.4 (SEQ ID NO: 34), GCaMP3 (SEQ ID NO: 35), GCaMPSg (SEQ ID NO: 36), GCaMP6m (SEQ ID NO: 37), GCaMP6s (SEQ ID NO: 38), GCaMP6f (SEQ ID NO: 39), and the like. Amino acid sequences of such GECIs are provided in FIG. 26A-26L. Other single-FP GECIs that find use in the present disclosure include genetically encoded calcium indicators for optical imaging (GECOs) such as, the green fluorescing indicators G-GECO1 (SEQ ID NO: 40), G-GECO1.1 (SEQ ID NO: 41) and G-GECO1.2 (SEQ ID NO: 42), the red fluorescing indicator R-GECO1 (SEQ ID NO: 43), the blue fluorescing indicator B-GECO1 (SEQ ID NO: 44), the emission ratiometic indicator GEM-GECO1 (SEQ ID NO: 45), and the excitation ratiometric GEX-GECO1 (SEQ ID NO: 46), and the like. Amino acid sequences of such GECIs are provided in FIG. 26M-26S.

Single-FP GECIs that are suitable for use include, but are not limited to those that comprise an amino acid sequence having at least 75%, at least 80%, at least 85%, at least 90%, at least 95%, at least 98%, or at least 99%, amino acid sequence identity to the amino acid sequences depicted in FIG. 26A-FIG. 26S.

For example, in some cases, multi-FP GECIs (e.g., two-FP GECIs, three-FP GECIs, four-FP GECIs) may find use in combination with a light-responsive polypeptide of the present disclosure as tools for the effective mapping of functional connection between brain regions. Multi-FP GECIs that find use in the present disclosure include, but are not limited to, TN-XXL (depicted in FIG. 27A), Yellow Cameleons (e.g., YC3.6 (depicted in FIG. 27B)), D3CPVenus (depicted in FIG. 27C), and the like.

Multi-FP GECIs that are suitable for use comprise an amino acid sequence having at least 75%, at least 80%, at least 85%, at least 90%, at least 95%, at least 98%, or at least 99%, amino acid sequence identity to the amino acid sequences depicted in FIG. 27A-27C.

Host Cells

The present disclosure provides genetically modified host cells (e.g., isolated genetically modified host cells; in vitro genetically modified host cells; in vivo genetically modified host cells) that are genetically modified with a nucleic acid of the present disclosure or a recombinant expression vector of the present disclosure. In some cases, a subject isolated genetically modified host cell can produce a light-responsive polypeptide of the present disclosure. In some cases, a genetically modified host cell of the present disclosure produces a light-responsive polypeptide of the present disclosure, such that the light-responsive polypeptide is present in the cell membrane.

Suitable host cells include eukaryotic host cells, such as a mammalian cell, an insect host cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method. In some cases, the cell is not a Tiarinafusus cell.

Suitable mammalian cells include primary cells and immortalized cell lines. In some cases, the mammalian cell is a neuron, e.g., a non-immortalized (primary) neuron. In other cases, the mammalian cell is an immortalized cell line. In some cases, the cell is a human primary cell. In some cases, the cell is a human neuron. In some cases, the cell is a cardiac cell. In some cases, the cell is a stem cell (e.g., a neural stem cell; a hematopoietic stem cell; a pluripotent stem cell; an embryonic stem cell). In some cases, the cell is a muscle cell.

Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

In some embodiments, the cell is a neuronal cell or a neuronal-like cell. The cells can be of human, non-human primate, mouse, or rat origin, or derived from a mammal other than a human, non-human primate, rat, or mouse. Suitable cell lines include, but are not limited to, a human glioma cell line, e.g., SVGp12 (ATCC CRL-8621), CCF-STTG1 (ATCC CRL-1718), SW 1088 (ATCC HTB-12), SW 1783 (ATCC HTB-13), LLN-18 (ATCC CRL-2610), LNZTA3WT4 (ATCC CRL-11543), LNZTA3WT11 (ATCC CRL-11544), U-138 MG (ATCC HTB-16), U-87 MG (ATCC HTB-14), H4 (ATCC HTB-148), and LN-229 (ATCC CRL-2611); a human medulloblastoma-derived cell line, e.g., D342 Med (ATCC HTB-187), Daoy (ATCC HTB-186), D283 Med (ATCC HTB-185); a human tumor-derived neuronal-like cell, e.g., PFSK-1 (ATCC CRL-2060), SK-N-DZ (ATCCCRL-2149), SK-N-AS (ATCC CRL-2137), SK-N-FI (ATCC CRL-2142), IMR-32 (ATCC CCL-127), etc.; a mouse neuronal cell line, e.g., BC3H1 (ATCC CRL-1443), EOC1 (ATCC CRL-2467), C8-D30 (ATCC CRL-2534), C8-S (ATCC CRL-2535), Neuro-2a (ATCC CCL-131), NB41A3 (ATCC CCL-147), SW10 (ATCC CRL-2766), NG108-15 (ATCC HB-12317); a rat neuronal cell line, e.g., PC-12 (ATCC CRL-1721), CTX TNA2 (ATCC CRL-2006), C6 (ATCC CCL-107), F98 (ATCC CRL-2397), RG2 (ATCC CRL-2433), B35 (ATCC CRL-2754), R3 (ATCC CRL-2764), SCP (ATCC CRL-1700), OA1 (ATCC CRL-6538).

In some cases, the cell is a neuron of the visual cortex. In some cases, the cell is a neuron of the primary visual cortex, e.g., a V1 neuron.

Suitable yeast cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like. Yeast cells can be used to produce a light-responsive polypeptide of the present disclosure.

Suitable prokaryotic cells include, but are not limited to, any of a variety of laboratory strains of *Escherichia coli, Lactobacillus* sp., *Salmonella* sp., *Shigella* sp., and the like. See, e.g., Carrier et al. (1992) J. Immunol. 148:1176-1181; U.S. Pat. No. 6,447,784; and Sizemore et al. (1995) Science 270:299-302. Examples of *Salmonella* strains which can be employed in the present invention include, but are not limited to, *Salmonella typhi* and *S. typhimurium*. Suitable *Shigella* strains include, but are not limited to, *Shigella flexneri, Shigella sonnei*, and *Shigella* disenteriae. Typically, the laboratory strain is one that is non-pathogenic. Non-limiting examples of other suitable bacteria include, but are not limited to, *Bacillus subtilis, Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like. Prokaryotic cells can be used to propagate a nucleic acid of the present disclosure.

In some cases, a genetically modified mammalian host cell of the present disclosure is genetically modified with a nucleic acid (or recombinant expression vector) comprising a nucleotide sequence encoding a light-responsive polypeptide of the present disclosure; and is also genetically modified with a nucleic acid (or recombinant expression vector) comprising a nucleotide sequence encoding a GECI, where suitable GECIs are described above.

In some cases, a genetically modified mammalian host cell of the present disclosure is genetically modified with a nucleic acid (or recombinant expression vector) comprising a nucleotide sequence encoding a light-responsive polypeptide of the present disclosure; and is also genetically modified with a nucleic acid (or recombinant expression vector) comprising a nucleotide sequence encoding a second light-responsive polypeptide. In some cases, the second light-responsive polypeptide is a depolarizing light-responsive polypeptide. In some cases, the second light-responsive polypeptide is a depolarizing light-responsive polypeptide that is activated in response to light of a wavelength that is different from the wavelength of light that activates a light-responsive polypeptide of the present disclosure. In some cases, the second light-responsive polypeptide is a hyperpolarizing light-responsive polypeptide. Suitable second light-responsive polypeptides are described hereinbelow.

Methods of Modulating the Activity of a Cell

The present disclosure provides methods for optogenetic modulation of action potentials in target cells. The subject methods generally involve introducing a light-responsive polypeptide of the present disclosure into a target cell and illuminating the target cell with light of an activating wavelength. Illumination of the target cell with light of an activating wavelength causes the light-activated polypeptide to allow one or more cations to pass through the plasma membrane of the target cell. The passage of the cations through the plasma membrane of the target cell has a desired effect, such as, e.g., modulating the membrane potential of the plasma membrane. In some cases, the passage of the cations species through the plasma membrane may be used to modulate one or more neurological responses or processes in a patient, and may therefore by used to treat a disease or condition in the patient. In some cases, the subject methods involve treating a patient for a condition, such as a neurological condition, using the systems and devices provided herein. The subject methods are now described in greater detail below.

In some cases, a method of the present disclosure for modulating the activity of a target cell comprises introducing into the target cell a light-responsive polypeptide of the present disclosure, or introducing into a target cell a nucleic acid (or recombinant expression vector) comprising a nucleotide sequence encoding a light-responsive polypeptide of the present disclosure, thereby generating a modified target cell that comprises the light-responsive polypeptide in its plasma membrane; and exposing the modified target cell to light of a wavelength (e.g., red light) that activates the light-responsive polypeptide. The modified target cell is exposed to light having a wavelength in a range of from 600 nm to 700 nm, e.g., from 600 nm to 625 nm, from 625 nm to 650 nm, from 650 nm to 675 nm, or from 675 nm to 700 nm. In some cases, the modified target cell is exposed to light having a wavelength of from 625 nm to 650 nm. In some cases, the modified target cell is exposed to light having a wavelength of 650 nm.

In some cases, a method of the present disclosure for modulating the activity of a target cell comprises introducing into the target cell a light-responsive polypeptide of the present disclosure, thereby generating a modified target cell that comprises the light-responsive polypeptide in its plasma membrane; and exposing the modified target cell to light of a wavelength (e.g., light having a wavelength in a range of from 600 nm to 700 nm; e.g., light having a wavelength of from 625 nm to 650 nm) that activates the light-responsive polypeptide.

In some cases, a method of the present disclosure for modulating the activity of a target cell comprises introducing into a target cell a nucleic acid comprising a nucleotide sequence encoding a light-responsive polypeptide of the present disclosure, thereby generating a modified target cell that comprises the light-responsive polypeptide in its plasma membrane; and exposing the modified target cell to light of a wavelength (e.g., light having a wavelength in a range of from 600 nm to 700 nm; e.g., light having a wavelength of from 625 nm to 650 nm) that activates the light-responsive polypeptide. In some cases, the target cell is a neuron, and the nucleotide sequence is operably linked to a neuron-specific promoter.

In some cases, a method of the present disclosure for modulating the activity of a target cell comprises introducing into a target cell a recombinant expression vector comprising a nucleotide sequence encoding a light-responsive polypeptide of the present disclosure, thereby generating a modified target cell that comprises the light-responsive polypeptide in its plasma membrane; and exposing the modified target cell to light of a wavelength (e.g., light having a wavelength in a range of from 600 nm to 700 nm; e.g., light having a wavelength of from 625 nm to 650 nm) that activates the light-responsive polypeptide. In some cases, the target cell is a neuron, and the nucleotide sequence is operably linked to a neuron-specific promoter.

In some cases, a target cell is an in vivo cell, e.g., a cell present in a multicellular organism, e.g., a mammal. Mammals include, e.g., humans; non-human primates; rodents, e.g., rats, mice; lagomorphs, e.g., rabbits; ungulates, e.g., caprines, equines, ovines, bovines, etc.; cats; dogs; etc. In some cases, the mammal is a human. In some cases, the mammal is a non-human primate. In some cases, the mammal is a rodent.

In some cases, the target cell is a neuron of the visual cortex. In some cases, the target cell is a neuron of the primary visual cortex, e.g., a V1 neuron.

Where the target cell is an in vivo cell, e.g., a cell present in an individual, e.g., a mammal, a recombinant expression vector (e.g., recombinant viral vector) comprising a nucleotide sequence encoding a light-responsive polypeptide of the present disclosure can be delivered by administering the recombinant expression vector to the individual. Administering the recombinant expression vector can be carried out by injecting a composition comprising the recombinant expression vector into the individual. For example, the recombinant expression vector can be injected at or near (e.g., within about 5 cm, within about 4 cm, within about 3 cm, within about 2 cm, within about 1 cm, or within about 0.5 cm) of the target cell or a target tissue comprising the target cell. In some cases, administering the recombinant expression vector can be carried out using a device or system, as described below, comprising a container that includes a composition comprising the recombinant expression vector. The container can be a syringe. The container can be totally or partially implanted within the individual. The targeted tissue structure may be genetically modified with a nucleic acid comprising a nucleotide sequence encoding a light-responsive polypeptide of the present disclosure such as by such as by viral mediated gene delivery, electroporation, ultrasound, hydrodynamic delivery, or introduction of naked DNA by direct injection or as complemented by additional facilitators such as cationic lipids or polymers.

In some cases, a nucleic acid comprising a nucleotide sequence encoding a light-responsive polypeptide of the present disclosure is introduced into the genome of a target cell. For example, in some cases, a nucleic acid comprising a nucleotide sequence encoding a light-responsive polypeptide of the present disclosure is introduced into the genome of a target cell using a CRISPR/Cas9 system. For example, a donor polynucleotide comprising a nucleotide sequence encoding a light-responsive polypeptide of the present disclosure is used in combination with a Cas9 polypeptide and a guide RNA to effect introduction of the nucleotide sequence encoding the light-responsive polypeptide into the genome of a target cell. The donor polynucleotide could include, e.g., an open reading frame (ORF) of a target gene in the target cell and a nucleotide sequence encoding a light-responsive polypeptide of the present disclosure, where the ORF and the nucleotide sequence encoding the light-responsive polypeptide are separated by an internal ribosome entry site or a nucleotide sequence encoding a 2A peptide; and the guide RNA could include, e.g., a nucleotide sequence that hybridizes to the 3' end of a promoter sequence that is operably linked to the ORF in the genome of the target cell. In some cases, the donor polynucleotide could include, e.g., sequence homologous to a non-coding region in a genome of a target cell, such a nucleic acid comprising a nucleotide sequence encoding a light-responsive polypeptide of the present disclosure in operable linkage with a neuron-specific promoter is introduced into a target cell (e.g., neuron) without affecting any endogenous gene expression.

Target cells are generally cells that carry or transmit electrical impulses, such as nerve cells. Target cells include neurons, cardiac cells, and stem cells. In some case, a target cell is a neuron. In some case, a target cell is a sensory neuron, a motor neuron, or an interneuron. Target cells can include cells of the central nervous system and/or cells of the peripheral nervous system. Target cells can be present in a target tissue. In some cases, a target tissue may include a plurality of nerve fibers, a nerve, a nerve cell ganglion, a neuromuscular junction, a tissue that is innervated by nerves, including but not limited to muscle, skin, or endocrine tissue, or an anatomical region, such as a portion or sub-portion of the brain or spinal cord. In some cases, a target tissue may be a portion of an individual cell, such as specific axon of a nerve cell.

Modulating Membrane Potentials in Target Cells

The present disclosure provides a method for modulating the activity of a target cell (e.g., a target mammalian cell), e.g., by modulating the membrane potential in the target cell. In some cases, a nucleic acid encoding a light-responsive polypeptide of the present disclosure is introduced into a target cell such that the target cell expresses the light-responsive polypeptide, e.g., where the light-responsive polypeptide is expressed and is present in the plasma membrane of the target cell. The target cell is then illuminated with light of an activating wavelength using a light-generating device. Illumination of the light-responsive polypeptide results in the movement of one or more cations through the plasma membrane of the cell in response to light. In some cases, light activation of a light-responsive polypeptide of the present disclosure results in depolarization of a cell expressing the light-responsive polypeptide. In certain embodiments, the activation of a light-responsive polypeptide results in depolarization of a nerve cell membrane and triggering of action potentials. In some embodiments, a method of the present disclosure for modulating the activity of a target cell involves use of a system or device of the present disclosure.

Target Cells and Tissues

As summarized above, aspects of the present disclosure include delivering a nucleic acid or a recombinant expression vector comprising a nucleotide sequence encoding a light-activated polypeptide of the present disclosure to a target cell. Target cells are generally cells that carry or transmit electrical impulses, such as nerve cells. In some case, a target cell is a sensory neuron, a motor neuron, or an interneuron. Target cells can include cells of the central nervous system and/or cells of the peripheral nervous system. Target cells can be present in a target tissue. In some cases, a target tissue may include a plurality of nerve fibers, a nerve, a nerve cell ganglion, a neuromuscular junction, a tissue that is innervated by nerves, including but not limited to muscle, skin, or endocrine tissue, or an anatomical region, such as a portion or sub-portion of the brain or spinal cord. In some cases, a target tissue may be a portion of an individual cell, such as specific axon of a nerve cell.

In some cases, the target cell is a neuron of the neocortex. In some cases, the target cell is a neuron of the visual cortex. In some cases, the target cell is a neuron of the primary visual cortex, e.g., a V1 neuron.

In some cases, a light-activated polypeptide of the present disclosure is expressed in the visual cortex; activation with red light can result in selectively ignite widespread population responses involving functionally-related neurons, and can result in correct and selective visual discrimination behavior even in the absence of sensory input.

Once a nucleic acid of the present disclosure has been delivered to a target cell or tissue, the nucleic acid enters the target cells and is expressed. In some cases, a subject nucleic acid may contain a tissue-specific promoter so that expression only occurs in target cells wherein the tissue-specific promoter is active. In this way, if a subject polynucleotide is delivered to cells other than a target cell, the polynucleotide will not be expressed (or will only be expressed at very low levels) in the non-target cells because the tissue-specific promoter will be inactive in those cells. In some cases, a subject polynucleotide may contain an inducible promoter, such that expression of the polynucleotide only takes place when an exogenously administered drug is present is a sufficient concentration within the cell to activate the promoter.

Additional Polypeptides

In some cases, a method of the present disclosure for modulating the activity of a target cell comprises introducing into a target cell a light-responsive polypeptide of the present disclosure, or introducing into a target cell a nucleic acid (or recombinant expression vector) comprising a nucleotide sequence encoding a light-responsive polypeptide of the present disclosure, thereby generating a modified target cell that expresses the light-responsive polypeptide in its cell membrane; and exposing the modified target cell to light of a wavelength (e.g., light having a wavelength in a range of from 600 nm to 700 nm; e.g., light having a wavelength of from 625 nm to 650 nm) that activates the light-responsive polypeptide, where the modified target cell expresses an additional heterologous polypeptide, such as a GECI, a second light-responsive polypeptide, and the like.

GECI

In some cases, a method of the present disclosure for modulating the activity of a target cell comprises introducing into a target cell a light-responsive polypeptide of the present disclosure, or introducing into a target cell a nucleic acid (or recombinant expression vector) comprising a nucleotide sequence encoding a light-responsive polypeptide of the present disclosure, thereby generating a modified target cell that expresses the light-responsive polypeptide in its cell membrane; and exposing the modified target cell to light of a wavelength (e.g., light having a wavelength in a range of from 600 nm to 700 nm; e.g., light having a wavelength of from 625 nm to 650 nm) that activates the light-responsive polypeptide, where the modified target cell expresses a GECI. Where the modified target cell expresses a GECI, the method can comprise detecting the level of intracellular calcium in the modified target cell after light activation of the light-responsive polypeptide present in the cell membrane of the modified target cell.

A GECI comprises a fluorescent protein, a calcium-binding domain (e.g., calmodulin, troponin C, and the like), and a domain that binds the calcium-binding domain (e.g., the M13 domain of the myosin light chain kinase, which binds calmodulin). Examples of GECI include Pericams, Cameleons, GCaMP, TN-XXL, and Twitch.

Fluorescent polypeptides that are suitable for use in a GECI include, but are not limited to, green fluorescent protein (GFP), blue fluorescent variant of GFP (BFP), cyan fluorescent variant of GFP(CFP), yellow fluorescent variant of GFP (YFP), enhanced GFP (EGFP), enhanced CFP (ECFP), enhanced YFP (EYFP), Venus, GFPS65T, Emerald, Topaz, GFPuv, destabilized EGFP (dEGFP), destabilized ECFP (dECFP), destabilized EYFP (dEYFP), HcRed, t-HcRed, DsRed, DsRed2, mCherry, t-dimer2, t-dimer2(12), mRFP1, mEos, pocilloporin, Renilla GFP, Monster GFP, paGFP, Kaede protein or a Phycobiliprotein, or a biologically active variant or fragment of any one thereof.

GECIs comprise a calcium-binding domain such as calmodulin or troponin C, fused to one or more (e.g., one, two, three, four, or more) fluorescent proteins (FPs). In single-FP GECIs, upon calcium binding, the fluorescence intensity of a circularly permutated FP (cpFP) may be modulated by calcium binding-dependent changes in the chromophore environment. In multiple-FP GECIs (e.g., two-FP GECIs, three-FP GECIs, four-FP GECIs), calcium binding modulates Förster resonance energy transfer (FRET) between FPs.

For example, in some cases, single-FP GECIs may find use in combination with light-responsive polypeptides as tools for the effective mapping of functional connection between brain regions. Single-FP GECIs that find use in the present disclosure may be a fusion product of a fluorescent protein, calmodulin and an M13 peptide sequence (e.g., GFP calmodulin-M13 GECI (GCaMP)), including, but are not limited to, GCaMPK (SEQ ID NO: 28), GCaMP2 (SEQ ID NO: 29), GCaMP2.1 (SEQ ID NO: 30), GCaMP2.2a (SEQ ID NO: 31), GCaMP2.2b (SEQ ID NO: 32), GCaMP2.3 (SEQ ID NO: 33), GCaMP2.4 (SEQ ID NO: 34), GCaMP3 (SEQ ID NO: 35), GCaMP5g (SEQ ID NO: 36), GCaMP6m (SEQ ID NO: 37), GCaMP6s (SEQ ID NO: 38), GCaMP6f (SEQ ID NO: 39), and the like. Amino acid sequences of such GECIs are provided in FIG. 26A-26L. Other single-FP GECIs that find use in the present disclosure include genetically encoded calcium indicators for optical imaging (GE-COs) such as, the green fluorescing indicators G-GECO1 (SEQ ID NO: 40), G-GECO1.1 (SEQ ID NO: 41) and G-GECO1.2 (SEQ ID NO: 42), the red fluorescing indicator R-GECO1 (SEQ ID NO: 43), the blue fluorescing indicator B-GECO1 (SEQ ID NO: 44), the emission ratiometric indicator GEM-GECO1 (SEQ ID NO: 45), and the excitation ratiometric GEX-GECO1 (SEQ ID NO: 46), and the like. Amino acid sequences of such GECIs are provided in FIG. 26M-26S.

Single-FP GECIs that are suitable for use include, but are not limited to those that comprise an amino acid sequence having at least 75%, at least 80%, at least 85%, at least 90%, at least 95%, at least 98%, or at least 99%, amino acid sequence identity to the amino acid sequences depicted in FIG. 26A-FIG. 26S.

For example, in some cases, multi-FP GECIs (e.g., two-FP GECIs, three-FP GECIs, four-FP GECIs) may find use in combination with a light-responsive polypeptide of the present disclosure as tools for the effective mapping of functional connection between brain regions. Multi-FP GECIs that find use in the present disclosure include, but are not limited to, TN-XXL (depicted in FIG. 27A), Yellow Cameleons (e.g., YC3.6 (depicted in FIG. 27B)), D3CPVenus (depicted in FIG. 27C), and the like.

Multi-FP GECIs that are suitable for use comprise an amino acid sequence having at least 75%, at least 80%, at least 85%, at least 90%, at least 95%, at least 98%, or at least 99%, amino acid sequence identity to the amino acid sequences depicted in FIG. 27A-27C.

Light-Responsive Polypeptides

In some cases, a method of the present disclosure for modulating the activity of a target cell comprises introducing into a target cell a light-responsive polypeptide of the present disclosure, or introducing into a target cell a nucleic acid (or recombinant expression vector) comprising a nucleotide sequence encoding a light-responsive polypeptide of the present disclosure, thereby generating a modified target cell that expresses the light-responsive polypeptide in its cell membrane; and exposing the modified target cell to light of a wavelength (e.g., light having a wavelength in a range of from 600 nm to 700 nm; e.g., light having a wavelength of from 625 nm to 650 nm) that activates the light-responsive polypeptide, where the modified target cell is also genetically modified to express a second light-responsive polypeptide. In some cases, the second light-responsive polypeptide is a depolarizing light-responsive polypeptide. In some cases, the second light-responsive polypeptide is a depolarizing light-responsive polypeptide that is activated by light of a wavelength that is different from the wavelength of light used to activate the light-responsive polypeptide of the present disclosure, e.g., where the second light-responsive polypeptide is a depolarizing light-responsive polypeptide that is activated by blue light, by yellow light, by green light, by orange light, etc. In some cases, the second light-responsive polypeptide is a hyperpolarizing light-responsive polypeptide. In some cases, the second light-responsive polypeptide is a hyperpolarizing light-responsive polypeptide that is activated by light of a wavelength that is different from the wavelength of light used to activate the light-responsive polypeptide of the present disclosure, e.g., where the second light-responsive polypeptide is a hyperpolarizing light-responsive polypeptide that is activated by blue light, by yellow light, by green light, by orange light, etc.

In some embodiments, a depolarizing light-responsive polypeptide is a channelrhodopsin (ChR1—NCBI Gene ID: 5724518, ChR2—NCBI Gene ID: 5727376) derived from *Chlamydomonas reinhardtii*, wherein the polypeptide is capable of transporting cations across a cell membrane when the cell is illuminated with light. The light used to activate the light-responsive cation channel protein derived from *Chlamydomonas reinhardtii* can have a wavelength between about 460 and about 495 nm or can have a wavelength of about 480 nm. Additionally, light pulses having a temporal frequency of about 100 Hz can be used to activate the light-responsive protein. In some embodiments, activation of the light-responsive cation channel derived from *Chlamydomonas reinhardtii* with light pulses having a temporal frequency of about 100 Hz can cause depolarization of the excitable cells, e.g., neurons, expressing the light-responsive cation channel. The light-responsive cation channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive cation channel protein to regulate the polarization state of the plasma membrane of the cell. Additionally, the light-responsive cation channel protein can comprise one or more conservative amino acid substitutions and/or one or more non-conservative amino acid substitutions. The light-responsive proton pump protein containing substitutions, deletions, and/or insertions introduced into the native amino acid sequence suitably retains the ability to transport cations across a cell membrane. In some cases, a suitable channelrhodopsin is a ChR1 polypeptide that comprises an amino acid sequence having at least 75%, at least 80%, at least 85%, at least 90%, at least 95%, at least 98%, or at least 99%, or 100%, amino acid sequence identity to the amino acid sequence depicted in FIG. 28A (SEQ ID NO: 50). In some cases, a suitable channelrhodopsin is a ChR2 polypeptide that comprises an amino acid sequence having at least 75%, at least 80%, at least 85%, at least 90%, or 100%, at least 95%, at least 98%, or at least 99%, amino acid sequence identity to the amino acid sequence depicted in FIG. 28B (SEQ ID NO: 51).

In other embodiments, the light-responsive polypeptide is a step function opsin (SFO) protein or a stabilized step function opsin (SSFO) protein that can have specific amino acid substitutions at key positions in the retinal binding pocket of the amino acid sequence of ChR2. Further disclosure related to SFO or SSFO proteins can be found in International Patent Application Publication No. WO 2010/056970, the disclosure of which is hereby incorporated by reference in its entirety. In some cases, a suitable ChR2 SFO comprises an amino acid sequence having at least 75%, at least 80%, at least 85%, at least 90%, at least 95%, at least 98%, or at least 99%, or 100%, amino acid sequence identity to the amino acid sequence depicted in FIG. 28C (SEQ ID NO: 52). In some cases, a suitable ChR2 SSFO comprises an amino acid sequence having at least 75%, at least 80%, at least 85%, at least 90%, at least 95%, at least 98%, or at least 99%, or 100%, amino acid sequence identity to the amino acid sequence depicted in FIG. 28D (SEQ ID NO: 53).

In some embodiments, a suitable light-responsive polypeptide is a cation channel derived from *Volvox carteri* (VChR1—NCBI Gene ID: 9619570) and is activated by illumination with light of a wavelength of from about 500 nm to about 600 nm, e.g., from about 525 nm to about 550 nm, e.g., 545 nm. The light-responsive ion channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive ion channel protein to regulate the polarization state of the plasma membrane of the cell. Additionally, the light-responsive ion channel protein can comprise one or more conservative amino acid substitutions and/or one or more non-conservative amino acid substitutions. The light-responsive ion channel protein containing substitutions, deletions, and/or insertions introduced into the native amino acid sequence suitably retains the ability to transport ions across the plasma membrane of a excitable cell in response to light. In some cases, a suitable cation channel derived from *Volvox carteri* is a VChR1 polypeptide that comprises an amino acid sequence having at least 75%, at least 80%, at least 85%, at least 90%, at least 95%, at least 98%, or at least 99%, or 100%, amino acid sequence identity to the amino acid sequence depicted in FIG. 28E (SEQ ID NO: 54).

In other instances, the light-responsive polypeptide is a SFO or an SSFO based on VChR1. In some cases, an SFO or SSFO protein is capable of mediating a depolarizing current in the cell when the cell is illuminated with blue light. In some cases, the light has a wavelength of about 560 nm. Additionally, in some cases the light is delivered as a single pulse of light or as spaced pulses of light due to the prolonged stability of SFO and SSFO photocurrents. In some cases, activation of the SFO or SSFO protein with single pulses or spaced pulses of light can cause depolarization of an excitable cell, e.g., neuron, expressing the SFO or SSFO protein. In some embodiments, each of the disclosed step function opsin and stabilized step function opsin proteins can have specific properties and characteristics for use in depolarizing the membrane of an excitable cell in response to light. In some cases, a suitable VChR1 SFO comprises an amino acid sequence having at least 75%, at least 80%, at least 85%, at least 90%, at least 95%, at least 98%, or at least 99%, or 100%, amino acid sequence identity to the amino acid sequence depicted in FIG. 28F (SEQ ID NO: 55). In some cases, a suitable VChR1 SSFO comprises an amino acid sequence having at least 75%, at least 80%, at least 85%, at least 90%, at least 95%, at least 98%, or at least 99%, or 100%, amino acid sequence identity to the amino acid sequence depicted in FIG. 28G (SEQ ID NO: 56).

In other instances, the light-responsive cation channel protein is a C1V1 chimeric protein derived from the VChR1 protein of *Volvox carteri* and the ChR1 protein from *Chlamydomonas reinhardti*, wherein the protein comprises the amino acid sequence of VChR1 having at least the first and second transmembrane helices replaced by the first and second transmembrane helices of ChR1; is responsive to light; and is capable of mediating a depolarizing current in the cell when the cell is illuminated with light. In some cases, the C1V1 protein further comprises a replacement within the intracellular loop domain located between the second and third transmembrane helices of the chimeric light responsive protein, wherein at least a portion of the intracellular loop domain is replaced by the corresponding portion from ChR1. In another instance, the portion of the intracellular loop domain of the C1V1 chimeric protein can be replaced with the corresponding portion from ChR1 extending to amino acid residue A145 of the ChR1. In other cases, the CiVi chimeric protein further comprises a replacement within the third transmembrane helix of the chimeric light responsive protein, wherein at least a portion of the third transmembrane helix is replaced by the corresponding sequence of ChR1. In yet another embodiment, the portion of the intracellular loop domain of the C1V1 chimeric protein can be replaced with the corresponding portion from ChR1 extending to amino acid residue W163 of the ChR1.

In some embodiments, the C1V1 protein mediates a depolarizing current in the cell when the cell is illuminated with green light. In some cases, the light has a wavelength of between about 540 nm to about 560 nm. In some cases, the light can have a wavelength of about 542 nm. In some embodiments, the C1V1 chimeric protein is not capable of mediating a depolarizing current in the cell when the cell is illuminated with violet light. In some embodiments, the chimeric protein is not capable of mediating a depolarizing current in the cell when the cell is illuminated with light having a wavelength of about 405 nm. Additionally, in some embodiments, light pulses having a temporal frequency of about 100 Hz can be used to activate the C1V1 protein.

In some aspects, a suitable light-responsive polypeptide comprises substituted or mutated amino acid sequences, wherein the mutant polypeptide retains the characteristic light-activatable nature of the precursor C1V1 chimeric polypeptide but may also possess altered properties in some specific aspects. For example, the mutant light-responsive C1V1 chimeric proteins described herein can exhibit an increased level of expression both within an animal cell or on the animal cell plasma membrane; an altered responsiveness when exposed to different wavelengths of light, particularly red light; and/or a combination of traits whereby the chimeric C1V1 polypeptide possess the properties of low desensitization, fast deactivation, low violet-light activation for minimal cross-activation with other light-responsive cation channels, and/or strong expression in animal cells.

Accordingly, suitable light-responsive proteins include CIV1 chimeric light-responsive proteins that can have specific amino acid substitutions at key positions throughout the retinal binding pocket of the VChR1 portion of the chimeric polypeptide. In some cases, a suitable C1V1 chimeric light-responsive protein comprises an amino acid sequence having at least 75%, at least 80%, at least 85%, at least 90%, at least 95%, at least 98%, or at least 99%, or 100%, amino acid sequence identity to the amino acid sequence depicted in FIG. 28H (SEQ ID NO: 57).

In other instances, the light-responsive cation channel protein is a C1C2 chimeric protein derived from the ChR1 and the ChR2 proteins from *Chlamydomonas reinhardti*, wherein the protein is responsive to light and is capable of mediating a depolarizing current in the cell when the cell is illuminated with light. The light-responsive cation channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive cation channel protein to regulate the polarization state of the plasma membrane of the cell. Additionally, the light-responsive cation channel protein comprises one or more conservative amino acid substitutions and/or one or more non-conservative amino acid substitutions. The light-responsive proton pump protein containing substitutions, deletions, and/or insertions introduced into the native amino acid sequence suitably retains the ability to transport cations across a cell membrane. In some cases, a suitable C1C2 chimeric light-responsive protein comprises an amino acid sequence having at least 75%, at least 80%, at least 85%, at least 90%, at least 95%, at least 98%, or at least 99%, or 100%, amino acid sequence identity to the amino acid sequence depicted in FIG. 28I (SEQ ID NO: 58).

In some aspects, a depolarizing light-responsive polypeptide is a SdChR polypeptide (GenBank Accession No.: AHH02138) derived from *Scherffelia dubia*, wherein the SdChR polypeptide is capable of transporting cations across a cell membrane when the cell is illuminated with light. The light used to activate the SdChR polypeptide can have a wavelength between about 440 and about 490 nm or can have a wavelength of about 460 nm. The SdChR protein can additionally comprise substitutions, deletions, and/or insertions introduced into a native amino acid sequence to increase or decrease sensitivity to light, increase or decrease sensitivity to particular wavelengths of light, and/or increase or decrease the ability of the SdChR protein to regulate the polarization state of the plasma membrane of the cell. In some instances, the SdChR protein comprises one or more conservative amino acid substitutions and/or one or more non-conservative amino acid substitutions. The SdChR protein containing substitutions, deletions, and/or insertions introduced into the native amino acid sequence suitably retains the ability to transport cations across a cell membrane. In some cases, a suitable SdChR protein comprises an amino acid sequence having at least 75%, at least 80%, at least 85%, at least 90%, at least 95%, at least 98%, or at least 99%, or 100%, amino acid sequence identity to the amino acid sequence depicted in FIG. 28J (SEQ ID NO: 59).

In some aspects, a depolarizing light-responsive polypeptide can be, e.g. CnChR2 (Genbank Accession No.: AHH02139), derived from *Chlamydomonas noctigama*, wherein the CnChR2 polypeptide is capable of transporting cations across a cell membrane when the cell is illuminated with light. The light used to activate the CnChR2 polypeptide can have a wavelength between about 560 and about 630 nm or can have a wavelength of about 600 nm. The CnChR2 protein can additionally comprise substitutions, deletions, and/or insertions introduced into a native amino acid sequence to increase or decrease sensitivity to light, increase or decrease sensitivity to particular wavelengths of light, and/or increase or decrease the ability of the CnChR2 protein to regulate the polarization state of the plasma membrane of the cell. In some cases, the CnChR2 protein comprises one or more conservative amino acid substitutions and/or one or more non-conservative amino acid substitutions. The CnChR2 protein containing substitutions, deletions, and/or insertions introduced into the native amino acid sequence suitably retains the ability to transport cations across a cell membrane. In some cases, a suitable CnChR2 protein comprises an amino acid sequence having at least 75%, at least 80%, at least 85%, at least 90%, at least 95%, at least 98%, or at least 99%, or 100%, amino acid sequence identity to the amino acid sequence depicted in FIG. 28K (SEQ ID NO: 60).

In other embodiments, the light-responsive cation channel protein is a CsChrimson chimeric protein derived from a CsChR (Genbank Accession No.: AHH02144) protein of *Chloromonas subdivisa* and CnChR1 protein from *Chlamydomonas noctigama*, wherein the N terminus of the protein comprises the amino acid sequence of residues 1-73 of CsChR followed by residues 79-350 of the amino acid sequence of CnChR1; is responsive to light; and is capable of mediating a depolarizing current in the cell when the cell is illuminated with light. The CsChrimson protein can additionally comprise substitutions, deletions, and/or insertions introduced into a native amino acid sequence to increase or decrease sensitivity to light, increase or decrease sensitivity to particular wavelengths of light, and/or increase or decrease the ability of the CsChrimson protein to regulate the polarization state of the plasma membrane of the cell. Additionally, the CsChrimson protein can comprise one or more conservative amino acid substitutions and/or one or more non-conservative amino acid substitutions. A CsChrimson protein containing substitutions, deletions, and/or insertions introduced into the native amino acid sequence suitably retains the ability to transport cations across a cell membrane. In some cases, a suitable CsChrimson protein comprises an amino acid sequence having at least 75%, at least 80%, at least 85%, at least 90%, at least 95%, at least 98%, or at least 99%, or 100%, amino acid sequence identity to the amino acid sequence depicted in FIG. 28L (SEQ ID NO: 61).

In some aspects, a depolarizing light-responsive polypeptide can be, e.g. ShChR1 (Genbank Accession No.: AHH02106), derived from *Stigeoclonium helveticum*, wherein the ShChR1 polypeptide is capable of transporting cations across a cell membrane when the cell is illuminated with light. The light used to activate the ShChR1 protein derived from *Stigeoclonium helveticum* can have a wavelength between about 480 and about 510 nm or can have a wavelength of about 500 nm. The ShChR1 protein can additionally comprise substitutions, deletions, and/or insertions introduced into a native amino acid sequence to increase or decrease sensitivity to light, increase or decrease sensitivity to particular wavelengths of light, and/or increase or decrease the ability of the ShChR1 protein to regulate the polarization state of the plasma membrane of the cell. Additionally, the ShChR1 protein can comprise one or more conservative amino acid substitutions and/or one or more non-conservative amino acid substitutions. A ShChR1 protein containing substitutions, deletions, and/or insertions introduced into the native amino acid sequence suitably retains the ability to transport cations across a cell membrane. In some cases, a suitable ShChR1 protein comprises an amino acid sequence having at least 75%, at least 80%, at least 85%, at least 90%, at least 95%, at least 98%, or at least 99%, or 100%, amino acid sequence identity to the amino acid sequence depicted in FIG. 28M (SEQ ID NO: 62).

In some cases, a suitable hyperpolarizing light-responsive polypeptide is an Archaerhodopsin (Arch—Genbank Accession No.: ADB03111) proton pump (e.g., a proton pump derived from *Halorubrum sodomense*) that can transport one or more protons across the plasma membrane of a cell when the cell is illuminated with light. The Arch protein can additionally have substitutions, deletions, and/or insertions introduced into a native amino acid sequence to increase or decrease sensitivity to light, increase or decrease sensitivity to particular wavelengths of light, and/or increase or decrease the ability of the Arch protein to transport ions across the plasma membrane of a target cell. Additionally, the Arch protein can comprise one or more conservative amino acid substitutions and/or one or more non-conservative amino acid substitutions. An Arch protein containing substitutions, deletions, and/or insertions introduced into the native amino acid sequence suitably retains the ability to transport ions across the plasma membrane of a target cell in response to light. In some cases, a suitable Arch protein comprises an amino acid sequence having at least 75%, at least 80%, at least 85%, at least 90%, at least 95%, at least 98%, or at least 99%, or 100%, amino acid sequence identity to the amino acid sequence depicted in FIG. 28N (SEQ ID NO: 63).

In some cases, a suitable light-activated protein is an Archaerhodopsin (ArchT—Genbank Accession No.: ABT17417) proton pump (e.g., a proton pump derived from *Halorubrum* sp. TP009) that can transport one or more protons across the plasma membrane of a cell when the cell is illuminated with light. The light can have a wavelength between about 530 and about 595 nm or can have a wavelength of about 560 nm. The ArchT protein can additionally comprise substitutions, deletions, and/or insertions introduced into a native amino acid sequence to increase or decrease sensitivity to light, increase or decrease sensitivity to particular wavelengths of light, and/or increase or decrease the ability of the ArchT protein to transport ions across the plasma membrane of a target cell. Additionally, the ArchT protein can comprise one or more conservative amino acid substitutions and/or one or more non-conservative amino acid substitutions. The ArchT protein containing substitutions, deletions, and/or insertions introduced into the native amino acid sequence suitably retains the ability to transport ions across the plasma membrane of a target cell in response to light. In some cases, a suitable ArchT protein comprises an amino acid sequence having at least 75%, at least 80%, at least 85%, at least 90%, at least 95%, at least 98%, or at least 99%, or 100%, amino acid sequence identity to the amino acid sequence depicted in FIG. 28O (SEQ ID NO: 64).

In some cases, the light-responsive polypeptide is responsive to blue light and is a proton pump protein derived from *Guillardia theta*, wherein the proton pump protein is capable of mediating a hyperpolarizing current in the cell when the cell is illuminated with blue light; such a protein is referred to herein as a "GtR3 protein" or a "GtR3 polypeptide". The GtR3 (NCBI Gene ID: 17301498) protein can additionally comprise substitutions, deletions, and/or insertions introduced into a native amino acid sequence to increase or decrease sensitivity to light, increase or decrease sensitivity to particular wavelengths of light, and/or increase or decrease the ability of the GtR3 protein to regulate the polarization state of the plasma membrane of the cell. Additionally, the GtR3 protein can comprise one or more conservative amino acid substitutions and/or one or more non-conservative amino acid substitutions. The GtR3 protein containing substitutions, deletions, and/or insertions introduced into the native amino acid sequence suitably retains the ability to hyperpolarize the plasma membrane of an excitable cell, e.g., neuron, in response to light. In some cases, a suitable GtR3 protein comprises an amino acid sequence having at least 75%, at least 80%, at least 85%, at least 90%, at least 95%, at least 98%, or at least 99%, or 100%, amino acid sequence identity to the amino acid sequence depicted in FIG. 28P (SEQ ID NO: 65).

In some cases, a light-activated protein is an *Oxyrrhis marina* (Oxy—Genbank Accession No.: ADY17806) proton pump that can transport one or more protons across the plasma membrane of a cell when the cell is illuminated with light. The light can have a wavelength between about 500 and about 560 nm or can have a wavelength of about 530 nm. The Oxy protein can additionally comprise substitutions, deletions, and/or insertions introduced into a native amino acid sequence to increase or decrease sensitivity to light, increase or decrease sensitivity to particular wavelengths of light, and/or increase or decrease the ability of the Oxy protein to transport ions across the plasma membrane of a target cell. Additionally, the Oxy protein can comprise one or more conservative amino acid substitutions and/or one or more non-conservative amino acid substitutions. The Oxy protein containing substitutions, deletions, and/or insertions introduced into the native amino acid sequence suitably retains the ability to transport ions across the plasma membrane of a target cell in response to light. In some cases, a suitable Oxy protein comprises an amino acid sequence having at least 75%, at least 80%, at least 85%, at least 90%, at least 95%, at least 98%, or at least 99%, or 100%, amino acid sequence identity to the amino acid sequence depicted in FIG. 28Q (SEQ ID NO: 66).

In some embodiments, the light-responsive proton pump protein (referred to herein as "Mac protein"—NCBI Gene ID: 13287905) is responsive to light and is derived from *Leptosphaeria maculans*, wherein the Mac proton pump protein is capable of pumping protons across the membrane of a cell when the cell is illuminated with 520 nm to 560 nm light. The Mac protein can additionally comprise substitutions, deletions, and/or insertions introduced into a native amino acid sequence to increase or decrease sensitivity to light, increase or decrease sensitivity to particular wavelengths of light, and/or increase or decrease the ability of the Mac protein to regulate the polarization state of the plasma membrane of the cell. Additionally, the Mac protein can comprise one or more conservative amino acid substitutions and/or one or more non-conservative amino acid substitutions. A Mac protein containing substitutions, deletions, and/or insertions introduced into the native amino acid sequence suitably retains the ability to pump protons across the plasma membrane of an excitable cell, e.g., neuron, in response to light. In some cases, a suitable Mac protein comprises an amino acid sequence having at least 75%, at least 80%, at least 85%, at least 90%, at least 95%, at least 98%, or at least 99%, or 100%, amino acid sequence identity to the amino acid sequence depicted in FIG. 28R (SEQ ID NO: 67).

In some cases, a suitable light-responsive chloride pump protein is derived from *Natronomonas pharaonis*; such a protein is referred to herein as an "NpHR protein" or an "NpHR polypeptide." In some embodiments, the NpHR (NCBI Gene ID: 3702828) protein can be responsive to amber light as well as red light and can mediate a hyperpolarizing current in the excitable cell, e.g., the neuron, when the NpHR protein is illuminated with amber or red light. The wavelength of light that can activate the NpHR protein can be between about 580 and 630 nm. In some embodiments, the light can be at a wavelength of about 589 nm or the light can have a wavelength greater than about 630 nm (e.g. less than about 740 nm). In another embodiment, the light has a wavelength of around 630 nm. In some embodiments, the NpHR protein can hyperpolarize a neural membrane for at least about 90 minutes when exposed to a continuous pulse of light. Additionally, the NpHR protein can comprise substitutions, deletions, and/or insertions introduced into a native amino acid sequence to increase or decrease sensitivity to light, increase or decrease sensitivity to particular wavelengths of light, and/or increase or decrease the ability of the NpHR protein to regulate the polarization state of the plasma membrane of the cell. In some embodiments, the NpHR protein comprises one or more conservative amino acid substitutions. In some embodiments, the NpHR protein comprises one or more non-conservative amino acid substitutions. A NpHR protein containing substitutions, deletions, and/or insertions introduced into the native amino acid sequence suitably retains the ability to hyperpolarize the plasma membrane of an excitable cell in response to light. In some cases, a suitable NpHR protein comprises an amino acid sequence having at least 75%, at least 80%, at least 85%, at least 90%, at least 95%, at least 98%, or at least 99%, or 100%, amino acid sequence identity to the amino acid sequence depicted in FIG. 28S (SEQ ID NO: 68).

Further disclosure related to light-responsive chloride pump proteins can be found in U.S. Patent Application Publication Nos: 2009/0093403 and 2010/0145418 as well as in International Patent Application NO: PCT/US2011/028893, the disclosures of each of which are hereby incorporated by reference in their entireties.

In some embodiments, a suitable light-responsive ion channel protein is, e.g., a DsChR protein (Genbank Accession No.: AEY68833) derived from *Dunaliella salina*, wherein the ion channel protein is capable of mediating a hyperpolarizing current in the cell when the cell is illuminated with light. The light can have a wavelength between about 470 nm and about 510 nm or can have a wavelength of about 490 nm. The DsChR protein can additionally comprise substitutions, deletions, and/or insertions introduced into a native amino acid sequence to increase or decrease sensitivity to light, increase or decrease sensitivity to particular wavelengths of light, and/or increase or decrease the ability of the DsChR protein to regulate the polarization state of the plasma membrane of the cell. Additionally, the DsChR protein can comprise one or more conservative amino acid substitutions and/or one or more non-conservative amino acid substitutions. A DsChR protein containing substitutions, deletions, and/or insertions introduced into the native amino acid sequence suitably retains the ability to transport ions across the plasma membrane of an excitable cell, e.g., a neuron, in response to light. In some cases, a suitable DsChR protein comprises an amino acid sequence having at least 75%, at least 80%, at least 85%, at least 90%, at least 95%, at least 98%, or at least 99%, or 100%, amino acid sequence identity to the amino acid sequence depicted in FIG. 28T (SEQ ID NO: 69).

In some cases, the light-responsive protein is a chimeric protein comprising Arch-TS-p2A-ASIC 2a-TS-EYFP-ER-2 (Champ). A Champ protein of the present disclosure comprises an Arch domain and an Acid-sensing ion channel (ASIC)-2a domain. Light activation of Champ activates a proton pump (Arch domain) that activates the ASIC-2a proton-activated cation channel (ASIC-2a domain). In some cases, a suitable Champ protein comprises an amino acid sequence having at least 75%, at least 80%, at least 85%, at least 90%, at least 95%, at least 98%, or at least 99%, or 100%, amino acid sequence identity to the amino acid sequence depicted in FIG. 28U (SEQ ID NO: 70).

In some cases, a hyperpolarizing light-responsive ion channel is based on a depolarizing light-responsive ion channel, as described in, e.g., PCT App. No. PCT/US2015/23087, which is incorporated herein by reference. In some cases, a light-responsive anion channel polypeptide is based on a C1C2 protein (Genbank Accession No. AHA49646). In some cases, a suitable hyperpolarizing light-responsive polypeptide is based on the amino acid sequence of the protein ChR2 (Genbank Accession No. AER29835). In some cases, a suitable hyperpolarizing light-responsive polypeptide is based on the amino acid sequence of the protein C1V1 (Genbank Accession No. AEL28924).

Use of Indicator Dyes

In some cases, a target cell is modified such that it expresses in its cell membrane a light-responsive polypeptide of the present disclosure; where the modified target cell includes an indicator dye. The indicator dye can provide for detection of a change in the intracellular calcium ion concentration, a change in the intracellular sodium ion concentration, etc.

In some cases, the indicator dye is a fluorescent dye. In such cases, fluorescent dyes of interest include fluorescein, fluorescein isothiocyanate (FITC), rhodamine, tetramethylenerhodamine isothiocyanate (TRITC), sulforhodamine 101 acid chloride (Texas Red®), phycoerythrin (PE), allophycocyanin, phycoerythrin-Texas Red® (PETR), 4-methylumbelliferone, etc.

In some cases, the indicator dye is a calcium indicator dye. Suitable calcium indicator dyes include, e.g., Indo-1, Fura-2, and Fluo-3, Calcium Green@, Fluo-4, etc.

In some cases, the indicator dye is a sodium indicator dye. Suitable sodium indicator dyes include, e.g., sodium-binding benzofuran isophthalate (SBFI), Sodium Green™, CoroNa™ Green, CoroNa™ Red, etc.); and proton indicator dyes (2',7'-bis-(carboxyethyl)-5-(and-6)-carboxyfluorescein (BCECF), etc.

Devices

The present disclosure provides systems and devices that can be used to carry out aspects of the subject methods (methods of modulating the activity of a target cell; treatment methods). In some cases, a system of the present disclosure includes a light-activated polypeptide of the present disclosure, as described above, and one or more devices for delivering light of an activating wavelength to a target tissue or cell. Devices that find use in carrying out a method of the present disclosure include delivery devices that can be used to deliver a nucleic acid (or recombinant expression vector) comprising a nucleotide sequence encoding a light-activated polypeptide of the present disclosure to target cells and tissues; delivery devices that can be used to deliver a light-activated polypeptide of the present disclosure to target cells and tissues; light-generating devices that can be used to illuminate target cells that express a light-activated polypeptide of the present disclosure; and control devices that can be used to control the delivery of light to specific target cells or tissues. Each of these components is further described below.

Delivery Devices

Aspects of the present disclosure include delivery devices that can be used to deliver a light-activated polypeptide of the present disclosure, or a nucleic acid (or recombinant expression vector) comprising a nucleotide sequence encoding a light-activated polypeptide of the present disclosure, to a target cell. A delivery device of the present disclosure may provide regular, irregular, programmed, or clinician- or patient-activated doses of the light-activated polypeptide of the present disclosure, or the nucleic acid (or recombinant expression vector) comprising a nucleotide sequence encoding a light-activated polypeptide of the present disclosure, to one or more target cells to ensure that the target cells continue to express the light-activated polypeptide for a desired period of time.

The subject delivery devices may generally include various components, such as reservoirs, pumps, actuators, tubing components, needles, catheters, and any other suitable components for delivering the subject pharmaceutical compositions to a target cell or tissue of a patient. Delivery devices may also include components that facilitate computerized operation, such as a power source, a processor comprising a memory, a user input device, and/or a graphical user interface. In some cases, a delivery device may be completely or partially implantable within a patient. In some cases, a delivery device may be operated by a caregiver, wherein the device is introduced into a portion of the patient's body, e.g., into the patient's brain, and a subject pharmaceutical composition is delivered to a target tissue, e.g., a portion of the patient's brain. In some cases, following delivery of the pharmaceutical composition, the device may be removed. In other instances, the device may be kept in place for later delivery of additional pharmaceutical compositions.

Light-Generating Devices

Aspects of the present disclosure include light-generating devices that can be used to deliver light to target cells that express a light-activated polypeptide of the present disclosure. The terms "light-generating device", "optical applicator" and "light applicator" are used interchangeably herein. Light-generating devices in accordance with embodiments of the present disclosure can generally produce light of a variety of different wavelengths from one or more light sources on the device. In some cases, a light-generating device may include a light cuff or sleeve that can be placed around or near target cells expressing a light-activated polypeptide of the present disclosure. In some cases, a portion of the light source or the entire light source is implantable. The subject light-generating devices may be of any useful configuration for stimulating the light-activated proteins disclosed herein. In some cases, for example, a light-generating device (i.e., optical applicator) may comprise components that facilitate exclusive illumination of a target cell or tissue. For example, in some cases, a light-generating device may exclusively direct light to a target cell, a portion of a target cell, e.g., a particular axon of a nerve cell, or a specific anatomical structure, such as, e.g. a bundle of nerve fibers, a target tissue, or a portion of the spinal cord. By "exclusively direct light" is meant that the light-generating device only delivers light to the specific target structure, and does not illuminate other structures. For example, in some embodiments, a light-generating device may be configured to illuminate an axon of a nerve cell, but not to illuminate any other portion of the nerve cell. In this way, the light from the light-generating device only affects light-activated proteins in the specific target structure that is illuminated.

Aspects of the disclosure include light delivery devices (i.e., optical applicators) that include one or more optical sources that are configured to deliver light in one or more 2-dimensional and/or 3-dimensional patterns to one or more target locations, including but not limited to one or more portions (e.g., multiple layers) of a target tissue and/or anatomical structure. In certain instances, a light delivery device may include a plurality of light sources (e.g., a plurality of laser light sources, light-emitting diodes (LEDs), and the like), as well as any suitable number of light guides that are configured to bend or shape light in a desired manner. Examples of light delivery devices are provided in U.S. Pat. No. 8,545,543, the disclosure of which is hereby incorporated by reference in its entirety.

In some cases, a light-generating device (i.e., optical applicator) may not completely surround the region containing a target cell expressing a light-activated protein, but, rather, can have a U-shape. In some cases, a light-generating device can have an attachment arm that can be used to guide the light-generating device to a specific region or target structure, e.g., a specific neuronal region. The attachment arm can be removed following implantation of the light-generating device or can be left in place to fix the position of the light-generating device in proximity to the target cells of interest.

In some cases, the subject light-generating devices may comprise an inner body, the inner body having at least one means for generating light which is connected to a power source. In some embodiments, the power source can be an internal battery for powering the light-generating device. In some cases, an implantable light-generating device may comprise an external antenna for receiving wirelessly transmitted electromagnetic energy from an external source for powering the device. The wirelessly transmitted electromagnetic energy can be a radio wave, a microwave, or any other electromagnetic energy source that can be transmitted from an external source to power the light-generating device. In some embodiments, the light-generating device is controlled by, e.g., an integrated circuit produced using semiconductor or other processes known in the art.

In some cases, the light-generating device comprises a light emitting diode (LED). In some embodiments, the LED can generate blue and/or green light. In other embodiments, the LED can generate amber and/or yellow light. In some cases, several micro LEDs are embedded into the inner body of the light-generating device. In other cases, the light-generating device is a solid state laser diode or any other means capable of generating light. The light-generating device can generate light having a wavelength and intensity sufficient to activate a light-activated polypeptide of the present disclosure. In some cases, a light-generating device produces light having an intensity of any of about 0.05 $mW/mm^2$, 0.1 $mW/mm^2$, 0.2 $mW/mm^2$, 0.3 $mW/mm^2$, 0.4 $mW/mm^2$, 0.5 $mW/mm^2$, about 0.6 $mW/mm^2$, about 0.7 $mW/mm^2$, about 0.8 $mW/mm^2$, about 0.9 $mW/mm^2$, about 1.0 $mW/mm^2$, about 1.1 $mW/mm^2$, about 1.2 $mW/mm^2$, about 1.3 $mW/mm^2$, about 1.4 $mW/mm^2$, about 1.5 $mW/mm^2$, about 1.6 $mW/mm^2$, about 1.7 $mW/mm^2$, about 1.8 $mW/mm^2$, about 1.9 $mW/mm^2$, about 2.0 $mW/mm^2$, about 2.1 $mW/mm^2$, about 2.2 $mW/mm^2$, about 2.3 $mW/mm^2$, about 2.4 $mW/mm^2$, about 2.5 $mW/mm^2$, about 3 $mW/mm^2$, about 3.5 $mW/mm^2$, about 4 $mW/mm^2$, about 4.5 $mW/mm^2$, about 5 $mW/mm^2$, about 5.5 $mW/mm^2$, about 6 $mW/mm^2$, about 7 $mW/mm^2$, about 8 $mW/mm^2$, about 9 $mW/mm^2$, or about 10 $mW/mm^2$, inclusive, including values in between these numbers. In some embodiments, the light-generating device produces light at a frequency of at least about 5 Hz, such as up to about 20 Hz, at least about 10 Hz, such as up to about 25 Hz, such as up to about 50 Hz, such as up to about 75 Hz, such as up to about 100 Hz.

The subject light-generating devices are generally capable of generating light having a wavelength ranging from about 350 nm, up to about 360 nm, up to about 370 nm, up to about 380 nm, up to about 390 nm, up to about 400 nm, up to about 410 nm, up to about 420 nm, up to about 430 nm, up to about 440 nm, up to about 450 nm, up to about 460 nm, up to about 470 nm, up to about 475 nm, up to about 480 nm, up to about 490 nm, up to about 500 nm, up to about 510 nm, up to about 520 nm, up to about 530 nm, up to about 540 nm, up to about 550 nm, up to about 560 nm, up to about 570 nm, up to about 580 nm, up to about 590 nm, up to about 600 nm, up to about 610 nm, up to about 620 nm, up to about 630 nm, up to about 635 nm, up to about 640 nm, up to about 650 nm, up to about 660 nm, up to about 670 nm, up to about 680 nm, up to about 690 nm, up to about 700 nm, up to about 710 nm, up to about 720 nm, up to about 730 nm, up to about 740 nm, and/or up to about 750 nm. Subject light-generating devices of the present disclosure are capable of generating light having a wavelength sufficient to activate a subject light-activated protein. Such light-generating devices are capable of generating light having a wavelength ranging from about 550 nm to about 650 nm, from about 600 nm to about 700 nm, from about 650 nm to about 750 nm.

In some cases, a light generating device may generate red light having a wavelength ranging from about 600 nm to about 775 nm. For example, a light generating device may generate red light having a wavelength ranging from about 600 nm to about 650 nm, from about 625 nm to about 675 nm, from about 650 nm to about 700 nm, from about 675 nm to about 725 nm, from about 700 nm to about 750 nm, from about 725 nm to about 775 nm, from about 600 nm to about 700 nm.

In some cases, a suitable light-generating device may include one or more optical fibers that can transmit light from a light source and deliver the light to a target structure. The optical fibers may comprise plastic or glass materials, and in some embodiments may be suitably flexible to facilitate placement of the light-generating device in locations that could not be accommodated by rigid structures. For example, in some cases, a light-generating device may comprise a light source that generates light, as well as one or more optical fibers that can be placed in various locations on or in the patient's body. Light from the light source can pass through the optical fiber, passing around corners and bends in the optical fiber, and emerge at the end of the optical fiber to deliver light to a target structure.

In some cases, the subject light-generating devices may comprise a plurality of light sources that can be used to illuminate a target tissue with different wavelengths of light. For example, in some cases, a light-generating device may comprise a first light source that generates light of a first wavelength, e.g., red light, and a second light source that generates light of a second wavelength, e.g., blue light. Such light-generating devices may be used to simultaneously illuminate the same target tissue with light of both wavelengths, or may alternately illuminate the target tissue with light of the first wavelength and light of the second wavelength. In some cases, such light generating devices may be used to deliver light from the same light source to different target tissues. For example, in some instances a light-generating device may deliver light of a first wavelength to a first target tissue, and may deliver light of a second wavelength to a different target tissue.

Suitable light-generating devices can comprise an implantable optical applicator which is configured to deliver light to a target area, and an operatively coupled light source which is configured to generate light of certain intensities and wavelengths.

Control Devices

Aspects of the disclosure include a controller, processor (e.g., a computer) and computer readable medium that are configured or adapted to control or operate one or more components of the subject systems. In some cases, a system includes a controller that is in communication with one or more components of the systems, as described herein, and is configured to control aspects of the systems and/or execute one or more operations or functions of the subject systems. In some cases, a system includes a processor and a computer-readable medium, which may include memory media and/or storage media. Applications and/or operating systems embodied as computer-readable instructions on computer-readable memory can be executed by the processor to provide some or all of the functionalities described herein.

In some cases, a system includes a user interface, such as a graphical user interface (GUI), that is adapted or configured to receive input from a user, and to execute one or more of the methods as described herein. In some embodiments, a GUI is configured to display data or information to a user.

Aspects of the present disclosure include control devices that can control, or modulate, the amount of light that is emitted from the subject light-generating devices. In some embodiments, a control device may be configured to modulate the wavelength and/or the intensity of light that is delivered to a target tissue from a light-generating device. In some embodiments, a control device may be configured to modulate the frequency and/or duration of light that is delivered to a target tissue from a light-generating device. For example, in some embodiments, a control device may be configured to deliver pulses of light from the light-generating device to a target tissue. The control device can modulate the frequency and/or duration of the light pulses such that the target tissue is illuminated with light from the light-generating device, e.g., at a regular or irregular rate, according to a user input, etc. In some embodiments, a control device can produce pulses of light from the light-generating device that have a duration ranging from about 1 millisecond or less, up to about 1 second, up to about 10 seconds, up to about 20 seconds, up to about 30 seconds, up to about 40 seconds, up to about 50 seconds, up to about 60 seconds or more. In some embodiments, a control device can produce pulses of light from the light-generating device that have a frequency of 1 pulse per millisecond, up to about 1 pulse per second, up to about 1 pulse per minute, up to about 1 pulse per 10 minutes, up to about 1 pulse per 20 minutes, up to about 1 pulse per 30 minutes.

In some cases, a subject control device may comprise a power source that can be mounted to a transmitting coil. In some embodiments, a battery can be connected to the power source for providing power thereto. A switch can be connected to the power source, allowing an operator (e.g., a patient or caregiver) to manually activate or deactivate the power source. In some embodiments, upon activation of the switch, the power source can provide power to the light-generating device through electromagnetic coupling between the transmitting coil on the control device and an external antenna of an implantable light-generating device (such as a light cuff or sleeve). The transmitting coil can establish an electromagnetic coupling with the external antenna of the implantable light-generating device when in proximity thereof, for supplying power to the light-generating device and for transmitting one or more control signals to the light-generating device. In some embodiments, the electromagnetic coupling between the transmitting coil of the control device and the external antenna of the implantable light-generating device can be radio-frequency magnetic inductance coupling. When radio-frequency magnetic inductance coupling is used, the operational frequency of the radio wave can be between about 1 and 20 MHz, inclusive, including any values in between these numbers (for example, about 1 MHz, about 2 MHz, about 3 MHz, about 4 MHz, about 5 MHz, about 6 MHz, about 7 MHz, about 8 MHz, about 9 MHz, about 10 MHz, about 11 MHz, about 12 MHz, about 13 MHz, about 14 MHz, about 15 MHz, about 16 MHz, about 17 MHz, about 18 MHz, about 19 MHz, or about 20 MHz). However, other coupling techniques may be used, such as an optical receiver, infrared, or a biomedical telemetry system (See, e.g., Kiourti, "Biomedical Telemetry: Communication between Implanted Devices and the External World, Opticon1826, (8): Spring, 2010).

Systems

A system of the present disclosure is an optical stimulation system comprising a delivery device, a light-generating device, a control device. In some cases, a subject system comprises a container comprising a nucleic acid or recombinant expression vector of the present disclosure (where the nucleic acid or recombinant expression vector comprises a nucleotide sequence encoding a light-responsive polypeptide of the present disclosure), an implantable optical applicator, a light source operatively coupled to the implantable optical applicator, a controller (i.e., control device), a power supply and an implantable illuminance sensor. In some cases, a subject system comprises a container comprising a light-responsive polypeptide of the present disclosure, an implantable optical applicator, a light source operatively coupled to the implantable optical applicator, a controller (i.e., control device), a power supply and an implantable illuminance sensor. In some cases, the implantable optical applicator is configured to deliver light to a targeted tissue structure after implantation in a location adjacent to the targeted tissue structure. The controller of a subject system causes the power supply to allow current to flow to the light source to cause an emission of photons to the implantable light actuator based at least in part upon an output signal from the implantable illuminance sensor.

In some instances, a system of the present disclosure comprises an implantable illuminance sensor that is positioned such that it captures at least a portion of the photons directed toward the targeted tissue structure by the implantable light applicator. The system further may comprise an implantable input sensor configured to produce an output signal that is correlated to the illuminance of the implantable optical applicator at a position of photon emission before intersection of such photons with the targeted tissue structure. The controller (i.e., control device) may be operatively coupled to the implantable input sensor, such that it may compare the output signal from both the implantable input sensor and the implantable illuminance sensor to determine whether unexpected losses are being experienced. The controller may be configured to react to a loss level that is past a predetermined threshold loss level. The controller may be configured to react by flagging the event on the loss level being past the predetermined level in a software log file maintained by the controller. The controller may be configured to stop causing the power supply to allow current to flow to the light source.

The implantable illuminance sensor and input sensor of a system of the present disclosure can be a photovoltaic cell, a photodiode, a pyroelectric sensor, a photoresistor, a photoconductor, a phototransistor, or a photogalvanic sensor.

The system may further comprise a physiologic sensor configured to produce an output signal that is correlated with a physiologic parameter believed to be variable at least in part in response to the input of light to the target tissue structure. The physiologic sensor can be, e.g., an electromyogram sensor, an electroneurogram sensor, an electroencephalogram sensor, an electrocardiogram sensor, a pressure sensor, a temperature sensor, a chemometric sensor, a motion sensor, an accelerometer, a gyro, a strain sensor, an impedance sensor, or a capacitance sensor.

The controller of a system of the present disclosure may be configured to react to an output of the physiologic sensor being past a certain predetermined threshold. The controller may be configured to react by flagging the event on the loss level being past the predetermined level in a software log file maintained by the controller. The controller may be configured to stop causing the power supply to allow current to flow to the light source.

Utility

A method of the present disclosure for modulating the activity of a target cell is useful in a variety of research, diagnostic, imaging, and treatment applications. The subject methods generally involve introducing a light-activated polypeptide of the present disclosure, or a nucleic acid (or recombinant expression vector) comprising a nucleotide sequence encoding a light-activated polypeptide of the present disclosure, into a target cell, such that the target cell expresses a light-activated cation channel protein and inserts it into the membrane; and illuminating the target cell with light of an activating wavelength. Illumination of the target cell with light of an activating wavelength causes the light-activated cation channel protein to allow one or more cations to pass through the plasma membrane of the target cell. The passage of the cations through the plasma membrane of the target cell has a desired effect, such as, e.g., modulating the membrane potential of the plasma membrane. In some cases, the passage of the cation species through the plasma membrane may be used to modulate one or more neurological responses or processes in a patient, and may therefore by used to treat a disease or condition in the patient. As such, in some cases, the subject methods involve treating a patient for a condition, such as a neurological condition. In some cases, the subject methods involve treating a patient for a condition, such as a neurological condition, using the systems and devices provided herein.

Using the subject methods, the ordinarily skilled artisan will be able to perform in vivo recording and imaging of the activity of excitable cells, such as neurons. In some cases, in vivo calcium imaging may be performed substantially simultaneously on 100 or more neurons at 30 Hz or more for each neuron.

The subject methods also find use in analyzing or mapping the connectivity of neurons in target tissues, such as the brain. For example, the subject methods may be used to measure the individual activity of a plurality of neurons in a target tissue volume in response to a stimulus, either to one or more neurons in the local area of the target tissue that is being analyzed, or to sites distal to the measurement site. The stimulus may be a sensory stimulation, an electrical stimulation through an electrode, or an optical stimulation. By observing the pattern of activity of the measured neurons in response to various stimuli and other manipulations, one may deduce the connectivity of the neurons in the observed area of the target tissue.

In some embodiments, the neuronal regions targeted for measurement or stimulation by the subject methods include any neocortical region. With proper tissue exposure, suitable target neural regions include: the hypothalamus, entorhinal and hippocampal formation cortex, mammillary bodies, septum, bed nucleus of stria terminalis, dorsal and ventral striatum, thalamus, amygdala, accumbens, brainstem, and subcortical structures in general. The target location may include: a cell, a portion of a cell, a plurality of cells, a bundle of nerve fibers, a neuromuscular junction, a central nervous system (CNS) tissue, a peripheral nervous system (PNS) tissue, muscle or cardiac tissue, or an anatomical region.

Modeling of Diseases or Conditions Involving Action Potentials

In some cases, the subject methods can be used for studying and/or modeling certain diseases or conditions in a subject, such as conditions that involve or result from increased formation of action potentials and/or an improper promotion of action potential formation within a cell. For example, the subject methods may be used to specifically increase the formation of action potentials in target cells, such as specific target nerve cells, to study the effects of promoting action potential formation in those cells. In some embodiments, the subject methods may be used to selectively increase the formation of action potentials in certain portions of a target cell, such as an axon of a target nerve cell, to study the effects of promoting action potential formation in the selected portion of the target cell. Such methods may be used as models of diseases or conditions in which action potentials fire at abnormally high rates in a target cell or a portion thereof, or wherein action potentials are erroneously formed in a target cell or a portion thereof.

In some embodiments, the subject methods may be used in animal models (including but not limited to transgenic animal models) of diseases of conditions associated with abnormal formation of action potentials within target cells, or portions thereof, or associated with the increased formation of action potentials within target cells, or portions thereof. For example, in some embodiments, a target cell of an animal (such as a nerve cell, e.g., a brain cell of a rodent) may be contacted with a nucleic acid encoding a subject engineered light-activated cation channel protein so that the cation channel protein is expressed by the target cell. Next, the target cell is illuminated with light of an activating wavelength to promote the formation of action potentials in the target cell. The effect of the promotion of action potential formation within the target cell, or a portion thereof, on the animal can then be examined. The use of transgenic animals that overexpress one or more gene products, or the use of "knock-out" transgenic animals that fail to express one or more gene products, may be used to investigate the role of specific gene products in the formation of action potentials in target cells.

Methods of Screening

In some embodiments, the subject methods may be used, e.g., for screening compounds that may be effective in treating diseases or conditions involving the formation of action potentials in target cells, or the increased formation of action potentials in target cells. In some embodiments, the screening methods involve culturing cells in vitro, where the cultured cells comprise a light-activated polypeptide of the present disclosure. The cultured cell expressing the light-activated polypeptide of the present disclosure is contacted with a test compound; and the cell is then exposed to light of an activating wavelength to promote the formation of action potentials within the cell or a portion thereof. The ability of the test compound to elicit a desired effect or response from the cell while action potential formation is promoted may be useful in the treatment of a particular disease or condition.

In some embodiments, the subject methods find use in screening, in an in vivo non-human animal model, for neuronal circuit elements diagnostic of or causative for neuropsychiatric disease. For example, the non-human animal can be modified to express a light-responsive polypeptide of the present disclosure in one or more neuron cells, in a particular neuronal tissue, etc. Neuropsychiatric disease of interest may include disorders of mood and affect, anxiety, psychosis, personality, etc. The animal model may be any suitable model, including, but not limited to, rodents, cats, dogs, monkeys, and non-human primates. Perturbations used to model a neuropsychiatric disease include genetic models of neurological or psychiatric disease, such as autism; chronically induced models as with kainate or pilocarpine-induced epilepsy or chronic stress-induced depression; and acutely induced models as with hallucinogens or psychotogenic agents such as ketamine or phencyclidine (PCP). By comparing the difference in activity pattern between neurons in normal target tissue and neurons in abnormal target tissue, neural correlates of the neuropsychiatric disorder may be identified. Optical control of neurons in the target tissue may then allow identification of causative neuronal activity patterns for a particular neuropsychiatric disorder. These manipulations may potentially provide novel treatment targets.

In some embodiments, the subject methods find use in methods for identifying a treatment, e.g., a therapeutic treatment, with a desired activity on a group of neurons. If the desired outcome is known, then the present system and method may be used to screen for treatments, including, but not limited to, pharmacological agents, nonchemical based therapeutic treatment; behavioral treatment; electrical, magnetic, or optical based neural-modulation treatment; etc., that will bring about the desired neuronal activity pattern. The screening may be performed in any suitable animal model, either normal, or a model for a neurological disorder, such as Alzheimer's and Parkinson's disease, mild cognitive impairment, other dementias, and Down's Syndrome, as well as schizophrenia, autism, mood, affective, anxiety, and personality/developmental disorders.

Methods of Treatment

In some cases, a subject method involves modulating the activity of a target cell in vivo. In some cases, a nucleic acid (or recombinant expression vector) comprising a nucleotide sequence encoding a light-responsive polypeptide of the present disclosure is introduced into a target cell, where the encoded light-responsive polypeptide is produced in the target cell; and the light-responsive polypeptide is activated by exposure to light of an activating wavelength. In some cases, a nucleic acid (or recombinant expression vector) comprising a nucleotide sequence encoding a light-responsive polypeptide of the present disclosure is administered to an individual in need thereof, such that the light-responsive polypeptide is produced in a target cell (e.g., such that the light-responsive polypeptide is present on the plasma membrane of a target cell), thereby allowing the activity of the target cell to be modulated by light of an activating wavelength. In some cases, a light-responsive polypeptide of the present disclosure is administered to an individual in need thereof, such that the light-responsive polypeptide is introduced into a target cell (e.g., such that the light-responsive polypeptide is present on the plasma membrane of a target cell), thereby allowing the activity of the target cell to be modulated by light of an activating wavelength. Once a light-responsive polypeptide of the present disclosure is present in the plasma membrane of a target cell(s) in an individual, the target cell(s) is exposed to light of an activating wavelength, thereby depolarizing the target cell(s).

In some embodiments, the subject methods are used to treat a patient for a condition or disorder, such as a neurological condition or disorder, by optogenetically modulating the action potentials of target cells within the patient. In some embodiments, the subject methods involve introducing a light-responsive polypeptide of the present disclosure into a target tissue within the patient. In some embodiments, introduction of a light-responsive polypeptide of the present disclosure into the target tissue is accomplished using a subject delivery device. A polynucleotide (e.g., a recombinant expression vector) encoding a light-responsive polypeptide of the present disclosure is introduced into the target tissue, and the light-responsive polypeptide is expressed by target cells (e.g., nerve cells) in the target tissue and inserted into the plasma membrane of the target cells.

Next, a light-generating device is positioned to illuminate the target tissue with light of an activating wavelength when the light-generating device is activated. The light-generating device is activated (either by the patient, or by a caregiver (e.g., medical personnel)) to deliver light to the target tissue to cause the light-responsive polypeptide of the present disclosure to allow cations (e.g., sodium cations) to pass through the plasma membrane and depolarize the plasma membrane, thus promoting the formation of action potentials within the cell(s) of the target tissue.

As such, the formation of action potentials within the cell is increased for the duration of the effect of the light pulse and the resulting depolarization of the plasma membrane. Accordingly, the subject methods may be used to promote the formation of an action potential in a nerve cell by introducing a light-responsive polypeptide of the present disclosure into the nerve cell and illuminating the nerve cell with light of an activating wavelength from a light-generating device. As the duration of the action potential increase can be tailored to outlast the duration of a light pulse, increase of action potential formation may be achieved using pulsed light delivery, rather than continuous light delivery.

In some case, a method of the present disclosure involves treating a subject for a disorder by promoting the formation of action potentials in a target tissue. Accordingly, in some cases, the subject methods involve treating a subject by introducing into a target cell a light-responsive polypeptide of the present disclosure. Polynucleotides encoding these proteins are introduced into the target cell, and the proteins are expressed by the target cell and inserted into the plasma membrane of the target cell. Next, the target cell is illuminated with light of an activating wavelength from a light-generating device to cause the light-activated cation channel protein to allow cations (e.g., sodium cations) to flow through the plasma membrane from outside of the cell to the inside of the cell.

Once inside the cell, the cations depolarize the membrane to promote the formation of an action potential. The depolarization of the membrane promotes the formation of an action potential and therefore allows the cell to, e.g., generate action potentials in surrounding cells, e.g., neighboring nerve cells; mediate the release of neurotransmitters, modulators, or hormones; mediate muscle contraction; and the like until the effect of the membrane depolarization dissipates. Accordingly, the subject methods may be used to treat a subject for a disorder by promoting the formation of action potentials within a target cell. Since the duration of the membrane depolarization can be tailored to outlast the duration of the light pulse, promotion of action potential formation may be achieved using pulsed light delivery, rather than continuous light delivery.

A treatment method of the present disclosure may be used to treat any disease or condition in promoting or increasing the formation of an action potential a target cell, or along a particular portion of a target cell, would have a therapeutic effect for the patient. Examples of therapeutic applications of the subject methods include, without limitation, neurological disorders, such as visual impairment, memory disorders, and the like.

In some cases, the subject methods find use in the treatment of a condition or disorder, such as a neurological or psychiatric condition using optogenetic control (closed loop control). As real time activity of neurons is monitored using the subject methods, a controller may be configured to modulate the activity of neurons in response to the imaged activity signals in such a way as to treat or reduce symptoms of the condition or disorder, at the behavioral and/or physiological levels.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-44 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A light-activated polypeptide that comprises an amino acid sequence having at least about 85% amino acid sequence identity to a contiguous stretch of at least 250 amino acids of the following amino acid sequence:

(SEQ ID NO: 1)
MAHAPGTDQMFYVGTMDGWYLDTKLNSVAIGAHWSCFIVLTITTFYLGYE

SWTSRGPSKRTSFYAGYQEEQNLALFVNFFAMLSYFGKIVADTLGHNFGD

-continued

VGPFIIGFGNYRYADYMLTCPMLVYDLLYQLRAPYRVSCSAIIFAILMSG

VLAEFYAEGDPRLRNGAYAWYGFGCFWFIFAYSIVMSIVAKQYSRLAQLA

QDTGAEHSLHVLKFAVFTFSMLWILFPLVWAICPRGFGWIDDNWTEVAHC

VCDIVAKSCYGFALARFRKTYDEELFRLLEQLGHDEDEFQKLELDMRLSS

NGERLRRLS.

Aspect 2. The light-activated polypeptide of aspect 1, wherein the amino acid sequence comprises an H33R and/or an R136H substitution relative to the amino acid sequence depicted in aspect 1.

Aspect 3. The light-activated polypeptide of aspect 1 or aspect 2, comprising a heterologous membrane trafficking signal.

Aspect 4. The light-activated polypeptide of aspect 3, wherein the heterologous membrane trafficking signal comprises the amino acid sequence KSRITSEGEYIPLDQIDIN (SEQ ID NO: 7).

Aspect 5. The light-activated polypeptide of any one of aspects 1-4, comprising an endoplasmic reticulum (ER) export signal.

Aspect 6. The light-activated polypeptide of aspect 5, wherein the ER export signal comprises the amino acid sequence FCYENEV (SEQ ID NO: 13).

Aspect 7. A nucleic acid comprising a nucleotide sequence encoding the light-activated polypeptide of any one of aspects 1-6.

Aspect 8. The nucleic acid of aspect 7, wherein the nucleotide sequence is operably linked to a transcriptional control element that is functional in a eukaryotic cell.

Aspect 9. The nucleic acid of aspect 7 or aspect 8, wherein the transcriptional control element is an inducible promoter.

Aspect 10. The nucleic acid of aspect 7 or aspect 8, wherein the transcriptional control element is a neuron-specific promoter.

Aspect 11. A recombinant expression vector comprising the nucleic acid of any one of aspects 7-10.

Aspect 12. The recombinant expression vector of aspect 11, wherein the expression vector is a retroviral vector, a lentiviral vector, or an adeno-associated virus vector.

Aspect 13. A mammalian cell comprising the light-activated polypeptide of any one of aspects 1-6 in the cell membrane, wherein the light-activated polypeptide is capable of mediating a depolarizing current in the cell when the cell is illuminated with light of a wavelength of from about 600 nm to about 700 nm.

Aspect 14. The mammalian cell of aspect 13, wherein the cell is a neuronal cell.

Aspect 15. The mammalian cell of aspect 14, wherein the cell is a neuron of the neocortex.

Aspect 16. The mammalian cell of aspect 14, wherein the cell is a neuron of the primary visual cortex.

Aspect 17. A method of modulating the voltage potential of a mammalian cell in response to a light stimulus, the method comprising exposing a mammalian cell that comprises the light-activated polypeptide of any one of aspects 1-6 in the plasma membrane of the cell, wherein in response to exposure to a light stimulus, the voltage potential of the cell is modulated.

Aspect 18. The method of aspect 17, wherein the cell is a neuronal cell.

Aspect 19. The method of aspect 17 or 18, wherein the cell is in vitro.

Aspect 20. The method of aspect 17 or 18, wherein the cell is in vivo.

Aspect 21. The method of any one of aspects 17-20, wherein the light has a wavelength of from 600 nm to 700 nm.

Aspect 22. A method of modulating activity of a mammalian cell that comprises the light-activated polypeptide of any one of aspects 1-6, the method comprising activating the light-activated polypeptide with light.

Aspect 23. The method of aspect 22, wherein the light has a wavelength of from 600 nm to 700 nm.

Aspect 24. The method of aspect 22, wherein the cell is a neuronal cell.

Aspect 25. The method of any one of aspects 22-24, wherein the cell is in vivo.

Aspect 26. The method of aspect one of aspects 22-25, wherein the cell expresses a genetically encoded calcium indicator (GECI).

Aspect 27. The method of aspect 26, wherein the GECI comprises an amino acid sequence having at least 85% amino acid sequence identity to the amino acid sequence depicted in any one of FIGS. 26A-26S.

Aspect 28. The method of any one of aspects 22-27, wherein the cell further comprises a hyperpolarizing light-responsive polypeptide or a depolarizing light-responsive polypeptide other than the light-responsive polypeptide of aspect 1.

Aspect 29. The method of aspect 28, wherein the hyperpolarizing light-responsive polypeptide or depolarizing light-responsive polypeptide comprises an amino acid sequence having at least 85% amino acid sequence identity to the amino acid sequence depicted in any one of FIGS. 28A-28U.

Aspect 30. A device comprising: a) a container comprising the light-responsive polypeptide of any one of aspects 1-6, the nucleic acid of any one of aspects 7-10, or the recombinant vector of aspect 11 or 12; and b) a light source.

Aspect 31. The device of aspect 30, wherein the device is implantable.

Aspect 32. The device of aspect 30 or aspect 31, wherein the light source is an optical fiber.

Aspect 33. A system comprising: a) a container comprising the light-responsive polypeptide of any one of aspects 1-6, the nucleic acid of any one of aspects 7-10, or the recombinant vector of aspect 11 or 12; b) an implantable optical applicator configured to deliver light to a targeted tissue structure after implantation in a location adjacent to the targeted tissue structure; c) a light source operatively coupled to the implantable optical applicator; d) a controller; e) a power supply; and f) an implantable illuminance sensor, wherein the controller causes the power supply to allow current to flow to the light source to cause an emission of photons to the implantable light actuator based at least in part upon an output signal from the implantable illuminance sensor, wherein the implantable illuminance sensor is configured such that it can be positioned to capture at least a portion of the photons directed toward the targeted tissue structure by the implantable light applicator.

Aspect 34. The system of aspect 33, wherein the implantable illuminance sensor is selected from the group consisting of: a photovoltaic cell, a photodiode, a pyroelectric sensor, a photoresistor, a photoconductor, a phototransistor, and a photogalvanic sensor.

Aspect 35. The system of aspect 33, wherein the implantable input sensor is selected from the group consisting of: a photovoltaic cell, a photodiode, a pyroelectric sensor, a photoresistor, a photoconductor, a phototransistor, and a photogalvanic sensor.

Aspect 36. The system of aspect 33, further comprising a physiologic sensor configured to produce an output signal that is correlated with a physiologic parameter believed be variable at least in part in response to the input of light to the targeted tissue structure.

Aspect 37. The system of aspect 36, wherein the physiologic sensor is selected from the group consisting of: an electromyogram sensor, an electroneurogram sensor, electroencephalogram sensor, an electrocardiogram sensor, a pressure sensor, a temperature sensor, a chemometric sensor, a motion sensor, an accelerometer, a gyro, a strain sensor, an impedance sensor, and a capacitance sensor.

Aspect 38. A treatment method comprising delivering light of an activating wavelength to a target cell or tissue in an individual in need thereof, wherein the target cell or tissue comprises the light-activated polypeptide of any one of aspects 1-6 in the plasma membrane of the target cell or of a cell in the target tissue, wherein said delivering activates the light-activated polypeptide and depolarizes the target cell or cell in the target tissue.

Aspect 39. The method of aspect 40, wherein said depolarizing treats a neurological disease or disorder in the individual.

Aspect 40. A method for illuminating a target tissue of an individual, where the targeted tissue structure comprises the light-activated polypeptide of any one of aspects 1-6 in the plasma membrane of a cell in the targeted tissue, the method comprising: a) providing an implantable optical applicator configured to deliver light to the target tissue after implantation in a location adjacent to the target tissue; and b) operatively coupling the implantable optical applicator to a light source, a controller, a power supply, and an implantable illuminance sensor such that the controller causes the power supply to allow current to flow to the light source to cause an emission of photons to the implantable light actuator based at least in part upon an output signal from the implantable illuminance sensor, wherein the implantable illuminance sensor is positioned such that it captures at least a portion of the photons directed toward the target tissue by the implantable light applicator.

Aspect 41. The method of aspect 40, further comprising providing an implantable input sensor configured to produce an output signal that is correlated to the illuminance of the implantable optical applicator at a position of photon emission before intersection of such photons with the targeted tissue.

Aspect 42. The method of aspect 41, further comprising operatively coupling the controller to the implantable input sensor, such that it may compare the output signal from both the implantable input sensor and the implantable illuminance sensor to determine whether unexpected losses are being experienced.

Aspect 43. The method of aspect 40, wherein the implantable illuminance sensor is selected from the group consisting of: a photovoltaic cell, a photodiode, a pyroelectric sensor, a photoresistor, a photoconductor, a phototransistor, and a photogalvanic sensor.

Aspect 44. The method of aspect 41, wherein the implantable input sensor is selected from the group consisting of: a photovoltaic cell, a photodiode, a pyroelectric sensor, a photoresistor, a photoconductor, a phototransistor, and a photogalvanic sensor.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

To investigate V1 circuit elements and dynamics that may underlie behaviorally-potent detection of visual percepts, an integrated experimental paradigm was developed to test the role of specific activity patterns, delivered to large numbers of individually-specified V1 neurons defined by their natural response properties (a tuned ensemble), in guiding the dynamical responses of the local circuit and the elicited perception-driven behavior. An optical read-write system capable of kilohertz speed, three-dimensional (3D) access to tens to hundreds of individually-specified neurons across superficial to deep layers of cortex, and millimeter-scale spatial scope across the V1 region thought to be involved in visual perception was developed; this system was developed alongside and integrated with a new biological intervention capability derived from microbial opsin crystal structure-based genome mining, which allowed identification of a naturally-evolved optogenetic tool with unprecedented properties crucial for this biological question-through the conjunction of red-shifted light sensitivity, extremely large photocurrents alongside millisecond spike-timing fidelity, and compatibility with simultaneous two-photon $Ca^{2+}$ imaging via a green light-emitting fluorescent activity reporter. Use of this system allowed the measuring of naturally-occurring large-scale 3D ensemble activity patterns during visual experience, and then replay these patterns at the level of many individually-specified cells. This method allowed the recruitment of the broader network with dynamics corresponding to those elicited by actual visual stimuli (a phenomenon referred to as ignition), as well as to elicit the correctly selective behaviors, even in the absence of visual input. This approach allowed mapping of the cell numbers, layers, network dynamics, and plasticity dynamics underlying generation of behaviorally-potent percepts in neocortex, by enabling precise control over naturally-occurring, widely-distributed, and finely-resolved temporal and cellular elements of the corresponding neural representations.

Results

Marine Organism-Based Genomic Screen for New Classes of Microbial Opsin

Excitatory opsins that would jointly exhibit the required properties (all-optical capability, large photocurrents, high light-sensitivity, and robust performance over multiple stimuli) were first screened for via genomic sequencing of ocean-sourced organisms. Recent structural understanding of ChRs has enabled exploration of a much broader range of sequences than was previously feasible, guided by definitive knowledge that ion conductance is dependent upon certain residues in particular transmembrane (TM) helices (for example, cation-conducting ChRs (CCRs) use carboxylate moieties of TM2), and that ion selectivity depends upon overall surface electrostatic potential in the pore and vestibules of the channel (Kato et al. (2012) *Nature* 482:369, Kim et al. (2018) *Nature* 561:343, Kato et al. (2018) *Nature* 561:349). This knowledge was used to screen ~1000 suitable CCR-like sequences from transcriptome databases spanning>600 marine microbial organisms (Keeling et al. (2014) *PLoS Biol* 12: e1001889) (FIG. 1A), optimized the sequences for mammalian expression, and performed whole-cell patch clamp in cultured hippocampal neurons (collecting light-evoked action spectra over 390-650 nm, alongside comparisons to CsChrimson (Klapoetke et al. (2014) *Nat Meth* 11:338) and bReaChES (Rajasethupathy et al. (2015) *Nature* 526:653)). From this screen, a marine opsin gene (named here ChRmine to reflect both its deep red or carmine responsiveness, and its unique identification by ChR crystal structure-based mining) from Tiarinafusus, a ciliate phylogenetically distinct from green algae that have provided most known natural CCRs, was discovered (Klapoetke et al. (2014) *Nat Meth.* 11:338, Zhang et al. (2008) *Nat Neurosci* 11:631, Mattis et al. (2012) *Nat Meth* 9:159).

Figure 1G:
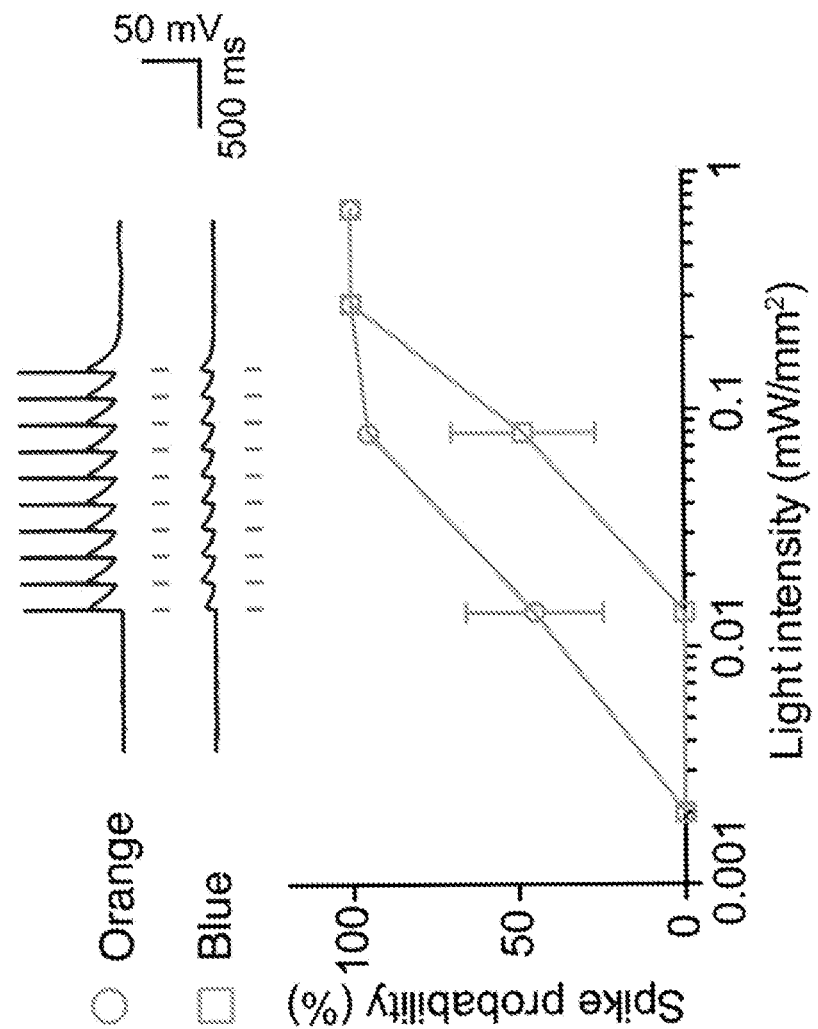
Figures 8A, 8B, 8C, 8D:
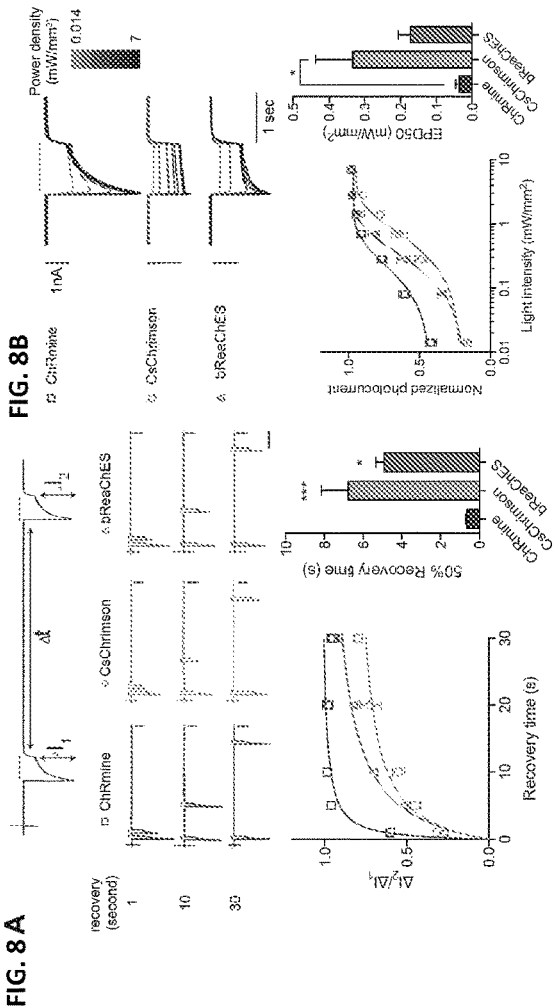

The new gene exhibited little similarity to previously known CCR genes (in fact showing more similarity to anion-conducting ChR (ACR) and proton-pumping proteorhodopsin (PR) genes; FIGS. 1B, 7) but expression in cultured neurons surprisingly gave rise to inward (excitatory) photocurrents driven by red-shifted light (4.1±0.53 nA at 585 nm) that were much stronger than for CsChrimson (0.9±0.05 nA) or bReaChES (1.9±0.36 nA; nanoamp-scale currents were observed even at 650 nm; FIG. 1C. The reversal potential of −5.64±1.39 mV (FIG. 1D) revealed robust $Na^+/K^+$ permeability ideal for driving spikes in neurons under typical physiological ion balance conditions, and recovery from desensitization in darkness (crucial for stationarity of performance over multiple stimuli (Mattis et al. (2012) *Nat Meth* 9:159, Berndt (2011) *Proc. Natl. Acad. Sci. U.S.A.* 108:7595)) was found to be an order of magnitude faster than for other red-shifted opsins (half-recovery time 0.63±0.08 s; FIG. 8A). Along with increased effective power density (EPD50, a measure of light sensitivity for opsin-expressing cells) for ChRmine (0.03±0.01 mW/mm², also many-fold improved compared with the other red-shifted opsins; FIG. 8B), these properties resulted in the capability of ChRmine to drive sustained spiking up to 40 Hz with red-shifted light (FIG. 8C). Finally, in another consequence of fast kinetics, large photocurrents, and high light sensitivity, ChRmine reliably induced spiking even with short red-shifted light pulses (100% spike success rate at 1 ms; FIG. 1E) and at low irradiance values (100% spike success rate at 0.08 mW/mm²; FIG. 1F, 1G). These properties have not been seen, even in isolation, in other fast red-shifted CCRs (Yizhar et al. (2011) *Nature* 477:171, Mattis et al. (2012) *Nat Meth* 9:159); appearing all together in a single opsin, these ChRmine data supported further testing.

FIG. 7. Structure-based sequence alignment of natural channelrhodopsin genes. The sequences are ChRmine (GenBank ID: TBD) (SEQ ID NO: 1), GtACR1 (GenBank ID: AKN63094.1) (SEQ ID NO: 21), GtACR2 (AKN63095.1) (SEQ ID NO: 22), CrChR1 (GenBank ID: 15811379) (SEQ ID NO: 23), CrChR2 (GenBank ID: 158280944) (SEQ ID NO: 24), VChR1 (UniProtKB ID: B4Y103) (SEQ ID NO: 25), and Chrimson (Genbank ID: AHH02126.1) (SEQ ID NO: 26). The sequence alignment was created using PROMALS3D and ESPript3, followed by manual re-alignment of TM1s, which were apparently misaligned. Predicted transmembrane domains are shown as coils. Structurally important residues are highlighted with red boxes and white font color, with other residues showing high sequence homology highlighted with blue boxes and red font color.

Simultaneous Optogenetics and Imaging in Cultured Neurons

Figure 1H:
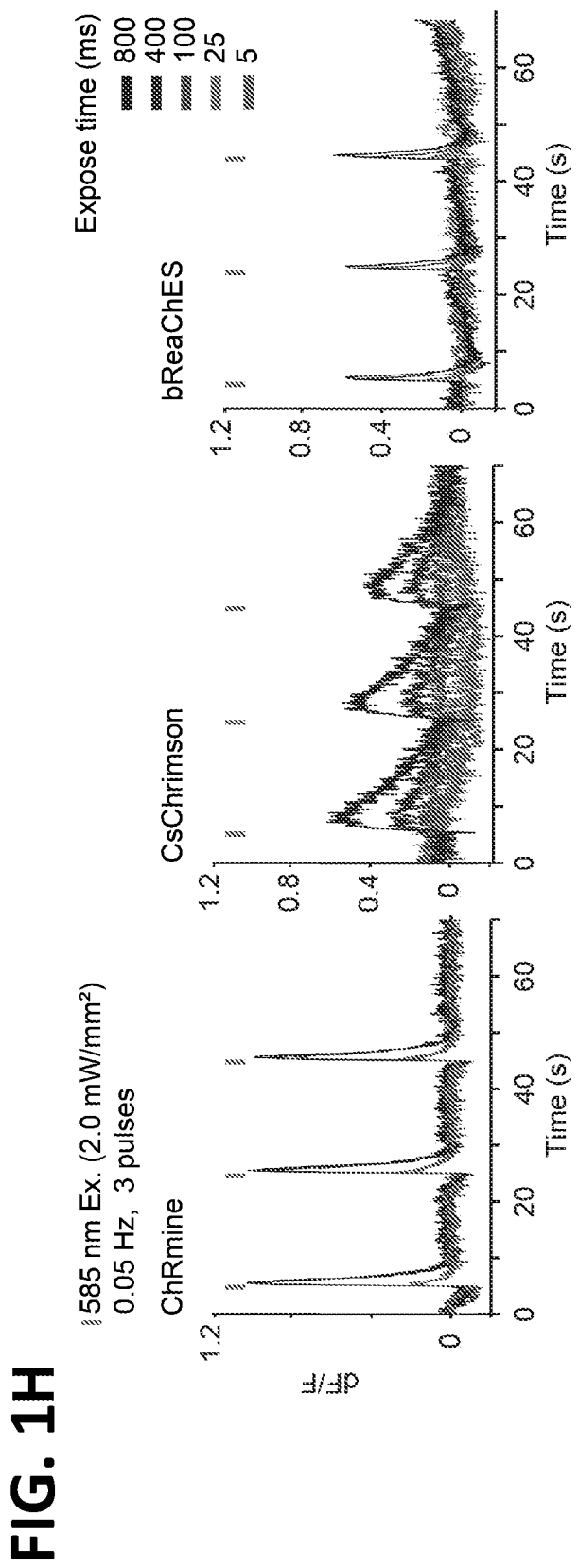
Figure 1J:
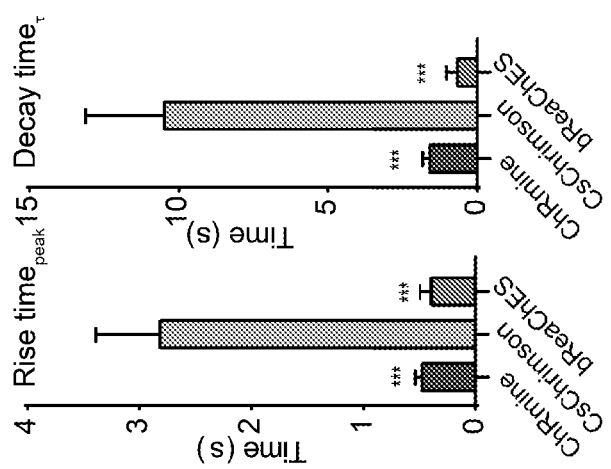
Figure 1I:
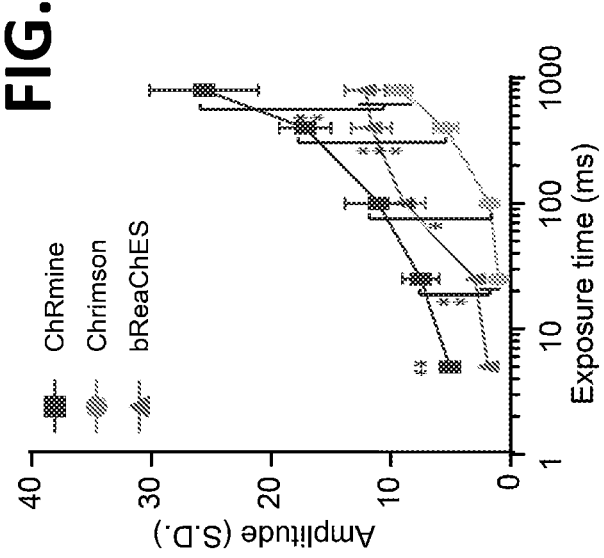

To test suitability for all-optical experiments, integrated wide-field one-photon stimulation and imaging was implemented with ChRmine and GCaMP6m in cultured neurons (Chen et al. (2013) Nature 499:295). Consistent with ChRmine photocurrent magnitude, much larger orange light-evoked GCaMP6m fluorescence signals were observed in ChRmine-expressing neurons compared with other ChR-expressing cells at the same light-exposure duration (FIG. 1H, 1I); moreover, as expected from its large fast photocurrents, ChRmine evoked faster rise and decay of evoked GCaMP6m signals at both orange (585 nm; FIG. 1H, 1J) and red (635 nm; FIG. 8D) wavelengths. Noting the slower kinetics of CsChrimson-mediated $Ca^{2+}$ signals (FIGS. 1J, 8D) and considering prior biochemical studies suggesting unusual pH-dependence of Chrimson, opsin-mediated GECI signals were imaged at external pH 7.0, 7.2 and 7.4 to test pH dependency across red-shifted opsins. Consistent with prior work (Kaufmann et al. (2017) J Biol Chem 292:14205, Urmann et al. (2017) Photochem Photobiol 93:782), CsChrimson use was associated with pH dependency of evoked $Ca^{2+}$ transients (slower rise-and-decay kinetics at pH 7.4 vs. 7.0), in contrast to ChRmine-evoked transients (FIG. 8E). Together, these remarkable properties of ChRmine as an excitatory opsin may be explained in part by an unusually strong predicted electronegative surface potential, as suggested by homology model-based comparison (FIG. 8F).

Figure 1K:
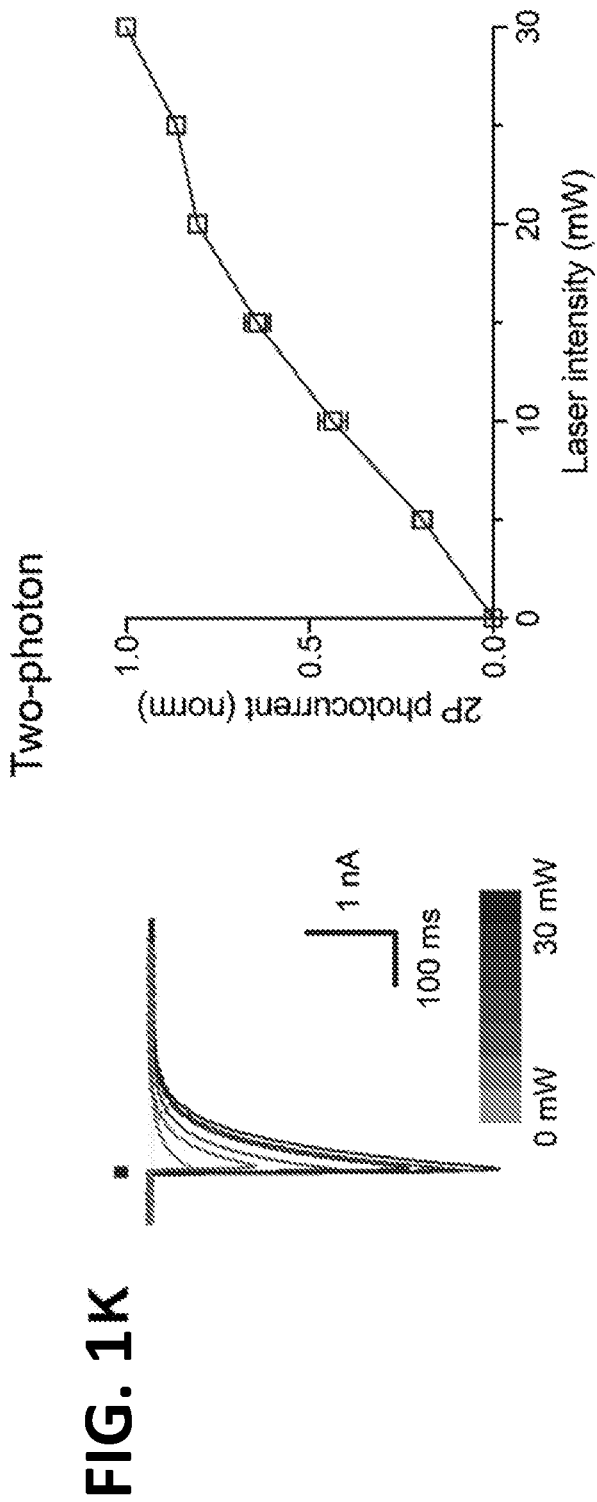
Figure 1L:
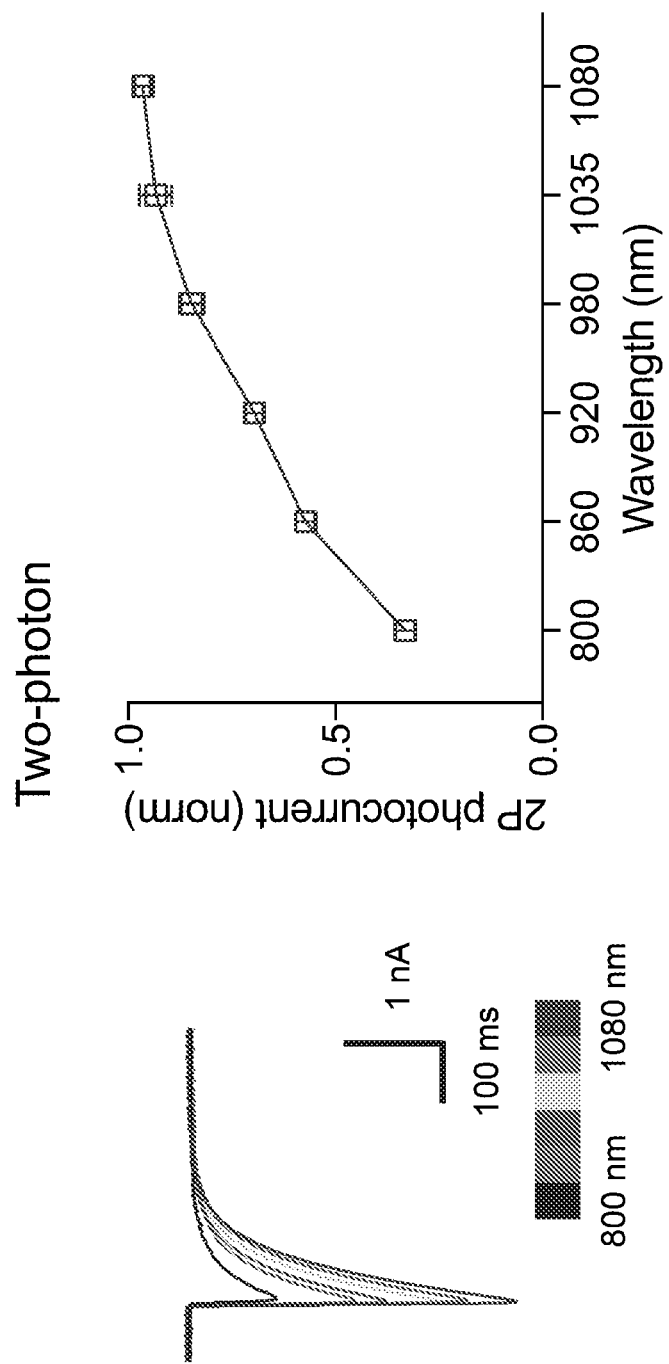

Since two-photon (2P) illumination is required for single-cell resolution in vivo, the next step included performing whole-cell recording during ChRmine recruitment via 2P spiral scanning over the soma. Mapping laser power from 0-30 mW (FIG. 1K) and illumination wavelengths from 800-1080 nm (FIG. 1L) revealed ChRmine photocurrents suitable in magnitude for 2P-driven spiking in all-optical experiments. Indeed, examining elicitation of spike trains with 2P photostimulation of ChRmine, reliable performance in trains up to 30 Hz was observed (FIG. 1M, 1N). Since a key limitation in all-optical neural control using red-shifted ChRs is persistent blue-light-driven cellular excitation which may occur as a side effect during imaging, ChRmine responses to blue light were characterized. With one-photon illumination, spikes were not elicited by 470 nm light over a broad range of light powers that reliably drove spiking at 585 nm (up to 100 W/mm$^2$; FIG. 1G); likewise, the 2P imaging laser (at 920 nm/80 MHz raster scanned at 90.8 ns/μm) over a broad range of powers from 0-60 mW, did not elicit spiking (FIG. 1M, 1N), further suggesting suitability for all-optical 2P experiments. Finally, a remarkable property of sub-millisecond spike jitter of 2P light-evoked spikes was observed (0.99±0.26 ms; FIG. 1O). Together these properties supported use of ChRmine as a tool with potentially unprecedented power and precision for 2P single-cell all-optical experiments.

FIG. 1. ChRmine: a novel class of opsin, suitable for high fidelity read-write experiments, derived from a marine environment. (A) Schematics of multi-step opsin-like genome mining. In silico screening was performed on data from the Marine Microbial Eukaryote Transcriptome Sequencing Project (Keeling et al. (2014) PLoS Biol. 12:e1001889). Subsequent phylogenetic analysis was performed to search for functionally novel opsin genes. To discover ChRs with predicted high cation conductance following the validated pore surface electrostatic model (Kim et al. (2018) supra; Kato et al. (2018) supra), the study focused on sequences with more negatively charged amino acids in transmembrane domains 1-3 and 7 along with the requisite lysine in TM7 as shown (red), defining putative ion-conducting pathways (Supplementary Text). Then, candidate opsin genes were transfected into primary cultured hippocampal neurons for in vitro electrophysiology, for testing both light sensitivity (1 s light at 390 nm, 485 nm, 513 nm, 585 nm and 650 nm; 0.7 mW/mm$^2$) and reversal potential (photocurrents measured with holding membrane potentials steps from −70 mV, every 10 mV stepwise to +60 mV). (B) Circular phylogenetic tree of multiple type-I opsin genes including ChRmine (left, arrow) and rectangular phylogenetic tree categorizing the opsins into different subfamilies (scale bar: fractional change in amino acid sequence. Phylogenetically ChRmine is situated uniquely, distinct from canonical cation-conducting ChRs, and closer to ion pumps and anion channels. (C) Left—representative voltage-clamp traces of red-shifted ChRs in cultured neurons responding to 1 s orange light (585 nm, 0.7 mW/mm$^2$) or red light (650 nm, 0.7 mW/mm$^2$). Right: action spectra in cultured neurons using peak currents after 1 s stim (0.7 mW/mm$^2$) (mean±s.e.m. n=5-7 cells. p<0.01, *p<0.001, one-way ANOVA with Tukey correction). (D) ChR I-V curves, −70 mV to +60 mV, in HEK cells. n=5-7 cells. (E) Probability of evoking spikes for different light pulse widths delivered at 5 Hz for 2 s and 0.7 mW/mm$^2$. (mean±s.e.m. n=5-7 cells. **p<0.0001, one-way ANOVA, Tukey correction). (F) Probability of evoking spikes at different intensities light at 5 Hz for 2 s, pulse width 5 ms (mean±s.e.m. n=5-7 cells. p<0.01, *p<0.001, one-way ANOVA, Tukey correction). (G) Top: current-clamp traces; ChRmine reliably induced spikes with orange light (585 nm, 5 ms pulse width, 5 Hz pulses at 100 W/mm$^2$) but less so with blue light (470 nm, 5 ms pulse width, 5 Hz pulses at 100 W/mm$^2$). Bottom: summary of ChRmine spike fidelity in response to orange or blue light (mean±s.e.m., n=5 cells) (H) Representative $Ca^{2+}$ imaging traces: 585-nm stimulation in cells expressing GCaMP6m and: ChRmine (left), CsChrimson (middle), or bReaChES (right) at $pH_{ext}$ 7.4. Responses to light pulses (orange) at indicated power and duration shown with blue intensity scale. Data collection across opsins was randomized and counterbalanced to minimize cross-group differences in expression. (I) Trial-averaged $Ca^{2+}$ peak-amplitude response to ChRmine (red), CsChrimson (orange) or bReaChES (green) stimulation with pulses of 2, 5, 25, 100, 400, or 800 ms (585 nm light as in (H). (J) Trial-averaged kinetics of ChRmine (red), CsChrimson (orange) and bReaChES (green). Data in (I) and (J) are mean±s.e.m., n=5-7 cells, p<0.01, ***p<0.001; one-way ANOVA, Tukey correction). (K) Two-photon power spectrum of ChRmine across 7 different powers at λ=1035 nm (0, 5, 10, 15, 20, 25, 30 mW). (L) Two-photon wavelength action spectrum of ChRmine: 6 different wavelengths, taken from voltage clamp recordings in neurons at holding voltage of −70 mV (n=6 cells, 20 mW, 12 rotations per spiral, 25 um diameter spirals, 4 ms duration, 80 MHz laser repetition rate; same setup as (K). (M) Spike fidelity across stimulation frequencies (left) alongside voltage clamp traces during different imaging exposure (right) (λ=920 nm, 2.8 Hz framerate). Note reliable 2P spiking fidelity at 5-30 Hz (left). With imaging power up to 60 mW, depolarization was minimal (right; <10 mV). (N) Summary of experiments in (M) (mean±s.e.m., n=6 for stimulation experiment and n=5 for imaging experiment). No spiking was observed under any imaging condition, whereas reliable (>60%) spiking fidelity was observed at stimulation frequencies up to 20-30 Hz. (O) Low jitter in 2P-elicited spikes: overlaid traces, 10 consecutive ChRmine spikes in train, aligned to 2P pulse timing (1035 nm, 20 mW, 12 rotations, 4 ms exposure).

FIG. 8. Electrophysiological and structural characterization of ChRmine. (A) Top—example traces showing channelrhodopsin recovery from desensitization after 1 s, 10 s and 30 s dark recovery times. Peak photocurrent magnitudes before ($\Delta I_1$, $I_{peak1}-I_{stationary1}$) and after ($\Delta I_2$, $I_{peak2}-I_{stationary2}$) the recovery time interval ($\Delta t$), and 1 second of light illumination periods (585 nm, 0.7 mW/mm$^2$, orange lines) are shown in the scheme. Bottom—time-dependent recovery plotted against the recovery time interval (left). Note that 50% recovery time constant of ChRmine was significantly faster than that of CsChrimson or bReaChES (right). (means±s.e.m. n=5-6 cells. * $p<0.05$, *** $p<0.001$ in one-way ANOVA with Dunnett's test). Vertical scale bars=1 nA current amplitude, horizontal scale bar=1 second. (B) Top—examples traces showing channelrhodopsin photocurrents across different light intensities. Photocurrents were measured with 585 nm, 1 sec light stimulation at power densities of (in mW/mm$^2$) 0.014, 0.08, 0.28, 0.7, 1.4, 2.8 and 7. Bottom—normalized photocurrents plotted against the light intensities (left). Note that Effective Power Density for 50% maximal photocurrent (EPD50) for ChRmine is significantly lower than that of CsChrimson (means±s.e.m. n=5-6 cells. * $p<0.05$ in one-way ANOVA with Dunnett's test). (C) Red-shifted channelrhodopsin spike fidelity. All spiking protocols used a train for 2 seconds and 0.7 mW/mm$^2$ light power was used for illumination. For light width, 1 ms for ChRmine and 5 ms for bReaChES and CsChrimson were used, as determined from the light sensitivity measurement from FIG. 1. (means±s.e.m. n=5-7 cells,  $p<0.01$ in one-way ANOVA with Tukey's test). (D) Left—Trial-averaged Ca$^{2+}$ response peak amplitude to ChRmine (red), CsChrimson (orange) and bReaChES (green) after pulses of 2, 5, 25, 100, 400, or 800 ms in response to 635 nm light. Right—Summary of rise and decay kinetics of Ca$^{2+}$ transients in response to 635 nm, 800 ms light pulses. bReaChES data not plotted in kinetics since the amplitude is too small for precise analysis (mean±s.e.m, n=5-7 cells,  $p<0.01$, *** $p<0.001$; one-way ANOVA with Tukey correction). (E) Left-representative Ca$^{2+}$ imaging traces response to indicated pH$_{ext}$ (7.0, 7.2, 7.4) at 585 nm light pulse, under the same experimental setup as indicated in (H). Right—trial-averaged Ca$^{2+}$ response kinetics to ChRmine (red) and CsChrimson (orange) at indicated pHs (mean±s.e.m of n=5-7 cells. * $p<0.05$,  $p<0.01$, * $p<0.001$ in two-tailed t-test). (F) Surface electrostatic potentials of the crystal structure of C1C2 (left) and homology model of ChRmine (right), built using RosettaCM (Song et al. (2013) supra), with C1C2 structure as a template. The surface is colored on the basis of electrostatic potential contoured from −15 kT (red) to +15 kT (blue). White denotes 0 kT. Surface potential was calculated using PDB2PQR (Dolinsky et al. (2004) *Nucleic Acids Res.* 32: W665) for both GtACR1 and C1C2 models. Note that homology model-based comparison indicates more electronegative surface potential of ChRmine than that of C1C2.

Kilohertz Control and Readout of 3D Ensembles Over mm$^2$ Domains of Neocortex In Vivo The precise temporal response and relatively low irradiance requirements to drive spiking with this high-potency opsin raised the prospect of control of unprecedented numbers of recruited neurons at kilohertz rates using safe illumination powers, potentially enabling new optical hardware designs that could elicit meaningful circuit dynamics and behavior by targeting large, arbitrarily-defined cellular ensembles at speeds consistent with fast neural circuit computations. For example, neocortical ensemble dynamics that are behaviorally potent may involve many cells that are sparsely and widely distributed, both transversely across cortical areas and axially across layers. To gain optical access across large volumes of cortex for single-cell photostimulation with kHz temporal resolution while simultaneously imaging local neural activity dynamics, a high-pixel-density (1536×1536 pixels) spatial light modulator (SLM) optimized for high-fidelity NIR hologram generation at high-speed (MacroSLM; ~85% diffraction efficiency in 2 ms at λ=1064 nm; Materials and Methods) was designed, fabricated, and optimized. The SLM was paired with custom optical elements and precise temporal sequencing protocols to access large volumes of cortex for single-cell, ensemble-scale photostimulation while simultaneously imaging local neural activity dynamics (Materials and Methods). To further improve temporal resolution to the kHz regime, multiple SLMs were incorporated along the same photo-stimulation path for multiplexed ensemble stimulation (MultiSLM, FIG. 2A, FIGS. 9-12, Materials and Methods, Supplementary Text).

Figure 2A:
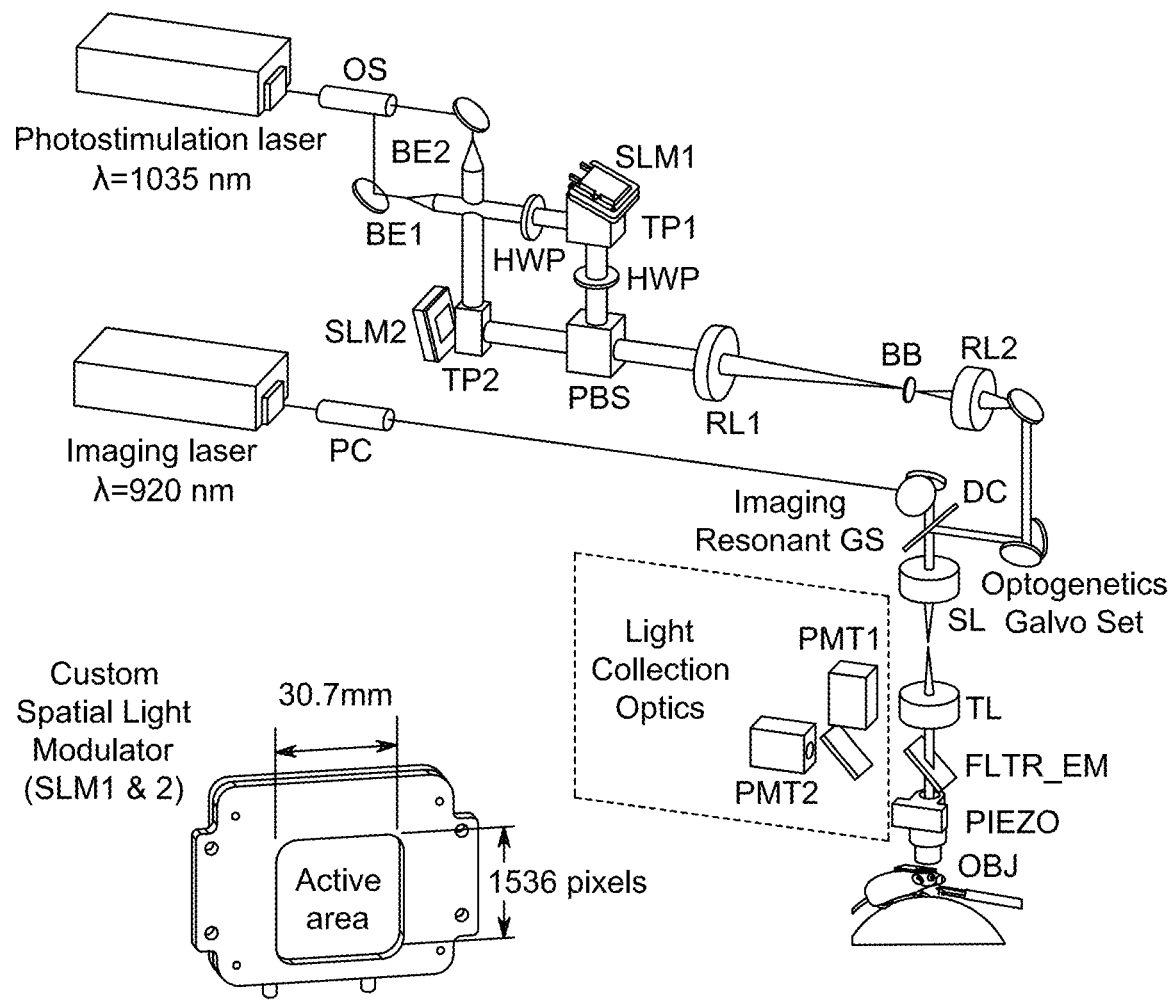
Figure 2B:
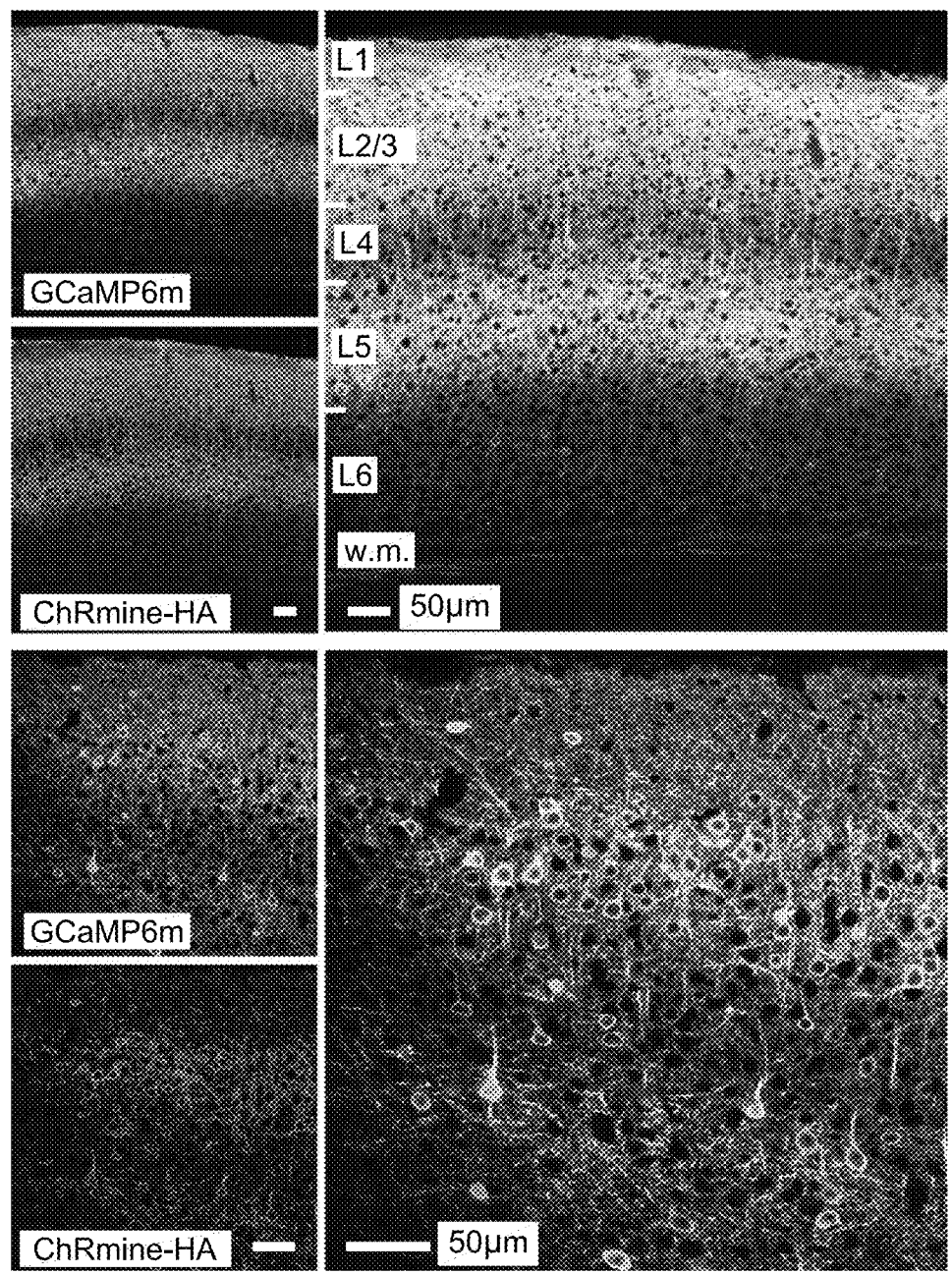

To test these new capabilities, mouse primary visual cortex (V1) was transduced with a single integrated ChRmine/GCaMP6m virus (AAV8-CaMKIIa-GCaMP6m-p2a-ChRmine-TS-Kv2.1-HA; Materials and Methods); this dual GECI/opsin construct achieved large-scale, homogeneous, highly reliable co-expression of reporter and actuator in cell bodies across layers 2/3 and 5, with very little expression in layer 4 (FIG. 2B). To leverage the exquisite temporal properties of ChRmine for high-fidelity timing of elicited spikes within individual neurons, a 210 μs spiral photostimulation protocol was developed, which along with novel high-speed hologram generation technology (termed MultiSLM), allowed realization of kHz ensemble stimulation over 1 mm$^2$ of superficial layer 2/3 in V1, with comparable efficiency across the entire imaging field-of-view (FIGS. 2C, 2D, 9A, 9B). Sequential addressing of neuronal ensembles at 1 kHz resolution was readily feasible with high success rates (FIGS. 2E, 2F, 9-10) and without off-target modulation of neighboring neurons (FIGS. 2G, 9D, 9E, 9G, 9H). This new high-performance SLM technology also allowed addressing of larger axial displacements with 3D holographic patterns (Yang et al. (2018) *Elife* 7: e32671, dal Maschio et al. (2017) *Neuron* 94:774, Mardinly et al. (2018) *Nature Neuroscience* 21:881); coupling this capability with 3D 2P imaging, all-optical physiology experiments were realized for tens to >100 individually-specified neurons across millimeter spatial scales across cortex and across cortical layers (layer 2/3 to layer 5; FIGS. 2C-2I; 9A, 9B, 9G, 9H).

FIG. 2. MultiSLM: large-volume temporally-precise all-optical microscope. (A) Hardware schematic detailing multi-photon 3D imaging and optogenetic stimulation light paths utilizing a pair of custom, large field-of-view spatial light modulators (MacroSLMs), an optogenetic galvanometer set for spiral scanning, and a piezo-coupled microscope objective for 3D image scanning. Custom SLM dimensions (inset). (B) Typical viral expression of GCaMP6m and ChRmine from the bicistronic virus at two magnifications (green: anti-GFP; magenta: anti-HA, as HA is conjugated to ChRmine-TS-Kv2.1) (Baker et al. (2016) *Elife* 5: e14193). ChRmine was found to be co-expressed with GCaMP6m in all cell bodies counted (n=610/610 soma across nine 40 μm V1 sections from n=3 mice; ChRmine expression was restricted to the membrane and GCaMP6m was cytosolic, as expected). Dense somatic expression is observed in layers 2/3 and 5, with minimal expression in layers 4 or 6. Unlike GCaMP6m, ChRmine is absent in axons in the white matter (w.m.) and markedly reduced in dendrites extending through layer 1, likely due to trafficking properties of the Kv2.1 soma-targeting motif (Baker et al. (2016) supra). (C) Simultaneous imaging and photoexcitation across a 1 mm² field-of-view, showing that successful optogenetic excitation does not depend on neuronal position (90 stimulations at 29 Hz, 20-30 mW per target, aggregation of 160 total targets across 6 groups of neurons, 10 MHz laser repetition rate, $\lambda$=1035 nm, spiral diameter=10 μm, 5 spiral revolutions). (D) Photostimulation shown of 2 representative cells (identified as C1 and C2), separated by 1.164 mm. (E) Temporal interleaving paradigm of the MultiSLM increases the temporal resolution at which N cell ensembles (denoted $e_N$) can be addressed (1 kHz address rate shown here at N=6). (F) Six nonoverlapping ensembles of ~27 neurons each were optogenetically excited every 1 ms, in a 1 kHz sequence (in total, 124/160 cells were successfully targeted at this speed in 5.2 ms, p<0.025 positive modulation versus baseline and post-stimulation epochs, Materials and Methods). Each of the six ensembles showed similar neuron-activation success rates, simultaneously exciting up to 23 neurons per 210 μs exposure (Materials and Methods). (G) Targeting precision is demonstrated; a single neuron (target iv) can be optogenetically driven in isolation (middle column), within a region of nearby, known-responsive cells as targeted on other trials (right column); drawn ROI outlines are slightly enlarged relative to analysis to prevent obscuring cell morphology in the visualization. (H) 3D imaging with simultaneous optogenetic control across cortical layers; drawn ROI labels are enlarged for visualization. (I) Simultaneous excitation of 27/30 total targets located across cortical layers 2/3 and 5 in V1 (90 exposures at 30 Hz, 10-20 mW per target, 30 total targets, single 0.63 ms exposure using a 15 μm diameter spiral with 8 revolutions, 10 MHz laser repetition rate; Materials and Methods). Note (F) and (I) on common z-score scale.

Selective Visual Network Recruitment by Functional Ensemble Stimulation

To explore how specific individually-defined cell ensembles in V1 may elicit specific local circuit dynamics, a series of experiments was initiated based on cellular-resolution stimulation of visually-tuned ensembles in V1 while recording from the surrounding neural population across layers 2/3 and 5 of cortex (FIGS. 3,4). Mice were head-fixed in the MultiSLM and free to run on a floating ball (FIGS. 3A,4A). In the first cohort (n=4 mice), there was no task-specific training before visual stimulus presentation, in vivo imaging and optogenetic stimulation (FIG. 3). In the second cohort (FIG. 4, n=5 mice), mice were first trained to discriminate visual stimuli before moving to imaging and optogenetics during perceptually-driven behavior; these two classes of cohort allow distinguishing whether similar or different patterns result from additional modulation related to training/plasticity or behavioral state (e.g., goal-directed attentional or top-down influences). Trained mice also crucially enabled testing whether specific visual network recruitment patterns could suffice to drive or behaviorally favor specific perceptual experiences or decisions, and to quantify the effect of individual neurons in specific layers on perceptual phenomena.

Figure 3A:
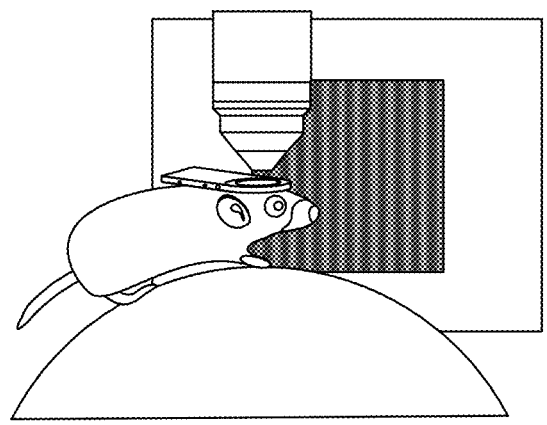
Figure 3B:
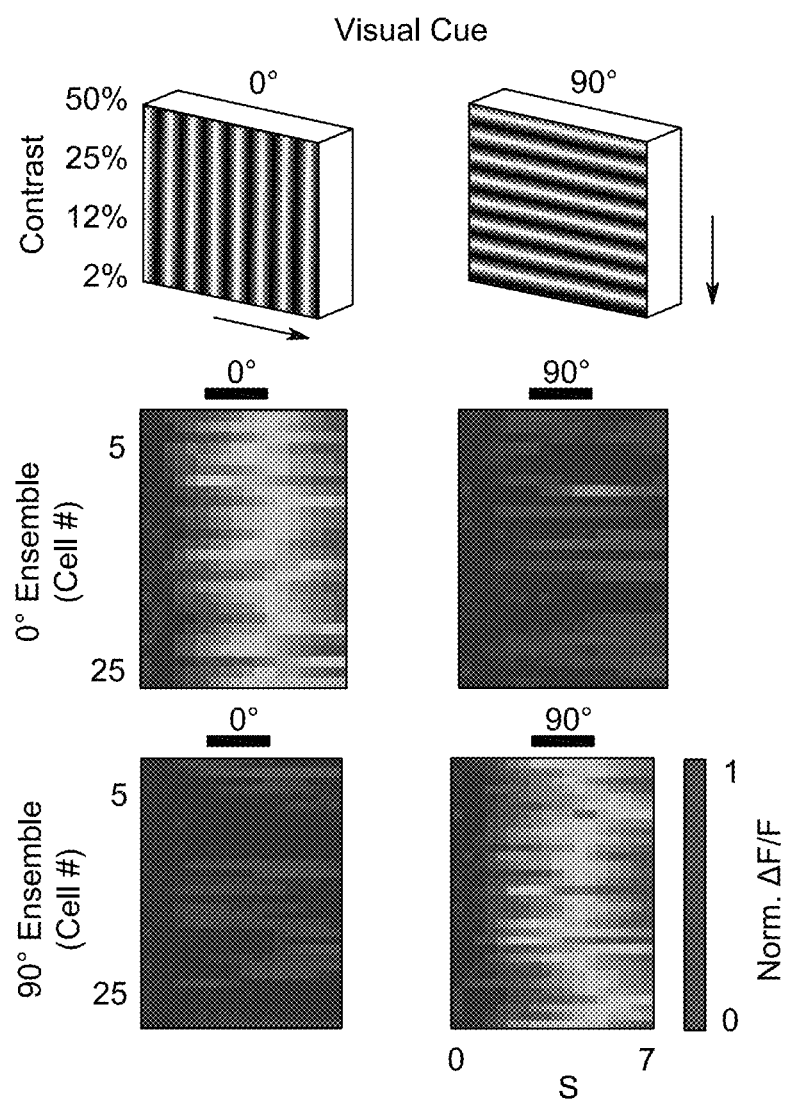
Figure 3C:
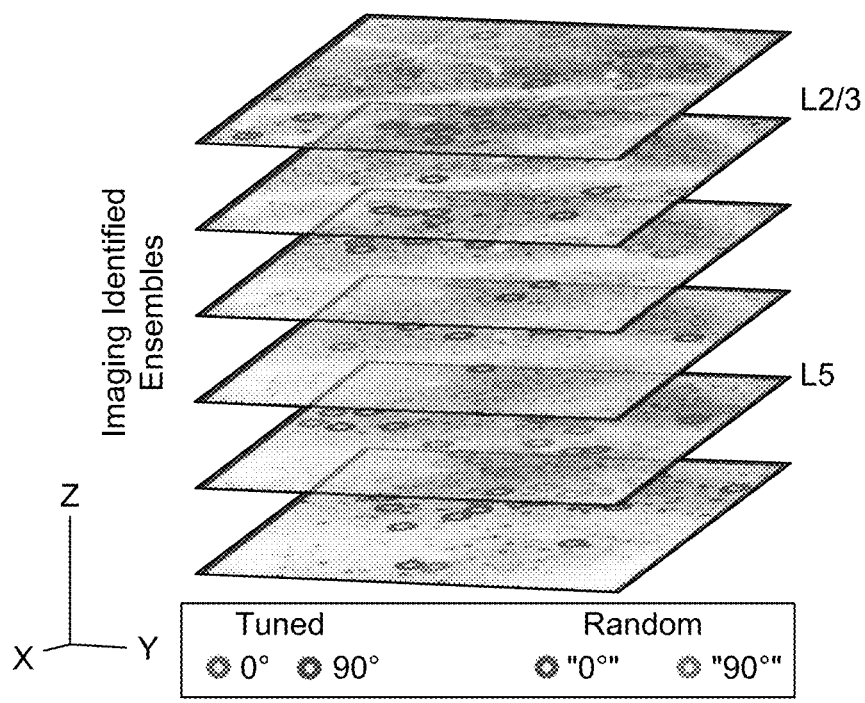
Figure 3D:
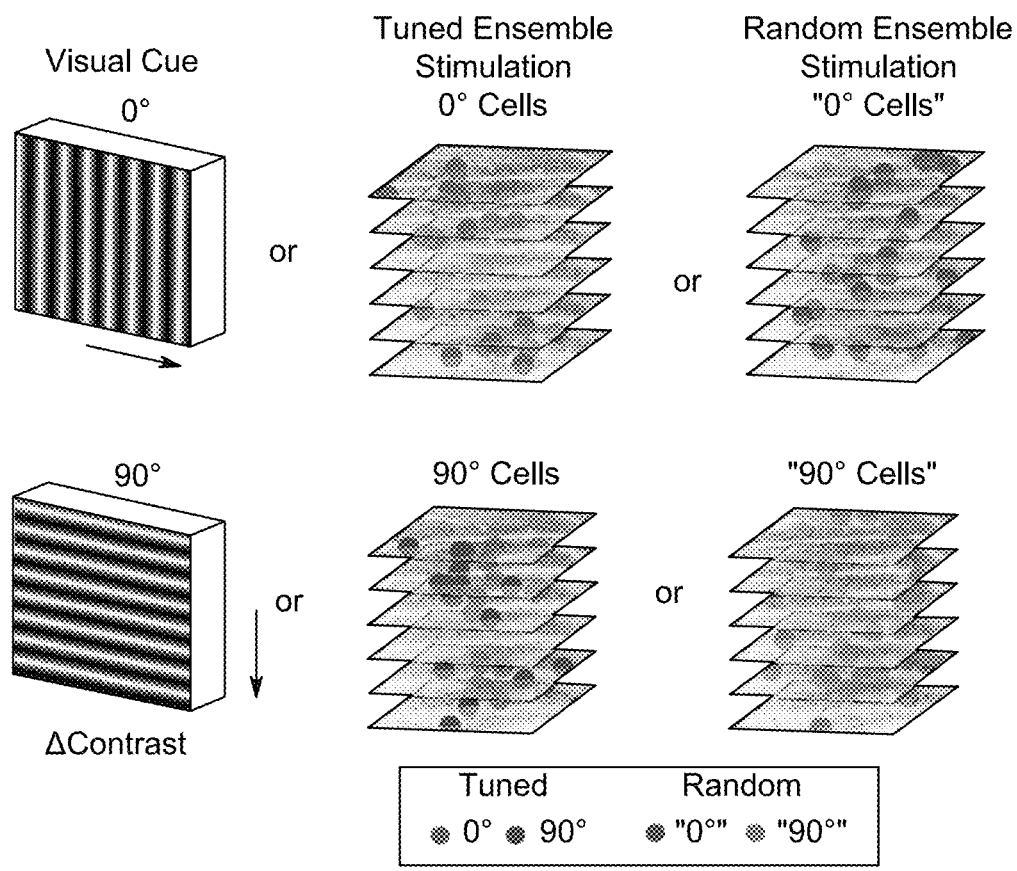
Figure 3E:
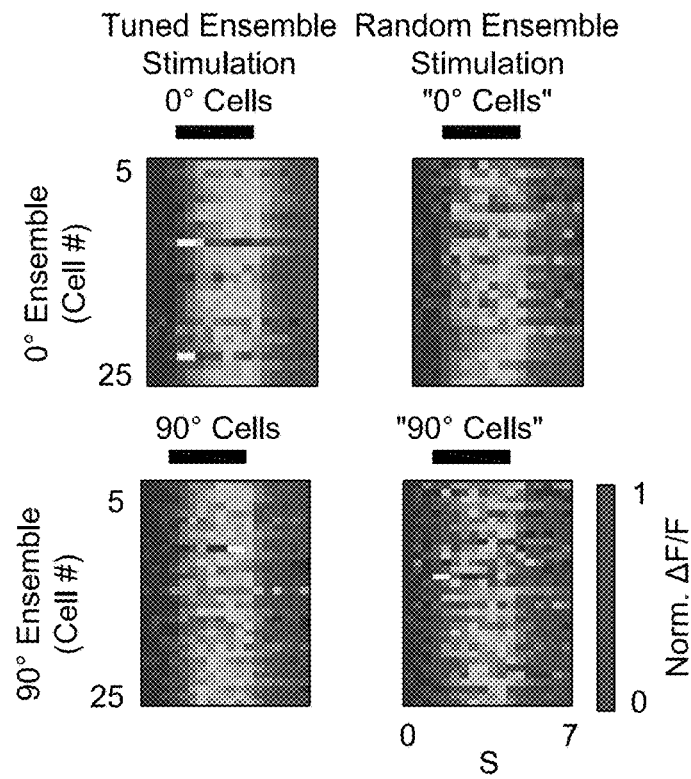
Figure 3F:
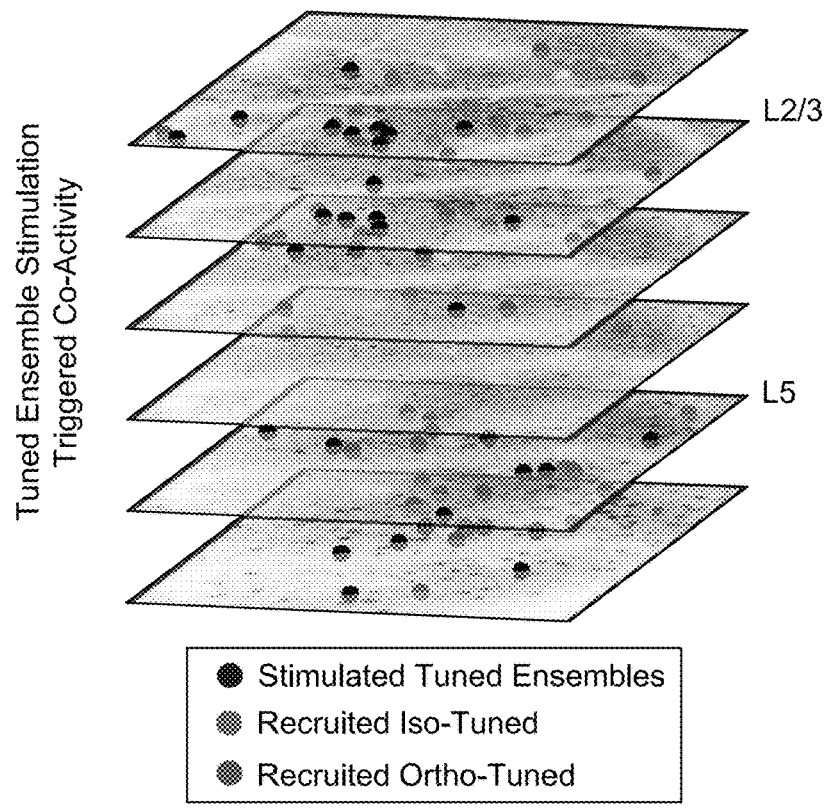

Mice transduced in V1 with AAV8-CaMKIIa-GCaMP6m-p2a-ChRmine-TS-Kv2.1-HA viewed drifting sine wave gratings while $Ca^{2+}$ signals were recorded across layers 2/3 and 5 with the MultiSLM (FIG. 3A-3C). Gratings were vertical (0°) or horizontal (90°) (FIG. 3B) and were presented in one of several contrasts on each trial (2, 12, 25, 50%). In this first cohort, each trial began with a 5 kHz tone and followed the same basic structure as for visually-trained mice discussed below except there was no training, i.e. no reward/punishment (see Materials and Methods). In each mouse, orientation-tuned ensembles were identified, comprised of dozens of neurons across layers with orientation selectivity index (OSI)>0.5 (FIG. 3B, 3C; 0°: mean=30.5 cells, range=[26 37]; 90°: mean=29.5 cells, range=[19 40]; Materials and Methods). Two additional ensembles were defined to match the number of cells in each orientation-tuned ensemble, but with member neurons selected at random from the surrounding population (FIG. 3C; Materials and Methods). The same neurons could be recorded and stimulated across sessions due to micron-scale precise alignment at each placement of the mouse in the MultiSLM (FIG. 13; Materials and Methods).

Figures 16I, 16J, 16K, 16L, 16M, 16N:
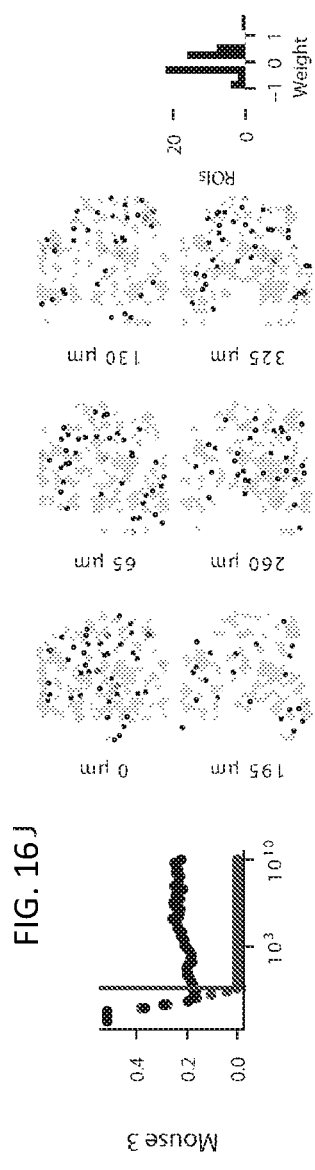

On randomly interleaved trials (FIG. 3D), sine-wave gratings were presented to the animal, or one of the cellular ensembles was stimulated (tuned or random ensembles, with comparable efficacy; FIG. 14C; Materials and Methods). Ensemble optogenetic stimulation was observed to drive robust time-locked responses in the targeted neurons in the absence of visual stimulation, emulating activity observed in the naturally-occurring (visual stimulus-evoked) ensembles (FIG. 3E); also observed was co-activation of non-stimulated neurons in the surrounding volume that were more likely to be similarly—than orthogonally-tuned to the targeted ensemble (FIGS. 3F and 16A, left, p=0.025; data from n=20 sessions in n=4 mice; Materials and Methods). This preferential recruitment of iso-tuned neurons in the surrounding population, even in the absence of visual stimulation, provided an initial indication that cortically-initiated activity in V1 cells defined by natural, visually-evoked activity recruits percept-specific downstream ensembles.

Figure 3G:
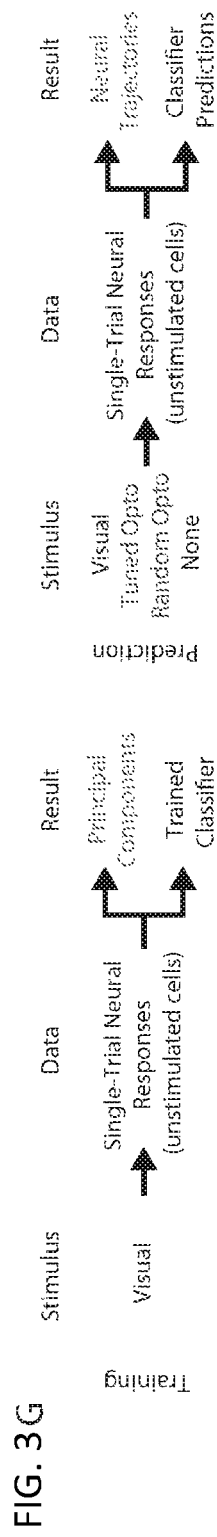
Figure 14A:
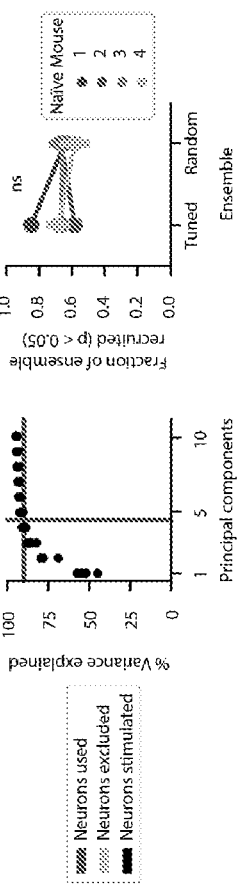

To further examine the potential encoding properties and computational significance of this pattern recruited in the surrounding network, a neural decoding approach involving both principal components analysis (PCA) and binary classification was developed (schematized in FIG. 3G). From each experimental animal, a subset of held-out neurons, termed "unstimulated neurons," that had never been optogenetically stimulated under any experimental circumstances—and also were not within spatial proximity to any stimulated neuron was identified (achieved by defining a cylindrical exclusion area around each optogenetic target neuron with 20 μm lateral radius and infinite axial extent; this exclusion protocol also applied for FIGS. 3F, 16A). This conservative approach excluded most neurons from further population analysis (1885±232 [mean±SD] neurons, or 46±4% of all neurons in each dataset, from n=4 mice; FIG. 14A) but crucially addressed the risk of neurons directly stimulated only by virtue of proximity to optogenetic targets becoming erroneously assigned as part of a downstream secondarily-recruited ensemble. The single-trial fluorescence responses of all remaining unstimulated neurons in response to each visual stimulus were examined (Materials and Methods). These visually-evoked population responses were used to identify principal component vectors for projecting population activity—not only for data collected during presentation of visual stimuli, but also for data collected during optogenetic stimulation. Leveraging the fact that each trial occurred during either the 0° or 90° stimulus, these single-trial visual responses were used to train binary classifiers to predict visual stimulus type from the held-out unstimulated neuron responses (via sparse logistic regression; Materials and Methods). These classifiers were trained only on visually-evoked responses, and were used to predict stimulus type for all experimental conditions (i.e. during visual, optogenetic, or no stimulation).

Figure 14B:
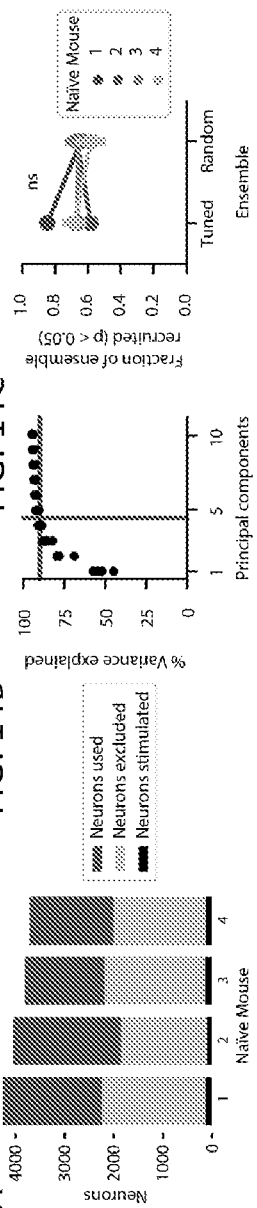
Figure 14D:
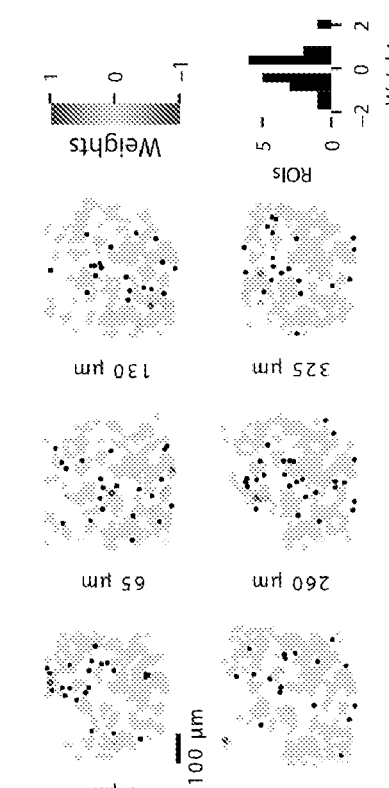
Figure 14E:
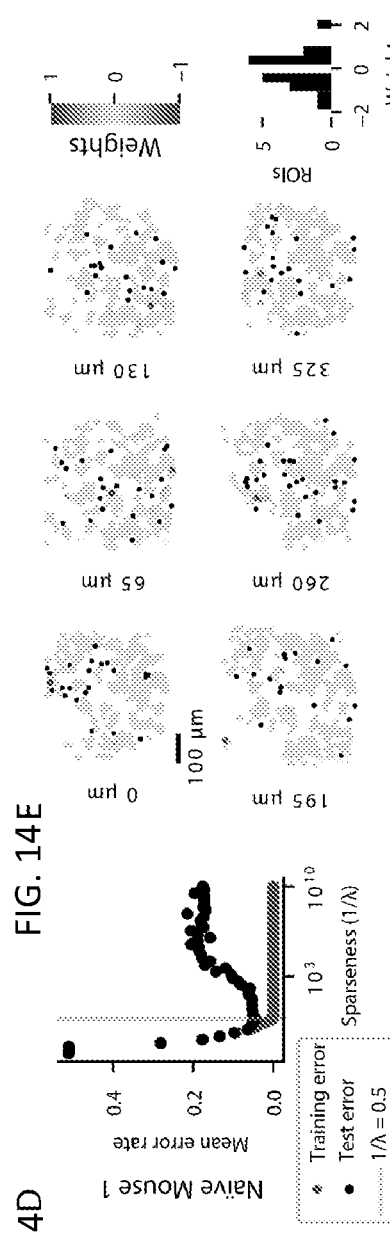
Figure 14F:
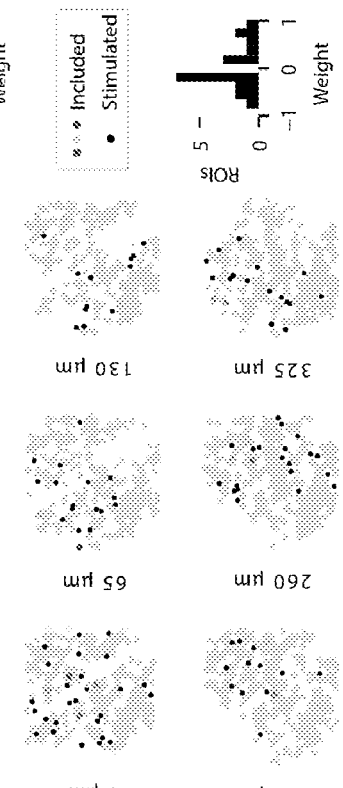
Figure 14G:
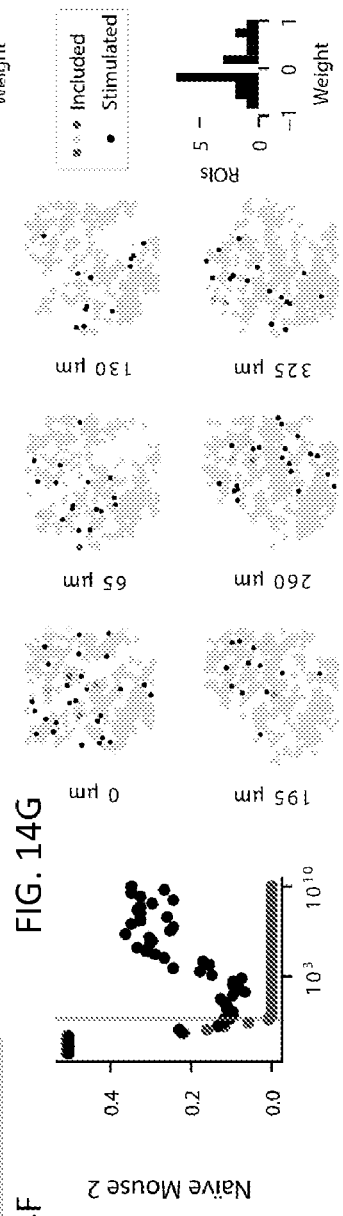

The PCA results can be seen in FIG. 3H for two representative mice (analyzed independently; top and bottom row). Each single line in this panel represents the average 19-frame (6.92 s) trajectory traversed by the unstimulated neuron population during 0° (blue) and 90° (red) trial conditions on each experimental day. At the first frame following stimulus onset (denoted by bold red or blue dots), trajectories clearly had begun to diverge as a function of visual stimulus type (left column). Interestingly, neural trajectories were similar between visual stimulus and tuned optogenetic ensemble stimulation conditions for both 0° (blue) and 90° (red) trial types (compare the first two columns). In contrast, there was no apparent segregation of neural trajectories arising from random stimulation (of cells that were not selective for either the 0° or 90° visual stimulus; third column), nor in the absence of any sort of stimulation (fourth column). This segregation of trajectories among held-out unstimulated-cell ensembles in different stimulus conditions was reproducible within individual mice and across mice: the top two principal components shown explained the majority of the variance seen in the visually-evoked data (FIG. 14B; top two components explain 76.21±2.09% and top four explain 89.96±0.46%).

The population activity of unstimulated neurons thus encodes the stimulus similarly during tuned optogenetic stimulation and visual stimulation, but not random optogenetic stimulation. This finding was developed in more quantitative detail with the use of binary classifiers. After training on the visual stimulation data alone, the classifiers were able to find a sparse set of weights on the unstimulated neurons that cleanly separated the two visual conditions (grating orientations) (FIG. 14D-14K). By subtracting the trial-averaged fluorescence responses of these neurons seen during the 0° visual conditions, from responses of these neurons seen during the 90° visual conditions, distinct groups of cells were resolved that exhibited differential recruitment during each visual stimulus (FIG. 3I, left column)—a pattern of neuron recruitment that was also largely reproduced with tuned optogenetic stimulation (FIG. 3I, second column) but seen neither with random stimulation nor unstimulated activity (FIG. 3I, third and fourth columns; for summary data from these and additional mice see FIG. 15). Together, these results underscore that population responses among the unstimulated neurons following tuned optogenetic stimulation are similar to those observed during visual stimulation—but distinct from those seen during random optogenetic stimulation (FIG. 3J). By examining classifier prediction accuracy, these results were confirmed quantitatively: classifier performance was evaluated for each experimental condition (i.e. visual, tuned, random, and no stimulation), and each condition was tested for five days in four different mice. No significant difference in prediction accuracy was found between random ensemble stimulation and the unstimulated condition (p=0.46, n=20 total conditions of each type, pooled across 4 mice and 5 conditions/mouse; Wilcoxon signed-rank test; FIG. 3K), whereas data taken from tuned optogenetic stimulation conditions yielded predictions superior to those seen in random data (p<0.001, n=20 conditions of each type, Wilcoxon signed-rank test; FIG. 3K). Together these data point to the existence of distributed subnetworks encoding specific visual features, that can be specifically recruited by targeted optogenetic selection of multiple individually-specified neurons.

Figure 4A:
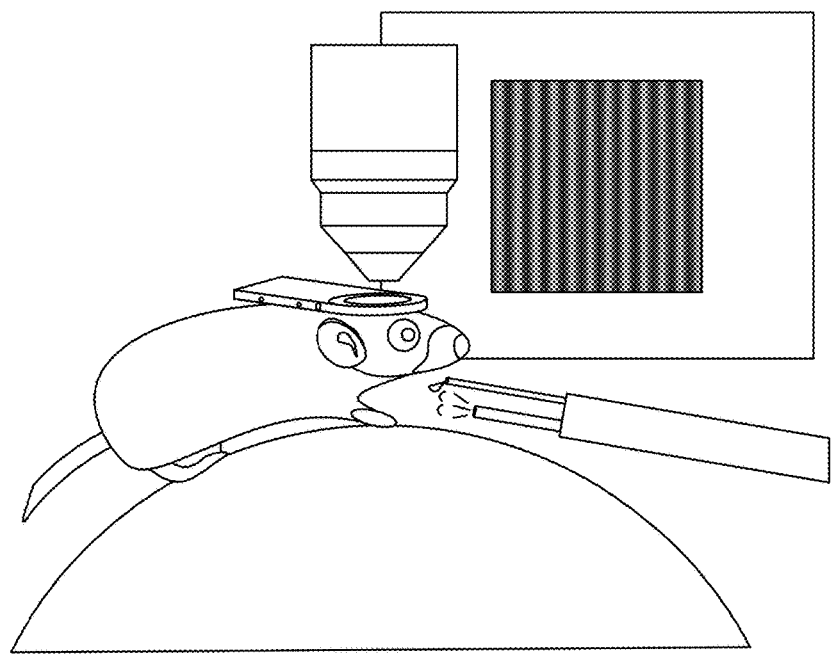
FIGS. 4A-4N depict eliciting a specific visual percept through targeting individually-identified neurons.
Figure 4B:
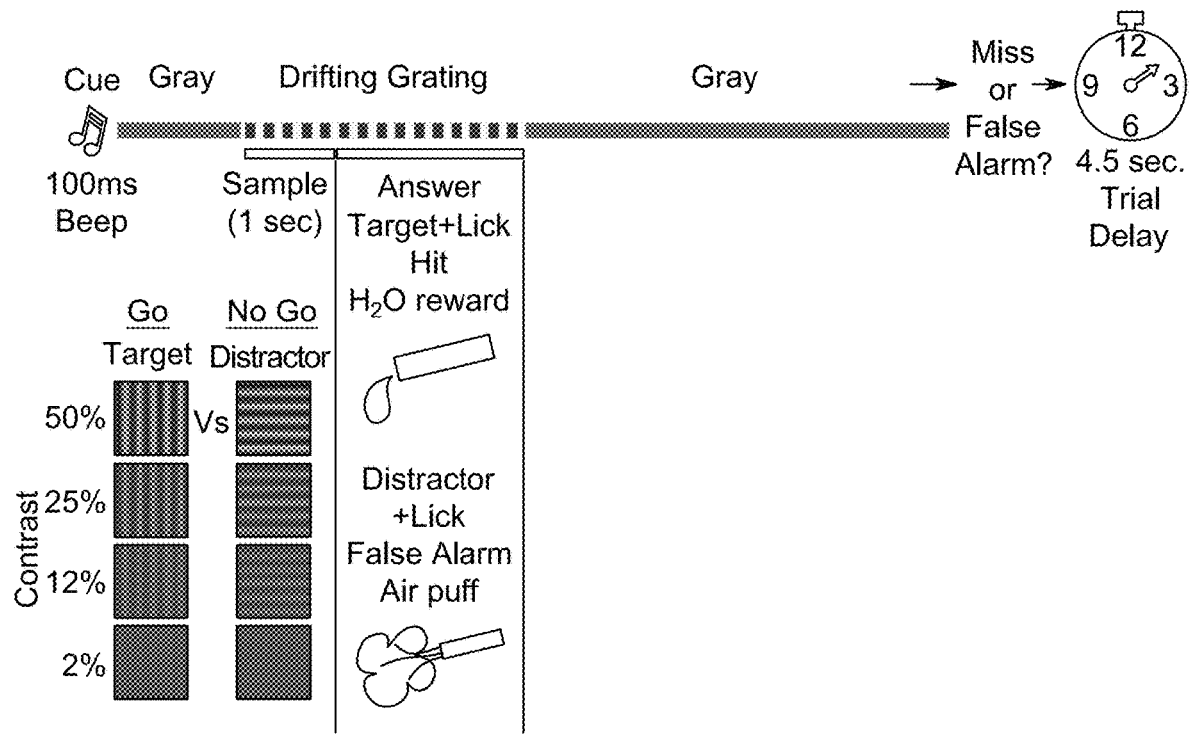
Figure 4C:
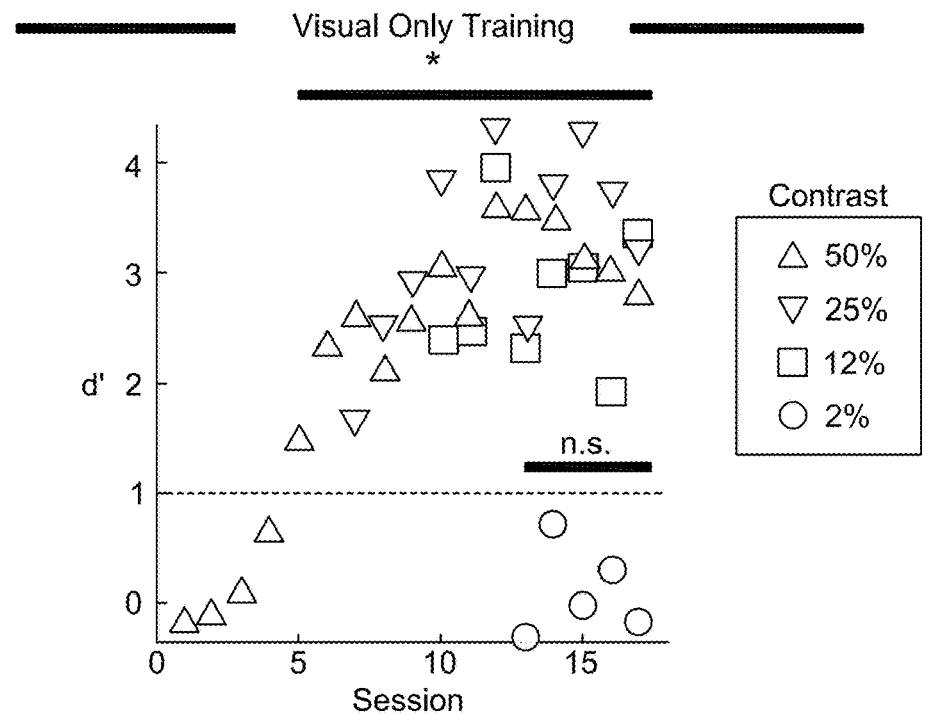

Recruiting Specific Percepts at Cellular Resolution: Behavioral and Physiological Readouts The next step was to test whether activation of these identified subnetworks could be capable of modulating or even eliciting specific percepts and behaviors, and to what extent potency of these subnetworks could be influenced by task-engagement, experience or plasticity. To enable a well-controlled behavioral readout, a second cohort of mice (n=5) was habituated on the floating ball and trained to discriminate the two drifting-grating orientations at high performance levels in a Go/No Go task (FIG. 4A-4C). Once mice reliably discriminated orthogonal visual stimuli (at 12%, 25% and 50% contrast; trained animals were unable to discriminate 2% contrast gratings (FIG. 4C), while performing well at 12%), ensembles composed of identified cells responding to either the Target (0°, Go) or Distractor (90°, No Go) stimulus (OSI>0.5) were identified by 2P $Ca^{2+}$ imaging with conservative criteria as before (here animals performed discrimination motivated by reward/punishment during image-based identification). Interestingly, using the same imaging/analysis criteria as in FIG. 3, more orientation-tuned neurons were found in the trained cohort vs. the naïve cohort (30±6.8 neurons [mean±SD] per naïve mouse ensemble, 40.7±8.7 [mean±SD] per trained mouse ensemble, p<0.05 two-tailed t-test), consistent with an increase in size, tuning sharpness and/or reliability of the population representation as a result of performing the visual discrimination task (Schoups et al. (2001) Nature 412:549, Poort et al. (2015) Neuron 86:1478). It was also noted that there was an insignificant difference in the mean size of Target (mean=43.2 cells, range [33 55]) versus Distractor (mean=38.2 cells, range [28 46]) ensembles across trained mice (p=0.29, two-tailed paired t-test comparing ensemble sizes, Materials and Methods); direct assessment of behavioral performance and neural dynamics were ensured using equally-sized ensembles in each mouse in later experiments (see FIG. 6).

Figure 4D:
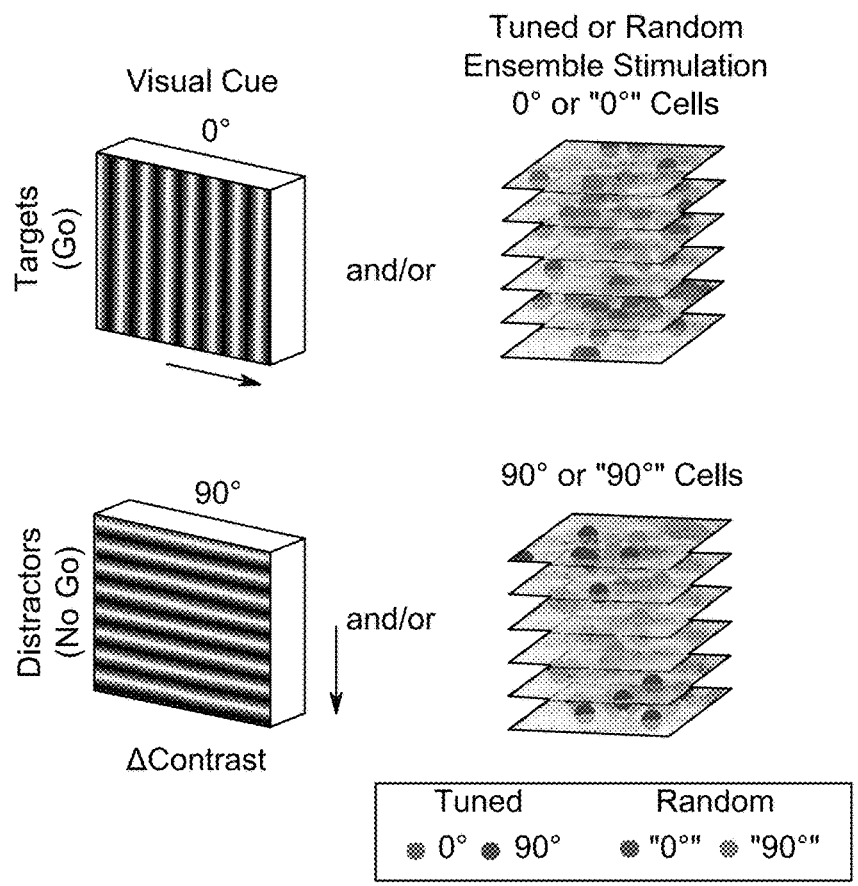
Figure 4E:
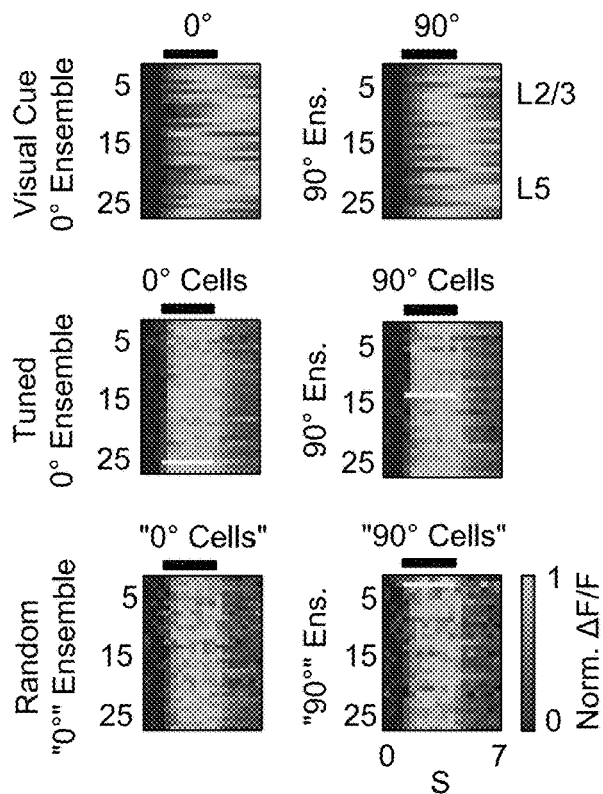
Figure 4F:
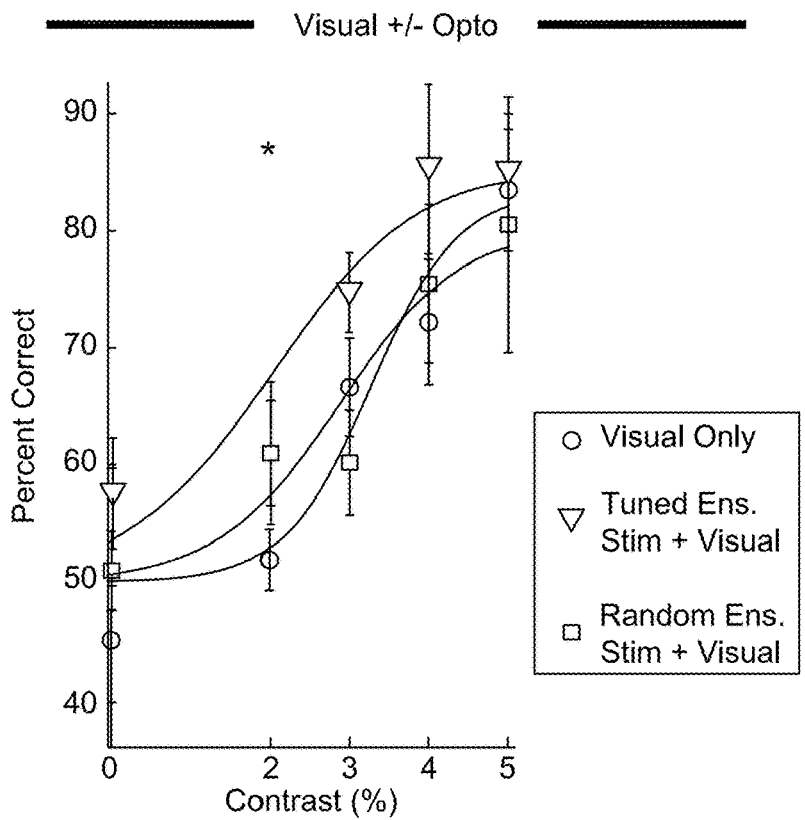

The trial structure then transitioned to one wherein, following a brief auditory cue, a drifting grating was presented alone, or a tuned or random ensemble was optogenetically stimulated without a drifting grating present, or a drifting grating was presented simultaneously with optogenetic stimulation of either a functionally-corresponding orientation-tuned ensemble or a random (but otherwise matched) ensemble (FIG. 4D, 4E). Used for subsequent sessions were the same two tuned ensembles in each mouse (termed Target for 0° cells, and Distractor for 900 cells), and two distinct neuron count-matched ensembles randomly selected from among the cells responding selectively to neither Target nor Distractor gratings (designated as random ensembles, one for use with each of the Target or Distractor conditions). While 75% of trials were maintained as high-contrast visual stimuli to promote task engagement and prevent extinction of the behavioral task, mice were presented with a subset of trials in which one of the ensembles was stimulated, but no visual stimulus was presented. Just as for the visual discrimination behavior, if the animal correctly licked during the answer window when the tuned or random Target ensembles were stimulated, water reward was delivered. Conversely, if licking occurred during stimulation of the tuned or random Distractor ensembles, an aversive air puff was provided along with a time out at the end of the trial; missed Target trials (false negatives) also led to a time out. In this way, licking behavior during tuned or random ensemble stimulation was consistently rewarded or punished according to each ensemble's associated visual percept.

While most of the mice did not immediately discriminate the optogenetically stimulated ensembles (n=4/5), interestingly, one mouse did correctly discriminate stimulation of the tuned ensembles alone (without any visual stimulation) in the course of the first session, (p<0.05, two-tailed Fisher's exact test, hit rate vs. false alarm rate, n=22 trials, d'=2.21). For all the other animals, the visual contrast of the paired visual/optogenetic condition was gradually increased from 2% to 5% contrast over the course of several sessions (typically one session per contrast; this process was termed the "contrast ramp"). In these mice, concomitant optogenetic stimulation of orientation-specific ensembles succeeded in improving behavioral discrimination across the contrast ramp, including at the perceptual threshold of the animals (FIG. 4F, ~3-4% contrast; p<0.05, two-way ANOVA, main effect of stimulation type, 4/4 mice that proceeded through training). Remarkably, after conclusion of the contrast ramp, under the no-visual-stimulus condition (0% contrast) mice achieved high performance discrimination of tuned ensemble optogenetic stimulation alone (FIG. 4G, 4H, p<0.01, n=5 mice, two-tailed paired t-test before vs. after contrast ramp, and tuned ensemble vs. no stimulation). Results were much more variable for random (non-orientation-tuned) ensemble stimulation across mice, with some mice significantly improving behavior (the fixed random ensembles had been consistently associated with either the Target grating, rewarded condition or the Distractor grating, no go/penalized condition) and others not (FIG. 4G, 4H; p=0.097, n=5 two-tailed paired t-test before vs. after contrast ramp; p=0.07 after ramp vs. no stimulation). Indeed, tuned ensemble stimulation drove higher performance across mice than did the random ensemble stimulation (p<0.05, two-tailed paired t-test, n=5). It was also observed that a higher fraction of neurons within tuned ensembles were recruited by optogenetic stimulation modulation than with stimulation of random ensembles (FIG. 16D, p<0.001, paired t-test, n=3 mice, Materials and Methods).

Given these apparent learning effects associated with the contrast ramp, the next step was to ask whether such a contrast ramp would be required to drive behaviorally-potent responses to any stimulated ensemble. To test this idea, a new population of cells were identified within the same receptive field in V1 (changing the origin of the z axis by $\Delta z = 30 \mu m$) during the visual-only task in order to identify entirely new tuned ensembles that had never been optogenetically stimulated. All mice that progressed through this new protocol (n=3), including one that had learned previously to correctly associate a random ensemble with the Target grating/reward condition (M3; behavior in FIG. 4H, 4I), were able to correctly discriminate stimulation of the entirely new orientation-tuned ensembles without any contrast ramp experiments (FIG. 4I, p<0.05, two-tailed paired t-test vs. no stim; each mouse also independently demonstrated significant discrimination performance to tuned ensembles stimulation, p<0.01 two-tailed Fisher's exact test comparing hit rate vs. false alarm rate for each mouse; 1-2 sessions per animal). Conversely, mice could not discriminate the new set of random ensembles (p=0.64, paired t-test, n=3), and tuned-ensemble stimulation performance far exceeded random-ensemble stimulation performance (p<0.01, two-tailed paired t-test, n=3). These results indicate that the optogenetic tuned-ensemble-driven performance is not simply the result of learning an association between cellular activity in an ensemble and reward (otherwise random-ensemble stimulation would work as well as tuned).

Discriminating random ensembles may indeed require additional learning/plasticity mechanisms, but tuned functional ensemble stimulation appears to support an immediately-interpretable and discriminable percept that can be used by the animal as it would use the visual percepts with which it had been trained.

The ability of some mice to learn to discriminate random ensembles, and the improvement observed for discrimination of tuned ensembles following the low-contrast pairing experiments, suggests that plasticity may occur in the visual cortical network to enhance specific perceptual pathways supporting behavior. Task learning has been hypothesized to strengthen specific pathways related to decision circuits (Law et al. (2009) *Nat Neurosci* 12:655, Petrov et al. (2005) *Psychol Rev* 112:715), and increased magnitude, tuning sharpness, and reliability of sensory responses have been observed in specific populations as a result of learning similar sensory-guided tasks including orientation discrimination (Schoups et al. (2001) supra, Yang et al. (2004) *J. Neurosci* 24:1617, Poort et al. (2015) supra), suggesting that local plasticity in V1 may indeed occur. Comparing recruitment of tuned networks in trained vs. naïve cohorts, it was observed that learning the visual task alone modestly enhanced specific network recruitment in response to visual stimuli (FIG. 16A, right, p<0.05; $\chi^2$ two tailed test, n=20 sessions in 4 mice); thus plasticity may indeed occur, but goal-directed attention, top-down modulation and general task-related states are likely to play a role as well (Zhang et al. (2014) *Science* 345:660).

Beyond changes associated with learning and performing the task itself, the next question was to ask what effects the pairing of visual stimuli with optogenetic ensemble-stimulation might have on specific visual circuit dynamics (FIG. 4 J-N). Whereas selective recruitment of iso-tuned (significantly more so than orthogonally-tuned) populations was observed for tuned ensemble stimulation before the contrast ramp in trained mice (FIG. 4J, p<0.05, $\chi^2$ two tailed test, n=6 session in 5 mice), as observed in naïve mice (FIG. 16A), random ensemble stimulation did not recruit visual-percept specific populations (FIG. 4 K, p=0.87, $\chi^2$ two tailed test, n=6 session in 5 mice). Following the contrast ramp experiments, tuned stimulation recruited much more powerfully the iso-tuned population (FIG. 4 L,N; p<0.0001, $\chi^2$ two-tailed test: iso-tuned vs. orthogonally tuned, n=15 sessions in 5 mice; p<0.0001, $\chi^2$ two-tailed test before vs. after the contrast ramp, same sessions as random-ensemble stimulation). Strikingly, random ensemble stimulation also now recruited the iso-tuned local populations (with tuning matching the grating direction with which that specific random ensemble had been paired during the contrast ramp training; FIG. 4 M, p<0.0001, $\chi^2$ two tailed test vs. orthogonally tuned). The magnitude of iso-tuned population recruitment also increased after vs. before contrast ramp experiments (FIG. 4 N, p<0.0001, $\chi^2$ two tailed test), consistent with the newly-learned ability of specific mice to perform random-ensemble discrimination (mouse identity legend as in FIGS. 4G, 4H, 4I, 4 J-N). Still, tuned ensembles were much more effective at recruiting iso-tuned populations than random ensembles (FIG. 4 N p<0.0001, $\chi^2$ two tailed test). Importantly, all of these local network recruitment analyses were conducted in the trial epoch before any reward or punishment was delivered, contingent on licking behavior (Materials and Methods).

This pattern of results dissociates specific network plasticity from more general, behavior-dependent brain state effects. That all mice immediately performed well in high-contrast visual conditions (range=[88.3% 96.8%] correct across n=5 mice for >12% visual contrast stimuli) at the outset of the contrast ramp experiments indicates that task-related brain states were likely already present. Yet, random-stimulation did not generalize from one ensemble to another and did not exhibit selective recruitment of visually-tuned populations until after the visual contrast ramp and optogenetic stimulation experiments (FIG. 4 M). In this way, the random-ensemble stimulation conditions help control for the influence of top-down and brain-state factors which would be present during the random-stimulation conditions as well as during tuned stimulation from the outset of the contrast ramp (though the possible role of selective feedback emerging after learning remains). These results point to connections being formed or strengthened between specific random ensembles and specific local visually-tuned and percept-selective populations, allowing mice to recruit appropriate visual pathways and perform appropriate discrimination associated with specific random-ensemble stimulation. While the mechanism of this linkage formation remains unclear, the functionally-broad inputs received by visual cortical neurons (Ko et al. (2011) *Nature* 473:87, Wertz et al. (2015) *Science* 349:70, Jia et al. (2010) *Nature* 464:1307, Chen et al. (2013) supra, Smith et al. (2013) *Nature* 503:115, Liu et al. (2011) *Neuron* 71:542), even if weak, may provide a pre-existing substrate in the network for learning new associations and building or linking pathways. Furthermore, synaptic plasticity mechanisms including sprouting of new synapses have been shown to occur over the time-frame of days—consistent with timescales present here (Trachtenberg et al. (2002) *Nature* 420:788). Local circuit plasticity, forming or strengthening specific connections between stimulated ensembles (both random and tuned) and surrounding populations, may serve to amplify specific cortical network activity originating from a fraction of the broader network.

Specific Naturally- or Artificially-Recruited Ensembles Support Behavior

Figure 13A:
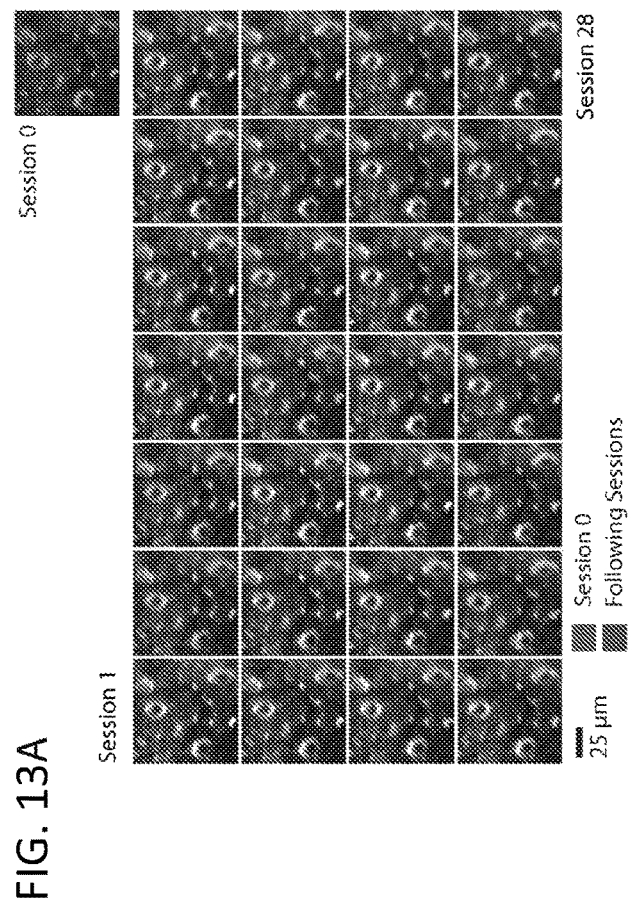
FIGS. 13A-13C depict targeting the same ensembles across weeks with cellular resolution.
Figure 13C:
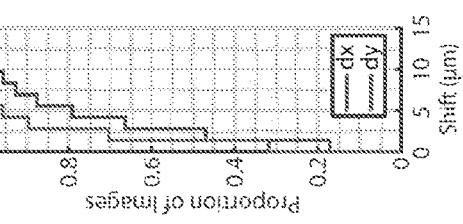
Figure 13B:
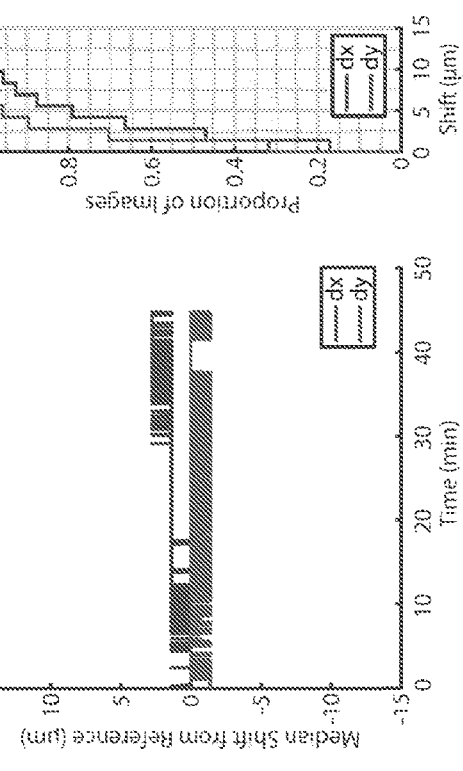

The ability to return to the same ensembles and surrounding populations with micron-level resolution allowed the exploration of the stability of visual-percept specific networks and artificial-percept discrimination behavior over several weeks (FIGS. 5,13). Mice performed both visual and artificial-percept discrimination behaviors with high performance over the course of many weeks, with statistically significant performance on almost every experimental session (FIG. 5A, 109/112 visual and 107/112 tuned ensemble sessions with p<0.05 hit rate vs. false alarm rate, two-tailed Fisher's exact test). Behavioral performance was nearly identical for visual orientation discrimination and optogenetic ensemble discrimination (FIG. 5B, 91.12±0.75% correct for visual discrimination vs. 89.47±0.78% correct [mean±SEM] for tuned ensemble discrimination, p=0.13, two-tailed paired t-test, n=112 sessions across 5 mice).

Figure 5A:
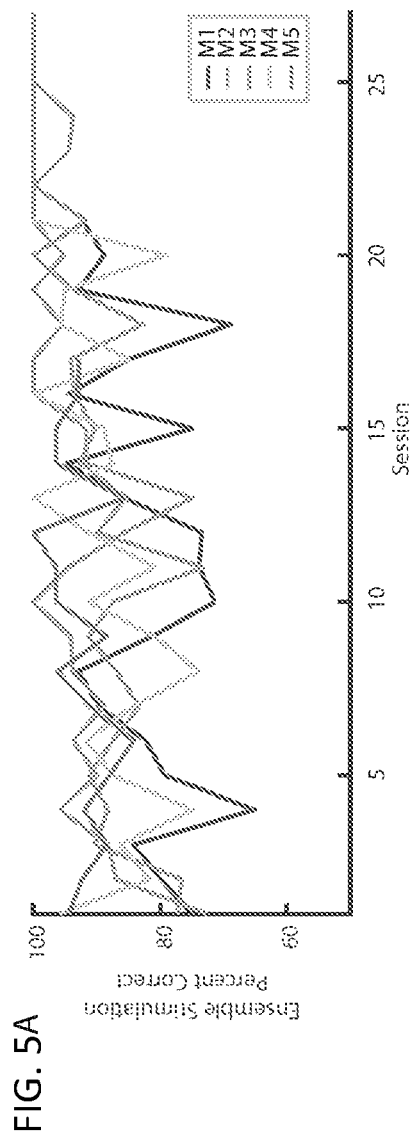
FIGS. 5A-5I depict dynamics of tuned and behaviorally potent visual ensembles.
Figure 5B:
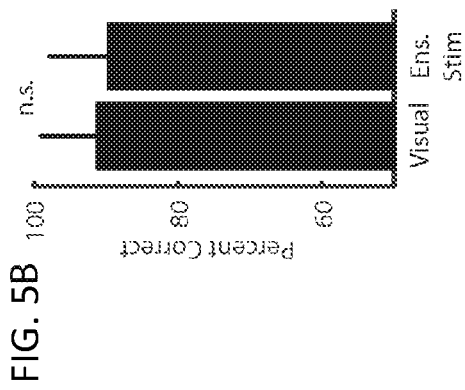
Figure 5C:
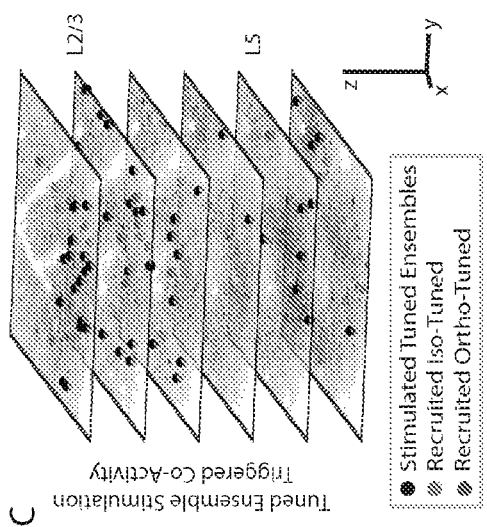
Figure 5D:
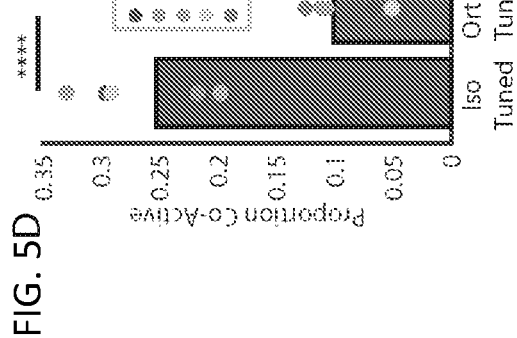
Figure 5E:
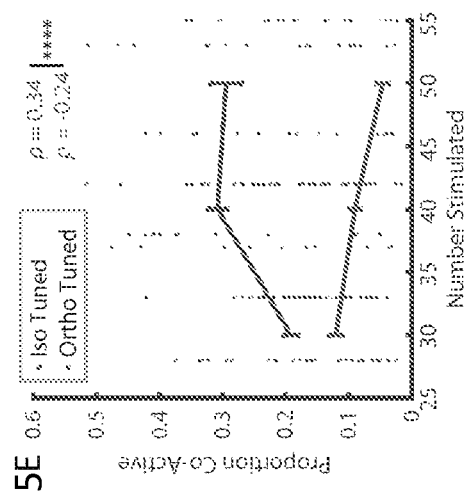

Recruitment of iso-tuned and orthogonally-tuned neurons was measured across all of these sessions; as before (FIGS. 3,4), finding co-active neurons among the held-out untargeted population across cortical layers during specific ensemble stimulation in the absence of visual stimulation (FIG. 5C). Iso-tuned neurons were much more likely to be thus recruited than were orthogonally-tuned neurons (FIG. 5D, p<0.0001, $\chi^2$ two tailed test, data from n=58 sessions in 5 mice). Iso-tuned population recruitment increased with the number of neurons stimulated (FIG. 5E; Spearman's ρ=0.34, p<0.001, n=116 data points across 5 mice). Conversely, recruitment of orthogonally tuned neurons decreased in probability as the number of stimulated neurons increased (FIG. 5E; Spearman's ρ=−0.24, p<0.01, n=116 data points across 5 mice), and thus selective recruitment was generally much more robust than orthogonal recruitment across all neuron-count conditions tested (FIG. 5E; p<0.0001, Fisher's z transformation).

Figure 5F:
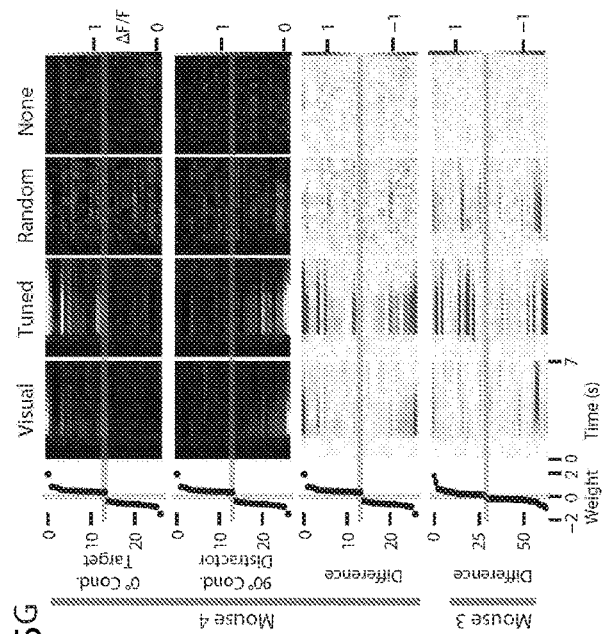

The elicited activity of neurons that had not been directly stimulated was further analyzed, as identified in each behavioral mouse in a manner identical to that used for the naïve mice (Materials and Methods; FIG. 16B; see FIG. 3G for a schematic of the analysis procedure). Principal component (PC) vectors were first identified using data taken during the presentation of visual stimuli and used these PC dimensions to project all of the experimental condition types (FIG. 5F). In a pattern like that observed in naïve mice (compare to FIG. 3H), the first two principal components explained the majority of the variance (the top two components explained 67.97±4.56% (mean±SEM) and the top four components accounted for 85.85±1.81%) (FIG. 16C). Neural trajectories during both visual and tuned stimulation closely matched each other, with the Target and Distractor trajectories separating upon stimulation onset (imaging frame following stimulus onset denoted by dark blue or red dot) in both the visual and tuned stimulation conditions, and exhibited far less separation during random stimulation (e.g. no separation detectable in Mouse 1 (FIG. 5F, top row, third column), and only slight separation in Mouse 3 (FIG. 5F; bottom row/third column)—a mouse that notably learned (FIG. 4H, 4I) to reliably discriminate random ensembles.

Further evidence supported the idea that these dimensions in PC space, whether visually or optogenetically-elicited, correspond to visual/perceptual dimensions rather than dimensions related to behavior/action. This is of critical importance to address, since behavioral task engagement can modulate activity in V1 (Fu et al. (2014) *Cell* 156:1139, Seitz et al. (2009) *Neuron* 61:700, Goltstein et al. (2018) *eLife* 7: e37683). The neural trajectories (reproduced in all mice and using multiple methods (Geladi et al. (1986) *Analytica Chimica Acta* 185:1, Remedios et al. (2017) *Nature* 550:388) in FIG. 18) from conditions where the mouse performed the incorrect licking behavior more than 50% of the time were indistinguishable from trajectories in conditions with high performance (see FIG. 5F, dark blue and red lines correspond to these low performance conditions). This result revealed independence of the V1 trajectories from strictly motor- or action decision-related effects, since trajectory type tracked with available percept rather than action taken.

Figure 5G:
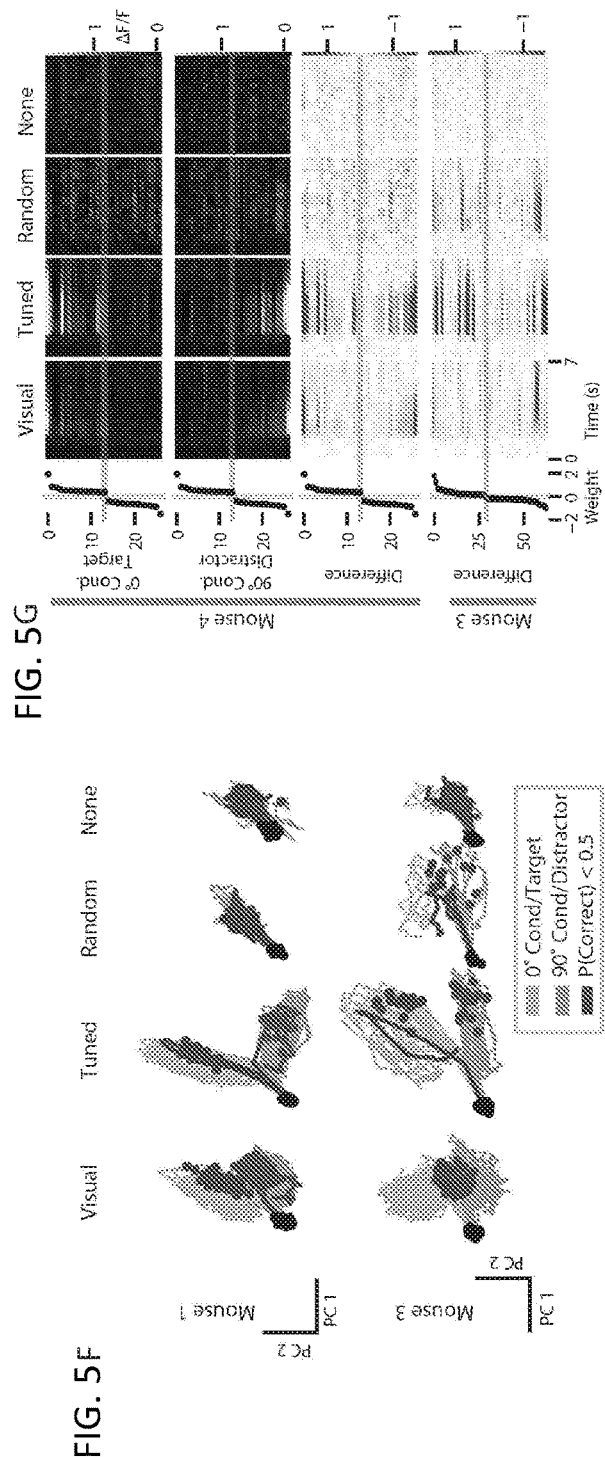
Figure 17:
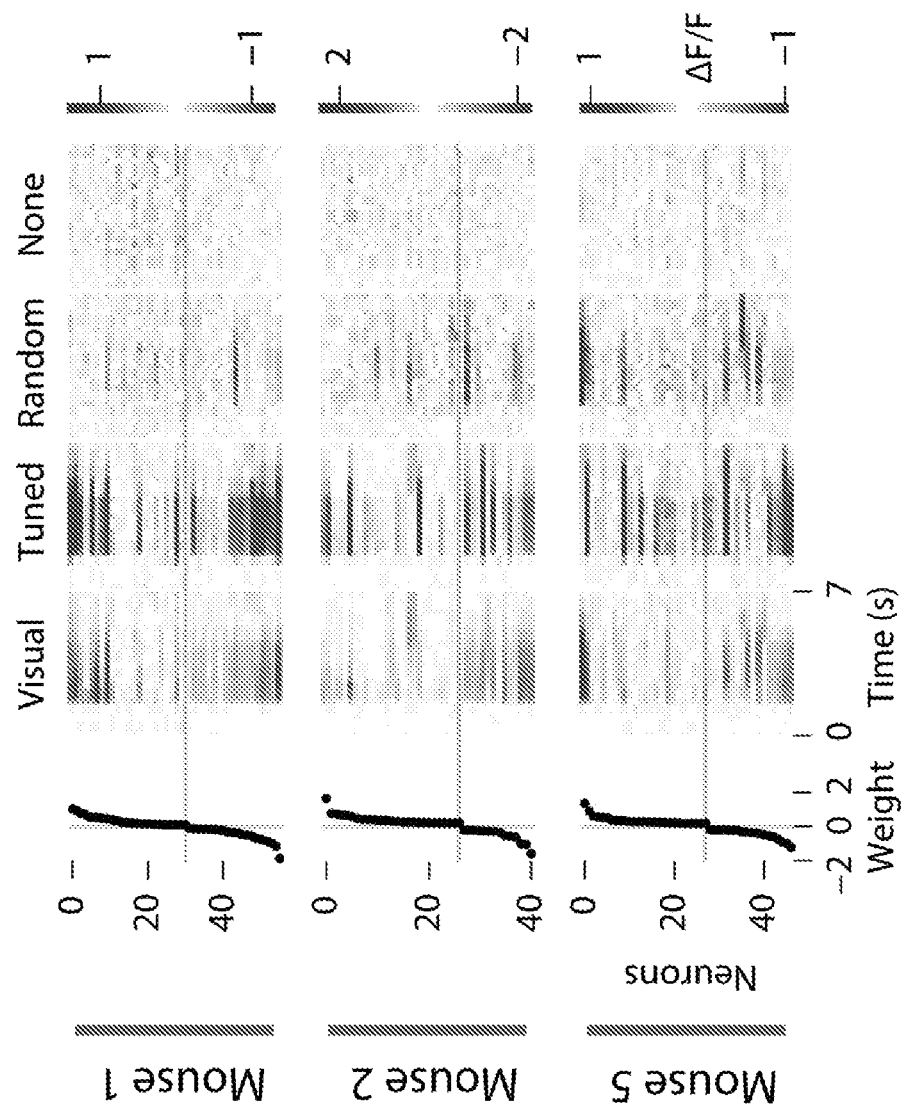
FIG. 17 depicts neural selectivity of additional behaviorally trained mice.

Upon application of binary classifiers trained only on data taken from the unstimulated neurons during presentation of visual gratings (FIG. 16E-16N), the learned classifier weights were found to correspond to neurons with selective responses for the 0° or 90° visual stimuli as expected—but crucially also to neurons selectively recruited by their corresponding optogenetic ensembles (FIG. 5G; three additional mice shown in FIG. 17). This result would be consistent with a model in which similar neural representations across conditions reveal the formation of a percept during optogenetic stimulation similar to that of the corresponding visual stimulus. Interestingly, the magnitude of this recruited population-response appeared even larger during tuned optogenetic ensemble stimulation than during visual stimulation (FIG. 5G, 5H), in contrast to the results seen in naïve animals. This pattern is consistent with training resulting in enhanced network recruitment of iso-tuned neurons, and may explain how random stimulation could in some cases yield population responses that weakly discriminate condition type (FIG. 5F-5H, bottom row, third column in each of those three panels). In contrast to this apparent effect of learning and task-related enhancement, random stimulation never evoked a large population response in naïve animals (FIGS. 3H-3K, 15).

Figure 5I:
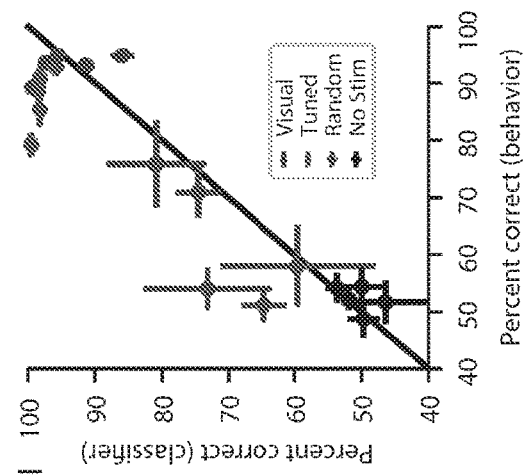
Figure 5H:
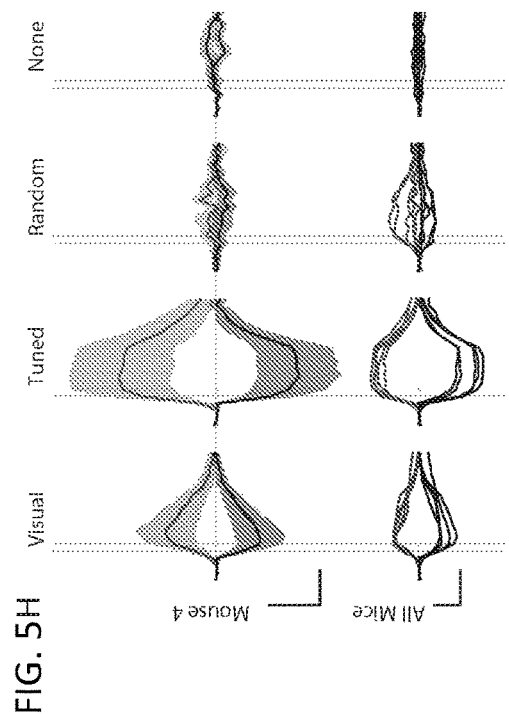

High correlation between mouse behavior and ensemble classifier performance was identified, across mice and condition type (FIG. 5I; $r^2=0.66$, $p<1e-70$). Both the classifier and behavioral data operated near saturation on real visual data, and on tuned stimulation conditions. In contrast, random stimulation resulted in lower, but still better-than-chance neural and behavioral discrimination (consistent with the local plasticity mechanisms described above). Together these results indicate that the selective stimulation of a small number of appropriate neurons is sufficient to ignite widespread network recruitment in V1 similar to that recruited by a visual stimulus, and that this specific ignition suffices to support corresponding specific behavior.

FIG. 3. Selective visual network recruitment by functionally-defined-ensemble stimulation. (A) Schematic of experimental arrangement. (B) Top, illustration of different experimental conditions. On a given trial, naïve mice were presented with one of two orthogonal visual stimuli at a specified contrast (contrasts were 2%, 12%, 25% and 50%, as for trained cohorts in FIG. 4). Bottom, mean, normalized $Ca^{2+}$ responses (GCaMP6m) for highly selective neurons (OSI>0.5) to 50% contrast; gray boxes indicate stimulus). (C) These tuned/selective ensembles were found intermingled across L2/3 and L5 (green, 0° cells, red, 900 cells). Two separate random ensembles were selected, matching the number of neurons in the tuned ensembles (magenta, ensemble designated as "0°", cyan, ensemble designated as "90°"). (D) Following the visual tuning characterization experiment in (B), conditions were added to the protocol to include selective or random ensemble optogenetic stimulation without a visual stimulus present (0% contrast). Ensemble stimulation trials were randomly interleaved alongside visual stimulus trials without optogenetic stimulation (visualizations not to scale). (E) Mean normalized $Ca^{2+}$ responses for all neurons within each selective or random ensemble during optogenetic stimulation trials (red or gray horizontal bars indicates stimulation time). (F) Locations of tuned neurons stimulated and recruited for one experimental session overlaid on average images from each imaging plane through the volume (negative image; black dots, directly-stimulated ensembles; green, secondarily recruited iso-tuned neurons; magenta, secondarily recruited orthogonally-tuned neurons; scale bars are 100 µm; see FIG. 16A for co-activity quantification, co-active neurons are found by two-tailed Wilcoxon signed-rank tests, $p<0.05$, sample window vs. baseline, Materials and Methods). (G) Schematic illustrating classifier and neural trajectory analysis. Classifiers and principal components (for neural trajectory visualization) were trained on fluorescence data taken from neurons that were never optogenetically stimulated. (H) Neural trajectories were computed individually for each experimental condition on each experimental day using Principal Components Analysis (PCA). Light blue trajectories show target conditions, light red trajectories show distractor conditions, black dots show trial start, and red and blue dots denote the $1^{st}$ frame following visual or optogenetic stimulus onset. (I) Top row: Mean 0° and 90° visual or optogenetic stimulation fluorescence responses (and their difference) in held out, unstimulated neurons, for one mouse. Mean time series traces taken from all neurons with large classifier weights: (abs(weight)>$99^{th}$ percentile). (J) Top row: Mean fluorescence response of all neurons included in the classifier analysis during 0° (positive lines) and 90° (negative lines) conditions multiplied by their classifier weights. Error bars, standard errors across neurons. Bottom row: weighted mean fluorescence responses shown for four mice. The activity from each mouse was normalized to its peak visual response to the 0° stimulus (this amplitude is indicated by the Y-axis scale bar). X-axis scale bar represents five volumes of activity (1.82 seconds). Vertical bars represent timepoints used for training the classifier. (K) Percent correct prediction performance of logistic classifiers trained on held-out neuronal responses indicated in panel (G) during visual stimulation (corresponding to the "sample window" time period in FIG. 4). Probabilities were computed using a Wilcoxon signed-rank test to determine if a condition type is decoded with higher efficacy than the one to its right in the plot. $p<0.01$, **$p<0.0001$.

FIG. 4. Eliciting a specific visual percept through targeting individually-identified neurons. (A) Mouse behavioral arena under the MultiSLM for simultaneous imaging and ensemble optogenetics. (B) Mice learn to discriminate orthogonal drifting gratings (Targets/Go: Vertical bars, Distractors/No Go: Horizontal bars) of varying contrast (trial timings shown; Materials and Methods). (C) Visual discrimination performance of representative mouse (statistical significance is seen with >12% contrast, $p<0.05$ Fisher's exact test, Target vs. Distractor conditions for each session). (D) Upon stable performance, GCaMP6m signals in visual cortex are imaged across cortical layers with the MultiSLM during task performance. Neurons (n=40.7±8.7 [mean±SD], across n=5 mice) with reliable and selective responses to one 50% contrast orientation (OSI>0.5; Materials and Methods) are used to constitute Target and Distractor Ensembles for all subsequent ensemble optogenetic experiments. Mice perform a variant of the visual discrimination task in which, on randomly interleaved trials, selective tuned (green, Target (00), or red, Distractor (90°), dots in schematic) or random ensembles (magenta, Target ("0"), or cyan, Distractor ("90°"), dots in schematic) are stimulated with or without corresponding visual stimuli. Reward and punishment contingencies are similarly applied for visual and/or optogenetic conditions. (E) Top: normalized mean visual responses (50% contrast) for Target (0°) and Distractor (90°) selective ensembles. Bottom: ensemble optogenetic stimulation responses of the same populations of tuned and of n-matched random ensembles. (F) The lowest-contrast stimulus is alternated from 0% contrast (no visual stimulus) to 2%, 3%, 4%, and 5% (typically in that order, with one low contrast tested in each behavioral session; 12%, 25% and 50% contrast trials are randomly interleaved). Discrimination behavior is significantly enhanced during tuned ensemble stimulation ($p<0.05$, two-way ANOVA, main effect of stimulation type, n=4 mice; tuned optogenetic ensemble=red, visual stimulus only=black, and random optogenetic ensemble=blue; logit function fits: 50% correct was subtracted from all mean values, values were divided by maximum performance ($P_{max}$), and values<0 were set to 0 for each fit; fits were re-scaled for plotting by multiplying each fit by ($P_{max}-0.5$) and adding 50%). A 5th mouse demonstrated significant discrimination on the first presentation of tuned ensemble stimulation in the absence of visual stimulation and thus immediately advanced to subsequent experiments. (G) Following these contrast-ramp experiments, mice demonstrated consistently high behavioral discrimination performance without a visual stimulus in response to stimulation of the tuned ensemble that had been paired with visual stimulus during training (left: $p<0.01$, n=5, paired t-test before vs. after ramp, 0% contrast), but the response to stimulation of the random ensemble that had been similarly paired with visual stimulus during training was variable and not significant across animals (right: p=0.097). Paired lines in (G-I) and dots in (J-N) are color-coded to reflect mouse identity, as indicated by legend. (H) Left, performance was high for tuned ensemble stimulation, compared with the condition of no visual or optogenetic stimulus present (p<0.01, n=5 paired t-test vs. no visual/optogenetic stimulation, two tailed). Intriguingly, a subset of mice appeared to improve performance with random ensemble stimulation vs. no stimulation (middle; overall p=0.07, n=5 paired t-test, two tailed), but mice performed better with tuned ensemble stimulation than random ensemble stimulation (right; p<0.05, paired t-test, two tailed; data points replotted across the three panels). (I) Mice immediately discriminated entirely new tuned ensembles that had never been stimulated during training ($\Delta z$=m shift to identify a new set of neurons within the same visual field) with high performance compared to no stimulation trials (left, p<0.05, two-tailed paired t-test, n=3) or compared to n-matched random ensembles (right, p<0.01, two-tailed paired t-test, n=3 mice), but mice showed no difference in performance for random ensemble stimulation vs. no stimulation (middle, p>0.1, two-tailed paired t-test, n=3; data points replotted across the three panels as in (H)). (J) Modest preferential recruitment of iso-tuned neurons versus orthogonally-tuned neurons during tuned ensemble stimulation (without a visual stimulus), before the visual-stimulus contrast ramp experiments. These mice were trained on the visual-only task (p<0.05 iso vs. orthogonally tuned, $\chi^2$ two tailed test, n=6 sessions in 5 mice; co-active neurons are found by two-tailed Wilcoxon signed-rank tests, sample window vs. baseline, p<0.05, Materials and Methods). (K) This effect is absent for stimulation of random ensembles initially (p>0.1, $\chi^2$ two tailed test, n=6 sessions in 5 mice). (L) Selective recruitment of iso-tuned neurons with tuned ensemble stimulation after contrast ramp pairing (p<0.0001, iso- vs orthogonally-tuned, $\chi^2$ two tailed test, n=15 sessions in 5 mice). (M) After the contrast ramp visual-stimulus and random-ensemble pairing, selective recruitment of iso-tuned neurons emerges for random ensemble stimulation (p<0.0001, $\chi^2$ two tailed test, n=13 sessions in 5 mice; same sessions as used for tuned ensemble stimulation in (N)—with the effect most apparent in mice that learned to discriminate the two ensembles as shown in (H, middle), (color coding for mouse identity preserved across all panels). (N) Tuned ensemble stimulation remains more potent than random ensemble stimulation at recruiting iso-tuned cells even after the contrast ramp pairing experiments (p<0.0001, $\chi^2$ two tailed test). The enhanced recruitment of iso-tuned populations after contrast ramp experiment for both tuned and random ensemble stimulation (p<0.0001, $\chi^2$ two tailed test) was consistent with observed improvements on task performance (panel (G)). Data were pooled across sessions and mice for each bar in the bar graphs of (J-N), and reported with Pearson's $\chi^2$ square test results; pooled data across sessions for each mouse are shown as colored dots (see Materials and Methods for stratified Cochran-Mantel-Haenszel (CMH) tests controlling for mouse identity). *p<0.05, p<0.01, **p<0.0001, †p<0.1, error bars mean+/−s.e.m. throughout figure.

FIG. 5. Dynamics of tuned and behaviorally potent visual ensembles. (A) All mice maintained high performance discrimination for tuned-ensemble stimulation over several weeks (behavioral session data from each mouse are shown as colored lines signifying mouse identity as in legend). Later sessions include fewer mice. (B) Ensemble optogenetic stimulation discrimination performance (right) was indistinguishable from visual discrimination performance (12% visual contrast behavior shown, left, p>0.1 paired t-test, two tailed, n=112 sessions across 5 mice; error bars are standard deviation of the mean). (C) Locations of tuned neurons stimulated and recruited for one experimental session overlaid on average images from each imaging plane through the volume (negative image; black dots, directly-stimulated ensembles; green, secondarily recruited iso-tuned neurons; magenta, secondarily recruited orthogonally-tuned neurons; scale bars are 100 µm). (D) Non-stimulated iso-tuned neurons are preferentially recruited by ensemble stimulation in the absence of visual stimuli, compared to orthogonally-tuned neurons (p<0.0001, $\chi^2$ two tailed test; co-active neurons are found by two-tailed Wilcoxon signed-rank tests, sample window vs. baseline, p<0.01, Materials and Methods). Data are pooled across sessions and mice for bars and reported Pearson's $\chi^2$ test results (n=58 sessions in 5 mice). Pooled data across sessions for each mouse are shown as colored dots (see legend for mouse identity; same legend corresponds to rest of figure, and FIG. 4; see Materials and Methods for CMH tests controlling for mouse identity). (E) Data from all experimental conditions of full ensemble stimulation in the absence of visual stimuli (n=232 data points from 58 sessions in 5 mice). As the number of neurons increases, more iso-tuned neurons are recruited (red, mean+/−s.e.m., Spearman's $\rho$=0.34, p<0.001, n=116). This effect reverses for recruited orthogonally-tuned neurons (blue, mean+/−s.e.m., Spearman's $\rho$=−0.24, p<0.01, n=116), with statistically-significant different correlation for recruited iso-tuned than recruited orthogonally-tuned neurons (p<0.0001, Fisher z transformation). (F) Neural trajectories were computed individually for each experimental condition on each experimental day using PCA. Only fluorescence time points before reward onset were used. Light blue trajectories show target conditions, light red trajectories show distractor conditions, black dots show trial start, and red and blue dots denote the $1^{st}$ frame following visual or optogenetic stimulus onset. Dark blue or red trajectories denote conditions wherein the mouse performed at <50%, indicating erroneous licking behavior on average. (G) Top row: Mean fluorescence time series for all neurons (in representative Mouse 4) with large classifier weights (abs (weight)>$95^{th}$ percentile) shown during target trials. Second row, distractor trials. Third row: first row (target trials)—second row (distractor trials). Bottom row: target—distractor fluorescence responses shown for 1 additional mouse. (H) Top row: Mean fluorescence response of all neurons included in classifier analysis during target (positive lines) and distractor (negative lines) conditions multiplied by their classifier weights. Error bars: standard errors across all neurons. Bottom row: weighted mean fluorescence responses for five mice. Activity from each mouse was normalized to its peak visual response to the target stimulus (amplitude is indicated by the Y-axis scale bar). X-axis scale represents five volumes of activity (1.82 seconds). Vertical bars: timepoints for training the classifier. (I) Behavioral performance vs. performance of logistic classifiers trained on unstimulated neuronal responses during visual stimuli. Points show different conditions from individual mice. Error bars: s.e.m. across sessions.

Figure 15:
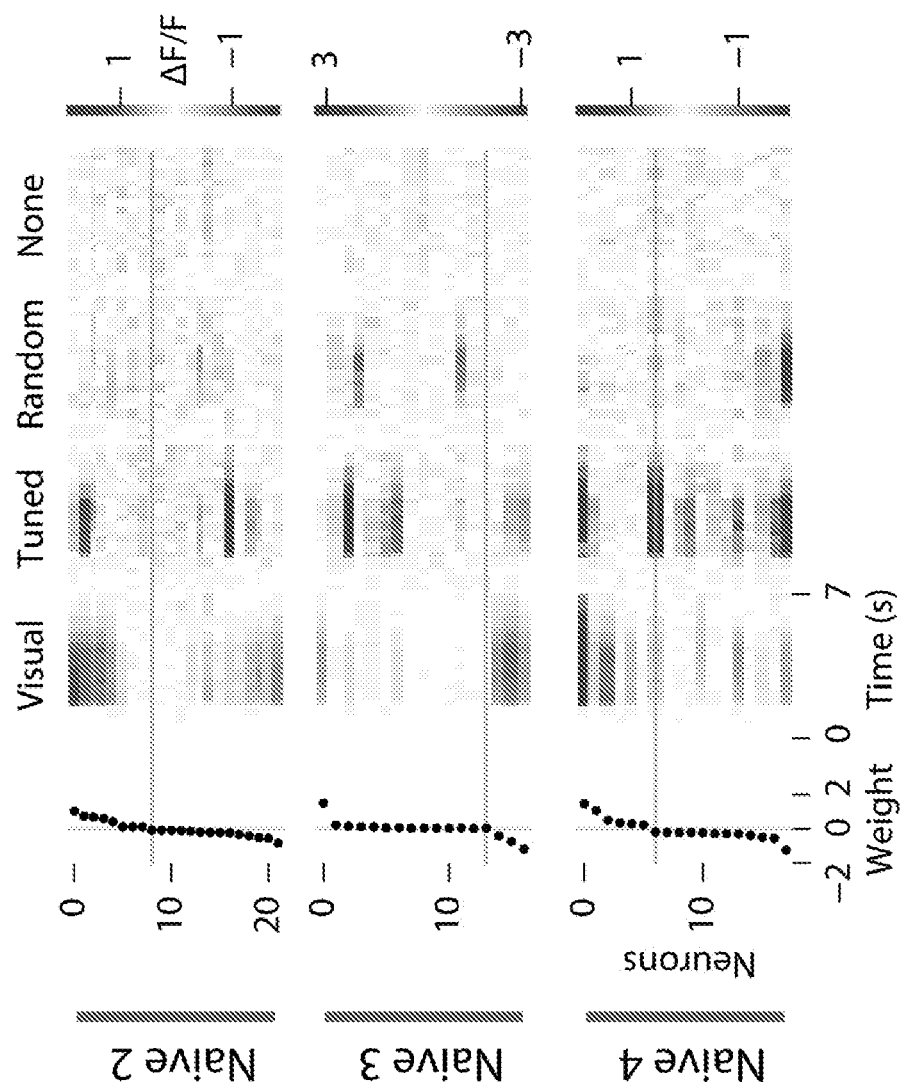
FIG. 15 depicts neural selectivity of additional behaviorally naïve mice.

FIG. 15. Neural selectivity of additional behaviorally naïve mice. Each row shows the trial-averaged fluorescence response of a neuron during the 0° visual stimulus minus its response during the 90° visual stimulus (or matched optogenetic stimulus) for all neurons with large classifier weights (defined as abs(weight)>$99^{th}$ percentile). This analysis is shown here for three naïve mice not shown in the main text. Dots on the left-hand side of each row indicate the classifier weight of each neuron. Blue indicates neural responses preferential to the 0° condition, red responses were stronger for the 90° condition.

FIG. 17. Neural selectivity of additional behaviorally trained mice. Each row shows the trial-averaged fluorescence response of a neuron during the 0° visual stimulus minus its response during the 90° visual stimulus (or matched optogenetic stimulus) for all neurons with large classifier weights (defined as abs(weight)>95$^{th}$ percentile). This analysis is shown here for three trained mice not shown in the main text. Dots on the left-hand side of each row indicate the classifier weight of each neuron. Blue indicates neural responses preferential to the 0° condition; red responses were stronger for the 90° condition.

Quantitative Circuit Architecture Underlying Layer-Specific Perceptual Thresholds The ability to record across cortical layers and return to the same populations each day (FIG. 13) next allowed systematic quantification of the influences of distinct numbers of stimulated neurons in each cortical layer on intra- and inter-laminar communication and behavior. In a subset of trials, subsets of neurons selected (at random) from the original tuned ensembles were stimulated, with particular attention to layer and total number of neurons stimulated. It was found that stimulating only layer 2/3 tuned ensembles led to selective recruitment of iso-tuned neurons in both layer 2/3 and layer 5, with stronger recruitment occurring within layer 2/3 (FIG. 6 A, $p<0.0001$ for all comparisons: recruited iso-tuned vs. ortho-tuned, and within layer 2/3 vs. layer 5, $\chi^2$ two tailed tests). Increasing the number of neurons stimulated in layer 2/3 led to an increase in the fraction of co-active iso-tuned cells within both layer 2/3 and layer 5 (FIG. 6 B, Spearman's $\rho=0.46$, $p<0.01$, n=46 data points, within layer 2/3, $\rho=0.51$, $p<0.01$, n=36 data points, within layer 5, $p=0.78$ two-tailed Fisher's z transformation comparing $\rho$ values).

Stimulating only layer 5 tuned ensembles led to selective recruitment within layer 5, but interestingly did not lead to robust recruitment in layer 2/3, and layer 5 to layer 2/3 recruitment was not visual-percept selective (FIG. 6 C, $p<0.0001$, iso vs. ortho tuned in layer 5, and layer 5 vs. layer 2/3 iso tuned, $\chi^2$ two tailed tests; recruitment in layer 2/3 was not significantly different between iso and ortho tuned populations, $p=0.58$, $\chi^2$ two tailed test). As the number of neurons stimulated increased in layer 5, a greater fraction of iso-tuned neurons in the surrounding population was recruited in layer 5 but not layer 2/3 (FIG. 6 D, Spearman's $\rho=0.62$, $p<0.01$, n=24 data points for layer 5 recruitment; $\rho=0.19$, $p=0.38$, n=24 data points for layer 2/3 recruitment), and the correlation was stronger for layer 5 than even the weak positive trend for layer 2/3 (FIG. 6 D, $p<0.05$, Fisher's z transformation). Enhanced recruitment of layer 5 was a consistent theme; stimulating full selective ensembles across layers led to selective recruitment within both layer 2/3 and layer 5, with the strongest iso-tuned recruitment in layer 5 (FIG. 19A, $p<0.0001$ all comparisons shown between iso vs. ortho-tuned and layer 2/3 vs. layer 5, $\chi^2$ two tailed tests). Furthermore, as the number of neurons stimulated in each respective layer was increased, the proportion of iso-tuned neurons in the surrounding population increased more rapidly within layer 5 (when layer 5 was stimulated) than within layer 2/3 (when layer 2/3 was stimulated) (FIG. 19B, $p<0.01$, ANCOVA, controlling for the covariate of number stimulated; corresponding data replotted from panels FIG. 6 B,D on the same axes).

These layer-specific results indicate selective functional connectivity within layer 2/3, to a greater extent within layer 5, and from layer 2/3 to layer 5. Strong functional connectivity is markedly lacking from layer 5 to layer 2/3, and functional effects of that projection appear non-specific in terms of the visual-percept information investigated here. This arrangement suggests V1 may implement a circuit capable of modular amplification of concordant information within layer 2/3 and within layer 5 independently, and provides a functionally selective link from layer 2/3 to 5 likely supporting influence of feedforward pathways converging on cortex from thalamus in vision (Douglas et al. (2004) Annu Rev Neurosci 27:419). Both superficial and deep layers support cortico-cortical connectivity between areas, but layer 5 is uniquely involved in certain long-range projections including to subcortical structures, and may be specially positioned in the circuit to convey information more broadly across the brain to influence ongoing dynamics supporting cognition and diverse behaviors (Felleman et al. (1991) Cerebral Cortex 1:1, Harris et al. (2015) Nat Neurosci 18:170, Sorensen et al. (2015) Cereb Cortex 25:433, Shepherd (2013) Nat Rev Neurosci 14:278, Hooks et al. (2011) PLOS Biology 9: e1000572, Tehovnik et al. (2009) Eur J Neurosci 29:1477, Tehovnik et al. (2002) Eur J Neurosci 16:751, Murphey et al. (2007) Curr Biol 17:862, Bak et al. (1990) Med Biol Eng Comput 28:257).

To test this prediction that layer 5 activity would be more potent in driving perceptual behavior than layer 2/3—and more generally, to quantify the sensitivity of network ignition and its relationship to behavior with single-cell resolution—the link between the number of iso-tuned neurons that were simultaneously optogenetically stimulated, and consequences on both network activation and behavior was examined. The binary classifiers described earlier were used to reveal that, across subjects, there was a critical number of stimulated neurons required for driving a robust population response that could drive high discrimination performance (FIG. 6 E-F; for psychometric curve fitting, see Materials and Methods and FIG. 19C-19G for results for individual mice). Classifier performance saturated at nearly 100% beyond a relatively small number of stimulated neurons (approximately 20), indicating that sufficient information is available in a small population for robust discrimination. This result from neural data agreed well with the same analysis applied to the aggregate behavioral performance (FIG. 6 G-H). However, behavioral performance was somewhat inferior to that of the classifier applied to neural data-evidenced by a lack of behavioral experiments with near perfect performance. This suggests that countervailing influences on behavior, such as attention, motivation, impulsivity or satiation, may prevent successful report of the percept on all trials, and may also indicate that V1 network recruitment does not always recruit the necessary brain-wide network for driving behavior. Importantly, in the great majority of cases, and adhering to a very similar threshold, percept-specific network ignition coincided with behavioral report of the specific percept.

The psychometric curves in FIG. 6 E,G further indicated that layer 5 neurons may be more potent at driving neural and behavioral discrimination than those in layer 2/3. To test this hypothesis in more detail, the analysis was restricted to only experiments where comparable numbers of neurons were stimulated between layers 2/3 and 5 (FIG. 6 F,H). This subset of data was used in a two-way ANOVA to compare the effect of laminar position on ensemble ability to influence classifier performance (FIG. 6 F) or animal behavior (FIG. 6 H). In each case, equivalent numbers of layer 5 neurons were more successful at driving high performance ($F_{1,49}$=8.11, p<0.01 for the classifier data; $F_{1,49}$=5.47, p=0.023 for behavioral data, main effect of layer).

To assess the minimum threshold for ensemble discrimination here, experiments were carried out to determine the fewest possible neurons needed to drive significant discrimination behavior in the most sensitive mouse. This mouse could discriminate two neurons per ensemble in layer 5 with high performance (d'=2.11, p=0.037, two-tailed Fisher's exact test, n=24 trials; a second mouse also demonstrated significant discrimination of two-neuron ensembles in layer 5, p=0.036), but could not discriminate single neurons (p>0.21 for 4 sets of single neurons tested). Relevant to perceptual thresholds for cortical neuron activity detection (Houweling et al. (2008) *Nature* 451:65, Huber et al. (2008) *Nature* 451:61), these results provide thresholds for specific ensemble discrimination related to natural percepts, with specific linkage to network recruitment and cortical layer.

Theory and Modeling of Low-Thresholds for Cortical Ignition

A striking finding of the experimental data is that stimulation of an exceedingly small number of selectively-tuned neurons can ignite the activity of a large fraction of the iso-tuned ensemble (FIG. 6 B,D,F). Despite such high sensitivity (low cell-count threshold for V1 ignition), spontaneous activity in V1 remains quite low, with a mean firing rate of about 0.2-2 Hz, depending on layer (Niell et al. (2008) *J Neurosci* 28:7520, Niell et al. (2010) *Neuron* 65:472). What then are the theoretical principles that enable such high sensitivity to small amounts of external stimulation, while still maintaining stable, low levels of spontaneous activity? An analytic theory of ignition (see Materials and Methods) based on a model of N neurons firing at a Poisson rate in the spontaneous state, representing a selective neural ensemble, was developed. Because fluctuations of the total number of active neurons in this ensemble are proportional only to the square-root of the ensemble size, it was found that it is possible to prove one can set very low thresholds for ignition, requiring stimulation of only order $\sqrt{N}$ neurons, without destabilizing the spontaneous activity. Calculations reveal (see Supplementary Text) that stimulating as few as 20-30 neurons may reliably ignite large V1 ensembles for biologically plausible assumptions about the total tuned ensemble size, spontaneous firing rates, and single neuron integration times.

Finally, a proof-of-principle instantiation of the phenomenon of low-threshold ignition in a model neural circuit (FIG. 6 I-K), of order 1000 excitatory and inhibitory neurons, was demonstrated. The key principles for generating low threshold ignition were found to be: (1) a fast recurrent excitatory subnetwork (which by itself would be highly unstable), (2) a slow inhibitory network that provides strong inhibition to the excitatory subnetwork, (3) recurrent excitatory connectivity not strong enough to destabilize a low spontaneous activity state in the combined excitatory-inhibitory network, and (4) this same recurrent excitation is strong enough that further excitation of a small number of excitatory cells can trigger ignition (FIG. 6 I). The slower inhibition then brings the excitation back down so the ignition is transient (FIG. 6 J). Thus overall, the combined technology development, experiment and theory suggest that, at least in the context of the percept discrimination behavior explored here, V1 operates in a striking and specific dynamic regime very close to a boundary of instability (FIG. 6 K), enabling stimulation of a very small number of neurons to reliably trigger neural ignition, and consequently, percept-guided behavior. Thus remarkably, V1 may be exquisitely organized to amplify activity input, without allowing spontaneous activity to trigger false percepts.

FIG. 6. Circuit architecture underlying layer-specific perceptual thresholds. (A) Recruitment probability for nontargeted cells with different tuning across layers, during stimulation of tuned ensembles in layer 2/3. Non-targeted iso-tuned neurons were preferentially recruited within layer 2/3 and layer 5 compared with ortho-tuned neurons (p<0.0001, $\chi^2$ two tailed test; co-active neurons are found by two-tailed Wilcoxon signed-rank tests, sample window vs. baseline, p<0.01, Materials and Methods; p<0.01, *p<0.001, ****p<0.0001 throughout the figure), and the proportion of recruited neurons was higher overall within layer 2/3 than within layer 5 during layer 2/3 stimulation across all experiments (p<0.0001, $\chi^2$ two tailed test). (B) The proportion of recruited iso-tuned neurons in each layer increased with high correlation within both layer 2/3 and layer 5 (Spearman's $\rho$=0.46, p<0.001 for layer 2/3, Spearman's $\rho$=0.51, p<0.0001 for layer 5; n=46 experiments in 5 mice, p>0.1, Fisher z transformation comparing p values; fit with logit function that assumes the fraction of recruited neurons will saturate to 1). (C) As in (A) but tuned ensembles in layer 5 instead of 2/3 were stimulated. Non-targeted iso-tuned neurons were preferentially recruited in layer 5 relative to ortho-tuned layer 5 neurons (p<0.0001, $\chi^2$ two tailed test), and relative to iso-tuned layer 2/3 neurons (p<0.0001, $\chi^2$ two tailed test), but selective recruitment of iso-tuned neurons was not observed to layer 2/3 (p>0.1, $\chi^2$ two tailed test). For (A) and (C), data were pooled across sessions and mice for each colored bar and reported with Pearson's $\chi^2$ square test results; pooled data across sessions for each mouse are shown as colored dots (see legend, per FIGS. 4H, 5D; Materials and Methods: stratified CMH tests controlling for mouse identity). (D) As the number of neurons stimulated in the tuned layer 5 ensemble increased, a greater fraction of iso-tuned layer 5 (Spearman's $\rho$=0.62, p<0.01) neurons were recruited. However, this correlation was not statistically significant for recruited layer 2/3 neurons (Spearman's $\rho$=0.19, p=0.38 versus no correlation), and the correlation was stronger for layer 5 vs the weak layer 2/3 trend (p<0.05, Fisher z transformation, n=24 experiments in 4 mice). (E,G) Logistic psychometric functions fit to predictions derived from logistic classifiers trained on either neural data (E) or behavioral data (G). Psychometric curve fits were generated against data pooled across 5 mice (see FIG. 19 for individual mouse data). Each curve relates the average performance of mice in response to stimulation of specific numbers of identified neurons from tuned ensembles. Individual points represent averages across the one or more sessions wherein a particular experimental condition was run (error bars show s.e.m.). Fits were generated independently for experiments where only neurons within layer 2/3 (purple) or layer 5 (green) were stimulated. (F,H): Data from (E) and (G) is re-plotted for only the ensemble sizes where comparable numbers of neurons were stimulated. Individual points correspond to experimental conditions taken from single days and single mice; mean±s.e.m. shown for each ensemble size bin (bin size across mice is 4 neurons). This subset of data was used to compute a two-way ANOVA to compare the effect of ensemble laminar position on classifier performance (F) or animal behavior (H). In each case, equivalent numbers of layer 5 neurons were more successful at driving performance (p<0.01 for classifier data, p=0.023 for behavioral data, main effect of layer; Target and Distractor ensembles differ in size by at most 1 neuron (E-H)). (I) In a model network of 1000 excitatory neurons and 1000 inhibitory neurons (Materials and Methods) stimulating a small number of excitatory neurons can lead to reliable ignition events, wherein the percent of the total excitatory neuron population that is secondarily recruited during stimulation exceeds 20% of the total population. Error bars reflect standard error in the estimate for the probability of ignition over 440 stimulation trials neurons (Materials and Methods). (J) Example traces showing ignition events wherein stimulation of only 30 neurons triggers transient activation of a substantial fraction of the entire excitatory population, while also maintaining low background probability of spontaneous ignition given certain properties of the network neurons (Materials and Methods). (K) Qualitatively, the excitatory subnetwork with low levels of constant inhibition behaves as a bistable system with two stable states corresponding to low and high fractions $f_e$ of active excitatory neurons (blue dots) separated by an unstable state of intermediate activation (red cross); these three fixed points correspond to $$\frac{df_e}{dt} = 0.$$

The network is poised near the boundary of instability in that the low stable spontaneous state is close to the unstable state, allowing the activation of a small number of neurons to push the network past the unstable state to trigger ignition to the high activity state. Slower rising inhibition (not shown) then brings the excitatory network back down, as in (J).

Materials and Methods

In Silico Opsin Screening, Molecular Cloning, and Imaging

For the purpose of finding new classes of opsin genes, in silico screening was performed on the data of the Marine Microbial Eukaryote Transcriptome Sequencing Project (Keeling et al. (2014) supra). Transcript sequences were obtained via tblastn search against the eukaryotic transcriptome data using known opsin sequences as a query with the threshold of e-value 0.1; duplicated sequences and sequences shorter than 750 bp were excluded. Then, phylogenetic analysis was performed to search for putative functionally-novel opsin genes; to find channelrhodopsins with high cation conductance, sequences with more negatively charged amino acids in the transmembrane domains 1, 2, 3, and 7 comprising the structure-resolved ion-conducting pathway and guided by the structure-derived pore surface electrostatic model were the focus (see Supplementary Text).

The amino acid sequence was human codon optimized and synthesized by Genscript in pUC57 vectors, the gene was subcloned into an adeno-associated viral vector fused with enhanced YFP (EYFP) along with the trafficking sequence (TS) and ER export signal and under control of either the CaMKIIα promoter for neuron expression or the Ef1α promoter for HEK293 cell expression. For confocal images of opsin-expressing neurons, coverslips of transfected neurons were fixed for 15 minutes in 4% paraformaldehyde and mounted with PVA-DABCO. Images were acquired with a Leica DM600B confocal microscope.

The opsin sequence described herein and discovered via this workflow (from Tiarina fusus strain LIS, SEQ_ID=MMETSPO472-20121206119186), which was named ChRmine, was edited and used for subsequent functional analysis. The edited sequence was deposited in the database (accession number TBD). All transcriptome data used in this study are available in the Marine Microbial Eukaryote Transcriptome Sequencing Project (MMETSP) (Keeling et al. (2014) supra).

Histology, immunohistochemistry and confocal imaging: Mice were anaesthetized with isoflurane and Beuthanasia-D, and transcardially perfused in cold 4% paraformaldehyde perfusion fix solution (Electron Microscopy Services, Hatfield, PA, USA). Brains were extracted and kept in the fixation solution for 24 hours at 4° C. and then transferred to 30% sucrose in PBS to equilibrate for 2 days at 4° C. 40 m slices were cut on a freezing microtome and stored in cryoprotectant at 4° C. Sections were washed three times for 10 minutes each in 1× phosphate buffered saline (Thermo Fisher Scientific) then incubated for 60 mins in blocking buffer (PBS+0.3% TritonX and 3% normal donkey serum), all at room temperature, while rocking. Sections were incubated with primary antibodies diluted 1:500 in blocking buffer overnight at 4° C. The two primary antibodies used were rabbit anti-GFP (Fisher Scientific A11122) and mouse monoclonal anti-HA tag (Fisher Scientific A26183). Sections were then washed in PBST and incubated in secondary antibodies against rabbit conjugated to Alexa Fluor@ 488 (A21206, Thermo Fisher Scientific) and against mouse conjugated to Alexa Fluor@ 647 (A-31571, Thermo Fisher Scientific) for three hours at room temperature, diluted 1:500 in blocking buffer. This was followed by three washes of ten minutes each in PBST. The nuclei were stained by DAPI (4',6-diamidino-2-phenylindole) diluted 1:50000 in PBS for 30 min at room temperature, then washed again and mounted on slides with PVA-DAPCO. Confocal imaging of GFP fluorescence (for GCaMP expression), HA antibody staining for localization of the opsin, and DAPI for cyto-architecture was performed using a Leica TCS SP5 confocal scanning laser microscope with a 20× or 40× oil objective. Co-localization was performed using 40× images (5-6 z slices through each section) by annotating GCaMP6m-expressing cell body locations and then overlaying these annotations and verifying expression in the anti-HA image. Images are displayed in the figure with 1% pixel saturation.

In Vitro Characterization with One-Photon Electrophysiology

The hippocampi of Sprague-Dawley rat pups (Charles River) were removed at postnatal day 0 (P0), and CA1/CA3 regions were digested with 0.4 mg/ml papain (Worthington, Lakewood, NJ) and plated onto 12 mm glass coverslips pre-coated with 1:30 Matrigel (Beckton Dickinson Labware). Cells were plated in 24-well plates, at a density of 65,000 cells per well. The cultured neurons were maintained in Neurobasal-A medium (Invitrogen) containing 1.25% FBS (Fisher Scientific), 4% B-27 supplement (Gibco), 2 mM Glutamax (Gibco) and 2 mg/mL fluorodeoxyuridine (FUDR, Sigma), and kept in a humid culture incubator with 5% $CO_2$ at 37° C.

Primary neuronal cultures were transfected 6-10 days in vitro (DIV). For each well to be transfected, a DNA-$CaCl_2$ mix containing with the following reagents was prepared: 2 μg of DNA (prepared using an endotoxin-free preparation kit (Qiagen)) 1.875 μl 2M $CaCl_2$, and sterile water added for a total volume of 15 μl. An additional 15 μl of 2× filtered HEPES-buffered saline (HBS, in mM: 50 HEPES, 1.5 $Na_2HPO_4$, 280 NaCl, pH 7.05 with NaOH) was added, and the resulting 30 μl mix was incubated at room temperature (20-25° C.) for 20 minutes. Meanwhile, the neuronal growth medium was taken out of the wells and kept at 37° C., and was replaced with 400 μl pre-warmed minimal essential medium (MEM). The DNA-$CaCl_2$—HBS mix was then added dropwise into each well, and the plates were transported to the culture incubator for 45-60 minutes. Each well was then washed three times with 1 mL of pre-warmed MEM, after which the MEM was removed and the original neuronal growth medium was added back into the wells. The transfected neuronal culture plates were placed in the culture incubator for another 6 days.

Recordings in hippocampal cultured neurons were performed 4-6 days after transfection in Tyrode's solution: 150 mM NaCl, 4 mM KCl, 2 mM $CaCl_2$, 2 mM $MgCl_2$, 10 mM glucose and 10 mM HEPES-NaOH pH 7.4. Tyrode was perfused at a rate of 1-2 ml $min^{-1}$ and was kept at room temperature. Intracellular solution contained 140 mM K-gluconate, 10 mM HEPES-KOH pH 7.2, 10 mM EGTA and 2 mM $MgCl_2$. Signals were amplified and digitized using the Multiclamp 700B and DigiData1400 (Molecular Devices, Sunnyvale, CA, USA). The Spectra X Light engine (Lumencor) served as a light source and was coupled into a Leica DM LFSA microscope. Borosillicate patch pipettes (4-6 MOhm) were pulled using a P2000 micropipette puller (Sutter Instruments, Novato, CA, USA). HEK293 cells (Thermo Fisher, cells identified by the vendor) were cultured as previously described (Kim et al. (2018) supra.). Cells were transfected using Lipofectamine 2000 (Life Technologies). Recordings in HEK293 cells were performed 12-36 hours after transfection in extracellular and intracellular solution as described above.

Voltage clamp recording was performed in the presence of bath-applied tetrodotoxin (TTX, 1 µM; Tocris). For initial screening of action spectra, cells were held at resting potential of −70 mV, with 0.7 $mW/mm^2$ light delivery for 1 second at wavelengths (in nm) of 390, 438, 485, 513, 585 and 650, which were generated using filters of corresponding peak wavelengths and 15-30 nm bandpass. Liquid junction potentials (LJPs) were corrected using the Clampex build-in LJP calculator by subtracting 15 mV from measured values. For reversal potential measurement, HEK293 cells expressing opsins were held at resting potentials from −70 mV to +60 mV (after LJP correction) in steps of 10 mV, with 585 nm, 0.7 $mW/mm^2$ light delivered for 1 s.

Current clamp measurements were performed in the presence of glutamatergic synaptic blockers: 6-cyano-7-nitroquinoxaline-2,3,-dione (CNQX; 10 µM, Tocris) for AMPA receptors and D(−)-2-amino-5-phosphonovaleric acid (APV; 25 µM, Tocris) for NMDA receptors. For light-sensitivity measurements, light was passed through a 585/29 nm filter (Thorlabs) and delivered through a 40×, 0.8 NA water immersion objective. For light pulse-width experiments, 585 nm light with 5 Hz frequency and 0.7 $mW/mm^2$ intensity was used at varying pulse-width values (in ms) of 0.1, 0.5, 1, 2, 5 and 10. For light sensitivity experiments, 585 nm light with 5 Hz frequency and 5 ms pulse-width was used at varying light power densities (in $mW/mm^2$) of 0.002, 0.014, 0.08, 0.28, 0.7, 1.4 and 2.8. For spike fidelity experiments, 585 nm light with 0.7 $mW/mm^2$ power density was used, with 1 ms pulse-width for ChRmine and 5 ms for bReaChES and CsChrimson. For all experiments, 5-7 cells were tested, and data collection across opsins was randomized and distributed to minimize across-group differences in expression time, room temperature, and related experimental factors.

In Vitro Characterization Preparatory to all-Optical Set-Up

Dissociated hippocampal neurons were cultured and transfected with both red opsin variants and GCaMP6m as previously described (Kim et al. (2018) supra). Coverslips of cultured neurons were transferred from the culture medium to a recording bath filled with Tyrode's solution containing (in mM, 129 NaCl, 5 KCl, 30 glucose, 25 HEPES-NaOH, pH 7.4, 1 $MgCl_2$ and 3 $CaCl_2$) supplemented with 10 µM CNQX and 25 µM APV to prevent contamination from spontaneous and recurrent synaptic activity. Optical stimulation and imaging were performed using a 40×/0.6-NA objective (Leica), sCMOS camera (Hamamatsu, ORCA-Flash4.0) and LED light source (Spectra X Light engine, Lumencor), all coupled to a Leica DMI 6000 B microscope. GCaMP6m was excited by 488 nm (Semrock, LL01-488-12.5) with the Spectra X Light engine. GCaMP6m emission was reflected off a dual wavelength dichroic mirror (Chroma, ZT488/594rpc) for orange light stimulation or another mirror (ZT488/640rpc) for red light stimulation, and passed through a 535-30-nm emission filter (Chroma, ET535/30 nm). Red-responsive opsins were activated with a Spectra X Light engine filtered either with 585 nm orange light (Semrock, FF01-585/29-25, 0.2 or 2.0 $mW/mm^2$) or 635 nm red light (Semrock, FF01-635/18-25, 0.2 or 2.0 $mW/mm^2$).

Low-intensity 488-nm laser light (12 $µW/mm^2$) was used for imaging GCaMP fluorescence without substantially activating red-responsive opsins. Images were acquired at 20 Hz using MicroManager (http://micro-manager.org). Light for stimulation was controlled by LabVIEW (National Instruments) and applied every 20 sec at an exposure time of 5, 25, 100, 400 and 800 msec. Imaging data were analyzed in MATLAB (MathWorks). Circular regions of interest (ROIs) were drawn manually based on the averaged image. Background subtraction was performed before calculating $Ca^{2+}$ signal. ΔF/F response was calculated to normalize the signal in each ROI by dividing by its mean value of total fluorescence intensity and subtracting 1. Noise was calculated as the standard deviation of the total ΔF/F fluctuation before the first stimulation. S.D. response was then computed as ΔF/F response divided by noise. Peak amplitude was calculated from the maximum value between the stimulus onset and 2 sec after the stimulus cessation. To compare red-responsive opsins to triggered GCaMP6m kinetics, 400 ms exposure-triggered $Ca^{2+}$ transients were calculated. Rise time ($t_{peak}$) was defined as the time-to-peak from the beginning of the light stimulus to the time point at which maximal-amplitude fluorescence was reached. The decay constants (tau) were determined by single exponential fit from the peak of the fluorescence response for 15 sec after stimulation.

In Vitro Characterization in Two-Photon Electrophysiology

All two-photon electrophysiology experiments were conducted on a commercial microscope (Bruker Ultima running PrairieView v5.4) using a Nikon 16×/0.8 NA (CFI75) long-working-distance objective for light delivery. For two-photon stimulation, spiral scanning was performed through a defined spiral ROI with 25 µm diameter, with 12 rotations per spiral, and 4 ms total exposure duration with 80 MHz laser repetition rate (Coherent Chameleon Ultra II). For imaging, a second 80 MHz laser (Coherent Chameleon Ultra II) was relayed through a resonant galvo path for 30 Hz imaging rates, to match the imaging characteristics present for the in vivo experiments. As each plane in the behavior in vivo imaging experiments was recorded at ~2.7 Hz, the imaging rate was appropriately modified by acquiring a new image every 370 ms such that the patched cell was sampled at ~2.7 Hz.

The two-photon stimulation and imaging light paths shared a common objective, tube lens and scan lens—but in contrast to the in vivo behavior imaging datasets, for the in vitro characterization data, the photostimulation galvanometer pair was smaller than the imaging galvanometer pair (3 mm vs. 6 mm). This effectively scaled down the actualized NA for photostimulation from the stated microscope objective values. Experiments were performed with cultured hippocampal neurons expressing ChRmine-EYFP through AAV transfection, and the same intracellular and extracellular solutions for one-photon electrophysiology characterization were used for recording.

For two-photon action spectra and power spectra characterization, recordings were done in voltage clamp mode at holding voltage of −70 mV. Action spectra were measured in randomized trial order at wavelengths (in nm) of 800, 860, 920, 980, 1035, 1080, at the laser power of 20 mW. Power spectra were measured in randomized trial orders at powers (in mW) of 0, 5, 10, 15, 20, 25, 30, at the two-photon wavelength of 1035 nm. All measurements were normalized by the maximum value of the single recording session. Experiments were done in 6 different cells.

For spike fidelity and imaging laser cross-stimulation experiments, recordings were done in current clamp mode, under the membrane potential at −65 mV to −70 mV. Spike fidelity was estimated by stimulation of cells at frequencies (in Hz) of 5, 10, 20, 30, with 1035 nm laser at 20 mW. For cross-stimulation experiments, membrane voltage was observed during image acquisition as a function of imaging power (920 nm, at 2.7 Hz frame-rate) at 0, 20, 40, and 60 mW. Data collection across opsin expressing neurons was randomized.

Electrophysiology Data Analysis pClamp 10.6 (Molecular Devices), and Prism 7 (GraphPad) software were used to record and analyze data. Statistical analyses were performed with two-tailed unpaired t-test or one-way ANOVA. Data is presented as mean±s.e.m. $P<0.05$ is defined to be statistically significant.

For preparation of phylogenetic trees, opsin sequences were first aligned using Clustal Omega server (https://www.ebi.ac.uk/Tools/msa/clustalo/) and later calculated using AQUAPONY (http://www.atgc-montpellier.fr/aquapony/aquapony.php) and TreeDyn (http://www.treedyn.org/) for circular and rectangular trees, respectively. The homology model of ChRmine was built using the C1C2 crystal structure (PDB ID: 3ug9) as a template, using RosettaCM method (Song et al. (2013) *Structure* 21:1735). All molecular graphics figures were prepared with Cuemol (http://www.cuemol.org).

Mouse In Vivo Experiments

Viral constructs: The genes for GCaMP6m (Chen et al. (2013) *Nature* 499:295) and soma-targeted (Baker et al. (2016) supra) ChRmine were cloned in a cis configuration separated by the ribosomal skip motif p2A under the CaMKIIα promoter in an AAV2 backbone. This construct was sequenced for accuracy, tested for in vitro expression in cultured hippocampal neurons and packaged by the Stanford Neuroscience Gene Vector and Virus Core (GVVC) as AAV8/Y733F to create AAV8-CaMKIIa-GCaMP6m-p2A-ChRnine-TS-Kv2.1-HA (used in all mice except for one). AAV8-CaMKIIa-GCaMP6m-p2a-ChRrnine-TS-HA was used in the remaining single mouse (mouse 2 in behavioral cohort). Map and sequences are available at http://optogenetics.org/ and prepackaged virus can be purchased from the Stanford GVVC.

Surgery: All animal procedures followed animal care guidelines approved by Stanford University's Administrative Panel on Laboratory Animal Care (APLAC) and guidelines of the National Institutes of Health. Male C57/BL6 mice (8-12 weeks) were anesthetized with 5% isoflurane for induction and ~1-2% isoflurane during surgery. The skull was exposed, cleaned and coated with a layer of Vetbond (3M). A circular (1 cm diameter, 1 mm height) titanium implant with a counter bore (8 mm outer diameter and 6 mm through hole) was affixed to the skull with Metabond dental cement (Parkell) centered on −2.75 mm (lateral) and −2.25 mm (posterior) from bregma over the lateral portion of primary visual cortex of the left hemisphere (imaging experiments were performed approximately 500 μm medial and posterior from this location, and thus were more centrally located within primary visual cortex). The mouse was transferred to a head clamp device designed to firmly hold the metal implant by an angled groove around its perimeter (this same head clamp device design was used to hold the animal under the two-photon microscope and thus had micron-level stability). A circular craniotomy was performed using a high-speed drill by slowly drilling away bone within the perimeter of the through hole of the implant. Once the bone was as thin as possible, but before drilling all the way through the bone, the remaining intact bone was pulled away with forceps to reveal the underlying cortex with the dura fully intact. A glass pipette injection needle (~25 μm diameter, angled tip) calibrated to the stereotaxic coordinates and filled with the virus was lowered into the cortex to a depth of ~400 μm. 500 nl of virus (typically $4 \times 10^{12}$ vg/ml) was injected over ~5 min and then the pipette was lowered to ~600 μm and another 500 nl was injected over an additional ~5 min. The pipette was left in place in the brain following injection for at least 3 minutes and then slowly retracted. A 4 mm glass coverslip affixed with UV-cured optical glue (Newport) to a titanium cannula of the same diameter (the cannula also had an ~8 mm flange at the top to register with the outer circular implant) was applied the surface of cortex and cemented in place with Metabond. For analgesia up to 72 hours, buprenorphine sustained release (SR) was injected pre-operatively at 0.3-1.0 mg/kg subcutaneously, or buprenorphine (0.05-0.1 mg/kg) was injected by subcutaneous or intraperitoneal injections.

Visual stimulation: Drifting sine wave gratings (0.2 cycles/degree spatial frequency; 2 Hz temporal frequency; 2, 3, 4, 5, 12, 25, or 50% contrast) were generated using custom software in Pyschtoolbox running on MATLAB (code available online adapted from (Marshel et al. (2011) *Neuron* 72:1040)) and presented on a calibrated liquid crystal display monitor placed 15 cm from the mouse's eye, centered on the retinotopically targeted location in V1 (Marshel et al. (2011) supra). The gratings subtended 60 deg of visual space and were surrounded by uniform gray around the rest of the screen. A trial began with a 100 ms, 5 kHz tone cue. 1.25 seconds later, the drifting grating was displayed for 3 seconds. The next trial began ~4.5-9 seconds later depending on whether the mouse made an error during the answer window and received a time out as penalty (no time outs were added for naïve mice or mice in the conditioning phase below). A uniform gray screen was presented between drifting grating presentation.

Behavioral training: Mice were kept on a reverse day/night cycle. Mice were habituated to the experimenter and to a floating Styrofoam ball and behavior apparatus (Phenosys) for approximately 3 days (the setup was either under the microscope or replicated in a behavioral chamber for initial training before imaging experiments; mice were briefly anesthetized with isoflurane prior to head fixation and allowed to fully recover before proceeding). For discrimination behavior training, mice were water restricted and first allowed to lick freely to trigger immediate water delivery from a lickport by triggering an infrared optical lickometer (Sanworks). This was repeated daily until the animal immediately and consistently consumed water once presented with the lickport. Then, mice were presented with visual stimuli (50% contrast 0 and 900 gratings, see below) using the same trial structure as above, without penalties. If the mice licked during the answer window (1-3 seconds after visual stimulus onset) during the 0° (target) stimulus, they immediately received a water reward (~6 µl). During this conditioning phase, mice always received ~6 µl of water at the end of target visual stimulus presentation, in addition to any lick-triggered reward. Once mice reliably licked to the target stimulus before the free water was delivered at the end of the trial (mean 6.8 days), they advanced to the discrimination task in which water was only delivered if they licked during the answer window during target stimulus presentation, and time outs (4.5 sec) were added to the end of error trials (misses/false alarms). If the mice did not show discrimination behavior improvement over the course of 4-5 days, a mild air puff directed toward the mouse's face was added as immediate penalty for false alarms. This air puff was eventually added for all mice for consistency. Training continued until mice had nearly 100% hit rates and discriminated 50% contrast gratings with >2 d' for at least 3 days (mean 9 days total). Then, an equal number of 25% contrast gratings trials were added to the protocol and training continued for 3 days. The same criteria were applied until the task included 2, 12, 25 and 50% contrasts (mice generally could not discriminate 2% contrast gratings). If not done so already, mice were additionally trained under the microscope until behavior was stable to all contrasts before advancing to all-optical experiments. d' was defined as norminv(Hit Rate)—norminv(False Alarm Rate) in MATLAB. For the d' calculation, rates equaling 100% or 0% were adjusted to 99% and 1% respectively. Percent correct was computed for a given condition(s) as [(Hits)+(Correct Rejections)]/(Total Trials).

In vivo visual and optogenetic stimulation experiments: Once trained (or in the case of naïve mice, once habituated to the head-fixed floating ball setup under the microscope), mice performed the task (or passively viewed visual stimuli) while volumetric two-photon $Ca^{2+}$ imaging was performed in V1 and visual stimuli were presented to the animal. A series of reference images were collected of the volume to aid in alignment to the same region on subsequent days. Neural $Ca^{2+}$ responses were analyzed as described below in order to identify ensembles for stimulation on subsequent days/experiments.

Mice returned to the microscope each day and the field of view was aligned to the reference images from the reference experiment. This was accomplished using an automated image registration algorithm (based on the same cross-correlation procedure described below for subsequent analysis) that reported the real-time offsets in pixels between the current imaging field of view (streamed from the microscope acquisition pipeline with minimal latency) and the reference images. In addition, a real-time overlay image was presented to allow the experimenter to optimize x, y, z and θ for precise alignment. This was done before beginning the stimulation experiment using several imaging planes throughout the volume. During the volumetric imaging and stimulation experiments, a similar program reported real-time offsets and displayed image overlays (allowing the experimenter to correct for any offsets online using the motorized translation stage), and could be alternated between imaging planes throughout the volume in order to confirm alignment across cortical layers (see FIG. 13).

On randomly interleaved trials, visual stimuli were presented to the animal or ensemble stimulation (tuned or random, target or distractor) ensembles were stimulated with the MultiSLM (see below). For naïve mice, contrasts included 12, 25 and 50%, as well as an equal number of 0% (no visual stimulus), and optogenetic ensemble stimulation occurred on 2/3 of 0% contrast trials (balanced tuned and random ensemble stimulation trials), but was never paired with visual stimulation. Trial order was pseudorandomized for all condition types, and re-randomized if the trial order contained>3 target, distractor, or low contrast (≤5%) conditions in a row. For the behavioral cohort, the same paradigm was used, except optogenetic stimulation could occur alone, or in combination with the visual stimuli (randomly interleaved, balanced trials), and the low contrast condition was exchanged from 0% to 2, 3, 4 or 5% and back to 0% over the course of the contrast ramp experiments. Following the contrast ramp experiments, the low contrast condition was kept at 0% for subsequent experiments (for example, layer-specific ensemble stimulation experiments described below). For the behavior cohort, licking during target stimuli (0° gratings, 0° tuned ensemble or size-matched "0°" designated random ensemble) during the answer window (1-3 sec after stimulus onset) triggered a water reward. Licking during distractor stimuli (90° grating, 90° tuned ensemble or size-matched "90°" designated random ensemble) during the answer window triggered an air puff. Errors (misses or false alarms) resulted in a time out (4.5 sec) at the end of the trial. Importantly, the microscope hardware performed the same operations on every trial, regardless of condition (e.g., galvanometer spiral scanning, laser shutter opening, imaging scanning pattern, spatial light modulator phase mask transition, etc.), with the exception of the laser power applied to the holograms (either 0 power or power calculated to stimulate the ensemble with 5 mW instantaneous power delivered to each cell for 0.63 ms at ~30 Hz, see below), such that all experiment sounds were the same between all conditions. All mice that proceeded through the contrast ramp with layer 2/3 and 5 stimulation experiments and proceeded onto the layer-specific stimulation experiments are included. Three additional mice proceeded only through the contrast ramp experiment, but laser stimulation power was increased beyond the typical protocol (i.e., to attempt to offset weaker stimulation responses). Including these mice in the behavioral analysis yielded comparable statistical results.

FIG. 13. Targeting the same ensembles across weeks with cellular resolution. (A) The same population of neurons is revisited for many weeks (29 sessions spanning 54 days) by precisely aligning the MultiSLM imaging/optogenetic volumetric stimulation systems to the original field of view (shown is a region of interest in layer 5 with 4 labeled cell bodies; overlay: green, original imaging session, magenta, each subsequent session of imaging and optogenetics). (B,C) Alignment is maintained online during the experiment using a real-time cross-correlation algorithm to compensate for the shift between the instantaneous image and the reference image (from day 0) for each slice through the volume (Materials and Methods). (B) Shift relative to the reference image over the duration of the experiment (dx, blue; dy, red; median data are plotted across 9 mice, optical z slices and sessions). (C) Shifts relative to reference image for all images (dx, blue, dy, red; 95% of all shifts were <8.34 µm (dx) and <4.17 µm (dy); ~2.5 million image shifts from reference across 9 mice from all optical z slices and sessions).

All-Optical Physiology Microscope Design and Characterization

As described in detail below, the all-optical (read/write) microscope was optimized to address neural ensembles distributed over large volumes beyond millisecond temporal precision for the first time. Achieving these biologically-important specifications required development and optimization of several components, including an entirely new, high-pixel-count, fast spatial light modulator (SLM) with new electronics and software interfaces (MacroSLM), new multiplexing strategies (MultiSLM; also see Supplementary Text and FIGS. 9-11,18,19), and a unique pairing with a three-dimensional (3D) imaging strategy during head-fixed mouse behavior.

In prior work, when realizing all-optical physiology using SLMs at high spatial resolution (e.g., NA>0.4), the addressable targeting volume has thus far been significantly constrained relative to the available imaging volume due to a ceiling on the number and size of available pixels provided with current commercial devices. Furthermore, generation of new ensemble-targeting hologram patterns in near-infrared wavelengths has been limited in overall refresh rate by the SLM response time and the stimulation durations required by previous multi-photon optogenetic opsins and protocols (see, for example, refs (Packer et al. (2015) *Nat Meth* 12:140, Yang et al. (2018) supra, dal Maschio et al. (2017) supra, Forli et al. (2018) *Cell Rep* 22:3087, Mardinly et al. (2018) supra)). This has restricted the ability to write in activity patterns at fundamental biological timescales (~1 ms) over volumes spanning several cortical layers and whole brain areas in the mouse (~0.5-1 mm spatial scale). Therefore, a solution was sought where the addressable optogenetic volume meets or exceeds the volume available for imaging, potentially spanning multiple functional areas/volumes across cortical layers—and developed a hardware and biological interface allowing millisecond-level precision of ensemble stimulation during behavior.

MacroSLM: To achieve the frame rates, trigger responsiveness, and 3D field of view used in this work, a custom liquid crystal was designed and built on silicon (LCoS) spatial light modulator (SLM). The MacroSLM achieves 500 Hz hologram-to-hologram frame rate at $\lambda$=1064 nm at 85% diffraction efficiency (FIG. 10A). The square 1536×1536 pixel array assures a uniform numerical aperture is available across the transverse dimensions of the sample and employs high-voltage (0-12V analog) pixel addressing, and carefully-timed transient voltages (also known as overdrive (Thalhammer et al. (2013) *Opt Express* 21:1779)), for increased liquid crystal (LC) response speed, requiring development of complex driving electronics. In addition, built-in temperature control allows the LC to operate at a fixed temperature where LC viscosity is low, while adjusting automatically for illumination- and data-throughput-related heating effects.

Figure 9C:
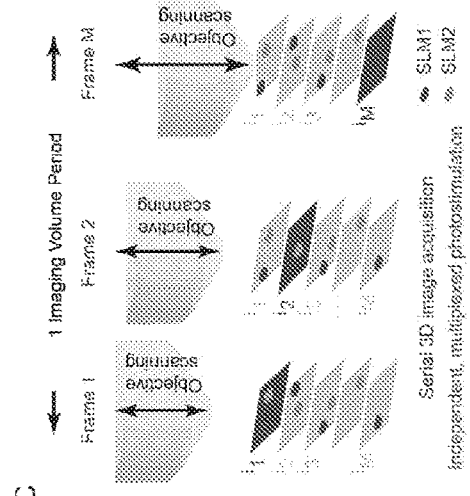
FIGS. 9A-9H depict theoretical and empirical properties of a microscope.
Figure 9F:
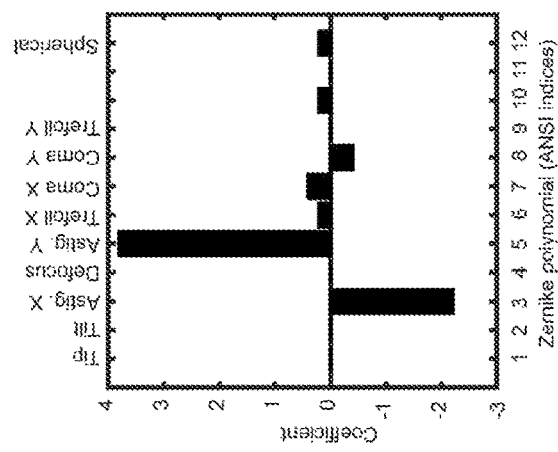
Figure 9B:
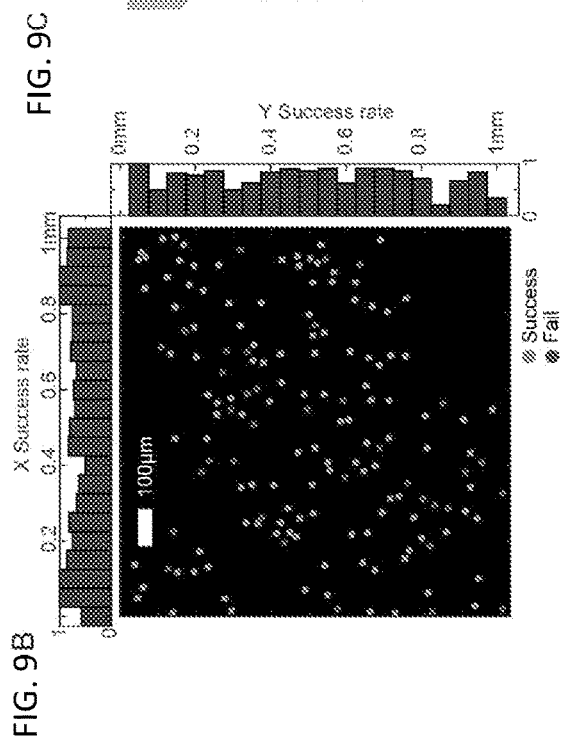
Figure 9E:
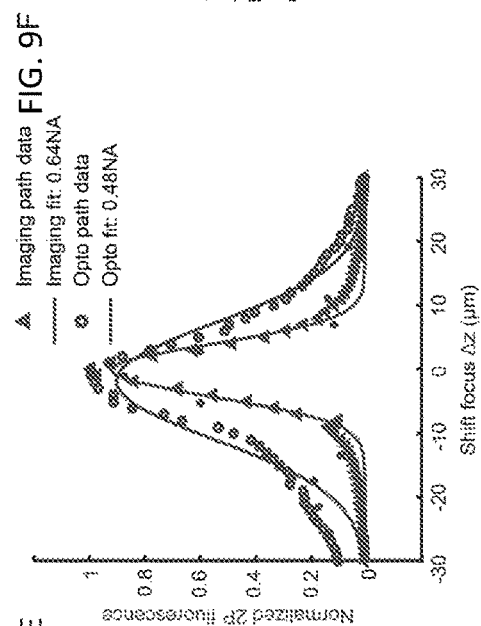
Figure 9A:
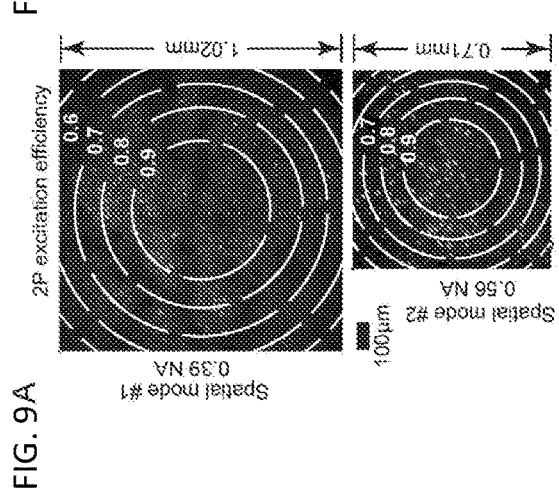
Figure 9D:
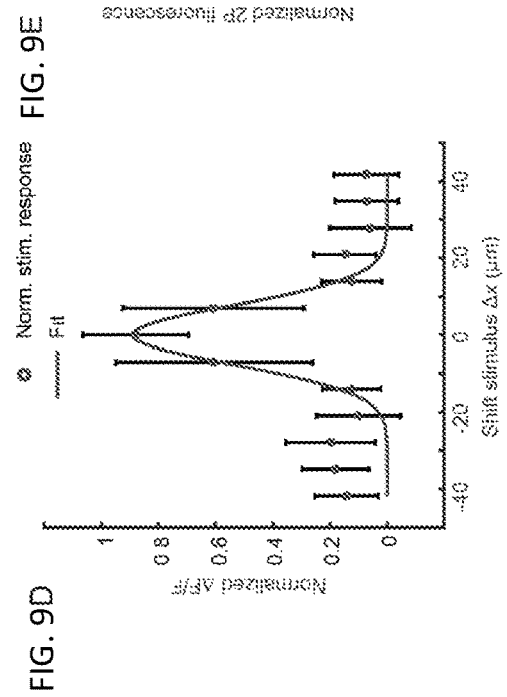

MacroSLM optimization for three dimensional fields of view: Achieving a large addressable field of view with high spatial precision was a key driving force behind the design of the MacroSLM, affecting the choice of pixel count and pixel size. Pixel count determines the holographic field of view of the microscope when the magnification of the optical system is designed to image the SLM onto the pupil of the objective lens. The MacroSLM 1536×1536 pixel array provides a theoretically addressable field of view of >>1 mm at high NA (>0.4) when using appropriate relay optics and microscope objectives (FIG. 9A). The SLM was designed with a relatively large 20 μm pixel pitch to achieve several advantages over smaller pixels. The large pixel pitch makes the effect of fringing fields small and minimizes interpixel cross-talk (that would otherwise act like an unwanted low-pass filter on the pattern that the SLM displays). This allows the SLM to maintain high diffraction efficiency (DE) at large steering angles, including when generating large numbers of excitation spots. The resulting large 30.7×30.7 mm array allows the input beam to be spread over a large square area which, along with internal light shielding layers, aids peak power handling. The large pixel pitch was also chosen for several important reasons: it enables large voltage swings (here 0-12 V analog), which in turn increases hologram transition speed; it is sufficient to store enough charge (178 fF) to hold the electric field across the liquid crystal while it is switching patterns; and it provides an extremely high fill factor since the active pixel (19.5 m width) is much larger than the gap between the pixel pads needed to prevent shorting (0.5 m). Ultimately, fill factor determines the DE ceiling of the device, with DE=(fill factor)*2× pixel reflectivity, or theoretically for this device (0.96)*2×0.95=0.88. This high DE improves overall efficiency of the system while minimizing potential artifacts from non-diffracted light. Also, achieving this DE value through realizing a high-fill-factor obviates the need for a dielectric mirror coating, which is typically used to increase DE, but dielectric mirrors increase the chances of unwanted optical artifacts. Lastly, larger pixels will be responsible for minimizing the lateral chromatic aberration inherent to using the SLM as a diffractive optic when addressing large fields-of-view (maximum deflection angle is 1.4°) and therefore improve the relative efficiency for multi-photon excitation at the focal spot (Yang et al. (2016) *Neuron* 89:269). Indeed, calculations indicate that when using the fixed-wavelength ultrafast laser source reported herein (Coherent Monaco 1035-80-60 at $\lambda$=1035 nm) at a pulse-width ($sech^2$) of $\Delta t \approx 300$ fs (spectral width of 4.5 nm), a maximum chromatic shift of only +/−0.64 μm would be present when addressing the full-width of the scanned imaged plane (reported herein as 710×710 μm).

MacroSLM liquid crystal speed response: High-voltage (0-12 V analog) pixel addressing makes the LC response fast, along with the use of high transient voltages (also known as "overdrive", see ref (Thalhammer et al. (2013) supra)). 'Phase wrapping' was implemented for each pixel to shorten the distance in phase between phase values in time. The LC temperature is also maintained with the use of backplane Peltier heating/cooling, allowing the device to operate at a temperature (45° C.) where LC viscosity is low while also adjusting for the varying heating effects of high-power laser illumination. The SLM thickness was optimized for the use of overdrive at the NIR (~1064 nm) target wavelength, and for maintaining full$\geq 2\pi$ phase modulation.

MacroSLM data handling: Data handling is another significant aspect of increasing speed, since the system must be capable of calculating the required transient voltages to achieve fast LC switching from phase to phase at each pixel, while loading the transient 1536×1536 images onto the SLM pixels at ~1250 Hz continuous frame rate. A custom field-programmable gate array (FPGA) solution was used for handling these high data rates, including on-board storage of 2045 images, on-board application of spatially-varying voltage calibrations, and on-board calculation of individual transient voltages for every pixel. The driver board receives data over PCIe on cable to a Xilinx Kintex-7 primary FPGA. This FPGA distributes the data to 8 secondary Kintex-7 FPGAs using the Xilinx Aurora high-speed serial interface. Each secondary FPGA is capable of performing the overdrive processing for, and supplies the data to, its own section of the SLM overdrive frames were precomputed and loaded into the on-board storage for these experiments). The primary FPGA also contains a Microblaze soft microcontroller that performs a number of additional functions, such as loading certain parameters over I2C, temperature monitoring, and automatic safety-shutdown for both the driver board and SLM head. Interruptible image downloads mean that new holograms can be triggered at arbitrary rates exceeding 1 kHz (rather than at integer multiples of the SLM's base refresh rate), without missing triggers. For integration into precisely timed and synchronized experiments, the high-speed triggering system instructs the SLM to transition to the next commanded hologram with low latency and jitter. The latency between a trigger arriving and the voltage changing on the SLM is 6 µs with a range of 3-9 µs, so that the transition to a new hologram can be very predictably initiated. A MATLAB-based software development kit (SDK) to interface with the SLM was developed. These conditions could trigger and cause a transition between different holograms at 330-500 Hz with 85-100% target hologram efficiency (FIG. 10A).

Figure 11A:
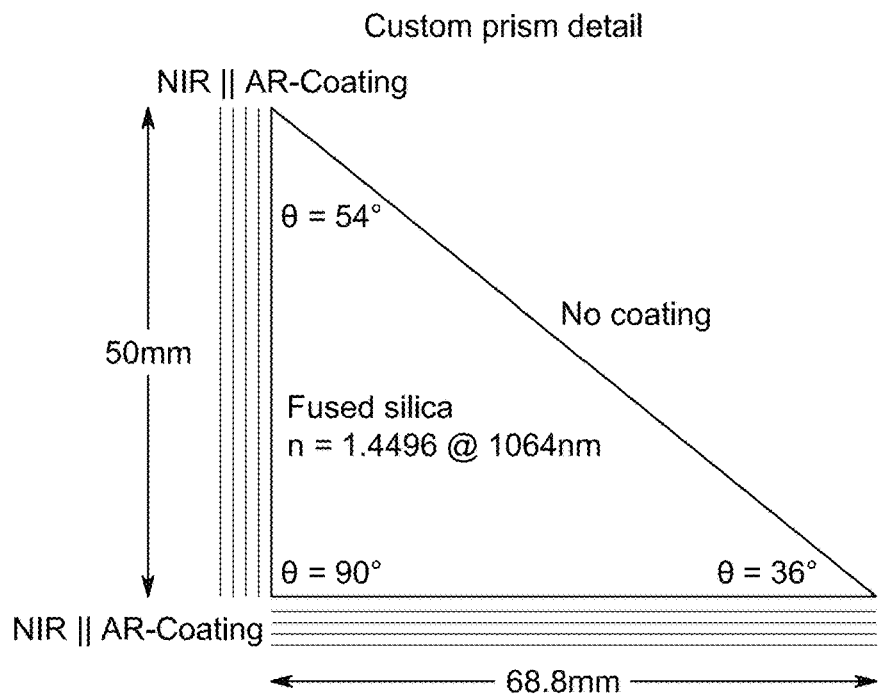
FIGS. 11A-11F depict the optomechanics for the Multi-SLM.
Figure 11B:
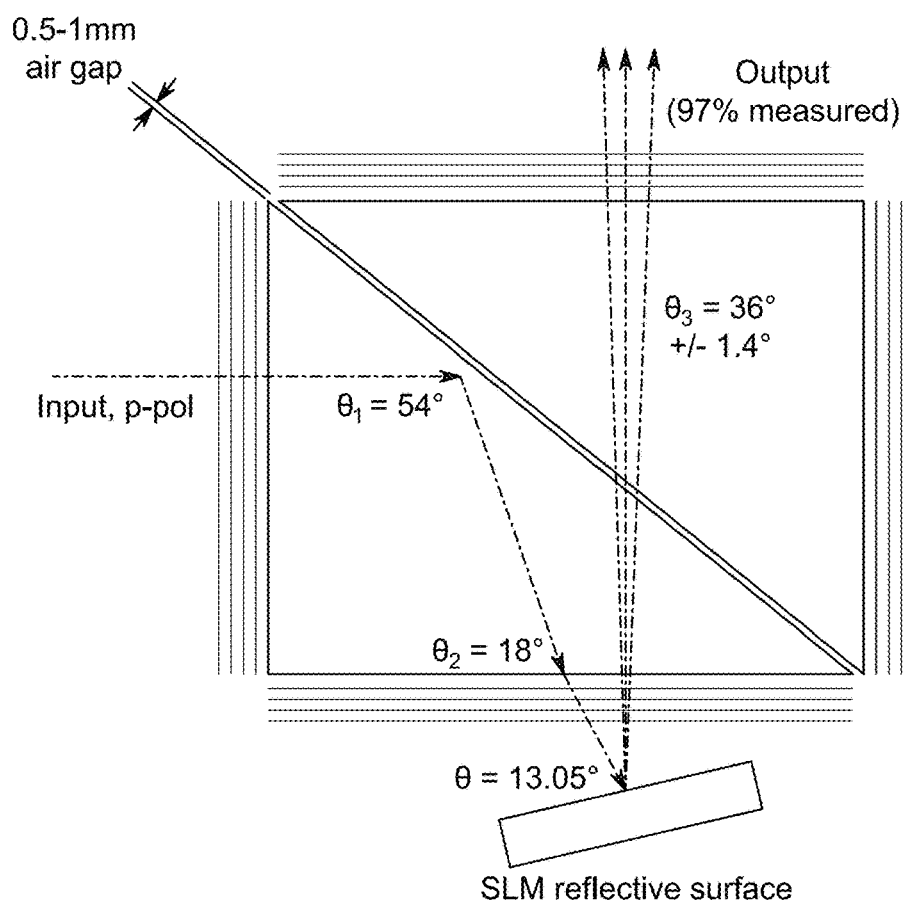
Figure 11C:
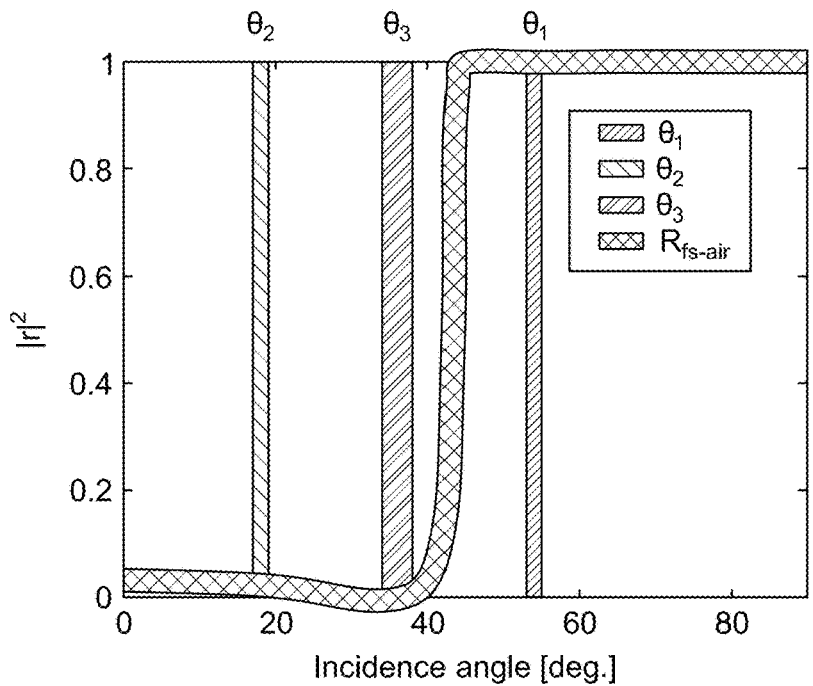
Figure 11D:
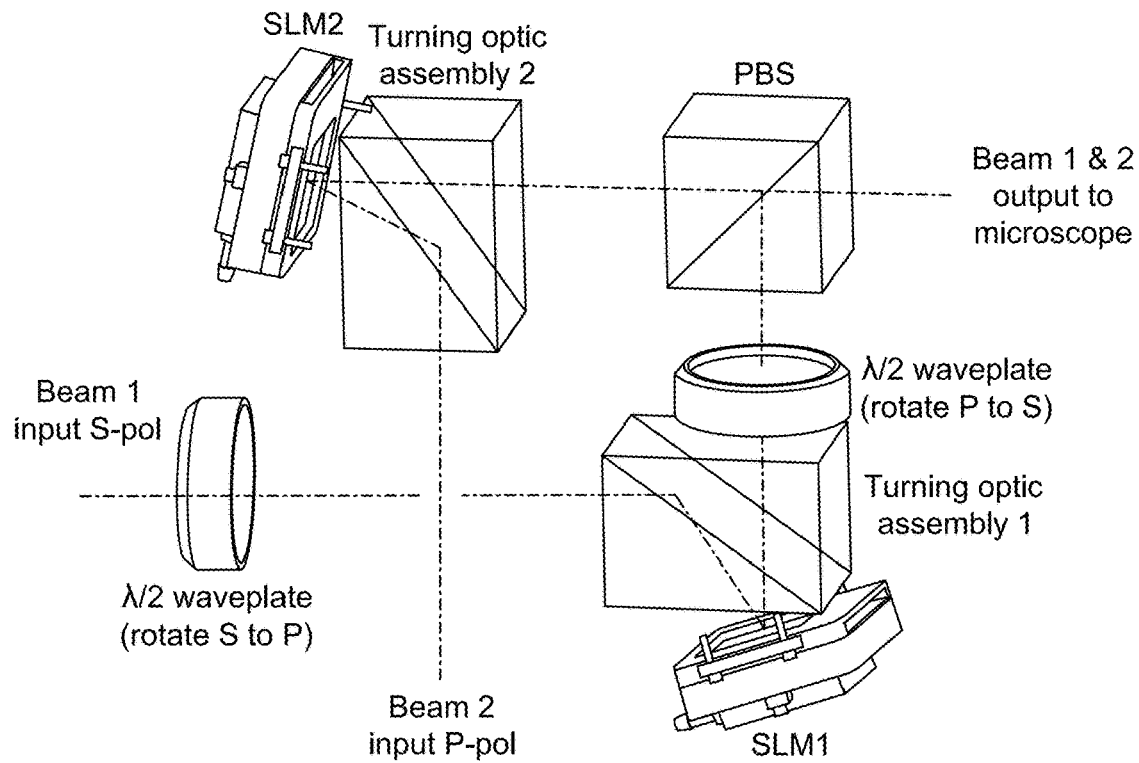
Figure 11E:
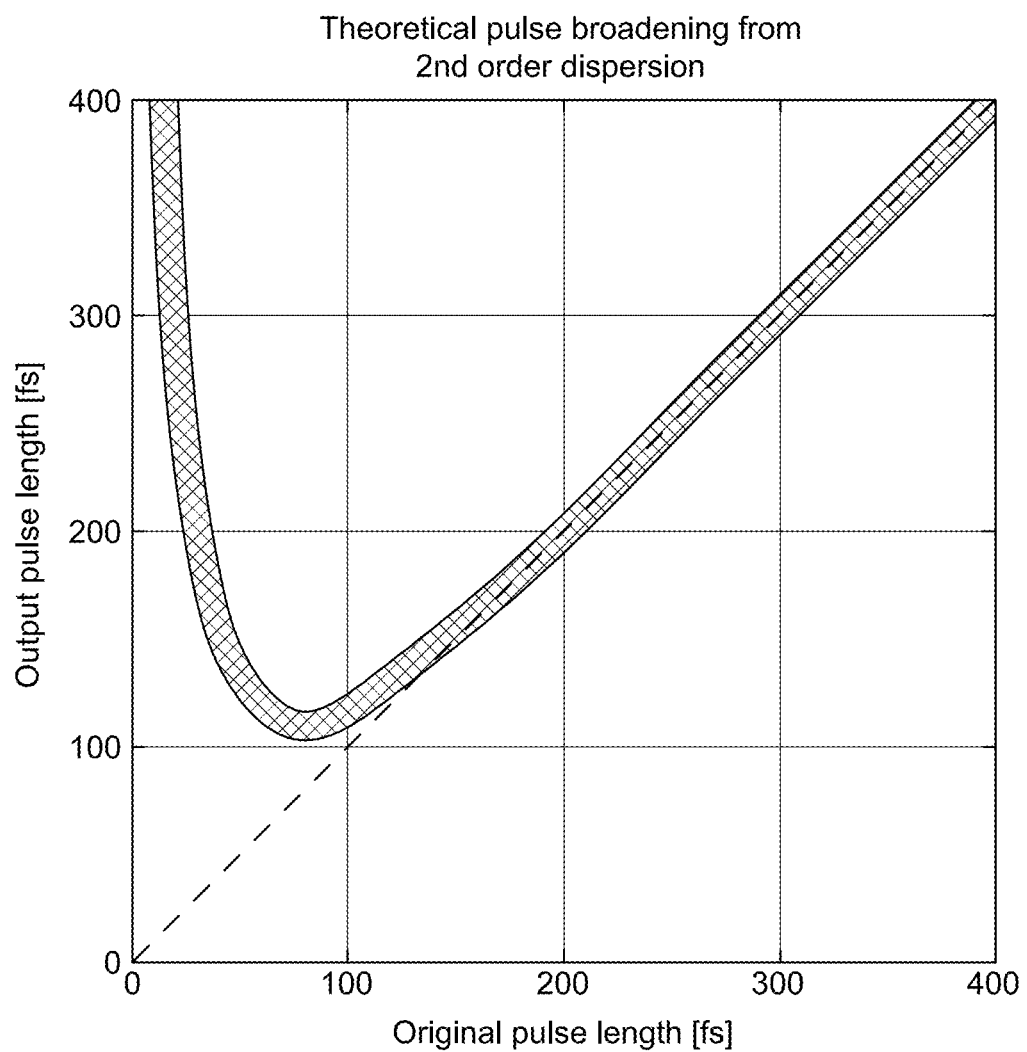
Figure 11F:
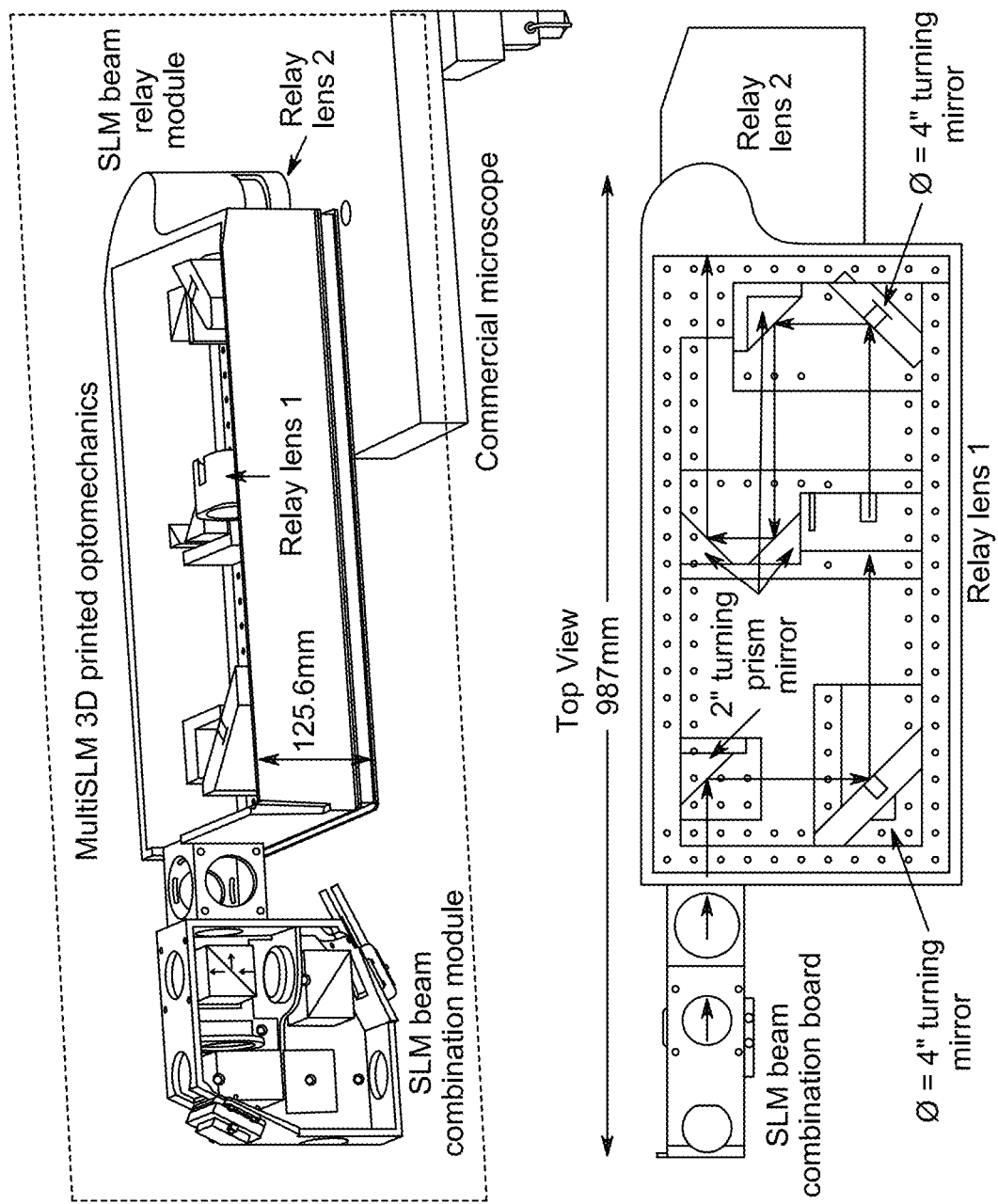

All-optical physiology microscope design: A custom MultiSLM photostimulation path that was integrated into a commercial multi-photon imaging microscope including a resonant-scanner imaging path and piezo-coupled microscope objective holder was developed (Bruker Nano Surfaces Division, Ultima, Middleton, WI). Custom optical elements and opto-mechanics were developed, alongside commercial elements when possible, to integrate the optogenetic stimulation path, including the multiple SLMs, into this microscope. The optical path was modeled in both Zemax OpticStudio (Zemax LLC, Kirkland, WA) and MATLAB (The Mathworks, Natick, MA) and optimized to maximize the field of view at the full available back aperture of the microscope (FIG. 9A). Integration is realized via a two-position drop-down mirror located before the existing uncaging galvanometer unit. For the imaging light path, a tunable-wavelength femtosecond pulsed light source is utilized (Coherent Chameleon Ultra II, $\lambda_{typ}$=920 nm, Santa Clara, CA). For the optogenetic stimulation, a fixed-wavelength ($\lambda$=1035 nm) femtosecond pulsed light source (Coherent Monaco 1035-80-60, Santa Clara, CA) is used at a user-selected 10 MHz pulse repetition rate. The integrated gate and power-modulation signals of the optogenetic laser were utilized to guarantee zero residual optogenetic-laser illumination on sample. An optical switch (Conoptics LTA360-80 with 302RM driver) (OS, FIG. 2A) is used to selectively direct the optogenetic stimulation light towards two alternative paths at 200 kHz temporal resolution, each path with a dedicated SLM. Each path has a 20× beam expander (Thorlabs GBE20-B) (BE, FIG. 2A) and a custom pair of turning prisms (Edmund Optics, 36°-54°-90° prism, NIRII coated, PN 913418) (TP1 and TP2, FIG. 2A, see also FIG. 11A-11C, 11E) to maintain a compact footprint, thereby minimizing mechanical drift issues as well as facilitating simple beam alignment by keeping the optics at 90° angles (FIG. 11D). One light path requires a pair of half-wave plates (Thorlabs WPH20ME-1064) (HWP, FIGS. 2A and 11D) in order to maintain optimal polarization alignment through the turning prisms, the SLM liquid crystal alignment layer and the beam combining polarization cube (Thorlabs PBS513) (PBS, FIG. 2A). A custom optical relay (Special Optics 54-44-783 AR-coated doublet and 54-8-750 AR-coated triplet) (RL1 and RL2, FIG. 2A) was designed to de-magnify the SLM active area at a 5:1 ratio, matching the SLM size to the clear aperture of the dedicated optogenetic galvanometers (OGS, 6 mm clear aperture, FIG. 2A) mounted within the commercial multi-photon microscope. This relay was optimized to correct for chromatic aberration, field curvature and distortion. To block residual DC signal from the un-diffracted optogenetic beam off the SLMs, a pair of magnets (D101-N52, K&J Magnetics, Inc, Pipersville, PA) are mounted to each side of a glass cover slip (Fisher Scientific, 12-546-2) and placed in the intermediate image plane of the microscope (located between the two lenses of the SLM relay, BB, FIG. 2A). A majority of the optogenetic optical path resides on custom 3D printed opto-mechanics which facilitates alignment and improves compactness as well as total costs (FIG. 11F, for individual mechanical parts the files are available through contacting the authors). The optogenetic galvanometers (OGS, FIG. 2A) are utilized to generate the temporal spiral raster scans which trace the SLM-diffracted beamlets across the neuron cell body membranes. The optogenetic and resonant-imaging beams are combined by a dichroic notch filter (Semrock NFDO1-1040) (DC, FIG. 2A). After both beams are combined, they pass through the commercial scan lens, tube lens and emission filter (SL, TL, and FLTR_EM, respectively, FIG. 2A) before reaching the microscope objective. Axial scanning during image acquisition was realized with a 1 mm-throw piezo-coupled microscope objective (objective for 3D scanning: Nikon 16×/0.8NA (16XLWD-PF), whereas the objective for 2D imaging: Olympus 10×/0.6NA). Optical fluorescence emission is collected by the appropriate microscope objective (OBJ, FIG. 2A) and redirected via the emission filter to a pair of PMTs (PMT1 and PMT2, FIG. 2A) which collect the red and green fluorescence channels (523/70 nm and 627/73 nm).

FIG. 11. Novel optomechanics for MultiSLM. The MultiSLM microscope utilizes a novel beam folding approach and 3D printed optomechanics to minimize size and promote mechanical stability. (A) A custom 36°-54°-90° prism was manufactured (Edmund Optics) of fused silica and anti-reflection (AR) coated on two faces to minimize air-to-glass interface reflections. (B) A pair of prisms, separated by an air gap, are used to redirect a P-polarized input beam to an SLM and to have the SLM output beam exit at a 90° angle, with minimal optical loss (97% throughput measured using a mirror as a proxy for SLM backplane). Note the three specified angles ($\theta_1$, $\theta_2$ and $\theta_3$) are all related to the angle of the beam when propagating from the fused silica into the associated air interface. (C) The specific angles of the prism were chosen to allow beam propagation through the turning prism assembly which is aligned to the peak and minimum Fresnel reflection coefficients ($|r^2|$=0 is total transmission, $|r^2|$=1 is total reflection) in order to allow maximum photon efficiency. The specific angles highlighted with a gray-scaled bar are associated with the angles identified in (B). $R_{fs\text{-}air}$ is the theoretical scalar coefficient of reflected intensity (e.g., the reflection coefficient of the first interface $\theta_1$, from the fused silica to the air-gap, is 1—indicating total reflection). (D) Two turning optic assemblies are utilized, along with beam polarization optics, to co-linearly combine the SLM outputs from a pair of input beams. Half-waveplates are utilized to control the light polarization for maximum transmission through the system. (E) Pulse propagation through di-electric material (e.g. glass) can induce a chromatic phase delay which leads to pulse broadening, and therefore less efficient multi-photon excitation. Theoretical modeling of femto-second pulses from the light source as it propagates through these turning prisms (118.8 mm of fused silica, blue curve) indicates that while sub-100 fs pulses would experience significant pulse broadening, minimal pulse broadening is expected using the current optogenetic stimulation light source (nominally between 250 and 300 fs) (Diels et al. (2006) *Ultrashort Laser Pulse Phenomena*, Jean-Claude Diels and Wolfgang Rudolph, $2^{th}$ Ed., Academic Press). (F)

3D printed optomechanics are used to mount and align the MultiSLM optogenetic path to the commercial microscope. Two distinct optomechanic groups represent the complete set of 3D fabricated parts—the SLM beam combination module and the SLM beam relay module. The SLM beam combination module provides convenient reference points to align and secure the SLMs as well as the beam turning prisms and polarization optics. The MacroSLMs were designed to use the mechanical face of the external SLM mount as a flush and parallel mount to the combination module using 4-40 # cap screws. The prism pair are kept parallel to each other and normal to the incident beam by reference groves in the seating of the 3D printed module. The SLM combination module mounts to the beam relay module by use of cap screws and/or Thorlabs cage railings in order to provide a reliable alignment. Within the beam relay module, the optical path is folded by use of 50 mm leg right-angle mirrors and 100 mm circular mirrors to ensure that zero beam vignetting occurs on this smaller footprint. Each 50 mm leg right-angle mirror has guide-points along each leg for precise placement on the 3D printed footings which directly bolt to a 12"×24" Thorlabs breadboard using the 1" hole-spacing. The custom beam relay lenses were aligned and mounted in custom 3D printed optomechanics within the module. By referencing to the 1" grid system of the breadboard, and keyed to other 3D printed components on the board, the relative positions of the two lenses could be readily optimized to ensure precise alignment and telecentricity. Note, both the relay lenses could be rapidly removed from the system to test or verify alignment using these custom opto-mechanics.

Precise temporal and spatial optogenetic control: To increase temporal resolution beyond that achievable by a single SLM capable of operating at up to 500 Hz (FIG. 10A), alternating optogenetic excitation from either SLM1 or SLM2 in the MultiSLM system was demonstrated (FIGS. 2C-2G and 10B). At the maximum temporal resolution tested, a $\Delta t_e$=210 µs spiral raster scan was designed using a 5-rotation, 10 µm diameter spiral for optogenetic light exposure and validated with the Olympus 10×/0.6 NA physiology objective at 20-30 mW/cell (FIGS. 2C-2G and 10C). This short stimulation-duration is many-fold faster than previously reported for in vivo two-photon optogenetics (e.g., see refs (Packer et al. (2015) supra, Yang et al. (2018) supra, Mardinly et al. (2018) supra)). Post-exposure, each SLM has 179 ms to load the next hologram in the sequence, ensuring that the hologram is nearly fully-formed to maximize fidelity and minimize DC illumination before exposing the sample. Therefore, when each SLM is running at 500 Hz and is temporally interleaved at uniform intervals, full 1 kHz temporal resolution is realized (FIGS. 2C-2G and 10D). This approach realizes efficient targeting precision across a full 1.03×1.03 mm field of view with no apparent roll-off in optogenetic excitation success rate vs position in the field (FIG. 2C, average of 8 randomized trials of the $e_1$-$e_6$ ensemble (FIG. 2F) photostimulation along with control, FIG. 9B). Alternatively, a burst-mode operation is available where both SLM1 and SLM2 are pre-loaded with the necessary holograms and each is sequentially illuminated to expose the sample to an optogenetic illumination pattern, with the sequential temporal difference limited only by the gating time of the Pockels cell (here, $\Delta t$=80 µs is conservatively applied). The burst mode operation was typically employed during all the visual in vivo experiments reported herein as a means to maximize the number of neurons stimulated per unit time. In those experiments all the targets in the ensemble were randomly distributed across two groups, and each group was assigned an individual SLM for the duration of the experiment. Note that all three-dimensional holograms are calculated as discussed in (Quirin et al. (2013) Optics Express 21, 16007).

In order to image multiple axial planes, a lighter microscope objective (Nikon 16×/0.8 NA) was used to reduce the inertial mass burden on the rapidly scanning piezo to help maintain its lifetime. Notably, this solution using a piezo-scanning objective does allow for rapid scanning across multiple axial layers while maintaining the ideal optical imaging performance of the microscope (FIG. 9C). Despite the temporal lag of acquiring an image from each axial slice (33 ms per slice), the optogenetic photoexcitation can be performed volumetrically, simultaneously. Using the viral vector approach taken here, selective expression is observed in layer 2/3 and layer 5 (FIG. 2B) and three-dimensional, simultaneous optogenetic excitation is realized across the full volume of 0.71×0.71×0.39 mm, capable of targeting layer 2/3 through layer 5 in this preparation (FIG. 9G, 9H, 30 Hz at 20 mW/cell at the objective, 0.63 ms, 9 rotations, 15 µm spirals). This was also the configuration used for all in vivo visual experiments, except the power was reduced to 10 mW/cell at the objective (see below); thus, the characterization measurements at higher power described here are conservative with regard to stimulation spatial precision.

Figures 9G, 9H:
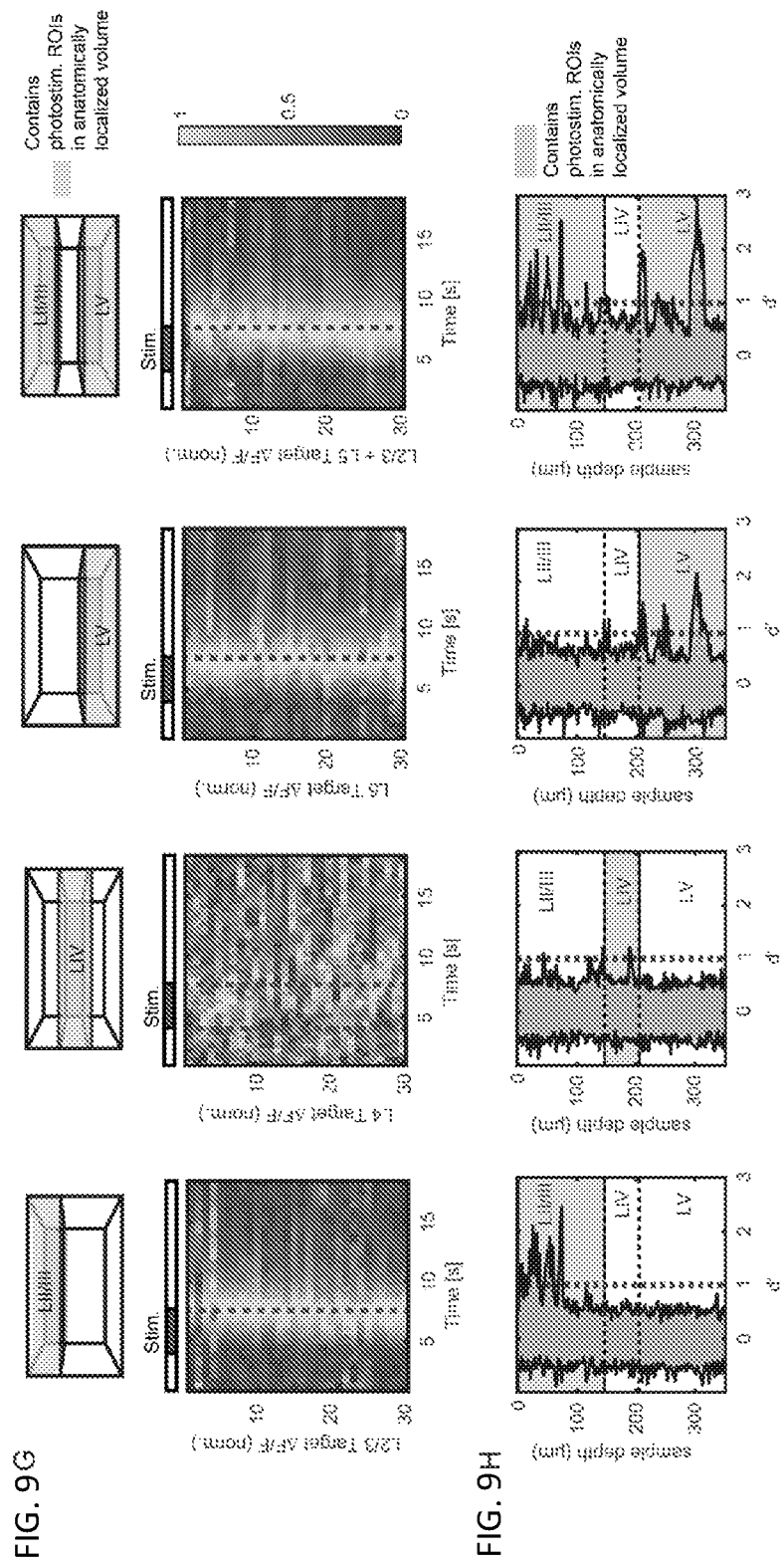

To assess axial precision of the stimulation system, optogenetic perturbation was selectively targeted only to layer 4, where expression is not present in the cell bodies. All resulting activity was measured in unbiased fashion across the entire imaged volume by subsampling the images into 8×8 pixel bins and reporting the modulation in fluorescence during optogenetic perturbation as a function of the tissue depth from the most superficially sampled image. As expected, based on the axial point spread function of the system (0.48 NA, FIG. 9E), layer 4 stimulation did not yield activity modulation in neighboring layers (FIG. 9G, 9H). In the same experiments, on randomly interleaved trials, neurons in layer 2/3 and/or 5 were stimulated for comparison, which elicited robust responses. It is also important to note that, as a result of the axial translation of the microscope objective during volumetric imaging, the spiral-scan stimulation will correspondingly be slightly tilted through the cell body, relative to normal. However, this is minimized in the setup due to the short exposure times required with this opsin/optics combination. As an example, the maximum axial slew rate of the objective in the experiments was ~2 µm/ms. Since all individual exposures in the protocols introduced in FIG. 10C-10F are below 0.63 ms, a maximum axial blur is expected due to microscope objective motion to be ≤1.2 µm.

FIG. 10. Temporal precision of the MultiSLM. (A) The maximum refresh rate of the large-format SLM is benchmarked at optimum diffraction efficiency (and slow refresh rate, red) in comparison to the operation using software overdrive at 500 Hz (blue) by placing a photodiode at the target A position. Alternating between holograms which alternatively place a spot at position A and alternative positions (e.g., position B) reveals that 85% of the optimum performance can be realized at a 500 Hz switching rate. Note, the measurement is at $\lambda$=1064 nm, in the wavelength range for operation, since LC response is often more than 3× faster at visible wavelengths (Peng et al. (2011) Opt Lett 36:2011). (B) A diagrammatic description of the temporal interleaving sequence using multiple SLMs. As each target/group hologram is exposed (e.g. solid bar SLM1/target 1A @ t=0 ms), the alternate SLM is already constructing the next hologram (e.g. dashed-line SLM2/target 2A @ t=0 ms).

The maximum temporal resolution of a single SLM is limited by the sum of the SLM rise time ($P_{SLM}$) and optogenetic exposure time (d; see Supplementary Text). (C) The MultiSLM with ChRmine technology allows significantly faster ensemble stimulation paradigms than previous studies. For example, a single hologram must be maintained for 5 ms duration to drive a spike in (Mardinly et al. (2018) supra). Exposures driving spikes in cell ensembles (i.e. e1) at 0.21 ms durations with spiral-scanning galvanometers across the cell membrane were reported. (D) Exploiting the fast optogenetic exposure and SLM dynamics, as well as temporal interleaving of multiple SLMs, results in a lower practical limit of 1.79 ms rise times and 0.21 ms exposures for a 1 kHz temporal resolution spike train for neuron ensembles e1-eN. (E,F) For a multiple SLM system, the system may run in a burst-mode where the interval between two successive ensembles, addressed by SLM1 and SLM2 respectively, can be continuously variable, down to the switching time of the Pockels cell (<50 μs). Note that all behavior optogenetic stimulation protocols in FIG. 3-6 were operated using condition (F) with a switching time of 100 μs.

Imaging and Optogenetic beam alignment: Spatial alignment of the targeting and imaging beams was accomplished by using the SLMs and optogenetic galvanometers to burn a constellation of holes into a thick fluorescent slab and then to register them to the collected imaging frame via manual identification of the hole centroids. A rigid, affine transform was defined for each axial position (at up to 7 axial planes) and a linear fit was implemented to characterize how each of the 9 affine transform coefficients would vary as a function of axial plane. This fit was stored and later recalled when generating the hologram patterns to be generated for targeting identified neurons in the sample. The axial localization of the imaging and optogenetic stimulation beams was characterized by measuring the fluorescence signal as a thin fluorescent slab (<5 μm) was translated through the beam (FIG. 9E).

The phase control afforded by the SLMs was exploited in two additional capacities to mitigate inherent optical challenges. First, due to the non-unity fill-factor of the SLM, a fixed amount of light will remain un-diffracted from the SLM and be focused in the sample plane unless mitigating steps are taken. First, this was addressed by placement of a beam block, in the form of a pair of magnets mounted to a cover slip (BB, FIG. 2A) in the intermediate image plane located between relay lens 1 and 2 (RL1 and RL2). This effectively blocked any light from undesirably focusing into the sample plane. To further address any potentially unblocked, un-diffracted light focusing in the sample, the beam expander was de-collimated (BE, FIG. 2A) such that the native foci of the SLMs were located approximately 300 μm above the native imaging plane of the microscope objective. This axial shift of the native SLM focal plane was compensated by adding a complementary focusing and spherical aberration correction term to the SLM phase mask, such that the un-diffracted illumination focuses ~300 μm above the targeting volume. The second capacity in which the SLMs were exploited to mitigate optical challenges was by employing an optical aberration correction algorithm which accounted for a) slight deviations from phase uniformity across the entire 30.7×30.7 mm face of the SLM and b) potential aberrations from optical misalignment or inherent to the optics. The aberration correction was realized by manually adjusting the weights of a linear summation of Zernike polynomials (up to $Z^{16}$) to account for the phase aberration (FIG. 9F), as measured by the fluorescence signal excited from a thin layer (<5 μm) of fluorescent material on a glass slide (Neil et al. (2000) *J Microsc* 200:105). The dominant phase errors were found to be astigmatism and spherical, with an additional defocus term which accounted for making the optogenetic target and the imaging plane effectively co-planar. The astigmatism phase correction likely compensated for any residual surface error not already corrected by the SLM look-up table.

FIG. 9. Theoretical and empirical properties of the microscope. (A) Theoretical multiphoton excitation efficiency curves for two alternative microscope objectives. The Olympus 10×/0.6NA multiphoton objective affords a large transverse field-of-view (1.02×1.02 mm) at a lower excitation NA (0.39) (top) while the Nikon 16×/0.8NA multiphoton objective compromises on the transverse field size (0.71× 0.71 mm) in order to realize a more precise axial point spread function (PSF) (NA=0.56) (bottom). White contour lines document the graded multi-photon excitation efficiency as a function of field position. (B) 160 target cells are identified as successful optogenetic stimulations (green) or unsuccessful (red) and used to map the success rate across the imaging field of view. Marginal projections of the spatially binned ratio of successful stimulation targets to the total number of targets are used to estimate the targeting efficiency across the field of view. (C) 3D imaging with optogenetic photoexcitation is realized by use of a piezo-coupled microscope objective for imaging while the SLM volumetrically addresses cells for optogenetic stimulation simultaneously across the entire volume. During each frame acquisition (frames 1 to N), all SLMs are able to volumetrically address the sample across N axial image planes ($i_1$ to $i_N$). Because of the piezo movement, the constellation of optogenetic targets will be axially offset during each frame acquisition, requiring a compensating quadratic phase offset to the SLM phase masks for each axial position. (D) The physiological response, as characterized by the percentage change in GCaMP fluorescence, when using a 15 μm diameter spiral for optogenetic photostimulation (9-spirals, 0.63 ms duration, as used in behavior experiments; n=10 neurons in vivo, mean response across 5 trials per stimulation location—the spiral was intentionally shifted from center of each cell by the defined lateral offset—randomized and interleaved, normalized to maximum for each cell, fit with a single gaussian function, error bars are s.e.m.). (E) Empirical, axial optical PSF measurements of both the optical imaging beam (FWHM=9.6 μm, NAest=0.64) and an optogenetic stimulation beam (FWHM=21.4 μm, NAest=0.48) using the Nikon 16×/0.8 NA microscope objective in the MultiSLM microscope. Data collected by translating a ~3 μm thick fluorescent slide through a focused beam. Best-fit to the empirical measurements was calculated using the square of a Gaussian function. (F) Representative adaptive optical correction to the SLM/optogenetic stimulation path as represented by Zernike polynomials. Application of the superposition of these polynomials as a compensatory phase mask results in the optimization of the optical PSF. The most significant aberrations are associated with astigmatism and possibly compensating for deformations across the face of the large-format SLMs (Neil et al. (2000) supra). (G) Optogenetic excitation of manually-selected targets with no known functional association, segregated by anatomical layer (L2/3 only, L4 only, L5 only, L2/3+L5), demonstrate positively responding neurons localized only in the anatomical layers associated with viral expression under the AAV8-CaMKIIa-GCaMP6m-p2a-ChRmine-TS-Kv2.1-HA construct. Averaged and normalized ΔF/F results from n=5 randomized trials across all four cases are presented in the lower row. The imaging conditions sample six planes, uniformly separated by 65 μm intervals across L23 to L5, and were held constant across all four stimulation conditions (which were randomly interleaved). Note that since little expression was localized to L4, the targets for that stimulation condition are generally not localized to cell bodies, but are used as a control for modulation of neighboring layers by the excitation light. (H) To measure to axial localization of the photostimulation response across the entire sampled volume, fluorescence modulations where quantified from every exclusive set of 8×8 pixel ROIs throughout the image acquisition volume. They are then organized according to sample depth during image acquisition and then aligned by the conditions in (G). Optogenetic modulation is measured by the d' (the difference in the mean number of counts acquired during photostimulation versus baseline, divided by the average of the standard deviation in counts of both time epochs) of each 8×8 pixel ROI. Supporting evidence that the optogenetic targeting is axially/anatomically localized is seen in the first, third and fourth columns where significant responses are isolated to L2/3, L5 and L2/3+L5, respectively. Conversely, when the same amount of optogenetic stimulation light is delivered to L4, no significant modulation is observed in the layers above or below. Whatever modulation is observed in L4 may be attributable to fluorescence modulation in the apical dendrites from L5.

Optical power considerations for all-optical physiology: It is worthwhile to note that in addition to considering instantaneous power, the time-averaged power into the sample (which is most likely related to brain heating) is minimal due to the very low duty cycles of each optogenetic photoexcitation exposure. For example, to target all 160 cells shown in FIG. 2C-2G required only:

$$\frac{30 \text{ mW}}{\text{cell}} \times 160 \text{ cell} \times \left(\frac{29 \text{ Hz} \times 0.21 \text{ ms}}{1000 \text{ ms}}\right) = 29.2 \text{ mW}$$

of average power during the 3 seconds of optogenetic stimulation. Further reducing time-averaged power into the brain, optogenetic stimulation epochs were generally a fraction of the total trial time (e.g., minimum 3 out of 8 seconds in behavioral trials).

In general, combined time-averaged power including imaging and optogenetic stimulation lasers during visual experiments was <50 mW. Instantaneously during either imaging or optogenetic stimulation (it was exceedingly rare that both occurred simultaneously on the microsecond scale for a given neuron due to raster scanning and very short optogenetic stimulation duration), it is estimated that each neuron experienced<20 mW imaging power or ~5 mW optogenetic stimulation power, when laser attenuation into the brain is accounted for (150 μm attenuation constant).

Mitigation of photo-stimulation artifact in images: As noted elsewhere (Yang et al. (2018) supra, Mardinly et al. (2018) supra), the optogenetic stimulation creates an image artifact due to the excitation of GCaMP in the targeted cells. Here, due to the low-duty cycle of the optogenetic stimulation, this artifact is present in only a small percentage of the imaging pixels (e.g., one 210 μs optogenetic stimulation will create artifact in only 0.6% of the total image). Furthermore, the artifact band is dithered across trials such that when the artifact pixels are excluded from any individual trials (see below), the trial-averaged results will reconstruct a full, artifact-free image (FIG. 12).

FIG. 12. Removal of photostimulation artifact in imaging channel of MultiSLM. (A) Targeted excitation of the opsin-fluorophore expressing neurons at λ=1035 nm results in a spatial block of pixels with increased background signal from co-excitation of the GCaMP6m reporter (here a bulk fluorescent slab serves as a phantom proxy), where the width of the artifact block is directly related to the excitation duration width. Note that optogenetic stimulation of each ensemble will result in an individual artifact band of width proportional to the ratio of the photostimulation duration (here 0.63 ms) to the imaging line-scan time (here, typical is 64.9 μs). Shown here are two ensemble stim artifacts, $e_1$ (SLM1) and $e_2$ (SLM2), analogous to FIG. 10F and the protocol applied in vivo. (B) Random offsets of the trial time (i), where $\tau \in \{-d, 0, +d\}$ and d is the optogenetic exposure duration, diversifies which image pixels which will have a photostimulation artifact. Representative recording of the optogenetic stimulation onset and frame start (where $\Delta t_{image}$ is frame acquisition time) which is used to track the relative timing and therefore the pixels which are contaminated by the artifact. (C) Trial mean intensity image taken from 10 trials of 30 Hz stimulation with trial-to-trial temporal shifting (dithering) of the onset ($\tau$). The randomized onset shift broadens the artifact on average but the diversity provides artifact-free access to every pixel for at least ⅓ of trials. (D) Result from artifact removal in the trial mean intensity image by omitting all pixels with artifact from the average on a per trial basis. (E) Comparison of this artifact removal in vivo. Top: Mean intensity image (one time-point averaged from 10 trials) when including the temporally shifted photostimulation artifact. Bottom: Mean intensity image (same time-point at above) when omitting the pixels associated with photostimulation artifact on a per trial basis. Areas representative of the increased contrast as a result of removing the additive photostimulation artifact are highlighted (cyan and red arrows). Note a Kalman filter (gain=0.8, noise=0.05) was applied to the time-series data after the artifact removal. All stimulation artifact fluorescence was completely removed from analyses of visual experiments by excluding artifact-contaminated pixels (Materials and Methods).

Data analysis of microscope performance: Multi-photon imaging data in FIGS. 2 and 9 were processed in MATLAB (R2017a, The Mathworks, Natick MA). Non-overlapping ROIs were defined from manual selection of targets. After defining the regions of interest (ROIs), the image movies were Kalman filtered (gain=0.5, noise=0.05) and data was then extracted by using each ROI as a binary mask and calculating the mean signal for each image frame. From this time-series ROI signal, the ΔF/F was calculated using the mean of the final ⅕ duration of the time-series data as the baseline measurement of each respective ROI. In FIG. 2C, for a neuron ROI to be deemed a positive optogenetic stimulation it must pass the following two criteria: a) the difference of the mean signal from the stimulation signal and the pre-stimulation baseline must be greater than 2σ (p≤0.025), and b) the difference of the mean signal and the post-stimulation baseline must be greater than 2σ (p≤0.025). Note that the trial-averaged artifact in FIG. 2C-2G was negligible due to: the phase offset of the image acquisition (30 Hz) and the optogenetic stimulation (29 Hz), which decreased the probability of the artifact being present in the same pixel across sequential frames; the minimal duration/line width of the artifact $$\left(\frac{210\ \mu s}{64.9\ \mu s/\text{line}}\right)$$

lines for each group in the stimulus, accounting for 3.8% of the image).

Data Analysis of In Vivo Visual Experiments

Preprocessing of in vivo visual experiment imaging data and selection of stimulated ensembles: Raw imaging data were loaded into MATLAB (R2016a, The Mathworks, Natick MA) and analyzed using built in functions, MATLAB Distributed Computing Server, and custom scripts. To reduce processing time by ~6 fold (n slices) and facilitate activity-guided experiments, raw images (~40,000 images per session, per channel) were processed in parallel in a computing cluster in which each optical slice (a defined depth in the volume) was processed by a single multi-core computing node. Data was served to each node by a high-performance data server in RAID 1+0 configuration in a 10-Gigabit network.

Any pixels in the image that were collected during optogenetic stimulation were replaced with "not a number" (NaN), and omitted from all subsequent analyses. Images from a single imaging plane in the volume were aligned to a reference image by determining the highest cross-correlation coefficient between each image and the reference image in a 20-pixel shift-window in X and Y. For the reference visual-only experiment, the reference image was defined as the average image of frames 10-50 from the imaging session. For each subsequent imaging session, the cross-correlation alignment procedure was repeated in the following order. First, the reference image was defined as the average of all images from the aligned, already motion-corrected visual-only experiment. The cross-correlation algorithm was applied to determine the optimal shifts to align Kalman filtered (gain=0.5, noise=0.05) imaging data from the current session to the reference experiment. These shifts were applied to the raw (non-Kalman filtered) data. A new reference image was defined as the mean image across the current, aligned dataset, and used to perform a final cross-correlation based motion correction for the current dataset. In this way, each session's dataset was aligned to the reference experiment using temporally-smoothed data, and further fast-motion corrected using its own reference.

Aligned imaging data from the reference visual-only experiment were input into the constrained nonnegative matrix factorization (CNMF) algorithm (Pnevmatikakis et al. (2016) *Neuron* 89:285-299). The spatial components estimated by CNMF were alone used to define a single set of cell masks across experimental sessions. Time courses for each cell were defined by averaging pixels within each cell mask for each image frame. Cell time course data were organized by trial, and baseline-normalized (to compute $\Delta F/F$) by the following formula: $(R_i-F)/F$, where $R_i$ is the cell's fluorescence at each time point i, and F is the cell's mean fluorescence during the three frames before a visual or optogenetic stimulus for each trial. The rigid alignment algorithm described above (well-suited for the high-speed imaging data, with minimal warping in each 33 ms frame), and alignment of the imaging volume to the reference experiment during each session (maintained in real-time using online cross-correlation software during image acquisition, see above), allowed the use of the same cell masks across sessions in order to conserve cell identity.

Tuned ensembles were defined as neurons (any mask segments resembling dendrites were removed by visual inspection) which responded robustly and reliably (at least 3 of 8 time points>0.3 $\Delta F/F$, and p<0.05 t-test stimulation epoch versus baseline) to either the 0° or 90° 50% contrast visual stimulus, with an orientation selectivity index (OSI) greater than 0.5. OSI was defined by the following formula: $(R_{pref}-R_{orth})/(R_{pref}+R_{orth})$, where $R_{pref}$ is the response during the visual stimulus to the preferred orientation, and $R_{orth}$ is the response to the orthogonal orientation. For these analyses of the reference visual experiment (but not subsequent analyses), cell time courses were Kalman filtered (gain=0.5, noise=0.05) before computing $\Delta F/F$. Tuned ensemble sizes were 0°: 32, 26, 27, 37 and 90°: 19, 40, 33, 26 for each mouse in the naïve cohort, respectively (Naïve Mouse 1-4). Tuned ensembles sizes were 0°: 55, 42, 33, 53, 33 and 90°: 38, 37, 28, 46, 42 for each mouse in the behavioral cohort, respectively (Trained Mouse 1-5). Random ensembles were randomly selected from the remaining population across the volume to match the number of neurons in the respective tuned ensembles. For stimulation of sub-ensembles in each cortical layer, either all of the neurons from the tuned ensemble from an anatomically-defined layer were used, or a randomly selected subset of those neurons was used, where the number of neurons was defined for each subset tested.

Statistical analysis of co-activity: Stimulated neurons and any neuron masks containing pixels within a 20.85 µm (15 pixels) radius, including any neurons above or below stimulated neurons within a cylinder with the same radius, were excluded from all analyses of co-activity. On each day, high contrast visual trials (50% contrast; no optogenetic stimulation) were used to find reliable (significant two-tailed Wilcoxon signed-rank test, MATLAB function, frames 5 and 6 versus baseline frames 2 and 3), orientation selective (OSI>0.5, calculated as above) neurons. Importantly, frames 5 and 6 occurred during the "Sample Window", that is during the visual or optogenetic stimulus but before any water reward or air puff was delivered. These reliable, orientation-selective neurons, which were distinct from the original tuned ensembles as described above, were used to define the tuned populations for network analyses. Neurons within these tuned populations that reliably increased fluorescence across trials of a specific optogenetic ensemble condition (significant two-tailed Wilcoxon signed-rank test, frames 5 and 6 versus frames 2 and 3) were deemed co-active. To define the fraction of co-active neurons for each condition, the number of co-active neurons was divided by the number of tuned neurons.

For scatter plots, each data point is the result from a single optogenetic ensemble stimulation condition from a single day. Relationships between the number of stimulated neurons and the fraction of co-active neurons were computed using the Spearman's correlation coefficient, with significance defined by a two-tailed test versus no correlation (built in MATLAB function). To statistically compare p values, a two-tailed Fisher's z transformation was performed.

Figures 19A, 19B, 19C:
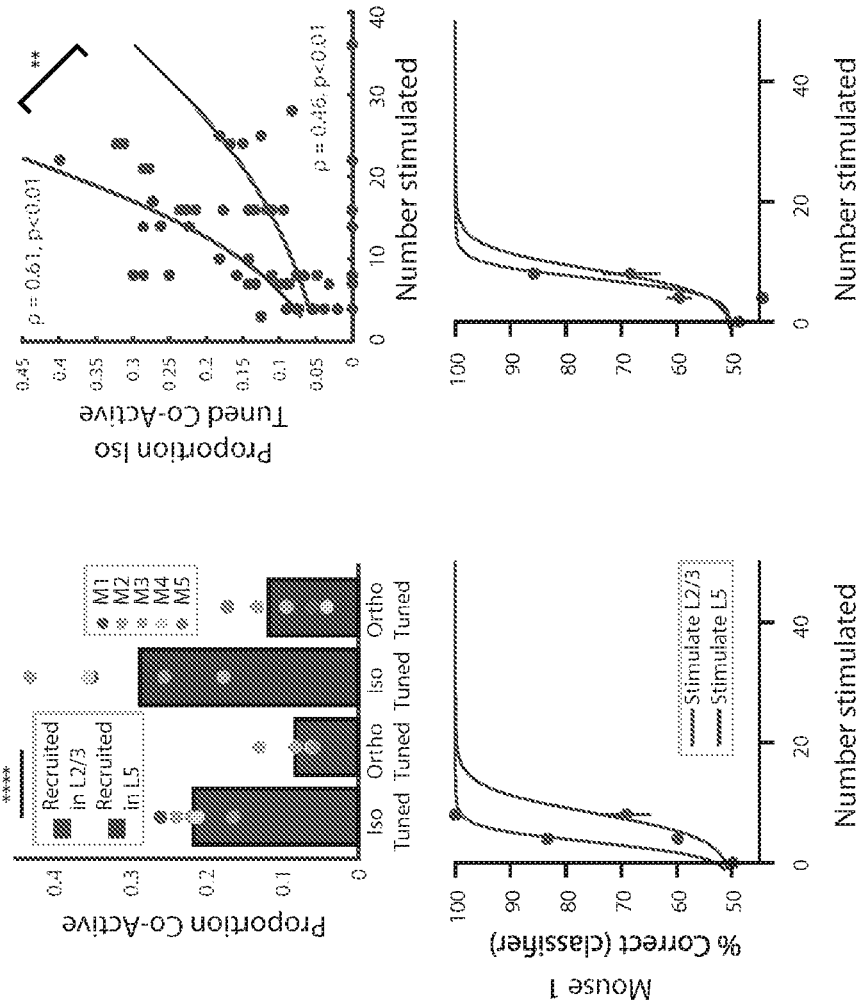
FIGS. 19A-19G depict selective laminar recruitment and ignition threshold visualized for five individual mice.
Figure 19D:
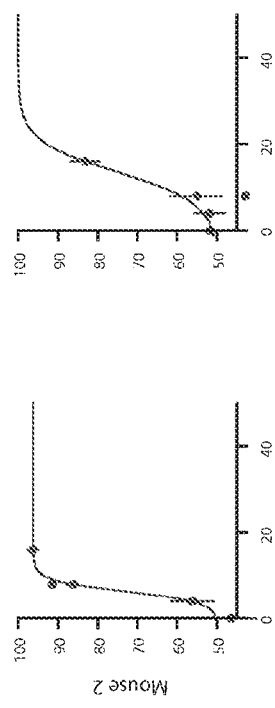
Figure 19E:
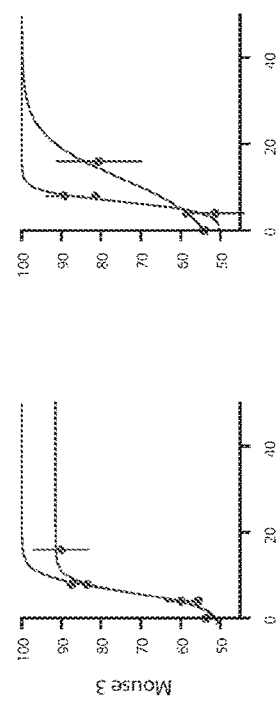
Figure 19F:
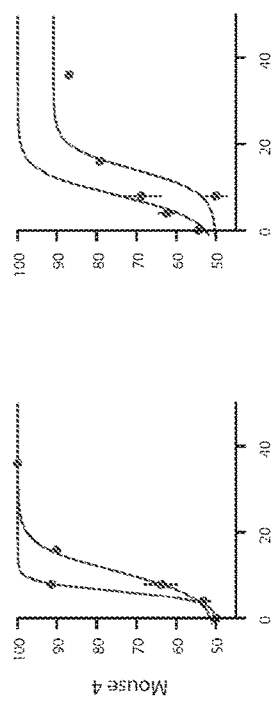
Figure 19G:
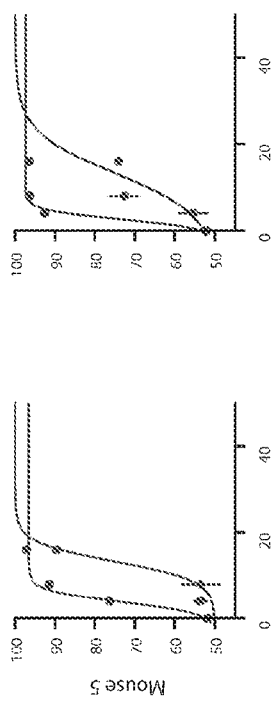

For bar graphs, the number of co-active neurons and tuned neurons neurons were each summed across sessions for each mouse to define each mouse-identified data point plotted on the figure, and across mice for summary data. A two-tailed Pearson's chi square test was used to statistically compare frequencies of co-activity on pooled data across mice between conditions (SPSS). To account for the contribution of mouse identity, additional statistics are presented here using the Cochran-Mantel-Haenszel (CMH) test, in which data are stratified by mouse identity. The CMH tests yielded comparable results to the Pearson's chi squared test in all instances. A Breslow-Day test was run to test the assumption of homogeneity of the odds ratio for each CMH test. The Breslow-Day test rejected the null hypothesis that the odds ratio was equal across mice for the following statistical tests, implying that an interaction may have existed between mouse identity and observed co-activity counts. These included Tuned After Contrast Ramp (FIG. 4 L), Random After Contrast Ramp (FIG. 4 M), Tuned vs. Random Before Contrast Ramp (FIG. 4 N), Tuned vs. Random After Contrast Ramp (FIG. 4 N), Iso vs. Ortho (FIG. 5E), Layer 2/3 vs Layer 5 Iso Tuned (FIG. 6 C), Layer 2/3 Iso vs. Ortho (FIG. 19A), and Layer 5 Iso vs. Ortho (FIG. 19A). Pearson's chi square tests were run independently for each mouse for each of these instances and were found to be significant to at least $p<0.05$ for 4/5, 4/5, 4/5, 3/5, 5/5, 3/4, 5/5, and 5/5 mice, with effect directions always matching the pooled data, for each of these comparisons respectively. Layer 2/3 vs. Layer 5 Iso Tuned (FIG. 19A) had 4/5 mice with significant Pearson's chi square tests ($p<0.001$) going in the direction of increased layer 5 recruitment vs. layer 2/3, and Mouse 3 had greater layer 2/3 recruitment than layer 5 ($p=0.046$).

FIG. 19. Selective laminar recruitment and ignition threshold visualized for five individual mice. (A) Stimulation of full tuned ensembles involving both layers 2/3 and 5 preferentially recruited iso-tuned neurons in both layer 2/3 and layer 5 ($p<0.0001$, $\chi^2$ two tailed test, iso vs. ortho in each layer; co-active neurons are found by two-tailed Wilcoxon signed-rank tests, $p<0.01$, sample window vs. baseline, Materials and Methods). A greater proportion of layer 5 iso-tuned neurons was recruited compared to layer 2/3 ($p<0.0001$, $\chi^2$ two tailed test, n=58 experiments in 5 mice). Data were pooled across sessions and mice for each colored bar and reported with Pearson's $\chi^2$ square test results; pooled data across sessions for each mouse shown as colored dots (see legend, per FIGS. 4H, 5D, 6A; Materials and Methods: stratified CMH tests controlling for mouse identity). $p<0.01$, $p<0.0001$ throughout. (B) Data from FIG. 6**B,D showing direct comparison of iso-tuned recruitment within each stimulated layer. Stimulation of layer 5 neurons recruits a greater fraction of layer 5 iso-tuned neurons more rapidly than layer 2/3 stimulation recruits iso-tuned layer 2/3 cells ($p<0.01$, ANCOVA controlling for the covariate of number stimulated; Spearman's $\rho=0.46$, $p<0.01$, n=46 data points, within layer 2/3 and Spearman's $\rho=0.61$, $p<0.01$, n=24 data points for layer 5 recruitment). (C) Logistic psychometric functions (solid lines) fit to predictions derived from a classifier trained on either neural (left column) or behavioral data (right column) taken from a single mouse. Each curve relates the mouse's performance to the stimulation of a specific number of neurons. Individual points represent averages across the one or more days where a particular experimental condition was run+/− the SEM Each plot shows fits to data for only conditions where ensembles resided in individual layers. (D-G) Results shown for four additional mice. Format matches (C). Target and Distractor ensembles stimulated in each mouse differ in size by at most 1 neuron. Importantly, the parameters underlying the psychometric function fits were not used for any quantitative statistical analysis and are presented only for illustrative purposes.

Statistical analysis of neuronal dynamics: All classifier and neural decoding analyses were performed in Python 3.6 and used open source libraries listed below. This analysis is presented in parts of FIG. 3, FIG. 5, and FIG. 6 as well as all of FIG. 14-19 (except for 16A).

FIG. 16. Parameter estimation for classifier analysis and tuned visual network recruitment in behaviorally trained mice. (A, left) Among the non-targeted cells in naïve mice, both iso-tuned and orthogonally-tuned neurons are secondarily recruited during tuned ensemble optogenetic stimulation, with a modest preference for iso-tuned in the absence of visual stimuli, ($p<0.05$, $\chi^2$ two tailed test). Data are pooled across sessions and mice for bars and statistics (n=25 sessions in 5 mice; co-active neurons are found by two-tailed Wilcoxon signed-rank tests, $p<0.05$, sample window vs. baseline, Materials and Methods). (A, right) Recruitment of iso-tuned populations is enhanced with training on the visual discrimination task ($p<0.05$, $\chi^2$ two tailed test, trained vs. naïve cohorts). Data for each mouse in each cohort are shown as shaded or color dots corresponding to stratified Cochran-Mantel-Haenszel (CMH) tests controlling for mouse identity (Materials and Methods, see legends: NM is Naïve Mouse, M corresponds to a trained mouse consistent with main figures and numbering throughout this figure). (B) Bar graph indicating the fraction of all imaged neurons that were used for classifier and neural trajectory analyses (neurons used are termed "unstimulated neurons"). The number of unstimulated neurons was 929±250 [mean±SD], or 21±5% of all neurons in each of the 5 mice in this cohort. (C) Plot indicating cumulative variance explained by increasing numbers of principal components as applied to the unstimulated neuronal traces during visual stimulus presentation. Results shown for five trained mice. Horizontal red line is at 90%. The vertical red line indicates that five principal components are necessary to explain at least 90% of the variance in all five mice. (D) The fraction of optogenetically stimulated tuned (left) and random (right) neurons that were significantly modulated by light is shown for n=3 trained mice that had at least 40 stimulation trials/neuron (using conservative metrics; line color corresponds legend in (A); see Materials and Methods). (E, G, I, K, M) Classifier performance shown for five trained mice as a function of the number of neurons with classifier regression weights equal to zero increases (which increases as a function of the parameter $1/\lambda$). A constant value ($1/\lambda=0.5$) was used across all five mice. It was found that this value approximately minimized each model's prediction error on held-out test data (that was not used for training). (F, H, J, L, N) Spatial map of all ROIs extracted across six cortical depths shown for five mice. Black dots (targets) were excited by 2P illumination in at least one experimental condition. Excluded ROIs (not shown, but counted in panel (A)) were within 20 microns of a target ROI at some depth or were contaminated by a 2P-induced stimulus fluorescence artifact and were excluded from the classifier analysis. Remaining ROIs (colors) were used for classifier analysis. Right histograms show weight values for ROIs that had weights>10% of the maximum weight obtained by any ROI. Scale bar is 100 µm.

Neural decoding analysis using sparse logistic regression: In order to select cells to include in the neural decoding analysis for a given mouse, all neurons that were ever optogenetically stimulated on any experimental day or condition were identified. Then a column of exclusion with an approximately 20.85 µm (15 pixel) radius around each of these stimulated neurons to conservatively identify any neuron that might have been erroneously stimulated during the experiments was defined. Other neurons whose fluorescence signals were contaminated by stimulation artifacts were also removed during this process (see above). This neuron selection procedure differs slightly from the one used for the statistical analysis of co-activity (see previous methods section) in that all neurons that were ever stimulated in a mouse (plus surrounding neurons) were excluded on all days to facilitate training regression models that generalize between experiments where different ensembles were optogenetically stimulated.

The regression models were trained only on experimental trials where mice watched a visual stimulus and no neurons were optogenetically stimulated. Specifically, for each experimental day, each condition where a visual stimulus was presented was found (at any contrast between 12-50%). Then from each one of these trials, the average fluorescence of each neuron across two fluorescence frames after stimulus onset was computed (frames 5 and 6 of 19 total imaging frames/trial; the same frames used for co-activity analyses above). These two frames were specifically chosen to eliminate the frame where fluorescence was rising at the onset of the visual stimulus (frame 4) and to also eliminate the later frames during the stimulus where either a water reward or punishing air puff could have been delivered. This process yielded a vector of length equal to the number of unstimulated neurons in each dataset, for each trial. Each of these vectors were concatenated into a matrix of size equal to the number of trials by the number of unstimulated neurons. Importantly, only this visual-stimulus-only data was ever used to train the regression models. The same models were then used to predict condition type (target vs. distractor) on all other kinds of data (i.e. during optogenetic stimulation of different types). This procedure was identically followed in both the behavioral cohort of mice (where reward and airpuff stimuli were present) and the naïve cohort of mice (where neither stimulus existed).

This data matrix and another vector containing the true stimulus type (target, 0° or distractor, 90°) were taken and used to fit a set of sparse logistic regression models. This procedure was repeated independently for each mouse. To perform the regression model fitting, a class in Python's scikit-learn package named LogisticRegression was used with the penalty argument set to 'L1.' Each of the five models was trained on a distinct random fifth of all of the trials presented (five-fold cross validation). Classifier weights and predictions reported are means across all five of the regression models trained for each mouse. Finally, it was found that across all n=5 behavioral mice (FIG. 14) and n=4 behaviorally naïve mice (FIG. 16), setting the sparseness parameter ($1/\lambda$) equal to 0.5 approximately minimized the training error in each case. Models generating all results reported had $1/\lambda$ set to this value.

Across n=4 behaviorally naïve mice (and 2 tuned+2 random ensembles for each mouse; 60 stimulation trials from each neuron were used in this analysis), tests showed that the effective size of the tuned and random optogenetically-stimulated ensembles was comparable. This was computed by using a Wilcoxon signed-rank test to compare the average fluorescence in the baseline period (frames 1 and 2) to the average fluorescence after optogenetic stimulus onset (frames 5 and 6) across all individual trials from each targeted neuron. The significantly recruited fraction of tuned ensembles ranged from 0.4-0.92. This fraction for random ensembles ranged from 0.37-0.74. A paired t-test revealed no significant difference between these two distributions, (p=0.48) (FIG. 14C).

This same analysis was also applied to n=3 behaviorally trained mice (40 stimulation trials/neuron were used for this analysis; there were 2 tuned and 2 random ensembles analyzed for each mouse). In contrast to the naïve mice, the conservative metric found that there was a significant difference in stimulation efficacy between the size-matched random and selective ensembles. The significantly recruited fraction for tuned ensembles ranged from 0.58-0.9. For random ensembles it ranged from 0.26-0.75. A paired t-test revealed a significant difference here, p<0.001.

FIG. 14. Parameter estimation for classifier analysis of behaviorally naïve mice. (A) Bar graph indicating the fraction of all imaged neurons that were used for classifier and neural trajectory analyses (neurons used are termed "unstimulated neurons"). (B) Plot indicating cumulative variance explained by increasing numbers of principal components as applied to the unstimulated neuronal traces during visual stimulus presentation. Results shown for four mice. Horizontal red line is at 90%. The vertical red line indicates that five principal components are necessary to explain at least 90% of the variance in all four mice. (C) The fraction of optogenetically stimulated tuned (left) and random (right) neurons that were significantly modulated by light is shown for n=4 naïve mice using 60 stimulation trials/neuron (using conservative metrics; see Materials and Methods). A paired t-test pooling across mice revealed no significant difference between these two distributions (p=0.48). (D, F, H, J) Classifier performance shown for four behaviorally naïve mice as a function of the number of neurons with classifier regression weights equal to zero increases (which increases as a function of the parameter $1/\lambda$). A constant value ($1/\lambda$=0.5) was used across all four mice. It was found that this value approximately minimized each model's prediction error on held-out test data (that was not used for training). (E, G, I, K) Spatial map of all ROIs extracted across six cortical depths shown for four naïve mice. Black dots (targets) were excited by 2P illumination in at least one experimental condition. Excluded ROIs (not shown, but counted in Panel A) were within 20 microns of a target ROI at some depth or were contaminated by a 2P-induced stimulus fluorescence artifact and were excluded from the classifier analysis. Remaining ROIs (colors) were used for classifier analysis. Right histograms show weight values for ROIs that had weights>10% of the maximum weight obtained by any ROI. Scale bar is 100 μm.

Neural trajectory analysis using PCA: In a similar manner to the procedure described above for the decoding analysis, Principal Components Analysis (PCA; scikit-learn class PCA) was used to visualize the average population response of all trials of an identical experimental condition, on a given experimental day. Principal components were identified using a data matrix composed of the mean fluorescence responses across all neurons to both the target, 0° and distractor, 900 visual stimuli (contrast ranged from 12 to 50%; in the absence of any optogenetic stimulation). Since each trial was 19 frames long, this yields a training matrix of size: (19×2)×number of neurons. The first two principal components estimated from this data matrix were used to plot all neural trajectories for an individual mouse in all experimental conditions.

A similar analysis using Partial Least Squares Regression (scikit-learn function PLSRegression) was performed with the identical data matrices, but also with ground truth visual stimulus information (target, 0° vs. distractor, 90°). This approach yielded nearly identical results to PCA—despite the fact that the latent dimensions were explicitly derived to separate target from distractor conditions, rather than to simply maximize variance explained (FIG. 18).

Figures 18A, 18B, 18C, 18D, 18E:
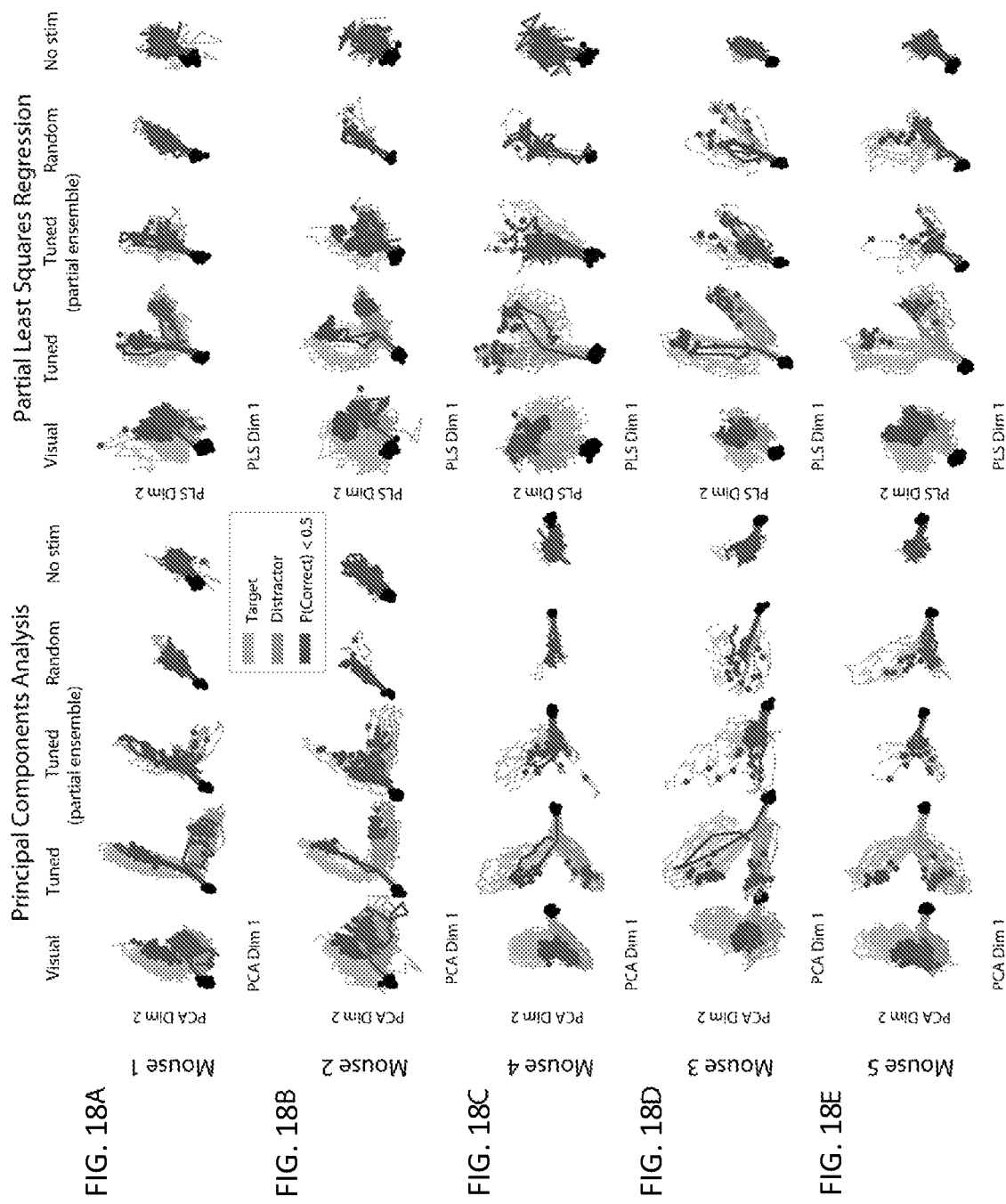
FIGS. 18A-18E depict visually evoked population activity is more similar to that evoked by stimulation of tuned ensembles than by random stimulation.

FIG. 18. Visually evoked population activity is more similar to that evoked by stimulation of tuned ensembles than by random stimulation. (A-E) Neural trajectories were computed individually for each experimental condition on each experimental day. The basis vectors were computed for each mouse with the visual only data, using either Principal Components Analysis (PCA, left column) or Partial Least Squares Regression (PLS, right column). Light blue trajectories represent data obtained during target conditions and light red trajectories represent distractor conditions. Dark blue and red trajectories denote target or distractor conditions that the mouse performed with mean performance less than 50% (meaning fewer than half of the trials on that condition and day elicited the correct behavioral response). Each trajectory is composed of neurons that were never optogenetically stimulated and that lie at least 20 microns away from any stimulated neuron. Principal component dimensions were computed using the visual data. Black dots represent the start of each trajectory. Red and blue dots mark the first frame following visual or optogenetic stimulus onset and are superimposed onto each trajectory. All but the tuned partial-ensemble panels from Mouse 3 and Mouse 4 were shown in FIG. 5, and are reproduced here for completeness. If motor behavior plays a role in the shape of these neural trajectories, it would be expected that in the case of the mouse making a large number of behavioral errors, those trajectories would look distinct from trajectories constructed from data where high behavioral performance was observed. Instead it is seen that the highlighted red and blue trajectories (where mean performance was <50%) look qualitatively indistinguishable from other red and blue trajectories from conditions where few errors were observed.

Psychometric curvefitting: To assess the relationship between either neural or behavioral performance and the size of an optogenetically stimulated ensemble, an open-source package called Psignifit-python (Schutt et al. (2016) Vision Res 122:105)) was used to fit logistic psychometric curves of the following form:

$$\psi(x) = \gamma + (1 + \lambda - \gamma)S(x; m, w)$$

$$S(x; m, w) = \frac{1}{1 + e^{-2\log\left(\frac{1}{0.05} - 1\right)\frac{X-m}{w}}}$$

Three parameters of the curve were fitted: the threshold m, width w, and the lapse rate A. The lower asymptote parameter, $\gamma$, was fixed to 50%. Psychometric curves fit in this manner are presented as a visual aid for interpreting the data and were statistically analyzed as described in the text.

Open source packages used: The following open source Python libraries were used in the statistical analyses of the data presented:
IPython (Perez et al. (2007) *Computing in Science Engineering* 9:21): https://ipython.org/
Numpy (Oliphant (2006) *Guide to NumPy*): http://www.numpy.org
Matplotlib (Hunter (2007) *Computing In Science & Engineering* 9:90): http://www.matplotlib.org
Psignifit 4 (Schutt et al. (2016) supra): https://github.com/wichmann-lab/python-psignifit
Pandas (McKinney (2010) Proceedings of the 9th Python in Science Conference): https://pandas.pydata.org/
Scikit-learn (Pedregosa et al. (2011) *Journal of Machine Learning Research* 12:2825): http://scikit-learn.org/stable/index.html
SciPy (Jones et al. (2001) *SciPy: Open source scientific tools for Python*): http://www.scipy.org
Seaborn: http://seaborn.pydata.org
Statsmodels (Seabold et al. (2010) Proceedings of the 9th Python in Science Conference): https://www.statsmodels.org/stable/index.html A Simple Theory of Neural Ignition in a Poisson Model Consider a population of N neurons that, in a spontaneous network state, all fire in a Poisson manner at a low spontaneous rate r. In the context of this work, this population of neurons corresponds to a selectively tuned neural ensemble of excitatory cells that are similarly tuned to the same oriented grating. Let n denote the total number of neurons that fire within a time window T. In the spontaneous state, n is then a Poisson random variable with mean $\mu$=NrT and standard deviation $\sigma$=$\sqrt{NrT}$. For large values of NrT n can be approximated as a Gaussian random variable with the same mean and standard deviation. Now further suppose the neurons are recurrently connected in a way such that if the total number of neurons n that fire within a time window T, either due to spontaneous fluctuations or due to external excitation, exceeds a threshold $\theta$, then the network undergoes an ignition event in which a large fraction of the network fires. This implies that if a number of $N_s$ neurons are optogenetically stimulated within a time window T, while the network is in the spontaneous state, an ignition event can be triggered with some probability $P(N_s)$. This probability should become close to 1 as $N_s$ becomes large. An interesting network property is the minimum number of neurons needed to stimulate so that an ignition event is obtained with a high probability, for example a probability of 0.95. This number of neurons required to obtain an ignition event with such high probability is denoted by $N_h$. The data suggests the intriguing observation that this minimal number $N_h$ required for ignition is much less than the total number of neurons N in the selectively tuned ensemble.

However, a goal is to ensure that the rate of spontaneous ignition events $r_s$ due to spontaneous activity remains low. This spontaneous ignition rate is given by $r_s$=P(0)/T where P(0) is the probability of ignition if $N_s$=0 cells are optogenetically stimulated. The key issue is then whether it is possible to choose biologically plausible parameters so that one can stimulate population ignition events with high probability with a very small $N_h \ll N$, while still ensuring the rate of spontaneous ignition events $r_s \ll 1$ Hz remains very small. To address this issue, both $r_s$ and $N_h$ are computed as a function of NrT and the ignition threshold $\theta$. First, it is noted that $P(N_s)$ is simply the probability that $n+N_s$ is greater than $\theta$, where n is the random number of neurons already spontaneously active during the stimulation window. Here it was assumed that the $N_s$ neurons that are being stimulated are not already spontaneously active, which is a good assumption when both n and $N_s$ are much smaller than N. This is the regime in which the data lies and the regime in which the theory will be applied. Thus $P(N_s)$ is simply the probability that a Gaussian random variable with mean NrT+$N_s$ and standard deviation $\sqrt{NrT}$ exceeds the threshold $\theta$. H(x) denotes the probability that a standard Gaussian variable with zero mean and standard deviation exceeds x; i.e.

$$H(x) = \int_x^\infty \frac{dz}{\sqrt{2\pi}} e^{-z^2/2}.$$

Then $P(N_s)$ is given by $$P(N_s) = H\left(z_\theta - \frac{N_s}{\sqrt{NrT}}\right),$$

where $$z_\theta = \frac{\theta - NrT}{\sqrt{NrT}}$$

is a z-scored version of the threshold for ignition that reflects how many neurons one needs to stimulate to go from the spontaneous mean $\mu=NrT$ to the threshold $\theta$, measured as a fraction of the spontaneous standard deviation $\sigma=\sqrt{NrT}$. The function $P(N_s)$ is a monotonically increasing function of $N_s$.

From this function, the following can be obtained:

$$T_s = H(z_\theta)/T.$$

And $N_h$ is obtained as the solution to $P(N_h)=0.95$. If $x_h$ is donated as the solution to $H(x_h)=0.95$, then the following can be obtained:

$$N_h = \sqrt{NrT}\,(z_\theta + |x_h|),$$

where the numerical value of $x_h$ is given by $x_h=-1.65$.

These results quantitatively capture the tradeoff induced by varying the threshold $\theta$. Increasing $\theta$ also increases the z-scored threshold $z_\theta$, and thereby decreases the spontaneous rate $r_s$ of ignition events, but also increases the minimum number of neurons $N_h$ needed to reliably trigger ignition with high probability. Conversely, decreasing $\theta$ makes the network more sensitive by reducing $N_h$, but also increases the rate $r_s$ of false positive spontaneous ignition events. However, varying $\theta$ yields dramatically different effects on $r_s$ and $N_h$. In particular, increasing $\theta$ (and therefore increasing the z-scored threshold $z_\theta$) exponentially suppresses $r_s$ but only leads to a modest, linear increase in $N_h$. Therefore, by setting a relatively low threshold for ignition so that the z-scored threshold $z_\theta$ is a fixed constant, independent of the network size N (i.e. say 5 or 10), then the spontaneous rate can be made exponentially small in $z_\theta$, while still ensuring that the minimum number of neurons $N_h$ needed to reliably trigger ignition remains proportional to the standard deviation of the spontaneous fluctuations, which grows only as the square-root of the tuned-ensemble size N. In essence, this corresponds to a situation in which the network ensemble has a low ignition threshold that lies just above what spontaneous fluctuations could reliably reach. However, the threshold is not so high that a small number of additional stimulated neurons of size proportional to the size of these same fluctuations, can push the network over the ignition threshold.

Biologically plausible numbers can now be employed to test this simple framework. Assuming that an estimate for the tuned-ensemble size is given by N of order of magnitude in the thousands, N=5000 is taken for simplicity. Previous studies of spontaneous activity in mouse primary visual cortex suggest a low spontaneous rate of r=0.2 Hz in layer 2/3 (Niell et al. (2008) *J Neurosci* 28:7520, Niell et al. (2010) *Neuron* 65:472) (with higher rates of ~2 Hz in layer 5 (Niell et al. (2010) supra)). A time window of T=20 ms, proportional to the typical membrane time constant over which neurons can integrate spikes, is considered. This yields a total population mean spike count of $\mu=NrT=20$ and spontaneous fluctuations of standard deviation $\sigma=\sqrt{NrT}=4.47$. Now suppose a threshold $\theta$ corresponding to a z-scored threshold $z_\theta=5$ is set. Then $r_s=H(z_\theta)/T=1.43*10^{-5}$ Hz. With this small rate of spontaneous events, on average 1 spontaneous ignition event every 19 hours would be observed. However, an ignition event could still be triggered by optogenetically stimulating only $N_h=\sqrt{NrT}\,(z_\theta+|x_h|)$ =4.47*(5+1.65)=30 neurons, which is much less than the ensemble size of N=5000, and similar to what is observed in the data. Thus overall, this analysis provides a simple and quantitative framework for thinking about how low thresholds for ignition can be. Furthermore, when combined with the experiments, this framework suggests that V1 may have organized its internal connectivity and thresholds so as to be highly sensitive to events that simultaneously excite exceedingly small numbers selectively tuned neurons, without suffering from unreasonable rates of false positive spontaneous ignition events.

A Nonlinear Neural Network Model of Neural Ignition

While the above simple analytic theory reveals that low thresholds for ignition in large neural populations can be feasible, it does not demonstrate a proof of principle for low ignition thresholds in an actual network model, and moreover leaves unspecified any network mechanism for ignition. Here one possible network model that can instantiate low thresholds for ignition is provided. The model consists of N=2000 rate neurons, characterized by their activity vector, x, which evolves in continuous time through the differential equation $\tau_k \dot{x}_k = -x_k + \sum_{l=1}^{N} J_{kl}\theta(x_l)$ where $\theta(x)$ is a heaviside function that is zero if its argument is negative, and 1 if its argument is positive. The population is split into two equal blocks of excitatory (e) and inhibitory (i) cells of size $$\frac{N}{2}$$

each. A, B are variables denoting the population identities, so that A, B$\in\{e,i\}$.

The connectivity from any neuron in population B to any neuron in population A is chosen to be random Gaussian, with a common variance $\sigma^2$, but a mean $\mu_{AB}$ that depends on both the source and target population. In particular, the inhibitory to inhibitory connections are chosen to have zero mean ($\mu_{ii}=0$), and the mean inhibitory to excitatory connectivity ($\mu_{ei}=-10$) is chosen to reflect strong inhibition of the excitatory subpopulation. The mean excitatory strength $\mu_{ee}$ and $\mu_{ie}$ were varied, finding a boundary in this two dimensional plane separating two regimes in which the fraction of spontaneously active excitatory neurons $f_e$ (where $f_A=\langle\theta(x_k)\rangle_k \forall k\in A$) is either high or low, depending on whether the mean recurrent $\mu_{ee}$ excitation is above or below a value set by $\mu_{ie}$. Intuitively, in parameter space there is an instability to all the excitatory neurons becoming strongly active if recurrent excitation is too high. The parameters were chosen so as to lie sufficiently below the boundary of instability such that the spontaneous ignition rate due to network fluctuations remained small, but close enough to this boundary such that a small excitatory stimulus can still transiently perturb the excitatory neurons to a high firing rate. This led to the choice of parameters $\mu_{ee}=15$ and $\mu_{ie}=11$, although there is a manifold of parameter choices that would yield similar results. Moreover, it is ensured that the excitatory population is fast, so that $\tau_k=1$ for all excitatory neurons, and it is ensured that the inhibitory neurons are slow, with $\tau_k=20$ for all inhibitory neurons. Finally, for computational purposes, the heaviside function was approximated as $\theta(x)=\frac{1}{2}\tanh(cx)+\frac{1}{2}$ where $c\gg 1$.

Overall, this network modeling reveals several principles required for low threshold ignition: (1) a fast excitatory subnetwork that by itself is highly unstable, (2) a slow inhibitory network that provides strong inhibition to the excitatory subnetwork, (3) recurrent excitatory connectivity that should not be so strong as to destabilize a low spontaneous-activity state in the combined excitatory-inhibitory network, and (4) this same recurrent connectivity should nevertheless be strong enough so that further excitation of a small number of excitatory cells can trigger ignition. After ignition is triggered in the fast excitatory population, this population will excite the inhibitory subpopulation, which will rise more slowly, and then this inhibitory population will later inhibit the excitatory population, bringing all the firing rates back down again, ensuring that ignition is a transient event. As demonstrated in the main figures, stimulation of order ~10-30 excitatory neurons in a network of 1000 excitatory neurons is sufficient to reliably trigger such transient ignition.

Structural Insights into the High Conductance of ChRmine

Although ChRmine was discovered through functional metagenomic screening targeting for joint exhibition of properties required for the experiments shown here, the mechanisms underlying its unique functionality remain unclear. However, recent advances in structural understanding of channelrhodopsins (ChRs) have provided a foundation for understanding of the basis of ion selectivity and spectral sensitivity (Kato et al. (2012) supra, Kim et al. (2018) supra, Kato et al. (2018) supra). Although ChRmine shows low similarity to previously studied ChRs, mechanistically important features, such as transmembrane domains 3, 6 and 7 comprising the retinal-binding pocket and ion-conducting pathway, exhibit high sequence homology (FIG. 7), suggest structural explanations for the properties of ChRmine based on structural and biochemical studies of other ChRs.

In ChRmine, Asp115 (Glu162 in C1C2 and Glu129 in CrChR2), which may form a counter-ion network along with Asp253 (Asp292 in C1C2 and Asp253 in CrChR2) to the protonated retinal Schiff base, is thus one carbon shorter than its glutamate counterparts in C1C2 or CrChR2 (FIG. 7). This difference may slightly destabilize the hydrogen-bonding network between the protonated Schiff base and its counter-ion, which would lead to elevation of the energy of the ground state of the protein and result in less energetic, more red-shifted photons sufficing for driving the transition to the light-activated state (Kato et al. (2018) supra). Moreover, the homology model (FIG. 8F, built on C1C2 crystal structure as a template) reveals that overall electrostatic surface potential of ChRmine is even more negatively charged than that of the lower-photocurrent cation-conducting channelrhodopsin C1C2, suggesting a more suitable ion-conducting pore/vestibule structure for deterring anion flux and thus allowing greater cation flux. This model would be consistent with prior findings showing how surface electrostatics determine ChR ion selectivity, and together may explain how ChRmine can give rise to higher photocurrent magnitude than other cation ChRs (Kim et al. (2018) supra, Kato et al. (2018) supra). Further structural and spectroscopic studies are clearly needed to completely understand the molecular mechanisms of ChRmine.

Temporal and Spatial Multiplexing of Spatial Light Modulators (MultiSLM)

A general description of the theory and possible embodiments of this brain interface, MultiSLM, are provided here. For more details on the instantiations, see Materials and Methods, and FIGS. 2, 9-11, 20. Additional instantiations are described in FIGS. 20, 21.

MultiSLM was designed as an optical hardware solution for spatially specific >kHz targeting of any of the thousands of neurons located throughout a three-dimensional (3D) volume of tissue. While imaging neural activity (e.g., fluorescent activity reporter), simultaneous photostimulation (e.g., with optogenetics) of user-specified targets is possible—both at high spatial resolution (<1 μm lateral). One to hundreds of diffraction limited spots can be generated in precise locations, simultaneously (within <1 ms), using holograms generated by combining high peak power lasers with an array of several customized, high-resolution spatial light modulators (SLMs) which are controlled by custom computational hardware and software.

Figure 20A:
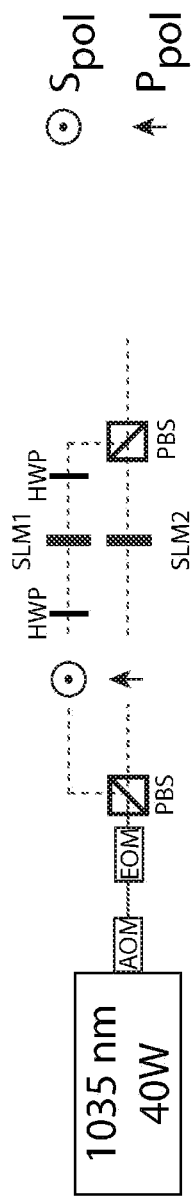
FIGS. 20A-20B depict MultiSLM designs and scalability.
Figure 20B:
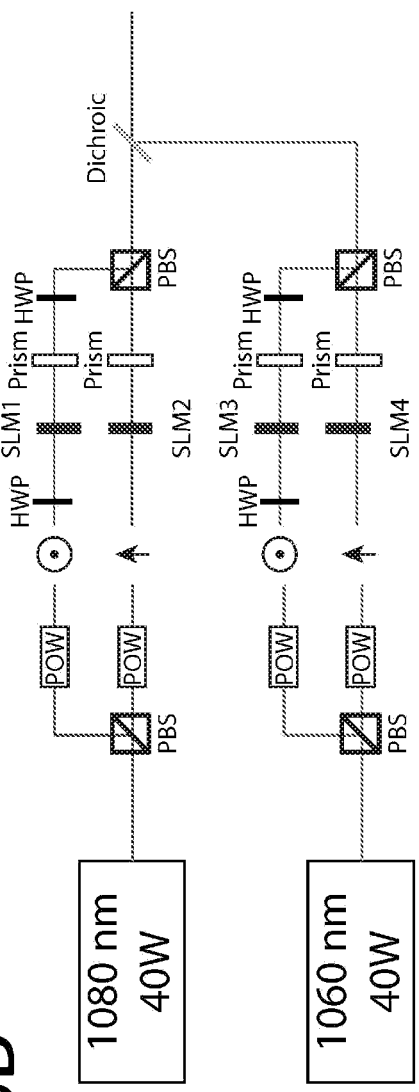
Figure 21A:
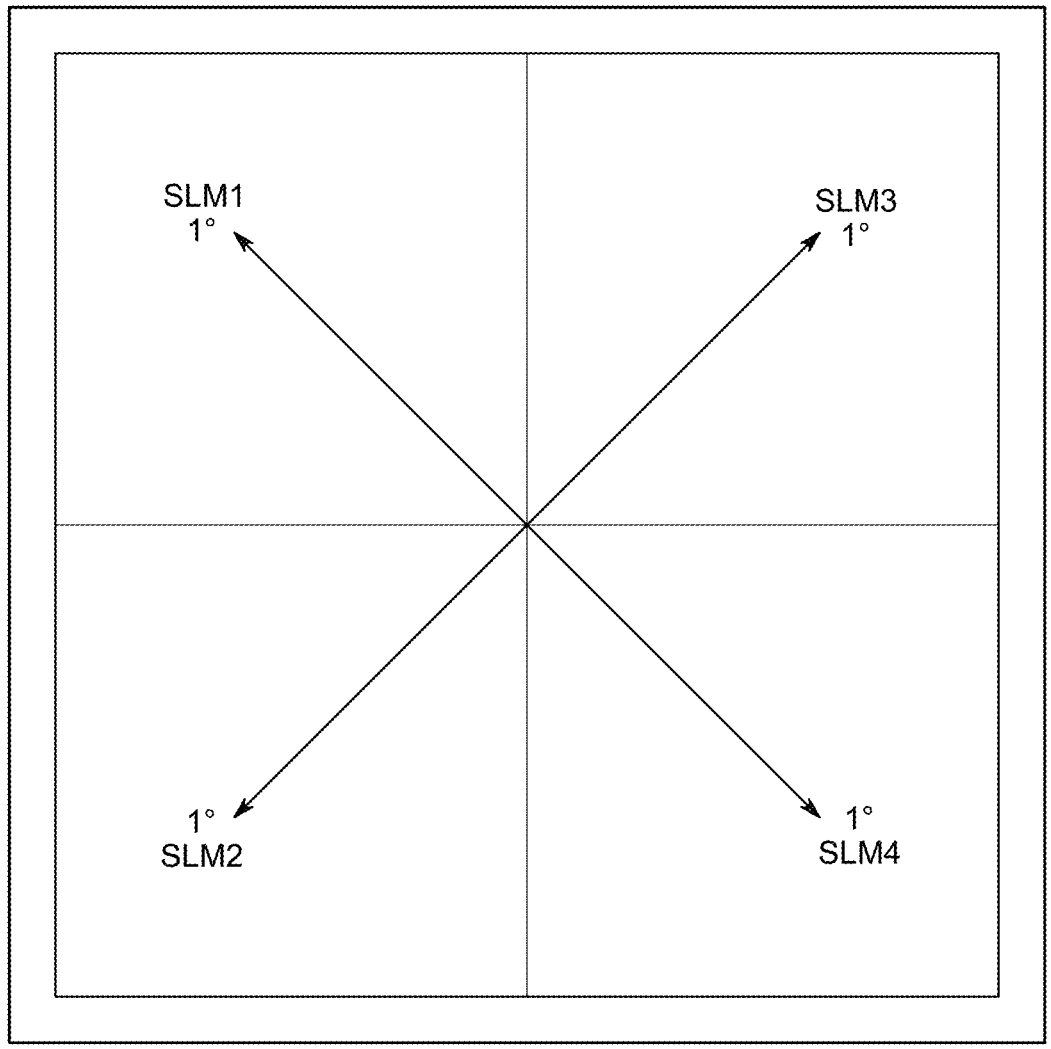
FIG. 21A-21G depict 4× MultiSLM for expanded addressable field of view.
Figure 21B:
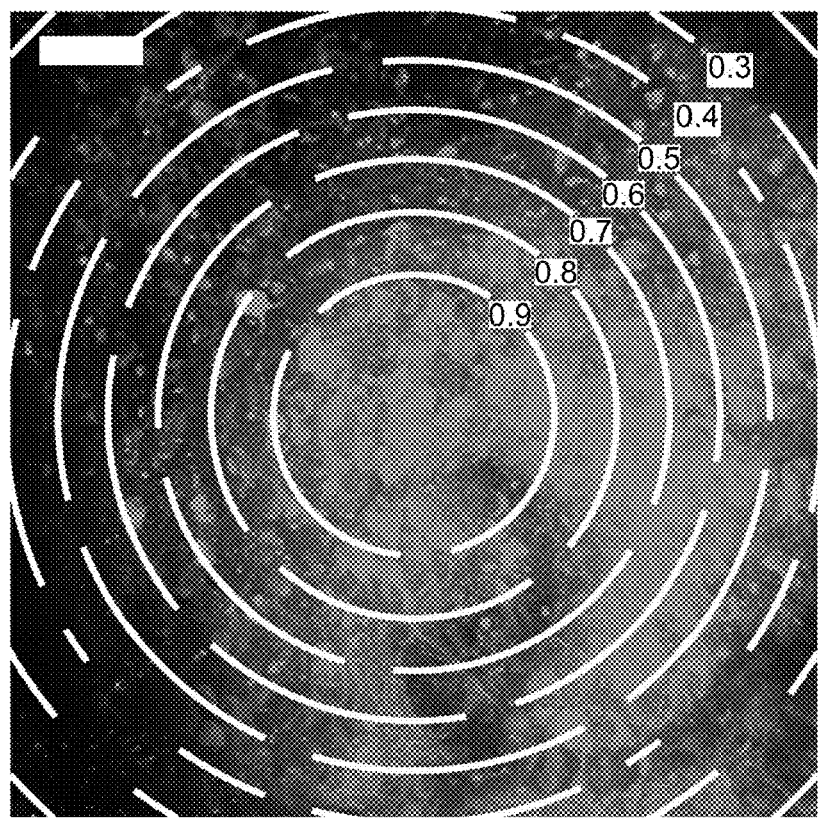
Figure 21C:
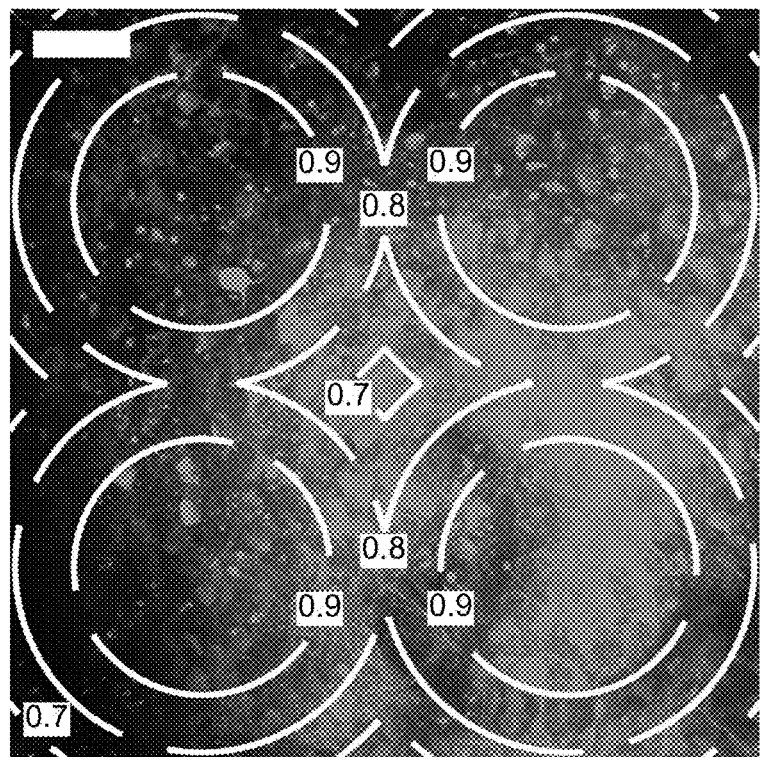
Figure 21D:
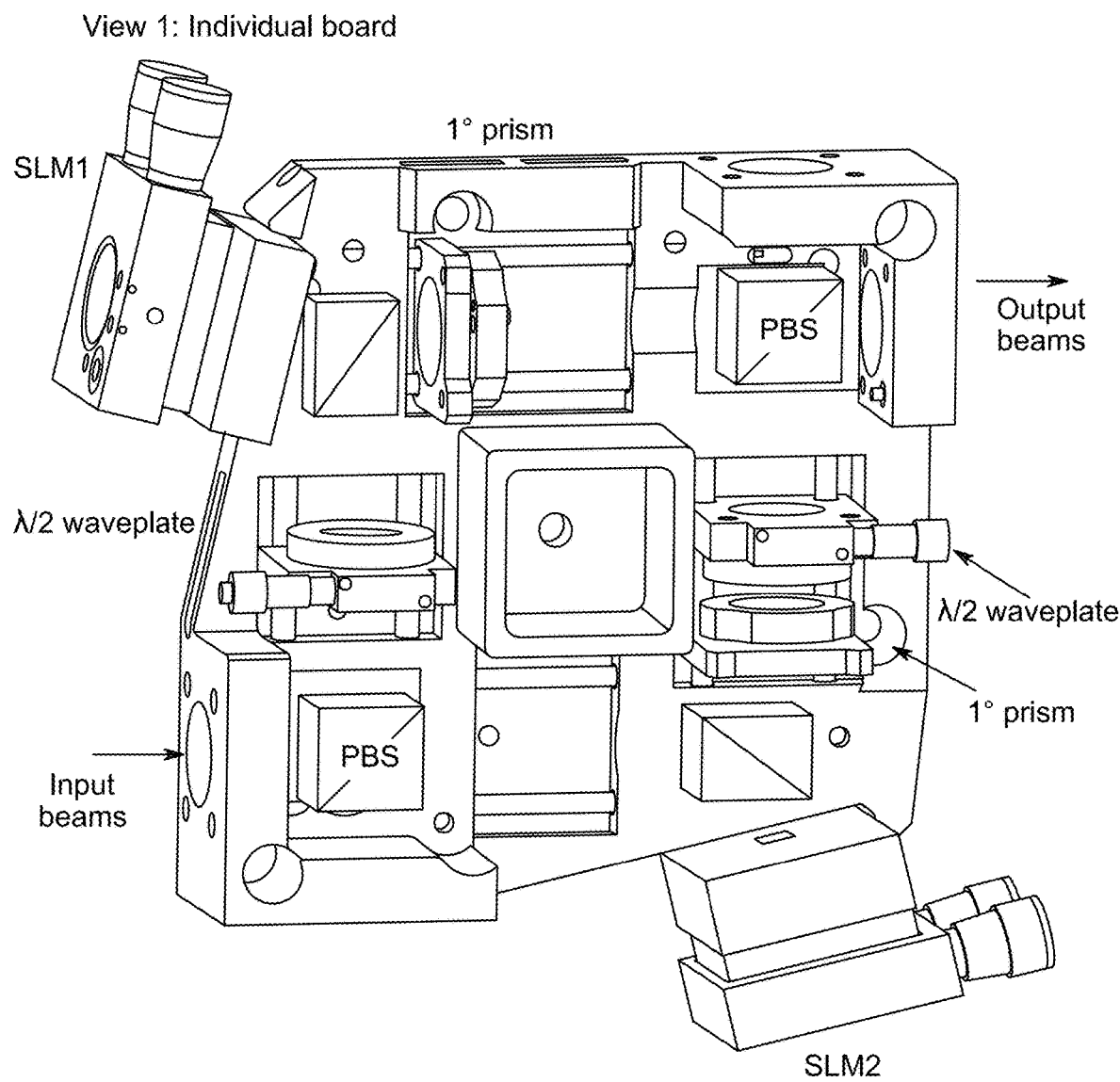
Figure 21E:
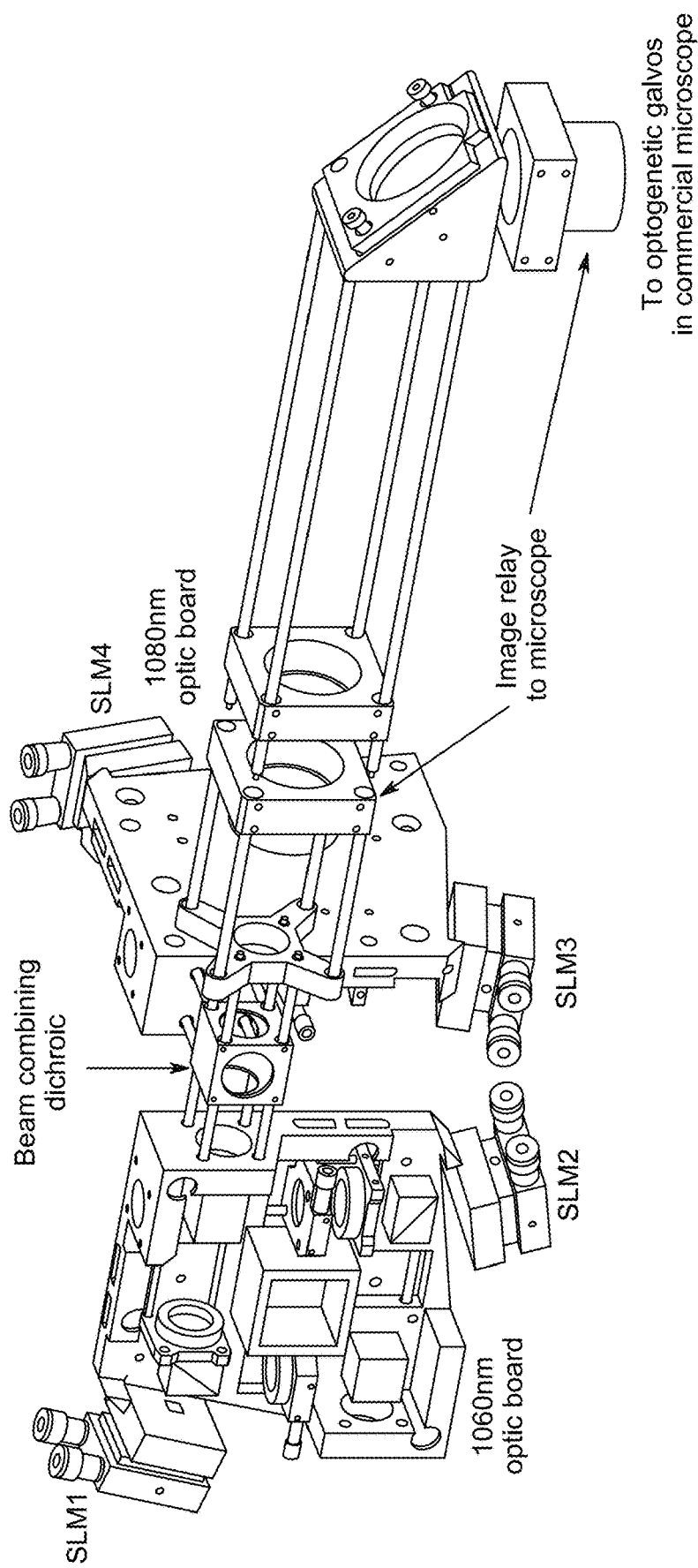
Figures 21F, 21G:
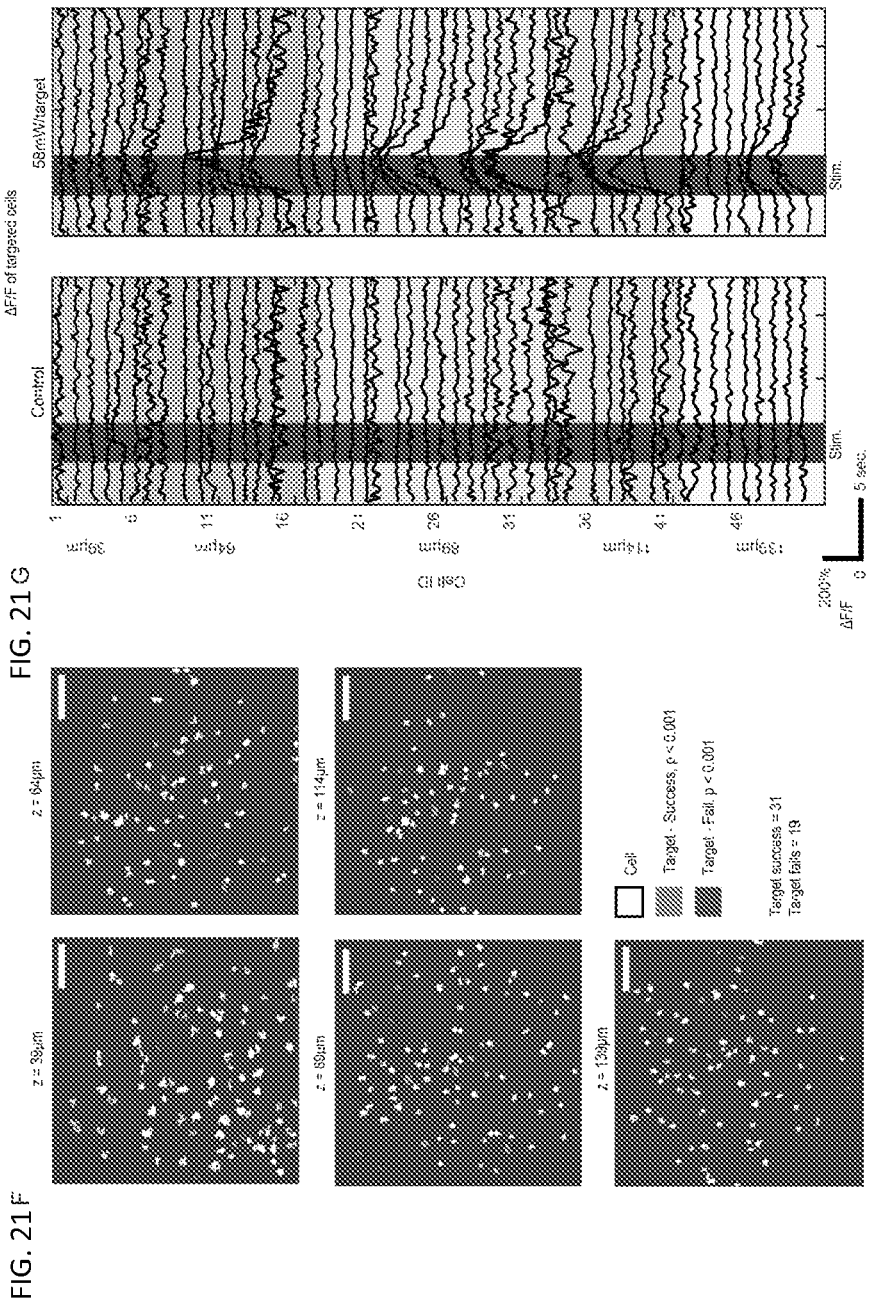
Figure 22:
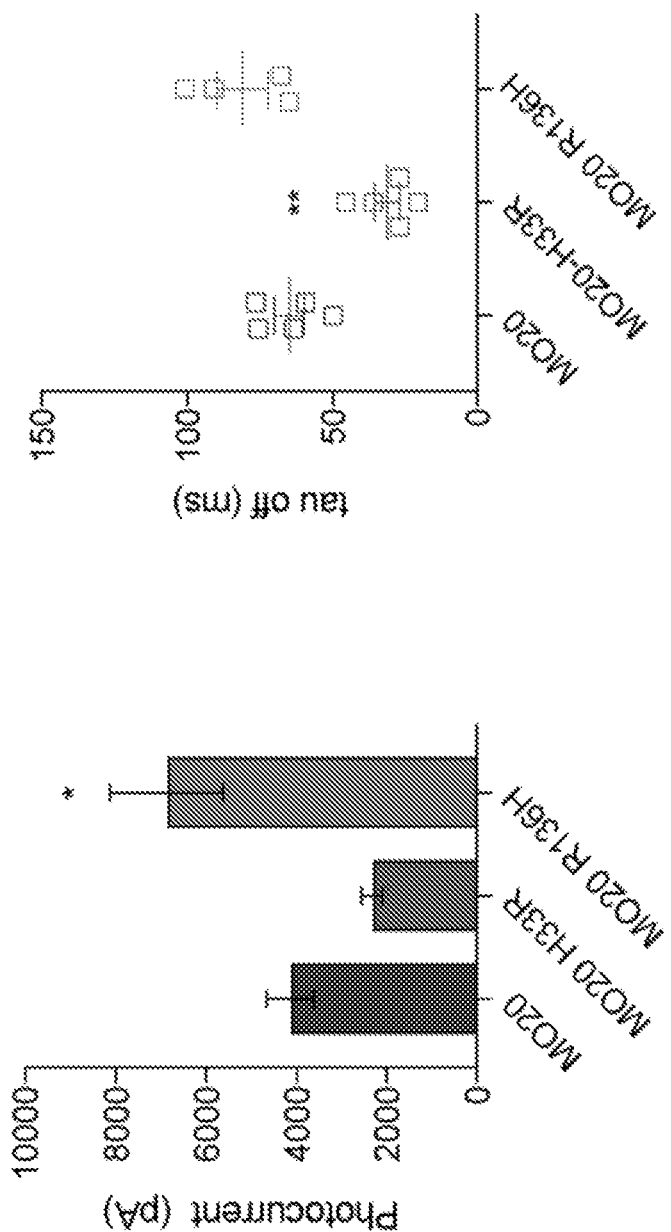
FIG. 22 depicts characteristics of ChRmine mutants.
Figure 25:
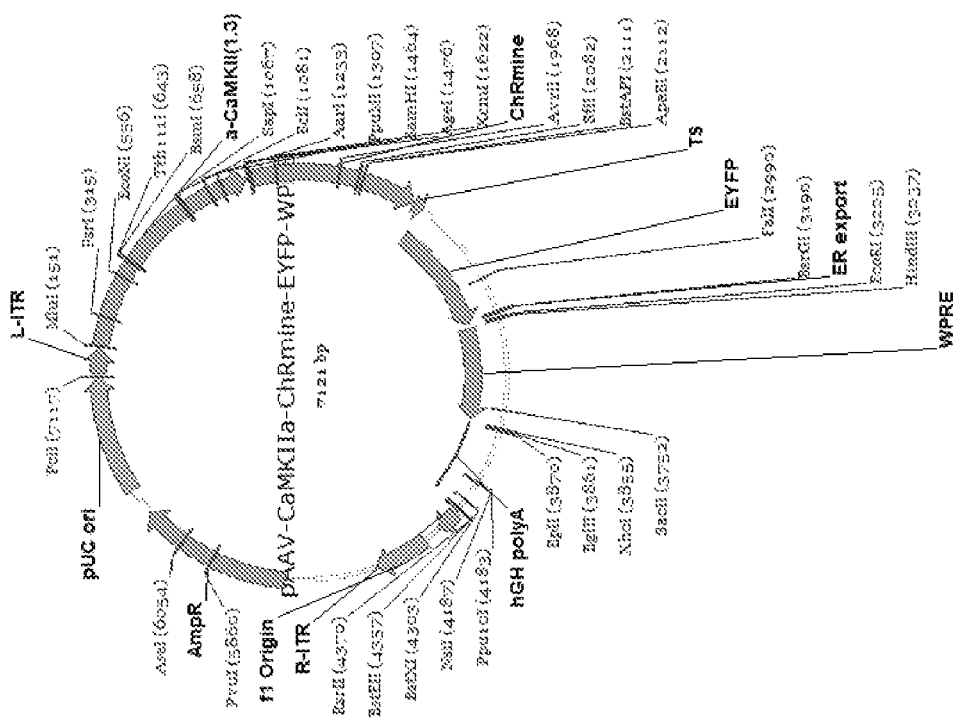
FIG. 25 depicts an expression vector comprising a nucleotide sequence encoding a light-responsive polypeptide of the present disclosure.

In addition to enhancing the individual performance of an SLM, the MultiSLM approach presented here utilizes multiplexing of multiple optical beams (e.g. using polarization-states or chromatic-dependent optics) to gain additional utility beyond a single SLM device. Generally, laser light can originate from 1 or more lasers and be de-multiplexed into at least 2 distinct channels. The channels can be de-multiplexed using an array of strategies for beam separation across multiple channels simultaneously, or directed to different channels (SLMs) in rapid sequence, with temporal precision on the order of microseconds. A number of strategies are available to add additional SLM modules—yielding 4 or more SLMs in one system (FIGS. 20 and 21). These channels are then multiplexed after the SLMs into a common optical axis by using dichroic mirrors, polarization beam splitters, high speed polarization switches (or electro-optic modulators) and/or 50/50 beamsplitters, which are carefully aligned with angle and polarization tuning.

When multiplexing across SLMs, two operation modes—sequential and simultaneous—can be realized and the choice of multiplexing mechanism will influence the performance of these two mode options, as discussed in more detail below. In Sequential Mode, the refresh times are staggered across individual SLMs (each with ~500 Hz refresh rate); thus, the effective temporal resolution of distinct ensemble addressing can exceed 1 kHz. In Simultaneous Mode, multiple SLMs are simultaneously projecting to the sample, allowing more neurons to be targeted at precisely the same time (for example, over a larger volume if the SLMs are spatially tiled; FIG. 21). In all designs, no optical interference is expected to occur between distinct MultiSLM system optical paths since different polarizations, wavelengths and/or optical path lengths are used (and in all presented instantiations, the femto-second, pulsed stimulation laser(s) are synchronized at the source and pulsed with low duty cycle on the nanosecond scale).

Temporal precision and excitation duration (<640 μs) are tightly controlled with custom software and electro-optic modulators (Pockels cells and/or polarization switches), for example, to drive a single spike in each targeted neuron using optogenetics. The SLM modulated light reflects off a set of high-speed galvanometer mirrors which move the SLM generated hologram rapidly in the volume, for example, to create a spiral motion spanning the size of a typical neuron. This pattern could be divided into multiple "mini-spirals" to span most of the neuron cell body more rapidly, with greater efficiency. This motion moves the spot around the cell body of the neuron using empirically-derived parameters for velocity and spatial resolution to reliably yield a spike in the neuron (reaching saturating photocurrent in the best case, or at least enough photocurrent to reliably elicit a spike). It should be noted that, alternatively, a disc of light or virtually any image pattern can be created using SLM-based holography to stimulate an entire neuron cell body, or other part of a neuron, such as a dendritic spine, without the need to move the galvanometer mirrors, but with a lower light power density and thus far lower multiphoton efficiency (in standard two-photon excitation, light power density—modeled as numerical aperture of the system producing the excitation spot—is thought to influence the multiphoton effect exponentially to the fourth power (Denk et al. (1990) *Science* 248:73), and is the single largest determinant of multiphoton excitation probability). Additionally, a grid of dots or other arbitrary pattern of light can be created to match the features (i.e., neuron cell body locations) in the volume for imaging or stimulation. In the instantiation presented here, the galvanometer mirrors are part of a modified two-photon microscope which has two additional sets of galvanometer mirrors, including a resonant scanner dedicated to imaging at high rates.

The wavelengths for SLM optogenetic stimulation are chosen to excite optogenetic actuators (e.g., ChRmine) at or near their peak excitation wavelengths, while minimally exciting neural activity sensors (e.g., GCaMP). This allows simultaneous opsin stimulation and neural activity imaging from the same population of neurons. Thus, the effects of stimulated patterns of activity on local dynamics can be read out in real time with neural activity imaging at single cell resolution. In low stimulation-duty cycle experiments, it may be advantageous to simply omit stimulation epochs from imaging data, since the stimulation laser will elicit some unwanted activity sensor fluorescence. More generally, synchronizing imaging and photostimulation lasers (typically kHz-MHz repetition rates of tens to hundreds of femtosecond pulses) could permit photostimulation to occur out of phase with imaging at the level of laser pulse times (by varying optical path lengths), such that light and fluorescence artifacts caused by optogenetic photostimulation could be completely removed with a lock-in amplifier, chopper circuit operating on the MHz or GHz scale (depending on the laser source repetition rates; fluorescence decay time constants of activity reporters, such as those based on green fluorescent protein (GFP), are likely to be on the order of a few nanoseconds and thus within a fraction of the period of high repetition rate lasers, e.g., 12.5 ns for 80 MHz). Even if lasers are not synchronized with each other, high-speed electronic acquisition circuits could at least partially remove photostimulation artifacts by precisely gating acquisition on laser pulse times. Similar high-speed, laser-synchronized electronic acquisition circuits have been demonstrated previously for spatiotemporal multiplexed two-photon imaging (Cheng et al. (2011) *Nat. Methods* 8:139). These approaches may thus have utility not only for artifact subtraction, but also for multiplexed imaging applications using MultiSLM holography for excitation of multiple points of interest at once in combination with non-scanning acquisition and computational methods that measure and estimate location information of recorded signals in 3D (Yang et al. (2015) *Opt Express* 23:32573, Yang et al. (2016) supra, Pnevmatikakis et al. (2016) *Neuron* 89:285).

As demonstrated, essentially any neurons in the three-dimensional field of view accessible with a single two-photon objective are addressable to stimulate with high precision. Thus, natural patterns of activity can be precisely replayed into the population, for example, to create artificial perceptions, or to artificially reinforce learning. Furthermore, the generated pattern of activity can be altered in precise ways, or combined with other experimental manipulations, to help understand the necessity and sufficiency of quantifiable features of the pattern on neural coding robustness, perception and behavior. In these ways, this novel device and experimental strategy may open fundamental new insights into the complexities of the brain.

FIG. 20. MultiSLM designs and scalability. (A) Simplified, modular design for multiplexing two SLMs. This basic design was used for figures in the main text to enable temporal multiplexing of two SLMs in time to achieve kilohertz hologram refresh rate. In this implementation, the laser contains an acousto-optic modulator (AOM) to rapidly modulate power (200 kHz). The electro-optic modulator (EOM; Pockels cell) rapidly switches polarization (200 kHz, between S polarization/$S_{pol}$, and P polarization/$P_{pol}$). A polarization beamsplitter (PBS) determines the subsequent optical path based on polarization of the beam, and therefore either SLM1 or SLM2, for hologram illumination. Half waveplates (HWP) rotate polarization before and after SLM1 to optimize illumination of the SLM ($P_{pol}$ is optimal for MacroSLM; alternatively, the SLM could be rotated 90° to achieve the same effect). A polarization beamsplitter (PBS) combines both SLM-modulated paths together onto a single beam path. In this configuration, only one SLM path is illuminated at any time. (B) Multiplexing four SLMs using polarization, similar to (A), and wavelength (proof of concept in FIG. 21). Power is modulated on each independent SLM path (POW; either a Pockels cell with PBS, or AOM in the setup). A prism after each SLM is used to add constant tilt to the beam, effectively increasing the maximum deflection angle of the modulated path. Adding this tilt at 90° rotations for each SLM path allows each quadrant of a larger FOV to be addressed. A PBS combines both polarizations of each single wavelength, and a dichroic mirror combines both wavelengths. All four SLM paths can be illuminated and combined fully simultaneously. In our setup, both lasers lines are synchronized to one another (and there are two 40 W laser amplifiers available at each wavelength, fully synchronized, such that all four SLMs can receive a full 40 W beam), and given inherently different path lengths for each SLM modulated beam, the combined beams from all beams do not interfere with one another given their low duty cycle on the femtosecond scale. Orthogonal polarizations should also effectively eliminate any interference, and wavelength differences should significantly reduce possible interference. Removing the prism from the beam paths (using a magnetic mount in the setup) re-centers each SLM on the same FOV, allowing full 4× multiplex of the same addressable volume in time.

FIG. 21. 4× MultiSLM for expanded addressable field of view. (A) Spatial multiplexing of the sample field-of-view (FOV) is realized by dividing the field into quadrants and assigning a unique SLM to each one. This is implemented by placement of wedge prisms (Edmund Optics #45-558) in the optical path near each SLM face—adding a fixed 1° tilt offset to each beam. Each of the four tilting prisms is rotated 90° from each other such that all four SLM beams are tilted radially outward. This tilt of the optical beam will be scaled by the relay optics to the microscope objective to effectively tile the full, square FOV. This configuration substantially improves two-photon efficiency of diffracted spots across an enlarged field of view. (B) Theoretical multi-photon excitation efficiency across the 450 μm FOV of an Olympus 25×/1.05NA objective when using a conventional SLM (512×512 pixel array, 15 μm pixels, BNS/Meadowlark) which is scaled to realize a 0.48 NA photostimulation path. (C) Theoretical multi-photon excitation efficiency of the spatially multiplexed approach addresses the full FOV at high multi-photon excitation efficiency (>0.7) (scale bars 50 μm). Values for two-photon efficiency (contours) take into account the quadratic dependence of the two-photon effect. (D) Mechanical layout of an individual SLM beam combination module dedicated for two SLM units. The layout is functionally similar to that described in FIG. 11F but scaled to accommodate the different sized SLMs. One additional utility of the board is to integrate the wedge prism close to the SLM face (the 1° prisms). Note that in this design there is only a single port where the optogenetic stimulation laser will enter before being selected by the polarizing beam splitter (PBS) to be directed to either of the two integrated SLMs. In this way, the input beam polarization can be rotated to continuously control the amount of power directed to either quadrant. The turning prism assembly for this design is a scaled version of that presented earlier so that it fit appropriately on the 3D printed assembly board. (E) Mechanical layout, combining two of the MultiSLM beam combination boards into a common optical path which is relayed to the optogenetic galvanometer set in the microscope. Each module has a dedicated laser and the two light sources are spectrally separated ($\lambda_1$=1060 nm vs. $\lambda_2$=1080 nm, Laser-femto Uranus). Each module can therefore be multiplexed onto a common optical axis by a beam combining dichroic (Semrock LPD02-1064RU), see FIG. 20B. The spectral- and polarization-multiplexed beams are then optically relayed into a commercial microscope (Bruker Ultima II) via a pair of lenses (Thorlabs AC508-400-B-ML, f=400 mm and Edmund Optics #49-391, f=150 mm, total magnification=0.375x) where the 6 mm clear aperture, optogenetic/uncaging galvanometers are utilized to generate the raster scanned spirals of the SLM-mediated focused points in the sample. (F) A random subset of 50 neurons expressing $C1V1_{T/T}$ and GCaMP6m are targeted for stimulation in a 450×450×100 μm volume of layer 2/3 cortical cells (green, targeted cell showing statistically significant GCaMP response, p<0.001, one-sided t-test, cyan, targeted cell not showing a response, white, other cells). (G) Comparison of the trial-averaged responses (N=5 trials each for control and optogenetic stimulation) across all cells identified for targeting during randomized, no optogenetic stimulation control trials (left) versus in the presence of the optogenetic stimulation (right) (20 μm diameter spirals, 2.11 ms exposure duration, 12 revolutions per spiral). The majority of targeted cells show a robust, statistically significant response in the stimulation period relative to the pre-stimulation baseline (p<0.001, one-sided t-test). Successful targets are found throughout the volume, regardless of position.

MultiSLM Sequential Mode: The MultiSLM design allows for the overall hologram generation rate of the system to surpass the hologram generation rate of any single SLM in the system, by staggering the triggering of individual SLMs in the system, each running at maximum hologram generation rate (plus dwell time on a given hologram). The following equations describe the design and limits on the Sequential Mode of operation.

$$P_{SLM} = L + r_{SLM} + (2 * \sigma_L) + (2 * \sigma_r)$$

Where $P_{SLM}$ is the period in time that the SLM takes to reach complete formation of a hologram (including time to load phase mask onto the SLM and time for the liquid crystal to respond and reach desired phase level to successfully generate the hologram, see FIG. 10B), $r_{SLM}$ is the mean hologram generation time of the SLM from start to completion, L is the mean latency from input trigger to beginning of hologram generation by the SLM, $\sigma_L$ is the standard deviation of latency from trigger input to the time the SLM begins transitioning to the next hologram, and $\sigma_r$ is the standard deviation of $r_{SLM}$. Assuming a normal distribution of L and $r_{SLM}$, this achieves an estimate of $P_{SLM}$ that is true 95% of the time.

Following from this, the hologram refresh rate of a given SLM in the system is:

$$P_{SLM} = \frac{1}{P_{SLM}}$$

The hologram refresh rate of the MultiSLM system in Sequential Mode, $R_{seq}$, that is the rate at which new holograms can be created, is:

$$R_{seq} = \frac{N_{SLM}}{P_{SLM} + d}$$

Where d is the duration that a formed hologram is displayed (e.g., to illuminate the sample for a desired period of time typically on the order of hundreds of microseconds), and $N_{SLM}$ is the number of SLMs in the MultiSLM system.

So far, this assumes that $P_{SLM}$ and d are each the same for all SLMs in the system. More generally, periods, durations, latencies and jitters can be determined for each SLM in the system and summed to determine $R_{seq}$:

$$R_{seq} = \sum_{i=1}^{N_{SLMs}} \frac{N_{SLM}}{P_{SLMi} + d_i}$$

The period of the MultiSLM system, $P_{seq}$, is:

$$P_{seq} = \frac{1}{R_{seq}}$$

The duty cycle of stimulation, D, is defined as:

$$D = \frac{d * N_{SLM}}{P_{seq}}$$

assuming equal interval in time between illumination of each SLM in the MultiSLM system. 100% duty cycle is achieved for all:

$$P_{seq} \leq d * N_{SLM}$$

The maximum hologram refresh rate of the MultiSLM system, MAX($R_{seq}$), occurs with 100% duty cycle when $$R_{seq} = d * N_{SLM}$$

and laser exposure duration times for each SLM in the MultiSLM system, $LaserExposure_{Time}$, are spaced sequentially in time such that:

$$LaserExposure_{Time_{i+1}} = LaserPulse_{Time_i} + \left(\frac{P_{seq}}{N_{SLM}}\right)$$

and the laser pulse duration, LaserExposure$_{Duration}$, equals d:

$$LaserExposure_{Duration} = d$$

and triggers to a given SLM, Ti, repeat with period P$_{trig}$, such that:

$$R_{trig} = P_{seq}$$

assuming that all SLMs in the system have equal P$_{SLM}$ (otherwise, timings should account for the different periods of each SLM to achieve the same effect). MAX(R$_{seq}$) increases as d approaches zero.

Furthermore, the improvement in hologram refresh rate of the MultiSLM compared to the hologram refresh rate of a single SLM in the system, R$_{SLM}$, is:

$$MAX(R_{seq}) = (R_{SLM} + d) * N_{SLM}$$

Increased temporal precision [beyond that afforded by the MAX(R$_{seq}$) at 100% duty cycle] can by generated for all:

$$P_{seq} > d * N_{SLM}$$

leading to lower than 100% duty cycle. This also has the effect of lowering the average power delivered to the sample proportional to the reduction in duty cycle (see below). Higher temporal precision could be applied in a burst mode (that is the array of SLMs are illuminated in rapid sequence at or near 100% duty at the higher rate and overall in less time than P$_{seq}$, followed by a time period to allow the completion of P$_{seq}$) or the higher temporal precision can be achieved while maintaining equal, sequential spacing between SLMs as described above for the 100% duty cycle implementation.

The maximum temporal precision, MAX(p), that is the precision in stimulation time that can be guaranteed by the system, is ultimately limited by the Pockels cell response time (or more generally whatever device is used to modulate the laser beam such as electro-optic modulator, acousto-optic modulator, polarization switch, shutter, etc), r$_{PC}$:

$$MAX(p) = r_{PC}$$

assuming modulator driver electronics with equal or better temporal precision as r$_{PC}$ (if this assumption is not met, then the limiting factor is driver signal sample rate). Furthermore, it is assumed that:

$$r_{PC} \ll d$$

A exposure of laser power to illuminate the hologram is calibrated in intensity depending on the hologram generated (e.g., calibrated to achieve equal hologram spot intensity regardless of imaging depth in scattering tissue), is created by a calibrated signal sent by the modulator electronics, which in conjunction with a polarizing beam splitter and beam dump, achieves the desired power level for the hologram after the light has passes through all optics and biological tissue. Additional software corrections in the hologram generation code can normalize the intensity of spots across the field of view (FOV) to account for diffraction efficiency fall off from the center of the FOV. The timing of the laser exposure for a given SLM should have duration d and be synchronized to start with the completion time of the hologram generation by an SLM, such that:

$$LaserExposure_{Time_i} = T_i + P_{SLM_i}$$

In Sequential Mode, the overall laser power stimulated at one time corresponds to the laser power of the laser exposure generated, LaserExposure$_{Power}$, at that time to illuminate a single hologram generated by a single SLM in the system, without overlap with illumination of other SLMs. Thus, the maximum exposure power, MAX(LaserExposure$_{Power}$), is limited to the maximum power allowable for any one SLM (SLM$_{damagethresh}$) or hologram (Hologram$_{thresh}$). The power may be further limited based on the peak power allowable into the biological tissue, PeakPower$_{biothresh}$, which may depend on the duration of d.

Thus:

$$LaserExposure_{Power} < SLM_{damagethresh}(d)$$

and $$LaserExposure_{Power} < Hologram_{thresh}$$

and $$LaserExposure_{Power} < PeakPower_{biothresh}(d)$$

Furthermore, an allowable average power limit may further constrain the allowable LaserExposure$_{Power}$, for example, in the case when accumulated heating over a longer period of time must be avoided, such as over the full period of the system, P$_{seq}$ (but other time durations can be used depending on the application). Depending on empirically determined limits of power into biological tissue, a limit may be set taking the form of:

$$\sum_{i=1}^{N_{SLM}} \frac{LaserExposure_{Power_i}}{P_{seq}} * D < AveragePower_{biothresh}$$

where lower duty cycle (D) can increase the allowable LaserExposure$_{Power}$, up to peak power limitations.

MultiSLM Simultaneous Mode: In some configurations, the MultiSLM system can be run in synchronized mode, such that independent holograms generated across all of the SLMs are illuminated by laser exposures at the same time, $$LaserExposure_{Time_i} = LaserExposure_{Time_i+1} = \ldots = LaserExposure_{Time_{N_{SLM}}}$$

In this configuration, the damage threshold of a single SLM can be overcome by distributing more power onto more than one SLM.

$$MAX(Power_{simul}) \leq SLM_{damagethresh}(d) * N_{SLM}$$

As in the case of Sequential Mode, power limits will still remain in place regarding peak and average power into the biological tissue, and would be summed across laser power used for each SLM in the system:

$$\sum_{i=1}^{N_{SLM}} LaserExposure_{Power_i} < PeakPower_{biothresh}(d)$$

$$\sum_{i=1}^{N_{SLM}} \frac{LaserExposure_{Power_i}}{P_{seq}} < AveragePower_{biothresh}$$

Some sources of noise depending on the stimulation pattern (hologram) could benefit from distributing the pattern generation across multiple SLMs, instead of a single SLM. For example, complex holograms involving generation of many spots, or complex shapes may be achieved with fewer artifacts (e.g., higher intensity spots or pattern with lower background and/or lower speckle). Since each laser source(s) can produce synchronized pulses across multiple optical paths (corresponding to each optical path in the MultiSLM system), with temporal delay lines for each path (as will occur easily given the extremely low duty cycle of the pulsed laser source and the typical length differences between optical paths on an optical table), the holograms are not generated simultaneously at the femtosecond timescale, but would be synchronized at the microsecond timescale. This design removes any chance of optical interference between the holograms generated on each SLM in the MultiSLM system.

In Simultaneous Mode, duty cycle would be lower than Sequential Mode; and depends on d and the period of the slowest SLM in the system:

$$D_{simul} = \frac{d}{MAX(P_{SLM})}$$

Since all SLMs are illuminated at the same time, the maximum period is limited by the period by the period of the slowest SLM in the system:

$$P_{simul} = MAX(P_{SLM}) + d$$

The refresh rate in Simultaneous Mode is comparable to the refresh rate of a single SLM:

$$R_{simul} \approx MAX(R_{SLM})$$

and is equal to the inverse of $P_{simul}$:

$$R_{simul} = \frac{1}{P_{simul}}$$

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A light-activated polypeptide that comprises an amino acid sequence having at least 99% amino acid sequence identity to the following amino acid sequence:

(SEQ ID NO: 1)
MAHAPGTDQMFYVGTMDGWYLDTKLNSVAIGAHWSCFIVLTITTFYLGYE

SWTSRGPSKRTSFYAGYQEEQNLALFVNFFAMLSYFGKIVADTLGHNFGD

VGPFIIGFGNYRYADYMLTCPMLVYDLLYQLRAPYRVSCSAIIFAILMSG

VLAEFYAEGDPRLRNGAYAWYGFGCFWFIFAYSIVMSIVAKQYSRLAQLA

QDTGAEHSLHVLKFAVFTFSMLWILFPLVWAICPRGFGWIDDNWTEVAHC

VCDIVAKSCYGFALARFRKTYDEELFRLLEQLGHDEDEFQKLELDMRLSS

NGERLRRLS;

and
   a heterologous membrane trafficking signal.

2. The light-activated polypeptide of claim 1, wherein the amino acid sequence comprises an H33R and/or an R136H substitution relative to the amino acid sequence depicted in claim 1.

3. The light-activated polypeptide of claim 1, wherein the heterologous membrane trafficking signal comprises the amino acid sequence KSRITSEGEYIPLDQIDIN (SEQ ID NO: 7).

4. The light-activated polypeptide of claim 1, comprising an endoplasmic reticulum (ER) export signal.

5. The light-activated polypeptide of claim 4, wherein the ER export signal comprises the amino acid sequence FCYENEV (SEQ ID NO: 13).

6. A mammalian cell comprising a light-activated polypeptide in the cell membrane,
   wherein the light-activated polypeptide comprises an amino acid sequence having at least 99% amino acid sequence identity to the following amino acid sequence:

(SEQ ID NO: 1)
MAHAPGTDQMFYVGTMDGWYLDTKLNSVAIGAHWSCFIVLTITTFYLGY

ESWTSRGPSKRISFYAGYQEEQNLALFVNFFAMLSYFGKIVADTILGHN

FGDVGPFIIGFGNYRYADYMLTCPMLVYDLLYQLRAPYRVSCSAIIFAI

LMSGVLAEFYAEGDPRLRNGAYAWYGFGCFWFIFAYSIVMSIVAKQYSR

LAQLAQDTGAEHSLHVLKFAVFTFSMLWILFPLVWAICPRGFGWIDDNW

TEVAHCVCDIVAKSCYGFALARFRKTYDEELFRLLEQLGHDEDEFQKLE

LDMRLSSNGERLRRLS, and
   wherein the light-activated polypeptide is capable of mediating a depolarizing current in the cell when the cell is illuminated with light of a wavelength of from about 600 nm to about 700 nm.

7. The mammalian cell of claim 6, wherein the cell is a neuronal cell.

8. The mammalian cell of claim 7, wherein the cell is a neuron of the neocortex.

9. The mammalian cell of claim 7, wherein the cell is a neuron of the primary visual cortex.

10. A method of modulating the voltage potential of a mammalian cell in response to a light stimulus, the method comprising exposing a mammalian cell that comprises a light-activated polypeptide in the plasma membrane of the cell,
   wherein the light-activated polypeptide comprises an amino acid sequence having at least 99% amino acid sequence identity to the following amino acid sequence:

(SEQ ID NO: 1)
MAHAPGTDQMFYVGTMDGWYLDTKLNSVAIGAHWSCFIVLTITTFYLGY

ESWTSRGPSKRISFYAGYQEEQNLALFVNFFAMLSYFGKIVADTILGHN

FGDVGPFIIGFGNYRYADYMLTCPMLVYDLLYQLRAPYRVSCSAIIFAI

LMSGVLAEFYAEGDPRLRNGAYAWYGFGCFWFIFAYSIVMSIVAKQYSR

LAQLAQDTGAEHSLHVLKFAVFTFSMLWILFPLVWAICPRGFGWIDDNW

TEVAHCVCDIVAKSCYGFALARFRKTYDEELFRLLEQLGHDEDEFQKLE

LDMRLSSNGERLRRLS, and
   wherein in response to exposure to a light stimulus, the voltage potential of the cell is modulated.

11. The method of claim 10, wherein the cell is a neuronal cell.

12. The method of claim 10, wherein the cell is in vitro.

13. The method of claim 10, wherein the cell is in vivo.

14. The method of claim 10, wherein the light has a wavelength of from 600 nm to 700 nm.

15. A method of modulating activity of a mammalian cell that comprises the light-activated polypeptide of claim 1, the method comprising activating the light-activated polypeptide with light.

16. The method of claim 15, wherein the light has a wavelength of from 600 nm to 700 nm.

17. The method of claim 15, wherein the cell is a neuronal cell.

18. The method of claim 15, wherein the cell is in vivo.

19. The method of claim 15, wherein the cell expresses a genetically encoded calcium indicator (GECI).

20. The method of claim 19, wherein the GECI comprises an amino acid sequence having at least 85% amino acid sequence identity to any one of the amino acid sequences of SEQ ID NOs: 28-46.

21. The method of claim 15, wherein the cell further comprises a hyperpolarizing light-responsive polypeptide or a depolarizing light-responsive polypeptide other than the light-responsive polypeptide of claim 1.

22. The method of claim 21, wherein the hyperpolarizing light-responsive polypeptide or depolarizing light-responsive polypeptide comprises an amino acid sequence having at least 85% amino acid sequence identity to any one of the amino acid sequences of SEQ ID NOs: 50-70.

* * * * *

UNITED STATES PATENT AND TRADEMARK OFFICE
CERTIFICATE OF CORRECTION

| | | |
|---|---|---|
| PATENT NO. | : 12,263,350 B2 | Page 1 of 1 |
| APPLICATION NO. | : 17/421346 | |
| DATED | : April 1, 2025 | |
| INVENTOR(S) | : Karl A. Deisseroth et al. | |

It is certified that error appears in the above-identified patent and that said Letters Patent is hereby corrected as shown below:

On the Title Page

Item (73), should read as follows:
(73) Assignee: The Board of Trustees of the Leland Stanford Junior University, Stanford, CA (US); The University of Tokyo, Tokyo (JP)

Signed and Sealed this
Twentieth Day of May, 2025

Coke Morgan Stewart
*Acting Director of the United States Patent and Trademark Office*